United States Patent
Deau et al.

(10) Patent No.: US 12,398,129 B2
(45) Date of Patent: Aug. 26, 2025

(54) IMIDAZOLONE DERIVATIVES AS INHIBITORS OF PROTEIN KINASES IN PARTICULAR DYRK1A, CLK1 AND/OR CLK4

(71) Applicant: PERHA PHARMACEUTICALS, Roscoff (FR)

(72) Inventors: Emmanuel Deau, Roscoff (FR); Pascal George, Roscoff (FR); Laurent Meijer, Roscoff (FR); Frédéric Miege, Lyons (FR)

(73) Assignee: PERHA PHARMACEUTICALS, Roscoff (FR)

( * ) Notice: Subject to any disclaimer, the term of this patent is extended or adjusted under 35 U.S.C. 154(b) by 518 days.

(21) Appl. No.: 17/997,324

(22) PCT Filed: Apr. 29, 2021

(86) PCT No.: PCT/EP2021/061349
§ 371 (c)(1),
(2) Date: Oct. 27, 2022

(87) PCT Pub. No.: WO2021/219828
PCT Pub. Date: Nov. 4, 2021

(65) Prior Publication Data
US 2023/0167104 A1 Jun. 1, 2023

(30) Foreign Application Priority Data

Apr. 30, 2020 (EP) .................... 20305421
Mar. 24, 2021 (EP) .................... 21305361

(51) Int. Cl.
*C07D 417/06* (2006.01)
(52) U.S. Cl.
CPC .................. *C07D 417/06* (2013.01)
(58) Field of Classification Search
CPC .................................................... C07D 417/06
See application file for complete search history.

(56) References Cited

U.S. PATENT DOCUMENTS

2015/0225421 A1* 8/2015 Hagiwara .......... A61P 25/00
548/149

FOREIGN PATENT DOCUMENTS

| WO | 2005082901 A1 | 9/2005 |
| WO | 2006040052 A1 | 4/2006 |
| WO | 2006106046 A1 | 10/2006 |
| WO | 2007103755 A2 | 9/2007 |
| WO | 2009050352 A2 | 4/2009 |

(Continued)

OTHER PUBLICATIONS

Mariano Marica et al, "Systematic diversification of benzylidene heterocycles yields novel inhibitor scaffolds selective for Dyrk1A, Clk1 and CK2", European Journal of Medicinal Chemistry, Elsevier, Amsterdam, NL, vol. 112, Feb. 9, 2016 (Feb. 9, 2016), p. 209-216.
Ching-Chi Chiu et al, "Upregulated Expression of MicroRNA-204-5p Leads to the Death of Dopaminergic Cells by Targeting DYRK1A-Mediated Apoptotic Signaling Cascade", Frontiers in Cellular Neuroscience, vol. 13, Sep. 13, 2019 (Sep. 13, 2019).
Tom Haltenhof et al, "A Conserved Kinase-Based Body-Temperature Sensor Globally Controls Alternative Splicing and Gene Expression", Molecular Cell 78, 57-69 Apr. 2, 2020 (Apr. 2, 2020).
Kunal Kumar et al, "DYRK1A Inhibitors as Potential Therapeutics for β-Cell Regeneration for Diabetes", Journal of Medicinal Chemistry. 2021, 64, 2901-2922.
Nalls et al, "Identification of novel risk loci, causal insights, and heritablerisk for Parkinson's disease: a meta-analysis of genome-wide association studies" The Lancet. vol. Dec. 18, 2019.

(Continued)

*Primary Examiner* — Timothy R Rozof
(74) *Attorney, Agent, or Firm* — WCF IP

(57) ABSTRACT

The present invention relates to a compound of formula (I) wherein $R^1$ represents a $(C_1-C_6)$alkyl group, a spiro$(C_5-C_{11})$ bicyclic ring, a fused phenyl group, a substituted phenyl group, a R'-L- group, wherein L is either a single bond or a $(C_1-C_3)$alkanediyl group, and R' represents a $(C_3-C_8)$cycloalkyl group, abridged $(C_6-C_{10})$cycloalkyl group, a $(C_3-C_8)$heterocycloalkyl group, or a $(C_3-C_8)$heteroaryl group, or a R'-L- group wherein L is a $(C_1-C_3)$alkanediyl group, and R' is an optionally substituted phenyl group, and wherein $R^2$ represents a hydrogen atom or a $(C_1-C_3)$alkyl group or any of its pharmaceutically acceptable salt. The present invention further relates to a composition comprising a compound of formula (I) and a process for manufacturing said compound as well as its synthesis intermediates. It also relates to said compound for use as a medicament, in particular in the treatment and/or prevention of cognitive deficits associated with Down syndrome; Alzheimer's disease; dementia; tauopathies; Parkinson's disease; CDKL5 Deficiency Disorder; Phelan-McDermid syndrome; autism; type 1 and type 2 diabetes; abnormal folate and methionine metabolism; osteoarthritis; Duchenne muscular dystrophy; several cancers; neuroinflammation, anemia and viral and unicellular infections and for regulating body temperature.

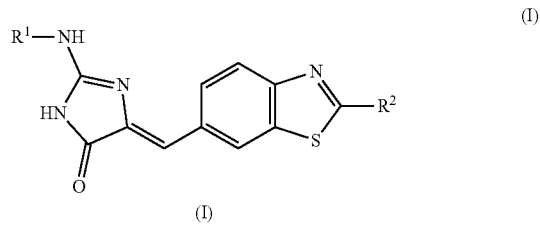

(I)

18 Claims, No Drawings

(56) References Cited

FOREIGN PATENT DOCUMENTS

| WO | 2021114314 | 6/2021 |
| WO | 2021114315 | 6/2021 |
| WO | 2021115489 | 6/2021 |

OTHER PUBLICATIONS

Thu Lan Nguyen et al, "Dual-specificity tyrosine phosphorylation-regulated kinase 1A (DYRK1A) inhibitors: a survey of recent patent literature", Expert Opinion on Therapeutic Patents, Aug. 2, 2017 (Aug. 2, 2017).

Thu Lan Nguyen et al., "Correction of cognitive deficits in mouse models of Down syndrome by a pharmacological inhibitor of DYRK1A" The Company of Biologists Ltd., Aug. 1, 2018 (Aug. 1, 2018).

Noemi Rueda et al, "Translational validity and implications of pharmacotherapies in preclinical models of Down syndrome" Progress in Brain Research, vol. 251 2019.

\* cited by examiner

IMIDAZOLONE DERIVATIVES AS INHIBITORS OF PROTEIN KINASES IN PARTICULAR DYRK1A, CLK1 AND/OR CLK4

FIELD OF THE INVENTION

The present invention relates to Leucettinibs, a class of new compounds useful as a medicament. Said new compounds are in particular useful as kinase inhibitors, and even more particularly as inhibitors of DYRK1A and/or CLK1 and/or CLK4. They are efficient for treating and/or preventing cognitive deficits associated with Down syndrome; Alzheimer's disease and related diseases; dementia; tauopathies; Parkinson's disease; other neurodegenerative diseases; CDKL5 Deficiency Disorder; type 1 and type 2 diabetes; abnormal folate and methionine metabolism; osteoarthritis; Duchenne muscular dystrophy; several cancers and leukemias, viral infections and for regulating body temperature.

Some of said compounds are further inhibitors of other kinases and namely other DYRKs (DYRK1B, 2, 3, 4) and the closely related cdc2-like kinases (CLKs) (CLK 2, 3, 4). Said compounds may then further be efficient for treating and/or preventing Phelan-McDermid syndrome; autism; viral infections, cancers, neuroinflammation, anemia and infections caused by unicellular parasites.

It further relates to the pharmaceutical compositions containing said new compounds and to the chemical synthesis processes for obtaining them.

BACKGROUND

The DYRK and CLK kinase families belong to the CMGC group of kinases which also includes the mitogen-activated protein kinases (MAPK), cyclin-dependent kinases (CDKs) and glycogen synthase kinase-3 (GSK-3). They phosphorylate many substrates involved in signaling pathways. DYRKs and CLKs play key roles in mRNA splicing, chromatin transcription, DNA damage repair, cell survival, cell cycle, differentiation, homocysteine/methionine/folate regulation, endocytosis, neuronal development and functions, synaptic plasticity.

DYRK1A and Down Syndrome (DS)

The gene encoding DYRK1A is located on chromosome 21, in particular in the "Down syndrome critical region" (DSCR), the triploidy of which is responsible for most DS-associated deficiencies. There is considerable genetic and pharmacological evidence showing that the mere 1.5-fold overexpression of DYRK1A is responsible for most cognitive deficits, especially memory and learning deficits, observed in DS patients (Rueda N et al., 2020. Translational validity and implications of pharmacotherapies in preclinical models of Down syndrome. Prog Brain Res 251, 245). Pharmacological or genetical normalization of DYRK1A levels restores cognitive functions (Nguyen T L et al., 2017. Dual-specificity tyrosine phosphorylation-regulated kinase 1A (DYRK1A) inhibitors: a survey of recent patent literature. Expert Opin. Ther. Pat. 27, 1183-1199; Nguyen T L et al., 2018. Correction of cognitive deficits in mouse models of Down syndrome by pharmacological inhibitor of DYRK1A. Dis. Model Mech. 11, dmm035634).

DYRK1A and Alzheimer's Disease (AD), Tauopathies

There is mounting evidence for a role of DYRK1A in the onset of AD. DYRK1A phosphorylates key substrates involved in AD and dementia: Tau, septin 4, amyloid precursor protein (APP), presenilin 1, neprilysin, Munc18-1, α-synuclein, RCAN1, β-Tubulin. There is evidence for abnormal expression and post-translational modifications of DYRK1A in AD. By modulating alternative splicing of exon 10, DYRK1A favors the production of the 3R-Tau splice isoform (characteristic for DS/AD/tauopathy) over the normal 4R-Tau isoform. DYRK1A inhibition promotes autophagy which could counterbalance the autophagy deficit seen in AD.

DYRK1A and Parkinson's Disease (PD) and Pick Disease

GWAS studies have revealed that DYRK1A is a risk factor for PD (Nalls M A et al., 2019. Identification of novel risk loci, causal insights, and heritable risk for Parkinson's disease: a meta-analysis of genome-wide association studies. Lancet Neurol 18, 1091). DYRK1A phosphorylates key factors for PD such as Parkin, septin 4, α-synuclein. Upregulation of micro-RNA specific for PD target DYRK1A expression (Chiu C C et al., 2019. Upregulated expression of microRNA-204-5p leads to the death of dopaminergic cells by targeting DYRK1A-mediated apoptotic signaling cascade. Front Cell Neurosci 13, 399). There is further evidence that DYRK1A expression is increased in PD. DYRK1A is overexpressed in Pick disease.

DYRK1A and Other Diseases (Viral Infections, Type 1 and Type 2 Diabetes, Cancers)

DYRK1A and DYRK1B are utilized during HCMV placental replication. Inhibition of DYRKs prevent replication of various viruses including Herpes virus, cytomegalovirus and HIV-1. DYRK1A inhibitors stimulate the proliferation of pancreatic, insulin-producing 0-cells, a promising approach to type 1 and type 2 diabetes (Ackeifi C et al., 2020. Pharmacologic and genetic approaches define human pancreatic β cell mitogenic targets of DYRK1A inhibitors. JCI Insight 5, e132594; Kumar K et al., 2021. DYRK1A inhibitors as potential therapeutics for j-Cell regeneration for diabetes. J Med Chem. 2021 Mar. 8. doi: 10.1021/acs.jmedchem.0c02050. Epub ahead of print. PMID: 33682417). There is abundant literature linking DYRK1A with cancer. The most prominent examples are megakaryoblastic leukemia, acute lymphoblastic leukemia, pancreatic cancer and brain tumor (glioblastoma).

Accordingly, abnormalities in DYRK1A dosage are associated with cognitive disorders observed in Down syndrome, and Alzheimer's disease. DYRK1A is a risk factor for Parkinson's disease. Inhibition of DYRK1A additionally triggers the proliferation of pancreatic, insulin-producing 0-cells. DYRK1A inhibitors may thus find applications in preventing and/or treating DS, AD, and other Tauopathies, dementia, PD, Niemann-Pick Type C Disease, CDKL5 deficiency disorder, type 1 and type 2 diabetes, viral infections, several cancers (leukemia, pancreatic cancer, glioblastoma), osteoarthritis, infections caused by unicellular parasites and for regulating body temperature.

Other DYRKs and Human Disease

DYRK1B is involved in the replication of various viruses including hepatitis C virus, Chikungunya virus, Dengue virus and SARS coronavirus, cytomegalovirus and human papillomavirus. Like DYRK1A, DYRK1B inhibition leads to the proliferation of pancreatic, insulin-producing 0-cells. DYRK1B is involved in neuroinflammation. Targeting DYRK1B provides a new rationale for treatment of various cancers such as liposarcoma or breast cancers.

DYRK2, in association with GSK-30, regulates neuronal morphogenesis. DYRK2 is involved in various ways in cancer development.

DYRK3 promotes hepatocellular carcinoma. DYRK3 couples stress granule condensation/dissolution to mTORC1 signaling. DYRK3 regulates phase transition of membraneless organelles in mitosis. DYRK3 and DYRK4 are involved in the regulation of cytoskeletal organization and process outgrowth in neurons.

DYRK1A decreases axon growth, DYRK3 and DYRK4 increase dendritic branching and DYRK2 decreases both axon and dendrite growth and branching.

CLKs and Human Disease

Note that CLK is a confusing abbreviation as it has the following meanings: (a) monooxygenase CLK-1 (human homologue COQ7); (b) Collectin-K1 (CL-K1, or CL-11), a multifunctional Ca(2+)-dependent lectin; (c) MAPK gene of the maize pathogen *Curvularia lunata*, Clk1; (d) mitochondrial membrane-bound enzyme Clock-1 (CLK-1); (e) *Colletotrichum lindemuthianum* kinase 1 (clk1).

CLKs play essential functions in alternative splicing. CLKs act as a body-temperature sensor which globally controls alternative splicing and gene expression. The activity of CLKs is indeed highly responsive to physiological temperature changes, which is conferred by structural rearrangements within the kinase activation segment (Haltenhof T et al., 2020. A conserved kinase-based body-temperature sensor globally controls alternative splicing and gene expression. Mol Cell 78, 57).

CLK1 and Human Disease

CLK1 triggers periodic alternative splicing during the cell division cycle. CLK1 regulates influenza A virus mRNA splicing and its inhibition prevents viral replication. CLK1 and CLK2 also regulates HIV-1 gene expression. CLK1 is an autophagy inducer. CLK1 inhibition may prevent chemoresistance in glioma and CLK1 inhibition by TG693 allows the skipping of mutated exon 31 of the dystrophin gene in Duchenne Muscular Dystrophy.

Other CLKs and Human Disease

Inhibition of CLK2 has been proposed as a way to improve neuronal functions and combat intellectual disability and autism in Phelan-McDermid syndrome (PMDS). Dual inhibition of CLK2 and DYRK1A by Lorecivivint is a potential disease-modifying approach for knee osteoarthritis. CLK2 inhibition compromises MYC-driven breast tumors, triple negative breast cancer and glioblastoma. Inhibition of CLK2 improves autistic features in Phelan-McDermid syndrome (PMDS). Alternative splicing of Tau exon 10 is regulated by CLK2 and other CLKs, leading to changes in the 3R/4R isoforms ratio and neurodegeneration in sporadic AD. Inhibition of CLK2, CLK3, CLK4 blocks HIV-1 production. By regulating alternative splicing CLKs modulate the balance between pro-apoptotic and anti-apoptotic regulators, and inhibition of CLKs may thus find applications in the treatment of numerous cancers.

CLK3 contributes to hepatocellular carcinoma and prostate cancer.

The following Table 1 summarizes the implication of the DYRKs and CLKs kinases in various diseases.

TABLE 1

| Kinase target | Disease |
| --- | --- |
| DYRK1A | Down syndrome (DS) |
| DYRK1A | Alzheimer's disease (AD) and other Tauopathies |
| DYRK1A | Parkinson's disease |
| DYRK1A | Pick disease |
| DYRK1A | CDKL5 Deficiency Disorder |
| DYRK1A | Type 1 and Type 2 diabetes |
| DYRK1A | Abnormalities in folate and methionine metabolism |
| DYRK1A | Glioblastoma |
| DYRK1A | Head and neck squamous cell carcinoma |

TABLE 1-continued

| Kinase target | Disease |
| --- | --- |
| DYRK1A | Pancreatic ductal adenocarcinoma |
| DYRK1A | Megakaryoblastic leukemia |
| DYRK1A | Acute Lymphoblastic Leukemia (ALL) |
| DYRK1A | Knee osteoarthritis |
| DYRK1A | Human immunodeficiency virus type 1 (HIV-1) |
| DYRK1A, | Human cytomegalovirus (HCMV) |
| DYRK1B | |
| DYRK1B | Hepatitis C virus, Chikungunya virus, Dengue virus and Severe acute respiratory syndrome coronavirus, Cytomegalovirus, Human papillomavirus |
| DYRK1B | Type 1 and Type 2 diabetes |
| DYRK1B | Neuroinflammation |
| DYRK1B | Liposarcoma, Breast cancer, Hedgehog/GLI-dependent cancer |
| DYRK2 | Triple-negative breast cancer (TNBC) and multiple myeloma (MM) |
| DYRK2 | Glioblastoma |
| DYRK3 | Hepatocellular carcinoma |
| DYRK3 | Influenza virus replication |
| DYRK3 | Anemia |
| DYRKs | Glioblastoma |
| DYRKs | Herpes simplex virus, cytomegalovirus, varicella-zoster virus |
| LmDYRK1 | Leishmaniasis |
| TbDYRK | *Trypanosoma brucei* |
| CLK1 | Glioblastoma |
| CLK1 | Duchenne muscular dystrophy |
| CLK1 | Influenza A |
| CLK2 | HIV-1 |
| CLK1/CLK2 | Triple-negative breast cancer |
| CLK2 | Autism, Phelan-McDermid syndrome (PMDS) |
| CLK2 | Knee osteoarthritis |
| CLK2 | Breast cancer, Triple negative breast cancer, Glioblastoma |
| CLK2 | Alzheimer's disease (alternative splicing of Tau exon 10) |
| CLK3 | Hepatocellular carcinoma, Prostate cancer |
| CLKs | Body temperature |
| CLKs | Prostate cancer, Gastrointestinal cancer |
| PfCLKs | Malaria |
| DYRKs/CLKs | Glioblastoma and numerous other cancers |

DYRKs and CLK Inhibitors

Several DYRK1A inhibitors have been reported in recent years. Most DYRK1A inhibitors also inhibit DYRK1B, 2, 3, 4, as well as the closely related CLK1, 2, 3, 4, with several possible inhibition profiles.

Some imidazolone derivatives, named Leucettines in the text below, were disclosed in WO2009/050352 as kinase inhibitors and more particularly as inhibitors of the DYRK1A kinase.

There is still a need to identify new compounds for treating and/or preventing the diseases as recited above, and particularly through the inhibition, and in particular selective inhibition, of DYRK1A, other DYRKs and the related CLKs kinases.

SUMMARY OF THE INVENTION

It has now been found that the compounds as defined in formula (I) herein after are useful in the treatment and/or prevention of a disease selected from cognitive deficits associated with Down syndrome; Alzheimer's disease and related diseases; dementia; tauopathies; Parkinson's disease; other neurodegenerative diseases; CDKL5 Deficiency Disorder; Phelan-McDermid syndrome; autism; type 1 and type 2 diabetes; abnormal folate and methionine metabolism; osteoarthritis; several cancers and leukemias; neuroinflammation, anemia, infections caused by unicellular parasites, viral infections and for regulating body temperature.

The present invention therefore relates to a compound of formula (I), as defined below.

The present invention further relates to a compound of formula (I) as defined below for use as a medicament.

The present invention further relates to a compound of formula (I) as defined below for use in the treatment and/or prevention of a disease selected from cognitive deficits associated with Down syndrome; Alzheimer's disease and related diseases; dementia; tauopathies; Parkinson's disease; other neurodegenerative diseases; CDKL5 Deficiency Disorder; Phelan-McDermid syndrome; autism; type 1 and type 2 diabetes; abnormal folate and methionine metabolism; osteoarthritis; several cancers and leukemias, neuroinflammation, anemia, infections caused by unicellular parasites, viral infections and for regulating body temperature.

The present invention further relates to a pharmaceutical composition comprising it and to a process for manufacturing it.

The present invention at last relates to synthetic intermediates of formula (II) as defined below.

Definitions

As used herein, the term "patient" refers to either an animal, such as a valuable animal for breeding, company or preservation purposes, or preferably a human or a human child, which is afflicted with, or has the potential to be afflicted with one or more diseases and conditions described herein.

In particular, as used in the present application, the term "patient" refers to a mammal such as a rodent, cat, dog, primate or human, preferably said subject is a human and also extends to birds.

The identification of those patients who are in need of treatment of herein-described diseases and conditions is well within the ability and knowledge of one skilled in the art. A veterinarian or a physician skilled in the art can readily identify, by the use of clinical tests, physical examination, medical/family history or biological and diagnostic tests, those patients who are in need of such treatment.

In the context of the invention, the term "treating" or "treatment", as used herein, means preventing, reversing, alleviating, inhibiting the progress of, or preventing the disease and its cognitive, motor or metabolic changes resulting from high DYRK1A kinase and/or CLK1 expression and activity, and optionally associated with the abnormalities in other DYRKs (DYRK1B, 2, 3, 4) and the closely related further cdc2-like kinases (CLKs) (CLK 2, 3, 4) and more particularly in connection to the diseases as described herein after in the paragraph "PATHOLOGIES".

Therefore, the term "treating" or "treatment" encompasses within the framework of the present invention the improvement of medical conditions of patients suffering from the diseases as described herein after in the paragraph "PATHOLOGIES", related to high expression and activity of any of the DYRK1A and CLK1 kinases, and optionally associated with the abnormalities in other DYRKs (DYRK1B, 2, 3, 4) and the closely related cdc2-like kinases (CLKs) (CLK 2, 3, 4).

As used herein, an "effective amount" refers to an amount of a compound of the present invention which is effective in preventing, reducing, eliminating, treating or controlling the symptoms of the herein-described diseases and conditions.

The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

The term "effective amount" includes "prophylaxis-effective amount" as well as "treatment-effective amount".

The term "preventing", as used herein, means reducing the risk of onset or slowing the occurrence of a given phenomenon, namely in the present invention, a disease resulting from abnormal DYRKs/CLKs kinase activity, in particular DYRK1A kinase activity.

As used herein, «preventing» also encompasses «reducing the likelihood of occurrence» or «reducing the likelihood of reoccurrence».

The term "prophylaxis-effective amount" refers to a concentration of compound of this invention that is effective in inhibiting, preventing, decreasing the likelihood of anyone of the hereabove described diseases.

Likewise, the term "treatment-effective amount" refers to a concentration of compound that is effective in treating the hereabove described diseases, e.g. leads to a reduction or normalization DYRK1A and/or CLK1 kinase activity, and optionally additionally of DYRKs/CLKs kinase activity in general, following examination when administered after disease has occurred.

As used herein, the term "pharmaceutically acceptable" refers to those compounds, materials, excipients, compositions or dosage forms which are, within the scope of sound medical judgment, suitable for contact with the tissues of human beings and animals without excessive toxicity, irritation, allergic response or other problem complications commensurate with a reasonable benefit/risk ratio.

DETAILED DESCRIPTION OF THE INVENTION

The inventors have surprisingly found that the compounds of formula (I) as disclosed herein after inhibit the DYRK1A, other DYRKs (DYRK1B, DYRK2, DYRK3, DYRK4) and CLKs (CLK1, CLK2, CLK3, CLK4). This assertion is based on data as illustrated in the following examples and more detailed herein after.

According to a first aspect, a subject-matter of the present invention relates to a compound of formula (I)

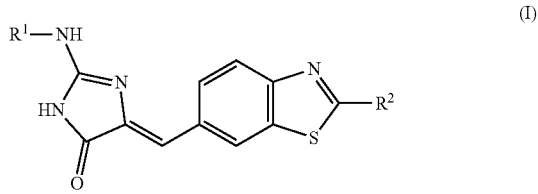

wherein $R^1$ represents:
(i). a $(C_1-C_6)$alkyl group substituted by one or two groups selected from a $—COOR^a$ group, a hydroxy group, a halogen atom, a $(C_1-C_4)$alkoxy group and a benzyloxy group, said benzyloxy being optionally substituted on its phenyl group by one to three halogen atoms,
(ii). a spiro$(C_5-C_{11})$bicyclic ring,
(iii). a fused phenyl group, selected from phenyl groups fused with a $(C_5-C_6)$cycloalkyl or $(C_5-C_6)$heterocycloalkyl, which $(C_5-C_6)$cycloalkyl and $(C_5-C_6)$heterocycloalkyl ring optionally comprise an insaturation and is optionally substituted by a $(C_1-C_4)$ alkyl group, a hydroxy group, a halogen atom, a $(C_1-C_3)$ alkoxy group or a $—COR^a$ group, (iv). a phenyl group, substituted by one or two groups selected from a $(C_1-C_8)$alkyl, a $(C_1-C_3)$fluoroalkyl, a fluoro$(C_1-C_4)$alkoxy group, a halogen atom, and a $(C_4-C_7)$heterocycloalkyl group, said $(C_4-C_7)$heterocycloalkyl group being itself optionally substituted by a $(C_1-C_4)$ alkyl group, or (v). a R'-L- group, wherein L is either a single bond or a $(C_1-C_3)$alkanediyl group, optionally substituted by a group selected from a hydroxy group and a $(C_1-C_3)$alkoxy group, and R' represents:
- (v.1) a $(C_3-C_8)$cycloalkyl group, optionally substituted by one, two or three groups selected from a $(C_1-C_4)$alkyl group, a hydroxy group, a halogen atom and a $(C_1-C_3)$ alkoxy group,
- (v.2) a bridged $(C_6-C_{10})$cycloalkyl group, optionally substituted by one to three groups selected from a $(C_1-C_4)$alkyl group, a $(C_1-C_4)$alkoxy group, a halogen atom, a hydroxy group, a —O—C(O)—$R^d$ group, a —O—C(O)—NH$R^d$ group and a —NH—C(O)—$R^d$ group, a —SO$_2$—$R^d$ group, a —N($R^e$)$_2$ group and a —COO$R^a$ group,
- (v.3) a $(C_3-C_8)$heterocycloalkyl group, optionally substituted by one to three groups selected from a —COO$R^a$ group, a hydroxy group, a halogen atom, a $(C_1-C_4)$alkyl group and an oxo group,
- (v.4) a $(C_3-C_8)$heteroaryl group, optionally substituted by one to three groups selected from a halogen atom, a $(C_1-C_4)$alkyl group, a $(C_1-C_4)$ alkoxy group and a N-methylpiperazinyl group, or
- (v.5) a bridged $(C_6-C_{10})$heterocycloalkyl group, or (vi). a R'-L- group wherein L is a $(C_1-C_3)$alkanediyl group, optionally substituted by a group selected from a —N$R^bR^c$ group, a $(C_1-C_4)$alkoxy group, a hydroxy group, a —COO$R^a$ group and a halogen atom, and R' is a phenyl group, optionally substituted by one to three groups selected from the group consisting of $(C_1-C_6)$alkyl group, a fluoro$(C_1-C_4)$alkyl group and a fluoro$(C_1-C_4)$alkoxy group, a halogen atom and a hydroxy group, $R^a$ represents a $(C_1-C_4)$alkyl group or a hydrogen atom,
$R^b$ and $R^c$ independently represent a $(C_1-C_6)$alkyl group or a hydrogen atom,
$R^d$ represents a $(C_1-C_4)$alkyl group or a cyclopropyl group,
$R^e$ represents a $(C_1-C_3)$alkyl group, and
$R^2$ represents a hydrogen atom or a $(C_1-C_3)$alkyl group, or any of its pharmaceutically acceptable salt.

The inventors have surprisingly discovered that compounds having the following scaffolds of formula (A) to (F) displayed much reduced kinase inhibitory activities on DYRK1A and other related kinases compared to their benzothiazole homologs (compounds according to the invention): IC$_{50}$ values were reduced by 10 to 1000-fold factors, and some compounds were completely inactive at the highest dose tested (10 PM).

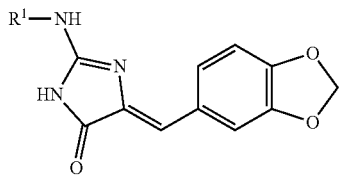

(A)

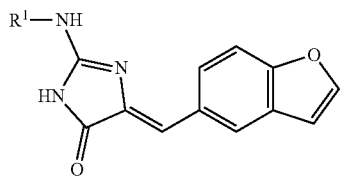

(B)

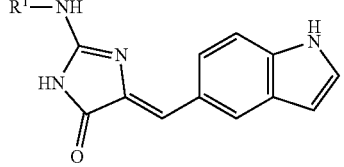

(C)

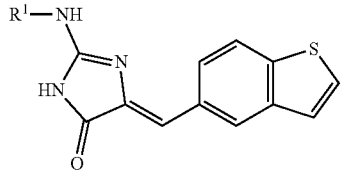

(D)

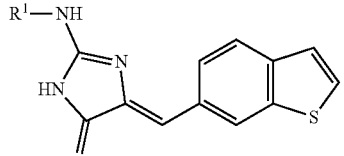

(E)

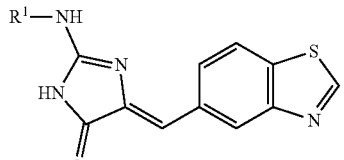

(F)

These much-reduced kinase inhibitory activities have been verified, for example, by individual comparison of a compound of formula (I) and of a compound having a scaffold of formula (A) to (F), wherein in both, $R^2$ is a hydrogen atom and $R^1$ is selected from the group consisting of cyclohexyl, cycloheptyl, cyclooctyl, 2-methoxy-1-phenyl-ethyl.

According to a particular embodiment, the present invention relates to a compound of formula (I) as defined herein above wherein $R^1$ represents:
- (i). a $(C_2-C_6)$alkyl group substituted by one or two groups selected from a —COO$R^a$ group, a hydroxy group, a halogen atom, a $(C_1-C_4)$alkoxy group and a benzyloxy group, said benzyloxy being optionally substituted on its phenyl group by one to three halogen atoms,
- (ii). a spiro$(C_7-C_9)$bicyclic ring,
- (iii). a fused phenyl group, selected from phenyl groups fused with a cyclopentyl or a heterocyclopentyl, which cyclopentyl and heterocyclopentyl group optionally comprise an insaturation and is optionally substituted by a $(C_1-C_4)$ alkyl group, a hydroxy group, a halogen atom, a $(C_1-C_3)$alkoxy group or a —CO$R^a$ group,
- (iv). a phenyl group, substituted by one or two groups selected from $(C_1-C_8)$alkyl, a $(C_1-C_3)$fluoroalkyl, a fluoro$(C_1-C_4)$alkoxy group a halogen atom, and a $(C_4-C_7)$heterocycloalkyl group, said $(C_4-C_7)$heterocycloalkyl group being itself optionally substituted by a $(C_1-C_4)$ alkyl group, or (v). a R'-L- group wherein
  L is either a single bond or a $(C_1-C_3)$alkanediyl group, optionally substituted by a group selected from a hydroxy group and a $(C_1-C_3)$alkoxy group, and R' represents:
  (v.1) a $(C_3-C_8)$cycloalkyl group, optionally substituted by one, two or three groups selected from a $(C_1-C_4)$alkyl group, a hydroxy group, a fluor atom and a $(C_1-C_3)$ alkoxy group,
  (v.2) a bridged $(C_7-C_{10})$cycloalkyl group, optionally substituted by one to three groups selected from a $(C_1-C_4)$alkyl group, a $(C_1-C_4)$alkoxy group, a hydroxy group, a halogen atom, a —O—C(O)—$R^d$ group, a —O—C(O)—NH$R^d$ group, a —NH—C(O)—$R^d$ group, a —SO$_2$—$R^d$ group, a —N($R^e$)$_2$ group and a —COO$R^a$ group,
  (v.3) a $(C_4-C_7)$heterocycloalkyl group, optionally substituted by one to three groups selected from a —COO$R^a$ group, a hydroxy group, a halogen atom, a $(C_1-C_4)$alkyl group and a oxo group,
  (v.4) a heteroaryl group, optionally substituted by one to three groups selected from a halogen atom, $(C_1-C_4)$alkyl group, a $(C_1-C_4)$alkoxy group, a N-methylpiperazinyl group, or
  (v.5) a bridged $(C_6-C_{10})$heterocycloalkyl group, or
(vi). a R'-L- group wherein
  L is a $(C_1-C_3)$alkanediyl group, optionally substituted by a group selected from a —N$R^bR^c$ group, a $(C_1-C_3)$alkoxy group, a hydroxy group, a —COO$R^a$ group and a halogen atom, and
  R' is a phenyl group, optionally substituted by one to three groups selected from the group consisting of $(C_1-C_6)$alkyl group, a fluoro$(C_1-C_4)$alkyl group and a fluoro$(C_1-C_4)$alkoxy group, a hydroxy group and a halogen atom,
$R^a$ represents a $(C_1-C_4)$alkyl group or a hydrogen atom,
$R^b$ and $R^c$ independently represent a $(C_1-C_6)$alkyl group or a hydrogen atom,
$R^d$ represents a $(C_1-C_4)$alkyl group or a cyclopropyl group,
$R^e$ represents a $(C_1-C_3)$alkyl group, and
$R^2$ represents a hydrogen atom or a $(C_1-C_3)$alkyl group,
or any of its pharmaceutically acceptable salt.

According to another particular embodiment, the present invention relates to a compound of formula (I) as defined herein above wherein $R^1$ represents:
  (i). a $(C_2-C_6)$alkyl group substituted by one or two groups selected from a —COOCH$_3$ group, a hydroxy group, a fluorine atom, a methoxy group, an ethoxy group, a tert-butoxy group, a cyclopropoxy group and a benzyloxy group, said benzyloxy being optionally substituted on its phenyl group by a fluorine atom,
  (ii). a spiro$(C_7-C_8)$bicyclic ring, in particular a spiro[3.3]heptyl, a spiro[2.5]octanyl or a 7-azaspiro[3.5]nonyl,
  (iii). a fused phenyl group, chosen from phenyl groups fused with a cyclopentyl or a heterocyclopentyl, which cyclopentyl and heterocyclopentyl group optionally comprise an insaturation and is optionally substituted by a methyl, a hydroxy group, a methoxy group and a —COCH$_3$ group,
  (iv). a phenyl group, substituted by one or two groups selected from a methyl, a hexyl, a trifluoromethyl, a difluoromethoxy group, a halogen atom, in particular a fluor atom, a morpholino group and a N-methylpiperazinyl group, or
  (v). a R'-L- group wherein L is either a single bond or a $(C_1-C_3)$alkanediyl group, optionally substituted by a group chosen from a hydroxy group and a $(C_1-C_3)$ alkoxy group, and R' is selected from the group consisting of:
    (v.1). a $(C_3-C_8)$cycloalkyl group in particular a cyclopropyl, a cyclobutyl, a cyclopentyl, a cyclohexyl, a cycloheptyl or a cyclooctyl, optionally substituted by one, two or three groups selected from a methyl, an isopropyl, a hydroxy group and a methoxy group,
    (v.2). a bridged $(C_7-C_{10})$cycloalkyl group, in particular an adamantyl or a bicyclo[3.1.1]heptyl, optionally substituted by one to three groups selected from a methyl group, a methoxy group, a hydroxy group, a fluorine atom, a —O—C(O)—CH$_3$ group, a —O—C(O)—C(CH$_3$)$_3$ group, a —O—C(O)—NH—C(CH$_3$)$_3$ group, a —NH—C(O)—CH$_3$ group, a —NH—C(O)—C$_3$H$_4$ group, a —S(O)$_2$—CH$_3$ group, a —S(O)$_2$—C$_3$H$_4$ group, a —N(CH$_3$)$_2$ group and a —C(O)—O—CH$_3$ group,
    (v.3). a $(C_5-C_8)$heterocycloalkyl group, in particular a tetrahydropyranyl, a piperidinyl, an oxetanyl, a tetrahydrofuranyl or an oxepanyl, a tetrahydrothiopyranyl, a pyrrolidinyl, a dioxepanyl or a piperidinyl, optionally substituted by one, two or three group(s) selected from a —COO$R^f$ group, a hydroxy group, a methyl group, and an oxo group, wherein $R^f$ represents either an ethyl or an isopropyl group,
    (v.4). a heteroaryl group, in particular a pyrimidinyl, a pyridinyl, a thiazolyl, a imidazolyl, a pyrazolyl, a thiadiazolyl, a pyridazinyl, a pyrazinyl, a furyl, optionally substituted by one to three groups selected from methyl group, a methoxy group and a N-methylpiperazinyl group, or
    (v.5). a bridged $(C_7-C_{10})$cycloalkyl group, in particular a quinuclidine-3-yl, or
  (vi). a R'-L- group wherein L is a $(C_1-C_3)$alkanediyl group, optionally substituted by a group selected from the group consisting of a —N$R^bR^c$ group, a $(C_1-C_4)$ alkoxy group, a hydroxy group, a —COO$R^a$ group and a halogen atom, in particular a fluor atom, and
    R' is a phenyl group, optionally substituted by one or two groups selected from the group consisting of methyl group, a trifluoromethyl group and a trifluoromethoxy group,
$R^a$ representing a $(C_1-C_3)$alkyl group,
$R^b$ and $R^c$ are independently chosen from a methyl group or a hydrogen atom, and
$R^2$ represents a hydrogen atom or a $(C_1-C_3)$alkyl group,
or any of its pharmaceutically acceptable salts.

According to another particular embodiment, the present invention relates to a compound of formula (I) as defined herein above wherein $R^1$ is a R'-L- group wherein L is selected from a group consisting of a —CH$_2$— group, a —CH(CH$_3$)— group, a —CH(CH$_2$OH)—CH$_2$— group, a —CH(CH$_2$OH)— group, a —CH(CH$_2$OCH$_3$)— group, a —CH(OH)—CH$_2$— group, a —CH$_2$—CH(CH$_2$OCH$_3$)— group, a —CH(OCH$_3$)—CH$_2$— group, a —CH$_2$—CH(COOCH$_3$)— group, a —CH(CH$_2$F)— group, a —CH(CH$_2$NH$_2$)— group, a —CH(CH$_2$NHCH$_3$)— group, a —CH(CH$_2$N(CH$_3$)$_2$)— group, a —CH$_2$—CH(CH$_2$OH)— group, a —CH(OCH$_3$)—CH$_2$— group, a —CH$_2$—CH(OCH$_3$)— group, a —CH$_2$—CH(OH)—CH$_2$— group, a —CH$_2$—CH(OCH$_3$)—CH$_2$ group, a —(CH$_2$)$_3$— group, a —(CH$_2$)$_2$— group and a —CH(CH$_2$OC(CH$_3$)$_3$) group or any of its pharmaceutically acceptable salts.

According to another particular embodiment, the present invention relates to a compound of formula (I) as defined herein above wherein $R^1$ is a R'-L- group wherein:

(v.1). when R' is a ($C_3$-$C_8$)cycloalkyl group, L is selected from the group consisting of a single bond, a —$CH_2$— group, a —$CH(CH_3)$— group, a —$CH(CH_2OH)$—$CH_2$— group, a —$CH(CH_2OH)$— group, a —CH($CH_2OCH_3$)— group and a —CH(OH)—$CH_2$— group and a —CH($OCH_3$)—$CH_2$— group, (v.2). when R' is a bridged ($C_7$-$C_{10}$)cycloalkyl group, L is a single bond, a —$CH_2$— group or a —$CH(CH_3)$— group, (v.3). when R' is a ($C_5$-$C_8$)heterocycloalkyl group including spiro($C_3$-$C_8$)heterocycloalkyls, L is a single bond or a —$CH_2$— group, (v.4). when R' is a phenyl, L is selected from the group consisting of a single bond, a —$CH_2$— group, a —$CH_2$—CH($COOCH_3$)— group, a —CH($CH_2F$)— group, a —CH($CH_2NH_2$)— group, a —CH($CH_2NHCH_3$)— group, a —CH($CH_2N(CH_3)_2$)— group, a —$CH_2$—CH($CH_2OH$)— group, a —CH($CH_2OH$)— group, a —CH($CH_2OCH_3$)— group, a —CH(OH)—$CH_2$— group, a —$CH_2$—CH($CH_2OCH_3$)— group, a —$CH_2$—CH(OH)—$CH_2$— group and a —$CH_2$—CH($OCH_3$)—$CH_2$ group, (v.5). when R' is a heteroaryl group, L is selected from the group comprising a single bond, a —$CH_2$— group, a —$(CH_2)_3$— group and a —$(CH_2)_2$— group.

According to another particular embodiment, the present invention relates to a compound of formula (I) as defined herein above, wherein $R^1$ represents:

an adamantyl group, optionally substituted by one to three groups, and in particular substituted by one group, selected from a methyl group, a methoxy group, a hydroxy group, a fluorine atom, a —O—C(O)—$CH_3$ group, a —O—C(O)—C($CH_3$)$_3$ group, a —O—C(O)—NH—C($CH_3$)$_3$ group, a —NH—C(O)—$CH_3$ group, a —NH—C(O)—$C_3H_4$ group, a —S(O)$_2$—$CH_3$ group, a —S(O)$_2$—$C_3H_4$ group, a —N($CH_3$)$_2$ group and a —C(O)—O—$CH_3$ group, the adamantyl group being preferably unsubstituted; or a R"—O—$CH_2$(R''')— group, wherein:
R" is a ($C_1$-$C_4$)alkyl group, preferably a methyl or ethyl group, and
R''' is a ($C_1$-$C_4$)alkyl group, in particular a ($C_3$-$C_4$)alkyl group, and preferably an isopropylmethyl group, or
R''' is a phenyl group, optionally substituted by one to three groups and in particular substituted by one group, selected from the group consisting of a ($C_1$-$C_6$)alkyl group, a fluoro($C_1$-$C_4$)alkyl group, a fluoro($C_1$-$C_4$)alkoxy group, a halogen atom and a hydroxy group, the phenyl group being preferably unsubstituted.

According to another particular embodiment, the present invention relates to a compound of formula (I) as defined herein above wherein $R^1$ represents:

a ($C_1$-$C_6$)alkyl group substituted by one or two groups selected from a —COOR$^a$ group, a hydroxy group, a fluorine atom, a ($C_1$-$C_4$)alkoxy group and a benzyloxy group, said benzyloxy group being optionally substituted on its phenyl group by a halogen atom, a spiro($C_5$-$C_{11}$)bicyclic ring, or a R'-L- group, wherein
L is either a single bond or a ($C_1$-$C_3$)alkanediyl group, optionally substituted by a group chosen from a hydroxy group and a ($C_1$-$C_3$)alkoxy group, and
R' is selected from the group consisting of:
a ($C_3$-$C_8$)cycloalkyl group, optionally substituted by one, two or three groups selected from a halogen atom, a ($C_1$-$C_4$)alkyl group, a hydroxy group and a ($C_1$-$C_3$) alkoxy group, and a bridged ($C_6$-$C_{10}$)cycloalkyl group, optionally substituted by one to three groups selected from a ($C_1$-$C_4$)alkyl group, a ($C_1$-$C_4$)alkoxy group, a halogen atom, a hydroxy group, a —O—C(O)—R$^d$ group, a —O—C(O)—NHR$^d$ group and a —NH—C(O)—R$^d$ group, a —SO$_2$—R$^d$ group, a —N(R$^e$)$_2$ group and a —COOR$^a$ group, R$^a$ representing a ($C_1$-$C_4$)alkyl group, R$^d$ representing a ($C_1$-$C_4$)alkyl group or a cyclopropyl group and R$^e$ representing a ($C_1$-$C_3$)alkyl group, and wherein $R^2$ represents a hydrogen atom or a ($C_1$-$C_3$)alkyl group, or any of its pharmaceutically acceptable salt.

Said sub-group of compounds are gathered under the "A1" type of compounds within the herein after table 1.

Still according to said embodiment, $R^1$ may more particularly represent a cyclopropylmethyl, a cyclopropyl, a cyclobutyl, a cyclopentyl, a cyclohexylmethyl, a cyclohexyl, a cycloheptylmethyl, a cycloheptyl, a cyclooctyl, a 3-hydroxy-2,2-dimethyl-propyl, a 2-benzyloxyethyl, a 2-methylcyclohexyl, a 1-cyclohexylethyl, a 1-adamantylmethyl, a 1-(1-adamantyl)ethyl, a 1-adamantyl, a 2-adamantyl, a 3,5-dimethyl-1-adamantyl, a 5-hydroxy-2-adamantyl, a 3-hydroxy-1-adamantyl, a 3-methoxy-1-adamantyl, a 2,6,6-trimethylnorpinan-3-yl, a 6,6-dimethylnorpinan-2-yl, a spiro[2.5]octan-2-yl, a spiro[3.3]heptan-2-yl, a 1,7,7-trimethylnorbornan-2-yl, norbornan-2-yl, a 2-isopropyl-5-methyl-cyclohexyl, a 1-(cyclohexylmethyl)-2-hydroxy-ethyl, a 1-(cyclopentylmethyl)-2-hydroxy-ethyl, a 1-(cyclobutylmethyl)-2-hydroxy-ethyl, a 1-(cyclopropylmethyl)-2-hydroxy-ethyl, a 1-(hydroxymethyl)-3-methyl-butyl, a 1-(methoxymethyl)-3-methyl-butyl, a 1-(hydroxymethyl)propyl, a 1-(fluoromethyl)-3-methyl-butyl, a 1-cyclohexyl-2-hydroxy-ethyl, a 1-cyclohexyl-2-methoxy-ethyl, a 2-cyclohexyl-2-hydroxy-ethyl, a 2-cyclohexyl-2-methoxy-ethyl, a 2-hydroxycyclopentyl, a 2-methoxycyclopentyl, a 2-hydroxycyclohexyl, a 3-hydroxycyclohexyl, a 4-hydroxycyclohexyl, a 2-methoxycyclohexyl, a 4-methoxycyclohexyl, a 2-hydroxycycloheptyl, a 3-hydroxycycloheptyl, a 2-methoxycycloheptyl, a —CH(COOCH$_3$)—CH(CH$_3$)$_2$, a —CH(COOCH$_3$)—CH$_3$, a —CH(COOCH$_3$)—CH$_2$—CH(CH$_3$)$_2$, a —CH(COOCH$_3$)—CHOH—CH$_3$, a 3,3-difluorocyclopentyl, a 4,4-difluorocyclohexyl, a 3,3-difluorocyclohexyl, a 2,2-difluorocyclohexyl, a 3,3-difluorocycloheptyl, a 3-acetoxy-1-adamantyl, a 3-pivaloyloxy-1-adamantyl, a 3-methoxycyclohexyl, a 4-hydroxycycloheptyl, a 3-methoxycycloheptyl, a 3-methoxycycloheptyl, a 4-methoxycycloheptyl, a 3-noradamantyl, 3-tert-butylcarbamoyloxy-1-adamantyl, 3-fluoro-1-adamantyl, 1-(tert-butoxymethyl)-3-methyl-butyl, 3-acetamido-1-adamantyl, 3-(cyclopropanecarbonylamino)-1-adamantyl, a 3-(methanesulfonamido)-1-adamantyl, a 3-(cyclopropylsulfonylamino)-1-adamantyl, a 3-(dimethylamino)-1-adamantyl, a 2-methoxycarbonyl-2-adamantyl, 3,5-dihydroxy-1-adamantyl, a 3,5,7-trifluoro-1-adamantyl, a 1-(ethoxymethyl)-3-methyl-butyl, a 1-(benzyloxymethyl)-3-methyl-butyl, a 1-[(4-fluorophenyl)methoxymethyl]-3-methyl-butyl or a 1-(cyclopropoxymethyl)-3-methyl-butyl.

According to another particular embodiment, the present invention relates to a compound of formula (I) as defined herein above wherein $R^1$ represents:

a fused phenyl group, chosen from phenyl groups fused with a ($C_5$-$C_6$)cycloalkyl or ($C_5$-$C_6$)heterocycloalkyl, which ($C_5$-$C_6$)cycloalkyl and ($C_5$-$C_6$)heterocycloalkyl group optionally comprise an insaturation and is optionally substituted by a $(C_1-C_4)$ alkyl group, a hydroxy group, a halogen atom, a $(C_1-C_3)$alkoxy group and a —COR$^a$ group, a phenyl group, substituted by one or two groups selected from $(C_1-C_8)$alkyl, a $(C_1-C_3)$fluoroalkyl, a fluoro$(C_1-C_4)$alkoxy group a halogen atom, and a $(C_4-C_7)$heterocycloalkyl group said $(C_4-C_7)$heterocycloalkyl group being itself optionally substituted by a $(C_1-C_4)$ alkyl group, or a R'-L- group, wherein L is a $(C_1-C_3)$alkanediyl group, optionally substituted by a group chosen from a hydroxy group, a $(C_1-C_4)$ alkoxy group, a —NR$^b$R$^c$ group, a —COOR$^a$ group and a halogen atom, and R' is a phenyl group, optionally substituted by one to three groups selected from the group consisting of $(C_1-C_6)$alkyl group, a fluoro$(C_1-C_4)$alkyl group and a fluoro$(C_1-C_4)$alkoxy group, a halogen atom and a hydroxy group, wherein R$^a$ is a $(C_1-C_4)$alkyl or a hydrogen atom and R$^b$ and R$^c$ are independently chosen from $(C_1-C_6)$alkyl and a hydrogen atom, and wherein R$^2$ represents a hydrogen atom or a $(C_1-C_3)$alkyl group, or any pharmaceutically acceptable salt thereof.

Said sub-group of compounds are gathered under the "A2" and "A5" type of compounds within the herein after table 1.

Still according to said embodiment, R$^1$ may more particularly represent a benzyl, an indan-2-yl, a (3,4-dimethylphenyl)methyl, a (2,4-dimethylphenyl)methyl, a [2-(trifluoromethyl)phenyl]methyl, a [2-(trifluoromethoxy)phenyl]methyl, a 2-hydroxyindan-1-yl, a 2-methoxyindan-1-yl, a —CH(COOCH$_3$)—CH$_2$-Ph, a —CH(CH$_2$F)Ph, a 2-amino-1-phenyl-ethyl, a 2-(methylamino)-1-phenyl-ethyl, a 2-(dimethylamino)-1-phenyl-ethyl, a 1-benzyl-2-hydroxy-ethyl, a 1-benzyl-2-methoxy-ethyl, a 2-hydroxy-1-phenyl-ethyl, a 2-methoxy-1-phenyl-ethyl, a 2-hydroxy-2-phenyl-ethyl, a 2-methoxy-2-phenyl-ethyl, a 2-hydroxy-3-phenyl-propyl, a 2-methoxy-3-phenyl-propyl, a 3-fluoro-4-methyl-phenyl, a 4-fluorophenyl, a 4-n-hexylphenyl, a 4-(4-methylpiperazin-1-yl)phenyl, a 3-(difluoromethoxy)phenyl, a 1-acetylindolin-6-yl, a 3-(trifluoromethyl)phenyl, an indan-5-yl, a 4-morpholinophenyl, a 1-methylindazol-7-yl or a 2-tert-butoxy-1-phenyl-ethyl.

According to another particular embodiment, the present invention relates to a compound of formula (I) as defined herein above wherein R$^2$ represents a hydrogen atom or a methyl group.

According to another particular embodiment, the present invention relates to a compound of formula (I) as defined herein above wherein R$^1$ represents a R'-L- group wherein:

R' is a $(C_3-C_8)$heteroaryl group, optionally substituted by one to three groups selected from a halogen atom, a $(C_1-C_4)$alkyl group, a $(C_1-C_4)$alkoxy group and a N-methylpiperazinyl group, and L is a $(C_1-C_3)$alkanediyl or a single bond, and wherein R$^2$ represents a hydrogen atom, or any pharmaceutically acceptable salt thereof.

Said sub-group of compounds are gathered under the "A3" and "A6" type of compounds within the herein after table 1.

Still according to said embodiment, R$^1$ may more particularly represent a (5-methylpyrazin-2-yl)methyl, a 2-pyridylmethyl, a 3-pyridylmethyl, a 4-pyridylmethyl, a (5-methyl-2-furyl)methyl, a (4-methylthiazol-2-yl)methyl, a 3-imidazol-1-ylpropyl, a 2-(2-pyridyl)ethyl, a 1,3-benzothiazol-2-ylmethyl, a 2-pyrimidinyl, a 2-pyridyl, a 1-methylpyrazol-3-yl, a 2-methoxy-6-methyl-3-pyridyl, a pyrimidin-5-yl, 3-pyridyl, a 1,3,4-thiadiazol-2-yl, a 5-(4-methylpiperazin-1-yl)-2-pyridyl, 6-(4-methylpiperazin-1-yl)-3-pyridyl, a 2-(4-methylpiperazin-1-yl)pyrimidin-5-yl, a 5-(4-methylpiperazin-1-yl)pyrimidin-2-yl, a 5-(4-methylpiperazin-1-yl)pyrazin-2-yl or a 6-(4-methylpiperazin-1-yl)pyridazin-3-yl.

According to another particular embodiment, the present invention relates to a compound of formula (I) as defined herein above wherein R$^1$ represents a R'-L- group wherein:

R' is a $(C_3-C_8)$heterocycloalkyl group, optionally substituted by one to three groups selected from a hydroxyl group, a $(C_1-C_4)$alkyl group, an oxo group and a —COOR$^a$ group wherein R$^a$ is as defined herein above, and L is a methylene or a single bond, and wherein R$^2$ represents a hydrogen atom, or any pharmaceutically acceptable salt thereof.

Said sub-group of compounds are gathered under the "A4" and "A7" type of compounds within the herein after table 1.

Still according to said embodiment, R$^1$ may more particularly represent a (1-methyl-4-piperidyl)methyl, a tetrahydropyran-4-yl-methyl, a 1-tert-butyloxycarbonylpiperidin-4-yl-methyl, a 7-methyl-7-azaspiro[3.5]nonan-2-yl, a tetrahydropyran-4-yl, a 1-tert-butyloxycarbonylpiperidin-4-yl, a 1-ethyloxycarbonylpiperidin-4-yl, a 1-methyl-4-piperidyl, a 1-methyl-3-piperidyl, an oxetan-3-yl, tetrahydrofuran-3-yl, a tetrahydropyran-3-yl, a 6,6-dimethyltetrahydropyran-3-yl, a 4-hydroxytetrahydropyran-3-yl, an oxepan-3-yl, a 2-oxo-piperidin-3-yl, a 2-oxo-piperidin-5-yl, a quinuclidin-3-yl, a tetrahydrothiopyran-3-yl, a 1,4-dioxepan-6-yl, a 2-oxo-pyrrolidin-3-yl, a 1-methyl-2-oxo-pyrrolidin-3-yl, a 4,4-dimethyl-2-oxo-pyrrolidin-3-yl, a 1-methyl-2-oxo-piperidin-3-yl, a 3-methyl-2-oxo-pyrrolidin-3-yl or a 1,3-dimethyl-2-oxo-pyrrolidin-3-yl.

In the context of the present invention, the term:

"halogen" is understood to mean chlorine, fluorine, bromine, or iodine, and in particular denotes chlorine, fluorine or bromine, "$(C_1-C_x)$alkyl", as used herein, respectively refers to a $C_1$-$C_x$ normal, secondary or tertiary monovalent saturated hydrocarbon radical, for example $(C_1-C_6)$alkyl. Examples are, but are not limited to, methyl, ethyl, propyl, n-propyl, isopropyl, butyl, isobutyl, sec-butyl, tert-butyl, pentyl, isopentyl, hexyl and isohexyl groups, and the like.

"$(C_1-C_3)$alkanediyl", as used herein, refers to a divalent saturated hydrocarbon radical which is branched or linear, comprises from 1 to 3 carbon atoms, and more particularly a methylene, ethylene or propylene, such as linear propylene or isopropylene, said alkanediyl may be substituted as it is apparent from the following description.

"$(C_3-C_8)$cycloalkyl", as used herein, refers to a cyclic saturated hydrocarbon, from 3 to 8 carbon atoms, saturated or partially unsaturated and unsubstituted or substituted. Examples are, but are not limited to, cyclopropyl, cyclobutyl, cyclopentyl, cyclohexyl, cycloheptyl and cyclooctyl.

"$(C_3-C_8)$heterocycloalkyl group", as used herein, refers to a $(C_3-C_8)$cycloalkyl group wherein one or two of the carbon atoms are replaced with a heteroatom such as oxygen, nitrogen or sulphur, and more particularly such as an oxygen or a nitrogen atom. Such heterocycloalkyl group may be saturated or partially saturated and unsubstituted or substituted. Examples are, but are not limited to, morpholinyl, piperazinyl, piperidinyl, pyrrolidinyl, aziridinyl, oxanyl, oxetanyl, tetrahydropyranyl, morpholinyl, tetrahydrofuranyl, oxepanyl, diazepanyl, dioxanyl and tetrahydrothiopyranyl, and more particularly piperidinyl and piperazinyl, and even more particularly piperazinyl.

"$(C_1-C_x)$alkoxy", as used herein, refers to a —O—$(C_1-C_x)$alkyl or —O—$(C_3-C_x)$cycloalkyl moiety, wherein alkyl and cycloalkyl are as defined above, for example $(C_1-C_6)$alkoxy. Examples are, but are not limited to, methoxy, ethoxy, 1-propoxy, 2-propoxy, cyclopropoxy, butoxy, tert-butoxy and pentoxy.

"spiro$(C_5-C_{11})$bicyclic ring" refers to two rings connected through a defining single common atom. Such spiro bicyclic alkyl generally comprises 5 to 11 carbon atoms referring to a "spiro$(C_5-C_{11})$bicyclic alkyl group". In a particular embodiment, one or more carbon atoms of the rings are replaced by heteroatom(s) such as oxygen, nitrogen or sulphur, and more particularly such as a nitrogen atom, forming a spiro$(C_5-C_{11})$bicyclic heteroalkyl group. Such spirobicyclic ring may be unsubstituted or substituted, in particular by at least one $(C_1-C_3)$alkyl group such as methyl. Examples are, but are not limited to spiro[3.3]heptanyl, spiro[2.5]octanyl, 7-azaspiro[3.5]nonanyl.

a "bridged $(C_6-C_{10})$cycloalkyl" group, as used herein, refers to a bi- or tricyclic compound where the cycles are cycloalkyls, the rings share three or more atoms and the bridge contains at least one atom, for example 1, 2 or 3 atoms. Such bridged cycloalkyl groups may be substituted by one or more $C_1-C_3$ alkyl. Examples are, but not limited to adamantyl, 2,6,6-trimethylbicyclo[3.1.1]heptyl, 6,6-dimethylbicyclo[3.1.1]heptyl, bicyclo[3.1.1]heptyl, 1,6,6-trimethylbicyclo[3.1.1]heptyl.

a "bridged $(C_6-C_{10})$heterocycloalkyl" group, as used herein, refers to a bridged $(C_6-C_{10})$cycloalkyl as defined herein above wherein one or more carbon atoms of the rings are replaced by heteroatom(s) such as oxygen, nitrogen or sulphur, and more particularly such as a nitrogen atom. Examples are, but not limited to quinuclidin-3-yl.

a "fused phenyl group" refers to a bicyclic radical that contains a phenyl moiety and may be substituted. Said fused phenyl group may be fused to a cycloalkyl or to a heterocycloalkyl and bound to the rest of the molecule either by its phenyl moeity or by said cycloalkyl or heterocycloalkyl. Examples are, but are not limited to indanyl, acetylindolinyl, methylindazolyl, hydroxyindanyl, benzothiazolyl, indolyl, indazolyl, methoxyindanyl and the like.

a $(C_5-C_{11})$heteroaryl group, as used herein, refers to a monocyclic aromatic group or to a bicyclic aromatic group where at least one of the ring is aromatic and wherein one to three ring carbon atom is replaced by a heteroatom, such as nitrogen, oxygen or sulphur. By way of examples of heteroaryl groups, mention may be made of, but not limited to: oxazole, isoxazole, pyridine, pyrimidine, pyridazine, triazine, pyrazine, oxadiazole, furane, pyrazole, thiazole, isothiazole, thiadiazole, imidazole, triazole and the like. In the framework of the present invention, the heteroaryl is advantageously pyridine, imidazole, pyrazine, furane, thiazole, pyrazole, thiadiazole, pyridazine and pyrimidine.

an aromatic ring means, according to Hückel's rule, that a molecule has $4n+2$ π-electrons.

a $(C_1-C_x)$fluoroalkyl group, as used herein, refers to a $(C_1-C_x)$alkyl as defined herein above in which one or more fluorines have been substituted by hydrogen. In one embodiment all the hydrogen atoms are replaced by fluor atoms, forming perfluoroalkyl groups, such as trifluoromethyl.

a $(C_1-C_x)$fluoroalkoxy, as used herein, refers to a $(C_1-C_x)$alkoxy as defined herein above in which one or more fluorines have been substituted for hydrogen such as trifluoromethoxy. In one embodiment all the hydrogen atoms are replaced by fluor atoms, forming perfluoroalkoxy groups, such as trifluoromethoxy.

In the context of the present invention, the terms "aromatic ring", and "heteroaryl" include all the positional isomers.

The nomenclature of the following compounds (1) to (216) was generated according to the principles of the International Union of Pure and Applied Chemistry, using Accelrys Draw 4.1 SP1. To avoid any confusion, the "(±)" symbol added to designate a racemic mixture; "cis" and "trans" prefixes were also used to assign the relative stereochemistry of two adjacent chiral centers.

According to a preferred embodiment of the present invention, the compound of formula (I) is chosen from:

(1). (4Z)-4-(1,3-Benzothiazol-6-ylmethylene)-2-(cyclopropylmethylamino)-1H-imidazol-5-one, (2). (4Z)-4-(1,3-Benzothiazol-6-ylmethylene)-2-(cyclopropylamino)-1H-imidazol-5-one, (3). (4Z)-4-(1,3-Benzothiazol-6-ylmethylene)-2-(cyclobutylamino)-1H-imidazol-5-one, (4). (4Z)-4-(1,3-Benzothiazol-6-ylmethylene)-2-(cyclopentylamino)-1H-imidazol-5-one, (5). (4Z)-4-(1,3-Benzothiazol-6-ylmethylene)-2-(cyclohexylmethylamino)-1H-imidazol-5-one, (6). (4Z)-4-(1,3-Benzothiazol-6-ylmethylene)-2-(cyclohexylamino)-1H-imidazol-5-one, (7). (4Z)-4-(1,3-Benzothiazol-6-ylmethylene)-2-(cycloheptylmethylamino)-1H-imidazol-5-one, (8). (4Z)-4-(1,3-Benzothiazol-6-ylmethylene)-2-(cycloheptylamino)-1H-imidazol-5-one, (9). (4Z)-4-(1,3-Benzothiazol-6-ylmethylene)-2-(cyclooctylamino)-1H-imidazol-5-one, (10). (4Z)-4-(1,3-Benzothiazol-6-ylmethylene)-2-[(3-hydroxy-2,2-dimethyl-propyl)amino]-1H-imidazol-5-one, (11). (4Z)-4-(1,3-Benzothiazol-6-ylmethylene)-2-(2-benzyloxyethylamino)-1H-imidazol-5-one, (12). (±)-(4Z)-4-(1,3-Benzothiazol-6-ylmethylene)-2-[[cis-2-methylcyclohexyl]amino]-1H-imidazol-5-one, (13). (4Z)-4-(1,3-Benzothiazol-6-ylmethylene)-2-[[(1R)-1-cyclohexylethyl]amino]-1H-imidazol-5-one, (14). (4Z)-2-(1-Adamantylmethylamino)-4-(1,3-benzothiazol-6-ylmethylene)-1H-imidazol-5-one, (15). (±)-(4Z)-2-[1-(1-Adamantyl)ethylamino]-4-(1,3-benzothiazol-6-ylmethylene)-1H-imidazol-5-one, (16). (4Z)-2-(1-Adamantylamino)-4-(1,3-benzothiazol-6-ylmethylene)-1H-imidazol-5-one, (17). (4Z)-2-(2-Adamantylamino)-4-(1,3-benzothiazol-6-ylmethylene)-1H-imidazol-5-one, (18). (4Z)-4-(1,3-Benzothiazol-6-ylmethylene)-2-[[3,5-dimethyl-1-adamantyl]amino]-1H-imidazol-5-one, (19). (4Z)-4-(1,3-Benzothiazol-6-ylmethylene)-2-[(trans-5-hydroxy-2-adamantyl)amino]-1H-imidazol-5-one, (20). (4Z)-4-(1,3-Benzothiazol-6-ylmethylene)-2-[(3-hydroxy-1-adamantyl)amino]-1H-imidazol-5-one, (21). (4Z)-4-(1,3-Benzothiazol-6-ylmethylene)-2-[(3-methoxy-1-adamantyl)amino]-1H-imidazol-5-one, (22). (4Z)-4-(1,3-Benzothiazol-6-ylmethylene)-2-[[(1R,2R,3R,5S)-2,6,6-trimethylnorpinan-3-yl]amino]-1H-imidazol-5-one,
(23). (4Z)-4-(1,3-Benzothiazol-6-ylmethylene)-2-[[(1S,2S,3S,5R)-2,6,6-trimethylnorpinan-3-yl]amino]-1H-imidazol-5-one,
(24). (4Z)-4-(1,3-Benzothiazol-6-ylmethylene)-2-[[(1R,2R,5R)-6,6-dimethylnorpinan-2-yl]methylamino]-1H-imidazol-5-one,
(25). (±)-(4Z)-4-(1,3-Benzothiazol-6-ylmethylene)-2-(spiro[2.5]octan-2-ylamino)-1H-imidazol-5-one,
(26). (4Z)-4-(1,3-Benzothiazol-6-ylmethylene)-2-(spiro[3.3]heptan-2-ylamino)-1H-imidazol-5-one,
(27). (4Z)-4-(1,3-Benzothiazol-6-ylmethylene)-2-[[(2R)-1,7,7-trimethylnorbornan-2-yl]amino]-1H-imidazol-5-one,
(28). (±)-(4Z)-4-(1,3-Benzothiazol-6-ylmethylene)-2-(norbornan-2-ylamino)-1H-imidazol-5-one,
(29). (4Z)-4-(1,3-Benzothiazol-6-ylmethylene)-2-[[(1R,2S,5R)-2-isopropyl-5-methyl-cyclohexyl]amino]-1H-imidazol-5-one,
(30). (4Z)-4-(1,3-Benzothiazol-6-ylmethylene)-2-[[(1R)-1-(cyclohexylmethyl)-2-hydroxy-ethyl]amino]-1H-imidazol-5-one,
(31). (4Z)-4-(1,3-Benzothiazol-6-ylmethylene)-2-[[(1R)-1-(cyclopentylmethyl)-2-hydroxy-ethyl]amino]-1H-imidazol-5-one,
(32). (4Z)-4-(1,3-Benzothiazol-6-ylmethylene)-2-[[(1R)-1-(cyclobutylmethyl)-2-hydroxy-ethyl]amino]-1H-imidazol-5-one,
(33). (4Z)-4-(1,3-Benzothiazol-6-ylmethylene)-2-[[(1R)-1-(cyclopropylmethyl)-2-hydroxy-ethyl]amino]-1H-imidazol-5-one,
(34). (4Z)-4-(1,3-Benzothiazol-6-ylmethylene)-2-[[(1R)-1-(hydroxymethyl)-3-methyl-butyl]amino]-1H-imidazol-5-one,
(35). (4Z)-4-(1,3-Benzothiazol-6-ylmethylene)-2-[[(1R)-1-(methoxymethyl)-3-methyl-butyl]amino]-1H-imidazol-5-one,
(36). (4Z)-4-(1,3-Benzothiazol-6-ylmethylene)-2-[[(1S)-1-(hydroxymethyl)-3-methyl-butyl]amino]-1H-imidazol-5-one,
(37). (4Z)-4-(1,3-Benzothiazol-6-ylmethylene)-2-[[(1S)-1-(methoxymethyl)-3-methyl-butyl]amino]-1H-imidazol-5-one,
(38). (4Z)-4-(1,3-Benzothiazol-6-ylmethylene)-2-[[(1R)-1-(hydroxymethyl)propyl]amino]-1H-imidazol-5-one,
(39). (4Z)-4-(1,3-Benzothiazol-6-ylmethylene)-2-[[(1S)-1-(hydroxymethyl)propyl]amino]-1H-imidazol-5-one,
(40). (±)-(4Z)-4-(1,3-Benzothiazol-6-ylmethylene)-2-[[1-(fluoromethyl)-3-methyl-butyl]amino]-1H-imidazol-5-one,
(41). (±)-(4Z)-4-(1,3-Benzothiazol-6-ylmethylene)-2-[(1-cyclohexyl-2-hydroxy-ethyl)amino]-1H-imidazol-5-one,
(42). (±)-(4Z)-4-(1,3-Benzothiazol-6-ylmethylene)-2-[(1-cyclohexyl-2-methoxy-ethyl)amino]-1H-imidazol-5-one,
(43). (±)-(4Z)-4-(1,3-Benzothiazol-6-ylmethylene)-2-[(2-cyclohexyl-2-hydroxy-ethyl)amino]-1H-imidazol-5-one,
(44). (±)-(4Z)-4-(1,3-Benzothiazol-6-ylmethylene)-2-[(2-cyclohexyl-2-methoxy-ethyl)amino]-1H-imidazol-5-one,
(45). (±)-(4Z)-4-(1,3-Benzothiazol-6-ylmethylene)-2-[[cis-2-hydroxycyclopentyl]amino]-1H-imidazol-5-one,
(46). (±)-(4Z)-4-(1,3-Benzothiazol-6-ylmethylene)-2-[[trans-2-hydroxycyclopentyl]amino]-1H-imidazol-5-one,
(47). (±)-(4Z)-4-(1,3-Benzothiazol-6-ylmethylene)-2-[[cis-2-methoxycyclopentyl]amino]-1H-imidazol-5-one,
(48). (±)-(4Z)-4-(1,3-Benzothiazol-6-ylmethylene)-2-[[trans-2-methoxycyclopentyl]amino]-1H-imidazol-5-one,
(49). (±)-(4Z)-4-(1,3-Benzothiazol-6-ylmethylene)-2-[[cis-2-hydroxycyclohexyl]amino]-1H-imidazol-5-one,
(50). (±)-(4Z)-4-(1,3-Benzothiazol-6-ylmethylene)-2-[[trans-2-hydroxycyclohexyl]amino]-1H-imidazol-5-one,
(51). (4Z)-4-(1,3-Benzothiazol-6-ylmethylene)-2-[[(1R,2S)-2-hydroxycyclohexyl]amino]-1H-imidazol-5-one,
(52). (4Z)-4-(1,3-Benzothiazol-6-ylmethylene)-2-[[(1S,2R)-2-hydroxycyclohexyl]amino]-1H-imidazol-5-one,
(53). (4Z)-4-(1,3-Benzothiazol-6-ylmethylene)-2-[[(1R,2R)-2-hydroxycyclohexyl]amino]-1H-imidazol-5-one,
(54). (4Z)-4-(1,3-Benzothiazol-6-ylmethylene)-2-[[(1S,2S)-2-hydroxycyclohexyl]amino]-1H-imidazol-5-one,
(55). (±)-(4Z)-4-(1,3-Benzothiazol-6-ylmethylene)-2-[[cis-3-hydroxycyclohexyl]amino]-1H-imidazol-5-one,
(56). (±)-(4Z)-4-(1,3-Benzothiazol-6-ylmethylene)-2-[[trans-3-hydroxycyclohexyl]amino]-1H-imidazol-5-one,
(57). (4Z)-4-(1,3-Benzothiazol-6-ylmethylene)-2-[(trans-4-hydroxycyclohexyl)amino]-1H-imidazol-5-one,
(58). (±)-(4Z)-4-(1,3-Benzothiazol-6-ylmethylene)-2-[[cis-2-methoxycyclohexyl]amino]-1H-imidazol-5-one,
(59). (±)-(4Z)-4-(1,3-Benzothiazol-6-ylmethylene)-2-[[trans-2-methoxycyclohexyl]amino]-1H-imidazol-5-one,
(60). (4Z)-4-(1,3-Benzothiazol-6-ylmethylene)-2-[(trans-4-methoxycyclohexyl)amino]-1H-imidazol-5-one,
(61). (±)-(4Z)-4-(1,3-Benzothiazol-6-ylmethylene)-2-[[cis-2-hydroxycycloheptyl]amino]-1H-imidazol-5-one,
(62). (±)-(4Z)-4-(1,3-Benzothiazol-6-ylmethylene)-2-[[trans-2-hydroxycycloheptyl]amino]-1H-imidazol-5-one,
(63). (4Z)-4-(1,3-Benzothiazol-6-ylmethylene)-2-[[(1R,2R)-2-hydroxycycloheptyl]amino]-1H-imidazol-5-one,
(64). (4Z)-4-(1,3-Benzothiazol-6-ylmethylene)-2-[[(1S,2S)-2-hydroxycycloheptyl]amino]-1H-imidazol-5-one,
(65). (±)-(4Z)-4-(1,3-Benzothiazol-6-ylmethylene)-2-[[cis-3-hydroxycycloheptyl]amino]-1H-imidazol-5-one,
(66). (±)-(4Z)-4-(1,3-Benzothiazol-6-ylmethylene)-2-[[trans-3-hydroxycycloheptyl]amino]-1H-imidazol-5-one,
(67). (±)-(4Z)-4-(1,3-Benzothiazol-6-ylmethylene)-2-[[cis-2-methoxycycloheptyl]amino]-1H-imidazol-5-one,
(68). (±)-(4Z)-4-(1,3-Benzothiazol-6-ylmethylene)-2-[[trans-2-methoxycycloheptyl]amino]-1H-imidazol-5-one,
(69). Methyl (2S)-2-[[(4Z)-4-(1,3-benzothiazol-6-ylmethylene)-5-oxo-1H-imidazol-2-yl]amino]-3-methyl-butanoate,
(70). Methyl (2S)-2-[[(4Z)-4-(1,3-benzothiazol-6-ylmethylene)-5-oxo-1H-imidazol-2-yl]amino]propanoate,
(71). Methyl (2S)-2-[[(4Z)-4-(1,3-benzothiazol-6-ylmethylene)-5-oxo-1H-imidazol-2-yl]amino]-4-methyl-pentanoate,
(72). Methyl (2R)-2-[[(4Z)-4-(1,3-benzothiazol-6-ylmethylene)-5-oxo-1H-imidazol-2-yl]amino]-4-methyl-pentanoate,
(73). Methyl (2S)-2-[[(4Z)-4-(1,3-benzothiazol-6-ylmethylene)-5-oxo-1H-imidazol-2-yl]amino]-3-hydroxy-butanoate,
(74). (4Z)-4-(1,3-Benzothiazol-6-ylmethylene)-2-(benzylamino)-1H-imidazol-5-one,
(75). (4Z)-4-(1,3-Benzothiazol-6-ylmethylene)-2-(indan-2-ylamino)-1H-imidazol-5-one,
(76). (4Z)-4-(1,3-Benzothiazol-6-ylmethylene)-2-[(3,4-dimethylphenyl)methylamino]-1H-imidazol-5-one, (77). (4Z)-4-(1,3-Benzothiazol-6-ylmethylene)-2-[(2,4-dimethylphenyl)methylamino]-1H-imidazol-5-one,
(78). (4Z)-4-(1,3-Benzothiazol-6-ylmethylene)-2-[[2-(trifluoromethyl)phenyl]methylamino]-1H-imidazol-5-one,
(79). (4Z)-4-(1,3-Benzothiazol-6-ylmethylene)-2-[[2-(trifluoromethoxy)phenyl]methylamino]-1H-imidazol-5-one,
(80). (±)-(4Z)-4-(1,3-Benzothiazol-6-ylmethylene)-2-[[cis-2-hydroxyindan-1-yl]amino]-1H-imidazol-5-one,
(81). (±)-(4Z)-4-(1,3-Benzothiazol-6-ylmethylene)-2-[[trans-2-hydroxyindan-1-yl]amino]-1H-imidazol-5-one,
(82). (4Z)-4-(1,3-Benzothiazol-6-ylmethylene)-2-[[(1R,2R)-2-hydroxyindan-1-yl]amino]-1H-imidazol-5-one,
(83). (4Z)-4-(1,3-Benzothiazol-6-ylmethylene)-2-[[(1S,2S)-2-hydroxyindan-1-yl]amino]-1H-imidazol-5-one,
(84). (±)-(4Z)-4-(1,3-Benzothiazol-6-ylmethylene)-2-[[cis-2-methoxyindan-1-yl]amino]-1H-imidazol-5-one,
(85). (±)-(4Z)-4-(1,3-Benzothiazol-6-ylmethylene)-2-[[trans-2-methoxyindan-1-yl]amino]-1H-imidazol-5-one,
(86). Methyl (2S)-2-[[(4Z)-4-(1,3-benzothiazol-6-ylmethylene)-5-oxo-1H-imidazol-2-yl]amino]-3-phenyl-propanoate,
(87). Methyl (2R)-2-[[(4Z)-4-(1,3-benzothiazol-6-ylmethylene)-5-oxo-1H-imidazol-2-yl]amino]-3-phenyl-propanoate,
(88). (±)-(4Z)-4-(1,3-Benzothiazol-6-ylmethylene)-2-[(2-fluoro-1-phenyl-ethyl)amino]-1H-imidazol-5-one,
(89). (±)-(4Z)-2-[(2-Amino-1-phenyl-ethyl)amino]-4-(1,3-benzothiazol-6-ylmethylene)-1H-imidazol-5-one dihydrochloride,
(90). (±)-(4Z)-4-(1,3-Benzothiazol-6-ylmethylene)-2-[[2-(methylamino)-1-phenyl-ethyl]amino]-1H-imidazol-5-one dihydrochloride,
(91). (±)-(4Z)-4-(1,3-Benzothiazol-6-ylmethylene)-2-[[2-(dimethylamino)-1-phenyl-ethyl]amino]-1H-imidazol-5-one,
(92). (±)-(4Z)-4-(1,3-Benzothiazol-6-ylmethylene)-2-[(1-benzyl-2-hydroxy-ethyl)amino]-1H-imidazol-5-one,
(93). (4Z)-4-(1,3-Benzothiazol-6-ylmethylene)-2-[[(1R)-1-benzyl-2-hydroxy-ethyl]amino]-1H-imidazol-5-one,
(94). (±)-(4Z)-4-(1,3-Benzothiazol-6-ylmethylene)-2-[(1-benzyl-2-methoxy-ethyl)amino]-1H-imidazol-5-one,
(95). (±)-(4Z)-4-(1,3-Benzothiazol-6-ylmethylene)-2-[(2-hydroxy-1-phenyl-ethyl)amino]-1H-imidazol-5-one,
(96). (4Z)-4-(1,3-Benzothiazol-6-ylmethylene)-2-[[(1R)-2-hydroxy-1-phenyl-ethyl]amino]-1H-imidazol-5-one,
(97). (4Z)-4-(1,3-Benzothiazol-6-ylmethylene)-2-[[(1S)-2-hydroxy-1-phenyl-ethyl]amino]-1H-imidazol-5-one,
(98). (±)-(4Z)-4-(1,3-Benzothiazol-6-ylmethylene)-2-[(2-methoxy-1-phenyl-ethyl)amino]-1H-imidazol-5-one,
(99). (±)-(4Z)-4-(1,3-Benzothiazol-6-ylmethylene)-2-[(2-hydroxy-2-phenyl-ethyl)amino]-1H-imidazol-5-one,
(100). (±)-(4Z)-4-(1,3-Benzothiazol-6-ylmethylene)-2-[(2-methoxy-2-phenyl-ethyl)amino]-1H-imidazol-5-one,
(101). (±)-(4Z)-4-(1,3-Benzothiazol-6-ylmethylene)-2-[(2-hydroxy-3-phenyl-propyl)amino]-1H-imidazol-5-one,
(102). (±)-(4Z)-4-(1,3-Benzothiazol-6-ylmethylene)-2-[(2-methoxy-3-phenyl-propyl)amino]-1H-imidazol-5-one,
(103). (4Z)-4-(1,3-Benzothiazol-6-ylmethylene)-2-[(5-methylpyrazin-2-yl)methylamino]-1H-imidazol-5-one,
(104). (4Z)-4-(1,3-Benzothiazol-6-ylmethylene)-2-(2-pyridylmethylamino)-1H-imidazol-5-one,
(105). (4Z)-4-(1,3-Benzothiazol-6-ylmethylene)-2-(3-pyridylmethylamino)-1H-imidazol-5-one,
(106). (4Z)-4-(1,3-Benzothiazol-6-ylmethylene)-2-(4-pyridylmethylamino)-1H-imidazol-5-one,
(107). (4Z)-4-(1,3-Benzothiazol-6-ylmethylene)-2-[(5-methyl-2-furyl)methylamino]-1H-imidazol-5-one,
(108). (4Z)-4-(1,3-Benzothiazol-6-ylmethylene)-2-[(4-methylthiazol-2-yl)methylamino]-1H-imidazol-5-one,
(109). (4Z)-4-(1,3-Benzothiazol-6-ylmethylene)-2-(3-imidazol-1-ylpropylamino)-1H-imidazol-5-one,
(110). (4Z)-4-(1,3-Benzothiazol-6-ylmethylene)-2-[2-(2-pyridyl)ethylamino]-1H-imidazol-5-one,
(111). (4Z)-2-(1,3-Benzothiazol-2-ylmethylamino)-4-(1,3-benzothiazol-6-ylmethylene)-1H-imidazol-5-one,
(112). (4Z)-4-(1,3-Benzothiazol-6-ylmethylene)-2-[(1-methyl-4-piperidyl)methylamino]-1H-imidazol-5-one,
(113). (4Z)-4-(1,3-Benzothiazol-6-ylmethylene)-2-(tetrahydropyran-4-ylmethylamino)-1H-imidazol-5-one,
(114). Tert-butyl 4-[[[(4Z)-4-(1,3-benzothiazol-6-ylmethylene)-5-oxo-1H-imidazol-2-yl]amino]methyl]piperidine-1-carboxylate,
(115). (4Z)-4-(1,3-Benzothiazol-6-ylmethylene)-2-[(7-methyl-7-azaspiro[3.5]nonan-2-yl)amino]-1H-imidazol-5-one,
(116). (4Z)-4-(1,3-Benzothiazol-6-ylmethylene)-2-(3-fluoro-4-methyl-anilino)-1H-imidazol-5-one,
(117). (4Z)-4-(1,3-Benzothiazol-6-ylmethylene)-2-(4-fluoroanilino)-1H-imidazol-5-one,
(118). (4Z)-4-(1,3-Benzothiazol-6-ylmethylene)-2-(4-hexylanilino)-1H-imidazol-5-one,
(119). (4Z)-4-(1,3-Benzothiazol-6-ylmethylene)-2-[4-(4-methylpiperazin-1-yl)anilino]-1H-imidazol-5-one,
(120). (4Z)-4-(1,3-Benzothiazol-6-ylmethylene)-2-[3-(difluoromethoxy)anilino]-1H-imidazol-5-one,
(121). (4Z)-2-[(1-Acetylindolin-6-yl)amino]-4-(1,3-benzothiazol-6-ylmethylene)-1H-imidazol-5-one,
(122). (4Z)-4-(1,3-Benzothiazol-6-ylmethylene)-2-[3-(trifluoromethyl)anilino]-1H-imidazol-5-one,
(123). (4Z)-4-(1,3-Benzothiazol-6-ylmethylene)-2-(indan-5-ylamino)-1H-imidazol-5-one,
(124). (4Z)-4-(1,3-Benzothiazol-6-ylmethylene)-2-(4-morpholinoanilino)-1H-imidazol-5-one,
(125). (4Z)-4-(1,3-Benzothiazol-6-ylmethylene)-2-[(1-methylindazol-7-yl)amino]-1H-imidazol-5-one,
(126). (4Z)-4-(1,3-Benzothiazol-6-ylmethylene)-2-(pyrimidin-2-ylamino)-1H-imidazol-5-one,
(127). (4Z)-4-(1,3-Benzothiazol-6-ylmethylene)-2-(2-pyridylamino)-1H-imidazol-5-one,
(128). (4Z)-4-(1,3-Benzothiazol-6-ylmethylene)-2-[(1-methylpyrazol-3-yl)amino]-1H-imidazol-5-one,
(129). (4Z)-4-(1,3-Benzothiazol-6-ylmethylene)-2-[(2-methoxy-6-methyl-3-pyridyl)amino]-1H-imidazol-5-one,
(130). (4Z)-4-(1,3-Benzothiazol-6-ylmethylene)-2-(pyrimidin-5-ylamino)-1H-imidazol-5-one,
(131). (4Z)-4-(1,3-Benzothiazol-6-ylmethylene)-2-(3-pyridylamino)-1H-imidazol-5-one,
(132). (4Z)-4-(1,3-Benzothiazol-6-ylmethylene)-2-(1,3,4-thiadiazol-2-ylamino)-1H-imidazol-5-one,
(133). (4Z)-4-(1,3-Benzothiazol-6-ylmethylene)-2-[[5-(4-methylpiperazin-1-yl)-2-pyridyl]amino]-1H-imidazol-5-one,
(134). (4Z)-4-(1,3-Benzothiazol-6-ylmethylene)-2-[[6-(4-methylpiperazin-1-yl)-3-pyridyl]amino]-1H-imidazol-5-one,
(135). (4Z)-4-(1,3-Benzothiazol-6-ylmethylene)-2-[[2-(4-methylpiperazin-1-yl)pyrimidin-5-yl]amino]-1H-imidazol-5-one,
(136). (4Z)-4-(1,3-Benzothiazol-6-ylmethylene)-2-[[5-(4-methylpiperazin-1-yl)pyrimidin-2-yl]amino]-1H-imidazol-5-one,
(137). (4Z)-4-(1,3-Benzothiazol-6-ylmethylene)-2-[[5-(4-methylpiperazin-1-yl)pyrazin-2-yl]amino]-1H-imidazol-5-one, (138). (4Z)-4-(1,3-Benzothiazol-6-ylmethylene)-2-[[6-(4-methylpiperazin-1-yl)pyridazin-3-yl]amino]-1H-imidazol-5-one,
(139). (4Z)-4-(1,3-Benzothiazol-6-ylmethylene)-2-(tetrahydropyran-4-ylamino)-1H-imidazol-5-one,
(140). Tert-butyl 4-[[(4Z)-4-(1,3-benzothiazol-6-ylmethylene)-5-oxo-1H-imidazol-2-yl]amino]piperidine-1-carboxylate,
(141). Ethyl 4-[[(4Z)-4-(1,3-benzothiazol-6-ylmethylene)-5-oxo-1H-imidazol-2-yl]amino]piperidine-1-carboxylate,
(142). (4Z)-4-(1,3-Benzothiazol-6-ylmethylene)-2-[(1-methyl-4-piperidyl)amino]-1H-imidazol-5-one,
(143). (±)-(4Z)-4-(1,3-Benzothiazol-6-ylmethylene)-2-[(1-methyl-3-piperidyl)amino]-1H-imidazol-5-one,
(144). (4Z)-4-(1,3-Benzothiazol-6-ylmethylene)-2-(oxetan-3-ylamino)-1H-imidazol-5-one,
(145). (4Z)-4-(1,3-Benzothiazol-6-ylmethylene)-2-[[(3R)-tetrahydrofuran-3-yl]amino]-1H-imidazol-5-one,
(146). (4Z)-4-(1,3-Benzothiazol-6-ylmethylene)-2-[[(3S)-tetrahydrofuran-3-yl]amino]-1H-imidazol-5-one,
(147). (4Z)-4-(1,3-Benzothiazol-6-ylmethylene)-2-[[(3R)-tetrahydropyran-3-yl]amino]-1H-imidazol-5-one,
(148). (4Z)-4-(1,3-Benzothiazol-6-ylmethylene)-2-[[(3S)-tetrahydropyran-3-yl]amino]-1H-imidazol-5-one,
(149). (±)-(4Z)-4-(1,3-Benzothiazol-6-ylmethylene)-2-[(6,6-dimethyltetrahydropyran-3-yl)amino]-1H-imidazol-5-one,
(149A). (4Z)-4-(1,3-Benzothiazol-6-ylmethylene)-2-[[(3R)/(3S)-6,6-dimethyltetrahydropyran-3-yl]amino]-1H-imidazol-5-one,
(149B). (4Z)-4-(1,3-Benzothiazol-6-ylmethylene)-2-[[(3R)/(3S)-6,6-dimethyltetrahydropyran-3-yl]amino]-1H-imidazol-5-one,
(150). (4Z)-4-(1,3-Benzothiazol-6-ylmethylene)-2-[[(3R,4R)-4-hydroxytetrahydropyran-3-yl]amino]-1H-imidazol-5-one,
(151). (±)-(4Z)-4-(1,3-Benzothiazol-6-ylmethylene)-2-(oxepan-3-ylamino)-1H-imidazol-5-one,
(152). (±)-3-[[(4Z)-4-(1,3-Benzothiazol-6-ylmethylene)-5-oxo-1H-imidazol-2-yl]amino]piperidin-2-one,
(153). (3S)-3-[[(4Z)-4-(1,3-Benzothiazol-6-ylmethylene)-5-oxo-1H-imidazol-2-yl]amino]piperidin-2-one,
(154). (5S)-5-[[(4Z)-4-(1,3-Benzothiazol-6-ylmethylene)-5-oxo-1H-imidazol-2-yl]amino]piperidin-2-one,
(155). (±)-(4Z)-4-(1,3-Benzothiazol-6-ylmethylene)-2-[(3,3-difluorocyclopentyl)amino]-1H-imidazol-5-one,
(156). (4Z)-4-(1,3-Benzothiazol-6-ylmethylene)-2-[(4,4-difluorocyclohexyl)amino]-1H-imidazol-5-one,
(157). (±)-(4Z)-4-(1,3-Benzothiazol-6-ylmethylene)-2-[(3,3-difluorocyclohexyl)amino]-1H-imidazol-5-one,
(158). (±)-(4Z)-4-(1,3-Benzothiazol-6-ylmethylene)-2-[(2,2-difluorocyclohexyl)amino]-1H-imidazol-5-one,
(159). (±)-(4Z)-4-(1,3-Benzothiazol-6-ylmethylene)-2-[(3,3-difluorocycloheptyl)amino]-1H-imidazol-5-one,
(160). (4Z)-4-(1,3-Benzothiazol-6-ylmethylene)-2-[[(1R)-1-(fluoromethyl)-3-methyl-butyl]amino]-1H-imidazol-5-one,
(161). (4Z)-4-(1,3-Benzothiazol-6-ylmethylene)-2-[[(1S)-1-(fluoromethyl)-3-methyl-butyl]amino]-1H-imidazol-5-one,
(162). [3-[[(4Z)-4-(1,3-Benzothiazol-6-ylmethylene)-5-oxo-1H-imidazol-2-yl]amino]-1-adamantyl] acetate,
(163). [3-[[(4Z)-4-(1,3-Benzothiazol-6-ylmethylene)-5-oxo-1H-imidazol-2-yl]amino]-1-adamantyl] 2,2-dimethylpropanoate,
(164). (4Z)-4-(1,3-Benzothiazol-6-ylmethylene)-2-[[(1R,2R)-2-methoxycyclopentyl]amino]-1H-imidazol-5-one,
(165). (4Z)-4-(1,3-Benzothiazol-6-ylmethylene)-2-[[(1S,2S)-2-methoxycyclopentyl]amino]-1H-imidazol-5-one,
(166). (4Z)-4-(1,3-Benzothiazol-6-ylmethylene)-2-[[(1R,2R)-2-methoxycyclohexyl]amino]-1H-imidazol-5-one,
(167). (4Z)-4-(1,3-Benzothiazol-6-ylmethylene)-2-[[(1S,2S)-2-methoxycyclohexyl]amino]-1H-imidazol-5-one,
(168). (±)-(4Z)-4-(1,3-Benzothiazol-6-ylmethylene)-2-[[cis-3-methoxycyclohexyl]amino]-1H-imidazol-5-one,
(169). (±)-(4Z)-4-(1,3-Benzothiazol-6-ylmethylene)-2-[[trans-3-methoxycyclohexyl]amino]-1H-imidazol-5-one,
(169A). (4Z)-4-(1,3-Benzothiazol-6-ylmethylene)-2-[[(1R,3R)/(1S,3S)-3-methoxycyclohexyl]amino]-1H-imidazol-5-one,
(169B). (4Z)-4-(1,3-Benzothiazol-6-ylmethylene)-2-[[(1R,3R)/(1S,3S)-3-methoxycyclohexyl]amino]-1H-imidazol-5-one,
(170). (±)-(4Z)-4-(1,3-Benzothiazol-6-ylmethylene)-2-[[cis-4-hydroxycycloheptyl]amino]-1H-imidazol-5-one,
(171). (±)-(4Z)-4-(1,3-Benzothiazol-6-ylmethylene)-2-[[trans-4-hydroxycycloheptyl]amino]-1H-imidazol-5-one,
(171A). (4Z)-4-(1,3-Benzothiazol-6-ylmethylene)-2-[[(1R,4R)/(1S,4S)-4-hydroxycycloheptyl]amino]-1H-imidazol-5-one,
(171B). (4Z)-4-(1,3-Benzothiazol-6-ylmethylene)-2-[[(1R,4R)/(1S,4S)-4-hydroxycycloheptyl]amino]-1H-imidazol-5-one,
(172). (±)-(4Z)-4-(1,3-Benzothiazol-6-ylmethylene)-2-[[cis-3-methoxycycloheptyl]amino]-1H-imidazol-5-one,
(173). (±)-(4Z)-4-(1,3-Benzothiazol-6-ylmethylene)-2-[[trans-3-methoxycycloheptyl]amino]-1H-imidazol-5-one,
(174). (±)-(4Z)-4-(1,3-Benzothiazol-6-ylmethylene)-2-[[cis-4-methoxycycloheptyl]amino]-1H-imidazol-5-one,
(175). (±)-(4Z)-4-(1,3-benzothiazol-6-ylmethylene)-2-[[trans-4-methoxycycloheptyl]amino]-1H-imidazol-5-one,
(176). (4Z)-4-(1,3-Benzothiazol-6-ylmethylene)-2-[[(1R)-2-methoxy-1-phenyl-ethyl]amino]-1H-imidazol-5-one,
(177). (4Z)-4-(1,3-Benzothiazol-6-ylmethylene)-2-[[(1S)-2-methoxy-1-phenyl-ethyl]amino]-1H-imidazol-5-one,
(178). (4Z)-4-(1,3-Benzothiazol-6-ylmethylene)-2-[[(2R)-2-hydroxy-2-phenyl-ethyl]amino]-1H-imidazol-5-one,
(179). (4Z)-4-(1,3-Benzothiazol-6-ylmethylene)-2-[[(2S)-2-hydroxy-2-phenyl-ethyl]amino]-1H-imidazol-5-one,
(180). (4Z)-2-[[(1R)-2-Amino-1-phenyl-ethyl]amino]-4-(1,3-benzothiazol-6-ylmethylene)-1H-imidazol-5-one dihydrochloride,
(181). (4Z)-2-[[(1S)-2-Amino-1-phenyl-ethyl]amino]-4-(1,3-benzothiazol-6-ylmethylene)-1H-imidazol-5-one dihydrochloride,
(182). (4Z)-4-(1,3-Benzothiazol-6-ylmethylene)-2-[[(3R)-quinuclidin-3-yl]amino]-1H-imidazol-5-one,
(183). (4Z)-4-(1,3-Benzothiazol-6-ylmethylene)-2-[[(3S)-quinuclidin-3-yl]amino]-1H-imidazol-5-one,
(184). (±)-(4Z)-4-(1,3-Benzothiazol-6-ylmethylene)-2-(tetrahydrothiopyran-3-ylamino)-1H-imidazol-5-one,
(185). (±)-(4Z)-4-(1,3-Benzothiazol-6-ylmethylene)-2-(1,4-dioxepan-6-ylamino)-1H-imidazol-5-one,
(186). (±)-(4Z)-4-(1,3-Benzothiazol-6-ylmethylene)-2-[(2-oxopyrrolidin-3-yl)amino]-1H-imidazol-5-one,
(187). (±)-(4Z)-4-(1,3-Benzothiazol-6-ylmethylene)-2-[(1-methyl-2-oxo-pyrrolidin-3-yl)amino]-1H-imidazol-5-one, (188). (±)-(4Z)-4-(1,3-Benzothiazol-6-ylmethylene)-2-[(4,4-dimethyl-2-oxo-pyrrolidin-3-yl)amino]-1H-imidazol-5-one,
(189). (3R)-3-[[(4Z)-4-(1,3-Benzothiazol-6-ylmethylene)-5-oxo-1H-imidazol-2-yl]amino]piperidin-2-one,
(190). (±)-3-[[(4Z)-4-(1,3-Benzothiazol-6-ylmethylene)-5-oxo-1H-imidazol-2-yl]amino]-1-methyl-piperidin-2-one,
(191). (±)-(4Z)-4-(1,3-Benzothiazol-6-ylmethylene)-2-[(3-methyl-2-oxo-pyrrolidin-3-yl)amino]-1H-imidazol-5-one,
(192). (±)-(4Z)-4-(1,3-Benzothiazol-6-ylmethylene)-2-[(1,3-dimethyl-2-oxo-pyrrolidin-3-yl)amino]-1H-imidazol-5-one,
(192A). (4Z)-4-(1,3-Benzothiazol-6-ylmethylene)-2-[[(3R)/(3S)-1,3-dimethyl-2-oxo-pyrrolidin-3-yl]amino]-1H-imidazol-5-one,
(192B). (4Z)-4-(1,3-Benzothiazol-6-ylmethylene)-2-[[(3R)/(3S)-1,3-dimethyl-2-oxo-pyrrolidin-3-yl]amino]-1H-imidazol-5-one,
(193). (4Z)-4-(1,3-Benzothiazol-6-ylmethylene)-2-[[(3S,4S)-4-hydroxytetrahydropyran-3-yl]amino]-1H-imidazol-5-one,
(194). (4Z)-2-(3-Noradamantylamino)-4-(1,3-benzothiazol-6-ylmethylene)-1H-imidazol-5-one,
(195). [3-[[(4Z)-4-(1,3-Benzothiazol-6-ylmethylene)-5-oxo-1H-imidazol-2-yl]amino]-1-adamantyl] N-tert-butylcarbamate,
(196). (4Z)-4-(1,3-Benzothiazol-6-ylmethylene)-2-[(3-fluoro-1-adamantyl)amino]-1H-imidazol-5-one,
(197). (4Z)-4-(1,3-Benzothiazol-6-ylmethylene)-2-[[(1R)-1-(tert-butoxymethyl)-3-methyl-butyl]amino]-1H-imidazol-5-one,
(198). (4Z)-4-(1,3-Benzothiazol-6-ylmethylene)-2-[[(1R)-2-tert-butoxy-1-phenyl-ethyl]amino]-1H-imidazol-5-one,
(199). N-[3-[[(4Z)-4-(1,3-Benzothiazol-6-ylmethylene)-5-oxo-1H-imidazol-2-yl]amino]-1-adamantyl]acetamide,
(200). N-[3-[[(4Z)-4-(1,3-Benzothiazol-6-ylmethylene)-5-oxo-1H-imidazol-2-yl]amino]-1-adamantyl]cyclopropanecarboxamide,
(201). N-[3-[[(4Z)-4-(1,3-Benzothiazol-6-ylmethylene)-5-oxo-1H-imidazol-2-yl]amino]-1-adamantyl]methanesulfonamide,
(202). N-[3-[[(4Z)-4-(1,3-Benzothiazol-6-ylmethylene)-5-oxo-1H-imidazol-2-yl]amino]-1-adamantyl]cyclopropanesulfonamide,
(203). (4Z)-4-(1,3-Benzothiazol-6-ylmethylene)-2-[[3-(dimethylamino)-1-adamantyl]amino]-1H-imidazol-5-one,
(204). Methyl 2-[[(4Z)-4-(1,3-benzothiazol-6-ylmethylene)-5-oxo-1H-imidazol-2-yl]amino]adamantane-2-carboxylate,
(205). (4Z)-2-(Cyclohexylamino)-4-[(2-methyl-1,3-benzothiazol-6-yl)methylene]-1H-imidazol-5-one,
(206). (4Z)-2-(Cycloheptylamino)-4-[(2-methyl-1,3-benzothiazol-6-yl)methylene]-1H-imidazol-5-one,
(207). (4Z)-2-[[(1R)-1-(Methoxymethyl)-3-methyl-butyl]amino]-4-[(2-methyl-1,3-benzothiazol-6-yl)methylene]-1H-imidazol-5-one,
(208). (4Z)-2-[[(1R)-2-Methoxy-1-phenyl-ethyl]amino]-4-[(2-methyl-1,3-benzothiazol-6-yl)methylene]-1H-imidazol-5-one,
(209). (4Z)-2-(1-Adamantylamino)-4-[(2-methyl-1,3-benzothiazol-6-yl)methylene]-1H-imidazol-5-one, and
(210). (4Z)-2-[(3-Hydroxy-1-adamantyl)amino]-4-[(2-methyl-1,3-benzothiazol-6-yl)methylene]-1H-imidazol-5-one,
(211). (4Z)-4-(1,3-Benzothiazol-6-ylmethylene)-2-[(3,5-dihydroxy-1-adamantyl)amino]-1H-imidazol-5-one,
(212). (4Z)-4-(1,3-Benzothiazol-6-ylmethylene)-2-[(3,5,7-trifluoro-1-adamantyl)amino]-1H-imidazol-5-one,
(213). (4Z)-4-(1,3-Benzothiazol-6-ylmethylene)-2-[[(1R)-1-(ethoxymethyl)-3-methyl-butyl]amino]-1H-imidazol-5-one,
(214). (4Z)-4-(1,3-Benzothiazol-6-ylmethylene)-2-[[(1R)-1-(benzyloxymethyl)-3-methyl-butyl]amino]-1H-imidazol-5-one,
(215). (4Z)-4-(1,3-Benzothiazol-6-ylmethylene)-2-[[(1R)-1-[(4-fluorophenyl)methoxymethyl]-3-methyl-butyl]amino]-1H-imidazol-5-one,
(216). (4Z)-4-(1,3-Benzothiazol-6-ylmethylene)-2-[[(1R)-1-(cyclopropoxymethyl)-3-methyl-butyl]amino]-1H-imidazol-5-one, or anyone of their pharmaceutically acceptable salts.

According to an even more preferred embodiment of the present invention, the compound of formula (I) is chosen from the group consisting of compounds (4), (5), (6), (7), (8), (9), (12), (13), (14), (16), (17), (18), (19), (20), (21), (22), (23), (24), (25), (27), (28), (30), (31), (32), (34), (35), (36), (38), (40), (41), (42), (43), (44), (46), (48), (49), (50), (51), (53), (55), (56), (57), (59), (60), (61), (62), (63), (64), (65), (66), (67), (68), (69), (70), (71), (72), (73), (74), (77), (78), (80), (81), (83), (85), (86), (89), (90), (92), (93), (94), (95), (96), (97), (98), (99), (104), (106), (108), (117), (119), (125), (127), (128), (135), (146), (147), (148), (149), (149A), (149B), (150), (151), (154), (155), (157), (158), (159), (160), (161), (162), (164), (165), (167), (168), (169), (169A), (169B), (170), (171), (171A), (171B), (172), (173), (174), (175), (176), (178), (179), (180), (181), (182), (184), (185), (191), (192), (192A), (194), (195), (196), (197), (198), (199), (200), (201), (203), (204), (208), (209), (210) and their pharmaceutically acceptable salts.

According to an even more preferred embodiment of the present invention, the compound of formula (I) is chosen from the group consisting of compounds (6), (7), (8), (9), (12), (14), (16), (17), (19), (20), (21), (22), (24), (25), (27), (28), (31), (32), (34), (35), (36), (38), (40), (41), (43), (44), (46), (48), (49), (51), (53), (55), (56), (57), (59), (61), (62), (63), (64), (65), (66), (67), (68), (69), (74), (77), (78), (81), (83), (85), (86), (89), (90), (92), (93), (95), (96), (97), (98), (99), (108), (119), (125), (146), (148), (149), (149A), (149B), (150), (151), (155), (157), (158), (159), (160), (161), (162), (164), (165), (167), (168), (169), (169A), (169B), (170), (171), (171A), (171B), (172), (173), (174), (175), (176), (178), (179), (180), (181), (182), (184), (185), (191), (192), (192A), (194), (195), (196) (197), (198), (199), (200), (201), (203), (204), (208), and their pharmaceutically acceptable salts.

According to an even more preferred embodiment of the present invention, the compound of formula (I) is chosen from the group consisting of compounds (9), (16), (17), (19), (20), (21), (22), (25), (27), (34), (35), (40), (48), (61), (65), (66), (78), (81), (83), (89), (95), (96), (97), (99), (158), (159), (160), (162), (169), (172), (173), (175), (176), (184), (194), (195), (196), (199), (200), (201), (203), (210) and their pharmaceutically acceptable salts.

According to an alternative embodiment of the present invention, the compound of formula (I) is chosen from the group consisting of compounds (1), (3), (4), (5), (6), (7), (8), (9), (10), (12), (13), (14), (16), (17), (19), (20), (21), (22), (23), (24), (25), (26), (27), (28), (30), (31), (32), (33), (34), (35), (36), (37), (38), (39), (40), (41), (42), (43), (44), (45), (46), (47), (48), (49), (50), (51), (53), (55), (56), (57), (58), (59), (60), (61), (62), (63), (64), (65), (66), (67), (68), (69), (70), (71), (72), (73), (74), (75), (76), (77), (78), (79), (80), (81), (82), (83), (85), (86), (88), (89), (90), (92), (93), (94), (95), (96), (97), (98), (99), (100), (101), (102), (103), (104), (105), (106), (107), (108), (109), (110), (111), (113), (117), (119), (120), (121), (126), (127), (128), (129), (130), (131), (132), (135), (137), (139), (141), (144), (145), (146), (147), (148), (149), (149A), (149B), (150), (151), (154), (155), (156), (157), (158), (159), (160), (161), (162), (163), (164), (165), (166), (167), (168), (169), (169A), (169B), (170), (171), (171A), (171B), (172), (173), (174), (175), (176), (178), (179), (180), (181), (182), (183), (184), (185), (191), (192), (192A), (192B), (194), (195), (196), (197), (198), (199), (200), (201), (203), (208), (209), (210), and their pharmaceutically acceptable salts.

According to a preferred embodiment of the present invention, the compound of formula (I) is chosen from the group consisting of compounds (1), (4), (5), (6), (7), (8), (9), (10), (12), (13), (14), (16), (17), (19), (20), (21), (22), (23), (24), (25), (26), (27), (28), (30), (31), (32), (33), (34), (35), (36), (38), (40), (41), (43), (44), (46), (48), (49), (51), (53), (55), (56), (57), (59), (61), (62), (63), (64), (65), (66), (67), (68), (69), (70), (71), (73), (74), (76), (77), (78), (79), (80), (81), (82), (83), (85), (86), (88), (89), (90), (92), (93), (94), (95), (96), (97), (98), (99), (100), (101), (102), (104), (105), (106), (108), (109), (113), (117), (119), (127), (128), (130), (131), (135), (139), (141), (146), (147), (148), (149), (149A), (149B), (150), (151), (155), (156), (157), (158), (159), (160), (161), (162), (163), (164), (165), (166), (167), (168), (169), (169A), (169B), (170), (171), (171A), (171B), (172), (173), (174), (175), (176), (178), (179), (180), (181), (182), (183), (184), (185), (191), (192), (192A), (192B), (194), (195), (196), (198), (199), (200), (201), (203), (210), and their pharmaceutically acceptable salts.

According to an even more preferred embodiment of the present invention, the compound of formula (I) is chosen from the group consisting of compounds (9), (16), (19), (20), (21), (35), (48), (61), (73), (78), (81), (95), (96), (155), (159), (160), (161), (169), (169A), (171A), (176), (184), (196), (199), (200), (201), (203), (210), and their pharmaceutically acceptable salts.

According to a further embodiment of the present invention, the compound of formula (I) is chosen from the group consisting of compounds (7), (8), (9), (10), (12), (16), (17), (19), (20), (21), (23), (25), (26), (28), (32), (33), (34), (35), (40), (41), (43), (44), (46), (48), (55), (56), (57), (59), (61), (62), (63), (65), (66), (67), (68), (69), (70), (73), (77), (78), (81), (83), (88), (89), (90), (95), (96), (97), (98), (99), (100), (101), (102), (104), (105), (106), (117), (119), (127), (131), (139), (148), (149), (149B), (151), (155), (156), (157), (158), (159, 160), (161), (164), (165), (167), (169), (169A), (169B), (170), (171), (171A), (171B), (172), (173), (176), (178), (179), (180), (181), (184), (185), (191), (192), (192A), (194), (196), (198), (199), (200), (201), (203), (210) and their pharmaceutically acceptable salts.

The groups of compounds as defined by the list of compounds as identified in Example 4 below through tables 4A to table 4F and specifically identified as most potent kinase inhibitors, as well as multi-target kinase inhibitors, also form part of the present invention.

According to another aspect, a subject-matter of the present invention relates to a compound of formula (I) as defined above or any of its pharmaceutically acceptable salts, or at least any of compounds (1) to (216) or any of its pharmaceutically acceptable salts, for use as a medicament.

«Pharmaceutically acceptable salt thereof» refers to salts which are formed from acid addition salts formed with inorganic acids (e.g. hydrochloric acid, hydrobromic acid), as well as salts formed with organic acids such as acetic acid, tartaric acid, succinic acid.

Suitable physiologically acceptable acid addition salts of compounds of formula (I) include hydrobromide, tartrate, hydrochloride, succinate and acetate.

The compounds of formula (I), and any of compounds (1) to (216) or any of their pharmaceutically acceptable salts may form solvates or hydrates and the invention includes all such solvates and hydrates.

The terms "hydrates" and "solvates" simply mean that the compounds (I) according to the invention can be in the form of a hydrate or solvate, i.e. combined or associated with one or more water or solvent molecules. This is only a chemical characteristic of such compounds, which can be applied for all organic compounds of this type.

The compounds of formula (I) can comprise one or more asymmetric carbon atoms. They can thus exist in the form of enantiomers or of diastereoisomers. These enantiomers, diastereoisomers and their mixtures, including the racemic mixtures, are encompassed within the scope of the present invention.

The compounds of the present invention can be prepared by conventional methods of organic synthesis practiced by those skilled in the art. The general reaction sequences outlined below represent a general method useful for preparing the compounds of the present invention and are not meant to be limiting in scope or utility.

| List of abbreviations: | |
| --- | --- |
| Abbreviation/ acronym | name |
| Ac | Acetyl |
| ACN | Acetonitrile |
| Alk | Alkyl |
| ATP | Adenosine triphosphate |
| br s | Broad singlet |
| c | Molar concentration |
| Cpd No | Compound number |
| d | Doublet |
| DCM | Methylene chloride |
| dd | Doublet of doublets |
| DIPEA | N,N-Diisopropylethylamine |
| DMF | Dimethylformamide |
| DMSO | Dimethylsulfoxide |
| DTT | Dithiothreitol |
| Eq | Equivalent |
| ESI | Electrospray ionization |
| Et | Ethyl |
| FC | Flash chromatography |
| GP | General protocol |
| GST | Glutathione S-transferase |
| Hal | Halogen |
| HEPES | 4-(2-Hydroxyethyl)-1-piperazineethanesulfonic acid |
| His-tagged | Polyhistidine-tagged |
| HPLC | High pressure liquid chromatography |
| $IC_{50}$ | Half maximal inhibitory concentration |
| m | Multiplet |
| M | Molarity |
| Me | Methyl |
| MS | Mass spectroscopy |
| MW | Molecular weight |
| NMR | Nuclear magnetic resonance |
| N/A | Not applicable |
| n.t. | Not tested |
| Piv | Pivaloyl |
| Rac | Racemic |
| r.t. | Room temperature |
| s | Singlet |
| SFC | Supercritical fluid chromatography |
| SDS-PAGE | Sodium dodecyl sulfate-polyacrylamide gel electrophoresis |
| t | Triplet |
| TEA | Triethylamine |
| TFA | Trifluoroacetic acid |

| Abbreviation/ acronym | name |
|---|---|
| THF | Tetrahydrofuran |
| TLC | Thin layer chromatography |
| T ° C. | Temperature in degrees Celsius |
| PTLC | Preparative thin layer chromatography |
| UV | Ultraviolet |
| v/v | Volume per volume |
| w/v | Weight per volume |
| $\delta_H$ | Hydrogen chemical shift |
| µw | Microwave irradiation |

The compounds of general formula (I) can be prepared according to scheme 1 below.

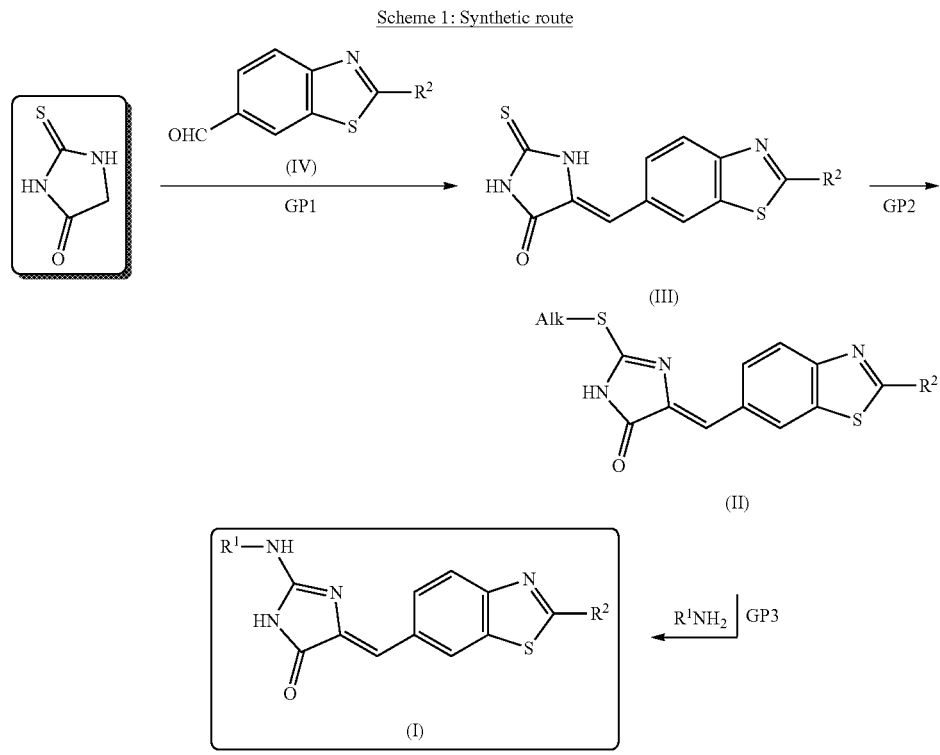

Scheme 1: Synthetic route

The synthesis of compounds according to the invention is based on a functionalization of a compound of formula (II) by an amine of formula $R^1NH_2$ wherein $R^1$ is as defined above, following the general protocol 3 (GP3), described herein after.

According to GP3, the compound of formula (II) may be placed in an aprotic solvent such as THF or dioxane, or a mixture of both. The amine of formula $R^1NH_2$ may be added, for example in a molar ratio ranging from 2 to 6, in particular of 4, with respect to the compound of formula (II). The reaction mixture may be placed in a sealed tube and may receive energy, for example from a heating block or from microwaves. Upon completion of the reaction, the mixture may be brought back to room temperature.

In an embodiment named GP3-A, the reaction mixture may be stirred at a temperature ranging from −10° C. to 10° C., for example at 0° C., for a duration ranging from 30 minutes to 2 hours, for example for 1 hour. Depending on the state of the product obtained (solid, precipitate), purification methods well-known by the person skilled in the art may be performed, for example filtering, washing, triturating, drying in vacuo, flash chromatography, precipitating and refluxing.

In an embodiment named GP3-B, wherein the product failed to precipitate, the reaction mixture may be concentrated, in particular in vacuo, and purified, in particular by flash chromatography. A second purification step may be performed, in particular selected from reprecipitation, trituration and recrystallization.

In another embodiment named GP3-C, wherein the product failed to precipitate, the reaction mixture may be concentrated, in particular in vacuo, and the resulting crude may be purified by trituration in a protic polar solvent such as ethanol. Said trituration may be performed at a temperature comprised between 20 and 100° C., in particular at room temperature. A second purification step may be performed, in particular selected from reprecipitation, trituration and recrystallization.

A compound of formula (II) as defined above may be obtained by the S-alkylation of a compound of formula (III) wherein $R^2$ is as defined above and Alk is a $(C_1$-$C_8)$alkyl.

According to the general protocol GP2, a compound of formula (III) may be placed in a polar aprotic solvent such as dimethylformamide (DMF). An alkylhalide of formula Alk-Hal wherein Hal is an halide such as iodine or bromine may then be added dropwise, for example in a molar ratio ranging from 0.75 to 1.50, in particular of 1.05, with respect to the compound of formula (III), in presence of an inorganic base such as $K_2CO_3$, for example in a molar ratio ranging from 0.7 to 1.5, in particular of 1, still with respect to the compound of formula (III). The reaction mixture may be stirred during the addition of the alkylhalide.

In a particular embodiment, the resulting mixture may then be stirred, for example from 8 to 16 hours, in particular for 12 hours at room temperature.

In another embodiment, the resulting mixture may be stirred, for example from 2 to 8 hours, in particular for 6 hours, at a temperature ranging from −10° C. to 10° C., in particular at 0° C.

A compound of formula (III) as defined above may be obtained from a compound of formula (IV) wherein $R^2$ is as defined above, following the general protocol GP1.

According to GP1, the compound of formula (IV) may be placed in a protic solvent such as ethanol in presence of 2-thiohydantoin, for example in a molar ratio ranging from 0.85 to 1.15, in particular of 1, with respect to the compound of formula (IV), in presence of an organic base such as piperidine in a molar ratio ranging from 0.85 to 1.15, in particular of 1, still with respect to the compound of formula (II), in presence of an organic acid such as acetic acid for example in a molar ratio ranging from 0.85 to 1.15, in particular of 1, still with respect to the compound of formula (IV). The reaction mixture may be placed in a sealed tube, stirred and heated at a temperature ranging for example from 60° C. to 130° C., in particular from 80° C. to a duration ranging from 10 to 100 minutes, in particular from 15 to 90 minutes. The reaction mixture may be irradiated, for example by microwaves.

Accordingly, the present invention further relates to the synthesis process for manufacturing new compounds of formula (I) as defined above, comprising at least a step of substituting a compound of formula (II) with a primary amine. The present invention relates to a synthesis process for manufacturing a compound of formula (I) as defined above or any of its pharmaceutically acceptable salt or any of the compounds (1) to (216) as defined above or any of their pharmaceutically acceptable salts, comprising at least a step of coupling a compound of formula (II) below

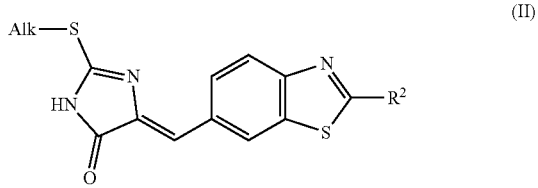

(II)

wherein Alk is a $(C_1-C_5)$alkyl,
with an amine of formula $R^1NH_2$ wherein $R^1$ and $R^2$ are as defined above.

The present invention further relates to a synthetic intermediate of formula (II) below

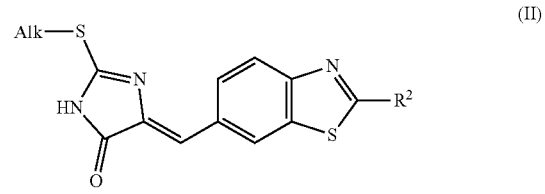

(II)

wherein Alk is a $(C_1-C_5)$alkyl, in particular Alk is selected from the group consisting of an ethyl and a methyl and $R^2$ is as defined above.

The chemical structures, the analytical and spectroscopic data of some compounds of formula (I) of the invention are illustrated respectively in the following Table 2 and Table 3.

Reactions were performed using oven-dried glassware under inert atmosphere of argon. Unless otherwise noted, all reagent-grade chemicals and solvents were obtained from commercial suppliers and were used as received. Reactions were monitored by thin-layer chromatography with silica gel 60 F254 pre-coated aluminium plates (0.25 mm). Visualization was performed under UV light and 254 or 312 nm, or with appropriate TLC stains including, but not limited to: phosphomolybdic acid, $KMnO_4$, ninhydrin, CAM, vanillin, p-anisaldehyde.

Microwave experiments were conducted in an Anton Paar Monowave 400® microwave reactor. The experiments were conducted in a monomode cavity with a power delivery ranging from 0 to 850 W, allowing pressurized reactions (0 to 30 bar) to be performed in sealed glass vials (4 to 30 mL) equipped with snap caps and silicon septa. The temperature (0 to 300° C.) was monitored by a contactless infrared sensor and calibrated with a ruby thermometer. Temperature, pressure, and power profiles were edited and monitored through a touch-screen control panel. Times indicated in the various protocols are the times measured when the mixtures reached the programmed temperature after a ramp period of 3 min.

Chromatographic purifications of compounds were achieved on an automated Interchim Puriflash XS420 equipped with 30 μm spherical silica-filled prepacked columns as stationary phase.

Some compounds of the invention are described with their structure in the below Table 2, which is merely illustrative and does not limit the scope of the present invention.

TABLE 2

Structure of compounds (1) to (216). Formulas and molecular weights were generated using Perkin Elmer's Chemdraw® version 17.1.0.105.

| Cpd N° | R¹—NH— | R² | Class | Formula | MW | Stereochemistry |
|---|---|---|---|---|---|---|
| 1 |  | —NH | H | A1 | $C_{15}H_{14}N_4OS$ | 298.36 | N/A |

TABLE 2-continued

| # | R group | | | Formula | MW | Notes |
|---|---|---|---|---|---|---|
| 2 | cyclopropyl-NH- | H | A1 | C₁₄H₁₂N₄OS | 284.34 | N/A |
| 3 | cyclobutyl-NH- | H | A1 | C₁₅H₁₄N₄OS | 298.36 | N/A |
| 4 | cyclopentyl-NH- | H | A1 | C₁₆H₁₆N₄OS | 312.39 | N/A |
| 5 | cyclohexyl-CH₂-NH- | H | A1 | C₁₈H₂₀N₄OS | 340.45 | N/A |
| 6 | cyclohexyl-NH- | H | A1 | C₁₇H₁₈N₄OS | 326.42 | N/A |
| 7 | cycloheptyl-CH₂-NH- | H | A1 | C₁₉H₂₂N₄OS | 354.47 | N/A |
| 8 | cycloheptyl-NH- | H | A1 | C₁₈H₂₀N₄OS | 340.45 | N/A |
| 9 | cyclooctyl-NH- | H | A1 | C₁₉H₂₂N₄OS | 354.47 | N/A |
| 10 | HOCH₂-C(CH₃)₂-CH₂-NH- | H | A1 | C₁₆H₁₈N₄OS | 330.41 | N/A |
| 11 | PhCH₂-O-CH₂CH₂-NH- | H | A1 | C₂₀H₁₈N₄O₂S | 378.45 | N/A |
| 12 | trans-2-methylcyclohexyl-NH- | H | A1 | C₁₈H₂₀N₄OS | 340.45 | trans-rac |

TABLE 2-continued

| | | | | | | |
|---|---|---|---|---|---|---|
| 13 | (R)-1-cyclohexylethylamine structure | H | A1 | C₁₉H₂₂N₄OS | 354.47 | (1R) |
| 14 | adamantylmethyl-NH structure | H | A1 | C₂₂H₂₄N₄OS | 392.17 | N/A |
| 15 | 1-adamantylethyl-NH structure | H | A1 | C₂₃H₂₆N₄OS | 406.55 | rac |
| 16 | 1-adamantyl-NH structure | H | A1 | C₂₁H₂₂N₄OS | 378.49 | N/A |
| 17 | 2-adamantyl-NH structure | H | A1 | C₂₁H₂₂N₄OS | 378.49 | N/A |
| 18 | dimethyladamantyl-NH structure | H | A1 | C₂₃H₂₆N₄OS | 406.55 | N/A |
| 19 | hydroxyadamantyl-NH structure | A | A1 | C₂₁H₂₂N₄O₂S | 394.49 | trans |
| 20 | 3-hydroxyadamantyl-NH structure | H | A1 | C₂₁H₂₂N₄O₂S | 394.49 | N/A |
| 21 | methoxyadamantyl-NH structure | H | A1 | C₂₂H₂₄N₄O₂S | 408.52 | N/A |
| 22 | (1R,2R,3R,5S)-pinanyl-NH structure | H | A1 | C₂₁H₂₄N₄OS | 380.51 | (1R,2R,3R,5S) |

TABLE 2-continued

| # | Structure | | | Formula | MW | Stereo |
|---|---|---|---|---|---|---|
| 23 | [bicyclic structure with (S),(S),(R),(S) stereocenters, H3C, H3C, CH3, NH] | H | A1 | C21H24N4OS | 380.51 | (1S,2S,3S,5R) |
| 24 | [bicyclic structure with (R),(R),(R) stereocenters, H, H, H, NH] | H | A1 | C21H24N4OS | 380.51 | (1R,2R,5R) |
| 25 | [spiro cyclohexane-cyclopropane with NH] | H | A1 | C19H20N4OS | 352.46 | rac |
| 26 | [spiro bicyclobutane with NH] | H | A1 | C18H18N4OS | 338.43 | N/A |
| 27 | [bicyclic structure with (R), H, NH] | H | A1 | C21H24N4OS | 380.51 | (2R) |
| 28 | [bicyclic structure with NH] | H | A1 | C18H18N4OS | 380.51 | rac |
| 29 | [cyclohexane with (S) isopropyl, (R), (R) NH, (R) methyl] | H | A1 | C21H26N4OS | 382.53 | (1R,2S,5R) |
| 30 | [HO-CH2-C(R)(NH)-CH2-cyclohexyl] | H | A1 | C20H24N4O2S | 384.50 | (1R) |
| 31 | [HO-CH2-C(R)(NH)-CH2-cyclopentyl] | H | A1 | C19H22N4O2S | 370.47 | (1R) |
| 32 | [HO-CH2-C(R)(NH)-CH2-cyclobutyl] | H | A1 | C18H20N4O2S | 356.44 | (1R) |
| 33 | [HO-CH2-C(R)(NH)-CH2-cyclopropyl] | H | A1 | C17H18N4O2S | 342.42 | (1R) |

TABLE 2-continued

| | | | | | | |
|---|---|---|---|---|---|---|
| 34 | HO—⟨(R)⟩—NH— (isobutyl) | H | A1 | $C_{17}H_{20}N_4O_2S$ | 344.43 | (1R) |
| 35 | MeO—⟨(R)⟩—NH— (isobutyl) | H | A1 | $C_{18}H_{22}N_4O_2S$ | 344.43 | (1R) |
| 36 | HO—⟨(S)⟩—NH— (isobutyl) | H | A1 | $C_{17}H_{20}N_4O_2S$ | 344.43 | (1S) |
| 37 | MeO—⟨(S)⟩—NH— (isobutyl) | H | A1 | $C_{18}H_{22}N_4O_2S$ | 344.43 | (1S) |
| 38 | HO—⟨(R)⟩—NH— (ethyl) | H | A1 | $C_{15}H_{16}N_4O_2S$ | 316.38 | (1R) |
| 39 | HO—⟨(S)⟩—NH— (ethyl) | H | A1 | $C_{15}H_{16}N_4O_2S$ | 316.38 | (1S) |
| 40 | F—⟨⟩—NH— (isobutyl) | H | A1 | $C_{17}H_{19}FN_4OS$ | 346.42 | rac |
| 41 | HO—⟨⟩—NH— (cyclohexyl) | H | A1 | $C_{19}H_{22}N_4O_2S$ | 370.47 | rac |
| 42 | MeO—⟨⟩—NH— (cyclohexyl) | H | A1 | $C_{20}H_{24}N_4O_2S$ | 384.50 | rac |
| 43 | cyclohexyl-CH(OH)-CH2-NH— | H | A1 | $C_{19}H_{22}N_4O_2S$ | 384.50 | rac |

TABLE 2-continued

| # | Structure | | | Formula | MW | Stereo |
|---|---|---|---|---|---|---|
| 44 | [cyclohexyl-CH(OMe)-CH2-NH-] | H | A1 | C₂₀H₂₄N₄O₂S | 384.50 | rac |
| 45 | [cyclopentyl with OH and NH, cis] | H | A1 | C₁₆H₁₆N₄O₂S | 328.39 | cis-rac |
| 46 | [cyclopentyl with OH and NH, trans] | H | A1 | C₁₆H₁₆N₄O₂S | 328.39 | trans-rac |
| 47 | [cyclopentyl with OMe and NH, cis] | H | A1 | C₁₇H₁₈N₄O₂S | 342.42 | cis-rac |
| 48 | [cyclopentyl with OMe and NH, trans] | H | A1 | C₁₇H₁₈N₄O₂S | 342.42 | trans-rac |
| 49 | [cyclohexyl with OH and NH, cis] | H | A1 | C₁₇H₁₈N₄O₂S | 342.42 | cis-rac |
| 50 | [cyclohexyl with OH and NH, trans] | H | A1 | C₁₇H₁₈N₄O₂S | 342.42 | trans-rac |
| 51 | [cyclohexyl (S)-OH (R)-NH] | H | A1 | C₁₇H₁₈N₄O₂S | 342.42 | (1R,2S) |
| 52 | [cyclohexyl (R)-OH (S)-NH] | H | A1 | C₁₇H₁₈N₄O₂S | 342.42 | (1S,2R) |

TABLE 2-continued
| | | | | | | |
|---|---|---|---|---|---|---|
| 53 | 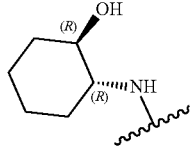 | H | A1 | $C_{17}H_{18}N_4O_2S$ | 342.42 | (1R,2R) |
| 54 | 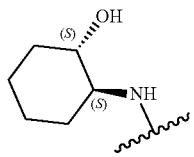 | H | A1 | $C_{17}H_{18}N_4O_2S$ | 342.42 | (1S,2S) |
| 55 | 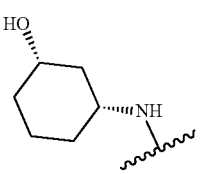 [SMILES: *N[C@@H]1CCC[C@H](O)C1] | H | A1 | $C_{17}H_{18}N_4O_2S$ | 342.42 | cis-rac |
| 56 | 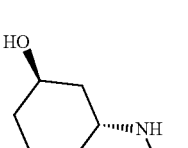 | H | A1 | $C_{17}H_{18}N_4O_2S$ | 342.42 | trans-rac |
| 57 | 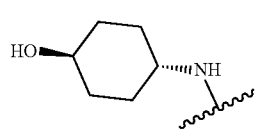 [SMILES: *N[C@H]1CC[C@H](O)CC1] | H | A1 | $C_{17}H_{18}N_4O_2S$ | 342.42 | trans |
| 58 | 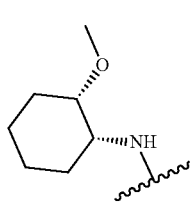 [SMILES: *N[C@@H]1CCCC[C@@H]1OC] | H | A1 | $C_{18}H_{20}N_4O_2S$ | 356.44 | cis-rac |
| 59 | 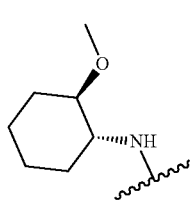 [SMILES: *N[C@@H]1CCCC[C@H]1OC] | H | A1 | $C_{18}H_{20}N_4O_2S$ | 356.44 | trans-rac |
| 60 | 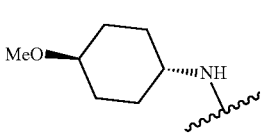 | H | A1 | $C_{18}H_{20}N_4O_2S$ | 356.44 | trans |
| 61 | 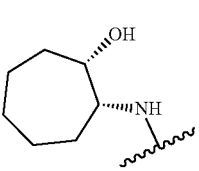 [SMILES: *N[C@@H]1CCCCC[C@@H]1O] | H | A1 | $C_{18}H_{20}N_4O_2S$ | 356.44 | cis-rac |

TABLE 2-continued

| | | | | | | |
|---|---|---|---|---|---|---|
| 62 | *cycloheptane with OH and NH substituents, trans* | H | A1 | $C_{18}H_{20}N_4O_2S$ | 356.44 | trans-rac |
| 63 | *cycloheptane with (R)-OH and (R)-NH* | H | A1 | $C_{18}H_{20}N_4O_2S$ | 356.44 | (1R,2R) |
| 64 | *cycloheptane with (S)-OH and (S)-NH* | H | A1 | $C_{18}H_{20}N_4O_2S$ | 356.44 | (1S,2S) |
| 65 | *cycloheptane with HO and NH, cis 1,3* | H | A1 | $C_{18}H_{20}N_4O_2S$ | 356.44 | cis-rac |
| 66 | *cycloheptane with HO and NH, trans 1,3* | H | A1 | $C_{18}H_{20}N_4O_2S$ | 356.44 | trans-rac |
| 67 | *cycloheptane with OMe and NH, cis* | H | A1 | $C_{19}H_{22}N_4O_2S$ | 370.47 | cis-rac |
| 68 | *cycloheptane with OMe and NH, trans* | H | A1 | $C_{19}H_{22}N_4O_2S$ | 370.47 | trans-rac |
| 69 | MeOOC–(S)CH(iPr)–NH– | H | A1 | $C_{17}H_{18}N_4O_3S$ | 358.42 | (2S) |
| 70 | MeOOC–(S)CH(Me)–NH– | H | A1 | $C_{15}H_{14}N_4O_3S$ | 330.36 | (2S) |

TABLE 2-continued

| # | Structure | | | Formula | MW | Config |
|---|---|---|---|---|---|---|
| 71 | MeOOC-CH(iBu)(S)-NH- | H | A1 | C₁₈H₂₀N₄O₃S | 372.44 | (2S) |
| 72 | MeOOC-CH(iBu)(R)-NH- | H | A1 | C₁₈H₂₀N₄O₃S | 372.44 | (2R) |
| 73 | MeOOC-CH(CH(OH)CH₃)(S)-NH- | H | A1 | C₁₆H₁₆N₄O₄S | 360.39 | (2S) |
| 74 | PhCH₂-NH- | H | A2 | C₁₈H₁₄N₄OS | 334.40 | N/A |
| 75 | 2-indanyl-NH- | H | A2 | C₂₀H₁₆N₄OS | 360.44 | N/A |
| 76 | 3,4-dimethylbenzyl-NH- | H | A2 | C₂₀H₁₈N₄OS | 362.45 | N/A |
| 77 | 2,4-dimethylbenzyl-NH- | H | A2 | C₂₀H₁₈N₄OS | 362.45 | N/A |
| 78 | 2-(CF₃)benzyl-NH- | H | A2 | C₁₉H₁₃F₃N₄OS | 402.40 | N/A |
| 79 | 2-(OCF₃)benzyl-NH- | H | A2 | C₁₉H₁₃F₃N₄O₂S | 418.39 | N/A |
| 80 | 2-hydroxy-1-indanyl-NH- | H | A2 | C₂₀H₁₆N₄O₂S | 376.43 | cis-rac |

TABLE 2-continued

| # | Structure | | | Formula | MW | Stereo |
|---|---|---|---|---|---|---|
| 81 | (trans indanol-NH) | H | A2 | C₂₀H₁₆N₄O₂S | 376.43 | trans-rac |
| 82 | (1R,2R indanol-NH) | H | A2 | C₂₀H₁₆N₄O₂S | 376.43 | (1R,2R) |
| 83 | (1S,2S indanol-NH) | H | A2 | C₂₀H₁₆N₄O₂S | 376.43 | (1S,2S) |
| 84 | (cis methoxy-indane-NH) | H | A2 | C₂₁H₁₈N₄O₂S | 390.46 | cis-rac |
| 85 | (trans methoxy-indane-NH) | H | A2 | C₂₁H₁₈N₄O₂S | 390.46 | trans-rac |
| 86 | (MeOOC-(S)-CH(Bn)-NH) | H | A2 | C₂₁H₁₈N₄O₃S | 406.46 | (2S) |
| 87 | (MeOOC-(R)-CH(Bn)-NH) | H | A2 | C₂₁H₁₈N₄O₂S | 406.46 | (2R) |
| 88 | (F-CH₂-CH(Ph)-NH) | H | A2 | C₁₉H₁₅FN₄OS | 366.41 | rac |

TABLE 2-continued

| # | Structure | | | Formula | MW | Stereo |
|---|---|---|---|---|---|---|
| 89 | H₂N group, •2HCl, phenyl, NH | H | A2 | C₁₉H₁₉Cl₂N₅OS | 436.36 | rac |
| 90 | HN(Me), •2HCl, phenyl, NH | H | A2 | C₂₀H₂₁Cl₂N₅OS | 450.48 | rac |
| 91 | N(Me)₂, phenyl, NH | H | A2 | C₂₁H₂₁N₅OS | 391.49 | rac |
| 92 | HO-CH₂, benzyl, NH | H | A2 | C₂₀H₁₈N₄O₂S | 378.45 | rac |
| 93 | HO-CH₂, (R), benzyl, NH | H | A2 | C₂₀H₁₈N₄O₂S | 378.45 | (1R) |
| 94 | MeO-CH₂, benzyl, NH | H | A2 | C₂₁H₂₀N₄O₂S | 392.48 | rac |
| 95 | HO-CH₂, phenyl, NH | H | A2 | C₁₉H₁₆N₄O₂S | 364.42 | rac |
| 96 | HO-CH₂, (R), phenyl, NH | H | A2 | C₁₉H₁₆N₄O₂S | 364.42 | (1R) |
| 97 | HO-CH₂, (S), phenyl, NH | H | A2 | C₁₉H₁₆N₄O₂S | 364.42 | (1S) |

TABLE 2-continued

| # | Structure | | | Formula | MW | Chirality |
|---|---|---|---|---|---|---|
| 98 | (1-methoxy-1-phenyl-ethyl)NH- | H | A2 | C₂₀H₁₈N₄O₂S | 378.45 | rac |
| 99 | (2-hydroxy-2-phenyl-ethyl)NH- | H | A2 | C₁₉H₁₆N₄O₂S | 364.42 | rac |
| 100 | (2-methoxy-2-phenyl-ethyl)NH- | H | A2 | C₂₀H₁₈N₄O₂S | 378.45 | rac |
| 101 | (2-hydroxy-3-phenyl-propyl)NH- | H | A2 | C₂₀H₁₈N₄O₂S | 378.45 | rac |
| 102 | (2-methoxy-3-phenyl-propyl)NH- | H | A2 | C₂₁H₂₀N₄O₂S | 392.48 | rac |
| 103 | (5-methylpyrazin-2-yl)methyl-NH- | H | A3 | C₁₇H₁₄N₆OS | 350.41 | N/A |
| 104 | (pyridin-2-yl)methyl-NH- | H | A3 | C₁₇H₁₃N₅OS | 335.39 | N/A |
| 105 | (pyridin-3-yl)methyl-NH- | H | A3 | C₁₇H₁₃N₅OS | 335.39 | N/A |
| 106 | (pyridin-4-yl)methyl-NH- | H | A3 | C₁₇H₁₃N₅OS | 335.39 | N/A |
| 107 | (5-methylfuran-2-yl)methyl-NH- | H | A3 | C₁₇H₁₄N₄O₂S | 338.39 | N/A |

TABLE 2-continued
| 108 | 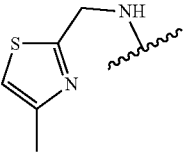 [SMILES: *NCc1nc(C)cs1] | H | A3 | $C_{16}H_{13}N_5OS_2$ | 355.43 | N/A |
| 109 | 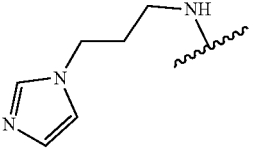 [SMILES: *NCCCn1ccnc1] | H | A3 | $C_{17}H_{16}N_6OS$ | 352.42 | N/A |
| 110 | 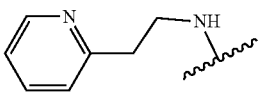 [SMILES: *NCCc1ccccn1] | H | A3 | $C_{18}H_{15}N_5OS$ | 349.41 | N/A |
| 111 | 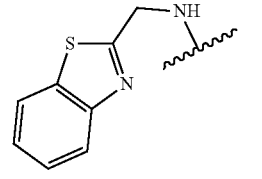 [SMILES: *NCc1nc2ccccc2s1] | H | A3 | $C_{19}H_{13}N_5OS_2$ | 391.47 | N/A |
| 112 | 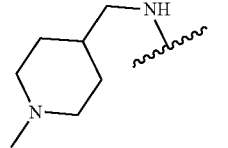 [SMILES: *NCC1CCN(C)CC1] | H | A4 | $C_{18}H_{21}N_5OS$ | 355.46 | N/A |
| 113 | 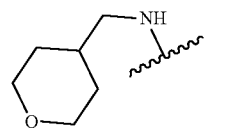 | H | A4 | $C_{17}H_{18}N_4O_2S$ | 342.42 | N/A |
| 114 | 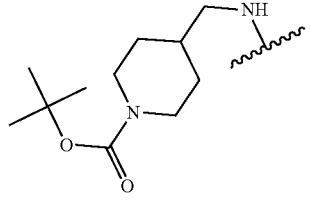 [SMILES: *NCC1CCN(C(=O)OC(C)(C)C)CC1] | H | A4 | $C_{22}H_{27}N_5O_3S$ | 441.55 | N/A |
| 115 | 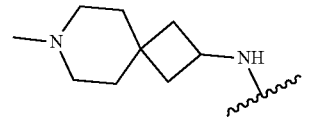 [SMILES: *NC1CC2(CCN(C)CC2)C1] | H | A4 | $C_{20}H_{23}N_5OS$ | 381.50 | N/A |
| 116 | 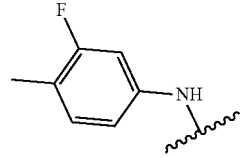 [SMILES: *Nc1ccc(C)c(F)c1] | H | A5 | $C_{18}H_{13}FN_4OS$ | 352.39 | N/A |
| 117 | 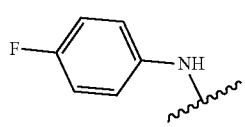 [SMILES: *Nc1ccc(F)cc1] | H | A5 | $C_{17}H_{11}FN_4OS$ | 338.37 | N/A |

TABLE 2-continued
| | | | | | | |
|---|---|---|---|---|---|---|
| 118 | 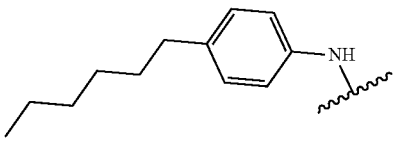 [SMILES: *Nc1ccc(CCCCCC)cc1] | H | A5 | $C_{23}H_{24}N_4OS$ | 404.53 | N/A |
| 119 | 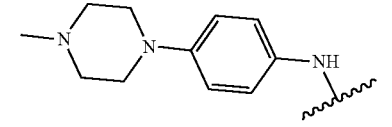 [SMILES: *Nc1ccc(N2CCN(C)CC2)cc1] | H | A5 | $C_{22}H_{22}N_6OS$ | 418.52 | N/A |
| 120 | 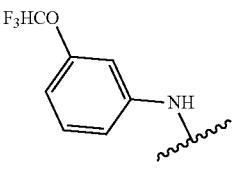 | H | A5 | $C_{18}H_{12}F_2N_4O_2S$ | 386.37 | N/A |
| 121 | 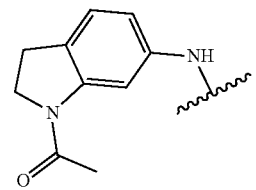 [SMILES: *Nc1ccc2c(c1)N(C(C)=O)CC2] | H | A5 | $C_{21}H_{17}N_5O_2S$ | 403.47 | N/A |
| 122 | 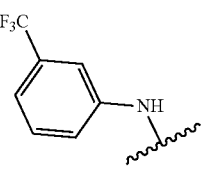 | H | A5 | $C_{18}H_{11}F_3N_4OS$ | 388.37 | N/A |
| 123 | 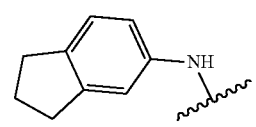 [SMILES: *Nc1ccc2c(c1)CCC2] | H | A5 | $C_{20}H_{16}N_4OS$ | 360.44 | N/A |
| 124 | 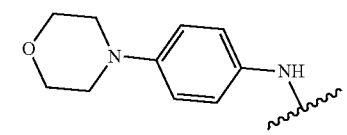 [SMILES: *Nc1ccc(N2CCOCC2)cc1] | H | A5 | $C_{21}H_{19}N_5O_2S$ | 405.48 | N/A |
| 125 | 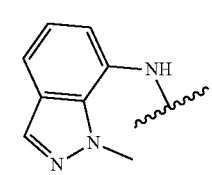 [SMILES: *Nc1cccc2cnn(C)c12] | H | A5 | $C_{19}H_{14}N_6OS$ | 374.42 | N/A |
| 126 | 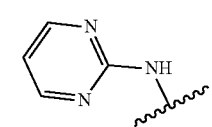 [SMILES: *Nc1ncccn1] | H | A6 | $C_{15}H_{10}N_6OS$ | 322.35 | N/A |
| 127 | 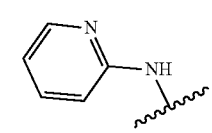 [SMILES: *Nc1ccccn1] | H | A6 | $C_{16}H_{11}N_5OS$ | 321.36 | N/A |

TABLE 2-continued

| # | Structure | R | Method | Formula | MW | Data |
|---|---|---|---|---|---|---|
| 128 | 1-methylpyrazol-3-yl-NH- | H | A6 | C₁₅H₁₂N₆OS | 324.37 | N/A |
| 129 | 2-methoxy-6-methylpyridin-3-yl-NH- | H | A6 | C₁₈H₁₅N₅O₂S | 365.41 | N/A |
| 130 | pyrazin-2-yl-NH- | H | A6 | C₁₅H₁₀N₆OS | 322.35 | N/A |
| 131 | pyridin-3-yl-NH- | H | A6 | C₁₆H₁₁N₅OS | 321.36 | N/A |
| 132 | 1,3,4-thiadiazol-2-yl-NH- | H | A6 | C₁₃H₈N₆OS₂ | 328.37 | N/A |
| 133 | 6-(4-methylpiperazin-1-yl)pyridin-3-yl-NH- | H | A6 | C₂₁H₂₁N₇OS | 419.51 | N/A |
| 134 | 6-(4-methylpiperazin-1-yl)pyridin-3-yl-NH- | H | A6 | C₂₁H₂₁N₇OS | 419.51 | N/A |
| 135 | 2-(4-methylpiperazin-1-yl)pyrimidin-5-yl-NH- | H | A6 | C₂₀H₂₀N₈OS | 420.50 | N/A |
| 136 | 5-(4-methylpiperazin-1-yl)pyrimidin-2-yl-NH- | H | A6 | C₂₀H₂₀N₈OS | 420.50 | N/A |
| 137 | 5-(4-methylpiperazin-1-yl)pyrazin-2-yl-NH- | H | A6 | C₂₀H₂₀N₈OS | 420.50 | N/A |
| 138 | 6-(4-methylpiperazin-1-yl)pyridazin-3-yl-NH- | H | A6 | C₂₀H₂₀N₈OS | 420.50 | N/A |

TABLE 2-continued

| # | Structure | | | Formula | MW | Stereo |
|---|---|---|---|---|---|---|
| 139 | [tetrahydropyran-4-yl-NH] | H | A7 | C₁₆H₁₆N₄O₂S | 328.39 | N/A |
| 140 | [Boc-piperidin-4-yl-NH] | H | A7 | C₂₁H₂₅N₅O₃S | 427.52 | N/A |
| 141 | [propoxycarbonyl-piperidin-4-yl-NH] | H | A7 | C₁₉H₂₁N₅O₃S | 399.47 | N/A |
| 142 | [1-methylpiperidin-4-yl-NH] | H | A7 | C₁₇H₁₉N₅OS | 341.43 | N/A |
| 143 | [1-methylpiperidin-3-yl-NH] | H | A7 | C₁₇H₁₉N₅OS | 341.43 | rac |
| 144 | [oxetan-3-yl-NH] | H | A7 | C₁₄H₁₂N₄O₂S | 300.34 | N/A |
| 145 | [(R)-tetrahydrofuran-3-yl-NH] | H | A7 | C₁₅H₁₄N₄O₂S | 314.36 | (3R) |
| 146 | [(S)-tetrahydrofuran-3-yl-NH] | H | A7 | C₁₅H₁₄N₄O₂S | 314.36 | (3S) |
| 147 | [(R)-tetrahydropyran-3-yl-NH] | H | A7 | C₁₆H₁₆N₄O₂S | 328.39 | (3R) |
| 148 | [(S)-tetrahydropyran-3-yl-NH] | H | A7 | C₁₆H₁₆N₄O₂S | 328.39 | (3S) |
| 149 | [2,2-dimethyltetrahydropyran-4-yl-NH] | H | A7 | C₁₈H₂₀N₄O₂S | 356.44 | rac |
| 149A | [2,2-dimethyltetrahydropyran-4-yl-NH, (R or S)] | H | A7 | C₁₈H₂₀N₄O₂S | 356.44 | Enantiomer A (3R) or (3S) |

TABLE 2-continued

| | | | | | | |
|---|---|---|---|---|---|---|
| 149B | [2,2-dimethyltetrahydropyran-3-yl-NH, (R or S)] | H | A7 | C₁₈H₂₀N₄O₂S | 356.44 | Enantiomer B (3R) or (3S) |
| 150 | [(3R,4R)-4-hydroxytetrahydropyran-3-yl-NH] | H | A7 | C₁₆H₁₆N₄O₃S | 344.39 | (3R,4R) |
| 151 | [oxepan-3-yl-NH] | H | A7 | C₁₇H₁₈N₄O₂S | 342.42 | rac |
| 152 | [2-oxopiperidin-3-yl-NH] | H | A7 | C₁₆H₁₅N₅O₂S | 341.39 | rac |
| 153 | [(3S)-2-oxopiperidin-3-yl-NH] | H | A7 | C₁₆H₁₅N₅O₂S | 341.39 | (3S) |
| 154 | [(5S)-2-oxopiperidin-5-yl-NH] | H | A7 | C₁₆H₁₅N₅O₂S | 341.39 | (5S) |
| 155 | [3,3-difluorocyclopentyl-NH] | H | A1 | C₁₆H₁₄F₂N₄OS | 348.37 | rac |
| 156 | [4,4-difluorocyclohexyl-NH] | H | A1 | C₁₇H₁₆F₂N₄OS | 362.40 | N/A |
| 157 | [3,3-difluorocyclohexyl-NH] | H | A1 | C₁₇H₁₆F₂N₄OS | 362.40 | rac |
| 158 | [2,2-difluorocyclohexyl-NH] | H | A1 | C₁₇H₁₆F₂N₄OS | 362.40 | rac |

TABLE 2-continued

| | | | | | | |
|---|---|---|---|---|---|---|
| 159 | [3,3-difluorocycloheptyl-NH-] | H | A1 | C₁₈H₁₈F₂N₄OS | 376.43 | rac |
| 160 | [(R)-1-(fluoromethyl)-3-methylbutyl-NH-] | H | A1 | C₁₇H₁₉FN₄OS | 346.42 | (1R) |
| 161 | [(S)-1-(fluoromethyl)-3-methylbutyl-NH-] | H | A1 | C₁₇H₁₉FN₄OS | 346.42 | (1S) |
| 162 | [3-AcO-adamantyl-NH-] | H | A1 | C₂₃H₂₄N₄O₃S | 436.53 | N/A |
| 163 | [3-PivO-adamantyl-NH-] | H | A1 | C₂₆H₃₀N₄O₃S | 478.61 | N/A |
| 164 | [(1R,2R)-2-methoxycyclopentyl-NH-] | H | A1 | C₁₇H₁₈N₄O₂S | 342.42 | (1R,2R) |
| 165 | [(1S,2S)-2-methoxycyclopentyl-NH-] | H | A1 | C₁₇H₁₈N₄O₂S | 342.42 | (1S,2S) |
| 166 | [(1R,2R)-2-methoxycyclohexyl-NH-] | H | A1 | C₁₈H₂₀N₄O₂S | 356.44 | (1R,2R) |
| 167 | [(1S,2S)-2-methoxycyclohexyl-NH-] | H | A1 | C₁₈H₂₀N₄O₂S | 356.44 | (1S,2S) |

TABLE 2-continued

| # | Structure | | | Formula | MW | Stereo |
|---|---|---|---|---|---|---|
| 168 | MeO-cyclohexyl-NH- (cis) | H | A1 | $C_{18}H_{20}N_4O_2S$ | 356.44 | cis-rac |
| 169 | MeO-cyclohexyl-NH- (trans) | H | A1 | $C_{18}H_{20}N_4O_2S$ | 356.44 | trans-rac |
| 169A | MeO-cyclohexyl-NH- (R,R) or (S,S) | H | A1 | $C_{18}H_{20}N_4O_2S$ | 356.44 | Enantiomer A (1R,3R) or (1S,3S) |
| 169B | MeO-cyclohexyl-NH- (R,R) or (S,S) | H | A1 | $C_{18}H_{20}N_4O_2S$ | 356.44 | Enantiomer B (1R,3R) or (1S,3S) |
| 170 | HO-cycloheptyl-NH- (cis) | H | A1 | $C_{18}H_{20}N_4O_2S$ | 356.44 | cis-rac |
| 171 | HO-cycloheptyl-NH- (trans) | H | A1 | $C_{18}H_{20}N_4O_2S$ | 356.44 | trans-rac |
| 171A | HO-cycloheptyl-NH- (R,R) or (S,S) | H | A1 | $C_{18}H_{20}N_4O_2S$ | 356.44 | Enantiomer A (1R,4R) or (1S,4S) |
| 171B | HO-cycloheptyl-NH- (R,R) or (S,S) | H | A1 | $C_{18}H_{20}N_4O_2S$ | 356.44 | Enantiomer B (1R,4R) or (1S,4S) |
| 172 | MeO-cycloheptyl-NH- | H | A1 | $C_{19}H_{22}N_4O_2S$ | 370.47 | cis-rac |

TABLE 2-continued

| # | Structure | | | Formula | MW | Config |
|---|---|---|---|---|---|---|
| 173 | MeO-cycloheptyl-NH (trans) | H | A1 | $C_{19}H_{22}N_4O_2S$ | 370.47 | trans-rac |
| 174 | MeO-cycloheptyl-NH (cis) | H | A1 | $C_{19}H_{22}N_4O_2S$ | 370.47 | cis-rac |
| 175 | MeO-cycloheptyl-NH (trans) | H | A1 | $C_{19}H_{22}N_4O_2S$ | 370.47 | trans-rac |
| 176 | MeO-CH2-CH(R)(Ph)-NH | H | A2 | $C_{20}H_{18}N_4O_2S$ | 378.45 | (1R) |
| 177 | MeO-CH2-CH(S)(Ph)-NH | H | A2 | $C_{20}H_{18}N_4O_2S$ | 378.45 | (1S) |
| 178 | Ph-CH(OH)-CH2(R)-NH | H | A2 | $C_{19}H_{16}N_4O_2S$ | 364.42 | (2R) |
| 179 | Ph-CH(OH)-CH2(S)-NH | H | A2 | $C_{19}H_{16}N_4O_2S$ | 364.42 | (2S) |
| 180 | H2N-CH2-CH(R)(Ph)-NH ·2HCl | H | A2 | $C_{19}H_{19}Cl_2N_5OS$ | 436.36 | (1R) |
| 181 | H2N-CH2-CH(S)(Ph)-NH ·2HCl | H | A2 | $C_{19}H_{19}Cl_2N_5OS$ | 436.36 | (1S) |

TABLE 2-continued

| | | | | | | |
|---|---|---|---|---|---|---|
| 182 | (quinuclidin-3-yl, R)-NH- | H | A7 | $C_{18}H_{19}N_5OS$ | 353.44 | (3R) |
| 183 | (quinuclidin-3-yl, S)-NH- | H | A7 | $C_{18}H_{19}N_5OS$ | 353.44 | (3S) |
| 184 | (tetrahydrothiopyran-3-yl)-NH- | H | A7 | $C_{16}H_{16}N_4OS_2$ | 344.45 | rac |
| 185 | (1,4-dioxepan-6-yl)-NH- | H | A7 | $C_{16}H_{16}N_4O_3S$ | 344.39 | N/A |
| 186 | (2-oxopyrrolidin-3-yl)-NH- | H | A7 | $C_{15}H_{13}N_5O_2S$ | 327.36 | rac |
| 187 | (1-methyl-2-oxopyrrolidin-3-yl)-NH- | H | A7 | $C_{16}H_{15}N_5O_2S$ | 341.39 | rac |
| 188 | (4,4-dimethyl-2-oxopyrrolidin-3-yl)-NH- | H | A7 | $C_{17}H_{17}N_5O_2S$ | 355.42 | rac |
| 189 | (2-oxopiperidin-3-yl, R)-NH- | H | A7 | $C_{16}H_{15}N_5O_2S$ | 341.39 | (3R) |
| 190 | (1-methyl-2-oxopiperidin-3-yl)-NH- | H | A7 | $C_{17}H_{17}N_5O_2S$ | 355.42 | rac |
| 191 | (3-methyl-2-oxopyrrolidin-3-yl)-NH- | H | A7 | $C_{16}H_{15}N_5O_2S$ | 341.39 | rac |

TABLE 2-continued

| # | Structure | R | Method | Formula | MW | Stereo |
|---|---|---|---|---|---|---|
| 192 | (1-methyl-3-methyl-2-oxopyrrolidin-3-yl)NH- | H | A7 | C₁₇H₁₇N₅O₂S | 355.42 | rac |
| 192A | (1-methyl-3-methyl-2-oxopyrrolidin-3-yl)NH- (R or S) | H | A7 | C₁₇H₁₇N₅O₂S | 355.42 | Enantiomer A (3R) or (3S) |
| 192B | (1-methyl-3-methyl-2-oxopyrrolidin-3-yl)NH- (R or S) | H | A7 | C₁₇H₁₇N₅O₂S | 355.42 | Enantiomer B (3R) or (3S) |
| 193 | (3S,4S)-4-hydroxytetrahydro-2H-pyran-3-yl-NH- | H | A7 | C₁₆H₁₆N₄O₃S | 344.39 | (3S,4S) |
| 194 | adamantan-1-yl-NH- | H | A1 | C₂₀H₂₀N₄OS | 364.47 | N/A |
| 195 | 3-((tert-butylcarbamoyl)oxy)adamantan-1-yl-NH- | H | A1 | C₂₆H₃₁N₅O₃S | 493.63 | N/A |
| 196 | 3-fluoroadamantan-1-yl-NH- | H | A1 | C₂₁H₂₁FN₄OS | 396.48 | N/A |
| 197 | (R)-1-(tert-butoxy)-4-methylpentan-2-yl-NH- | H | A1 | C₂₁H₂₈N₄O₂S | 400.54 | (1R) |

TABLE 2-continued
| | | | | | | |
|---|---|---|---|---|---|---|
| 198 | 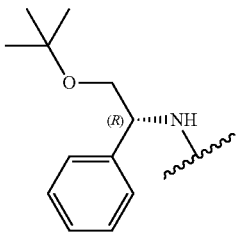 | H | A2 | $C_{23}H_{24}N_4O_2S$ | 420.53 | (1R) |
| 199 | 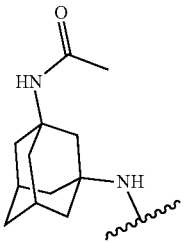 [SMILES: *NC12CC3CC(C1)CC(NC(C)=O)(C3)C2] | H | A1 | $C_{23}H_{25}N_5O_2S$ | 435.55 | N/A |
| 200 | 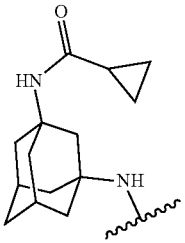 [SMILES: *NC12CC3CC(C1)CC(NC(=O)C1CC1)(C3)C2] | H | A1 | $C_{25}H_{27}N_5O_2S$ | 461.58 | N/A |
| 201 | 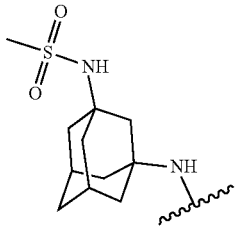 [SMILES: *NC12CC3CC(C1)CC(NS(C)(=O)=O)(C3)C2] | H | A1 | $C_{22}H_{25}N_5O_3S_2$ | 471.59 | N/A |
| 202 | 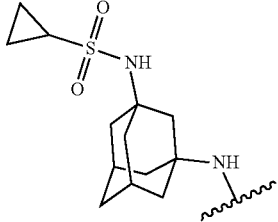 [SMILES: *NC12CC3CC(C1)CC(NS(=O)(=O)C1CC1)(C3)C2] | H | A1 | $C_{24}H_{27}N_5O_3S_2$ | 497.63 | N/A |
| 203 | 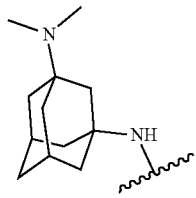 [SMILES: *NC12CC3CC(C1)CC(N(C)C)(C3)C2] | H | A1 | $C_{23}H_{27}N_5OS$ | 421.56 | N/A |
| 204 | 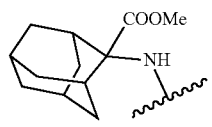 [SMILES: *NC1(C(=O)OC)C2CC3CC(C2)CC1C3] | H | A1 | $C_{23}H_{24}N_4O_3S$ | 436.53 | N/A |

TABLE 2-continued
| | | | | | | |
|---|---|---|---|---|---|---|
| 205 | 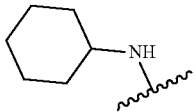 [SMILES: *NC1CCCCC1] | Me | A1 | $C_{18}H_{20}N_4OS$ | 340.45 | N/A |
| 206 | 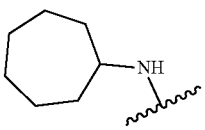 [SMILES: *NC1CCCCCC1] | Me | A1 | $C_{19}H_{22}N_4OS$ | 354.47 | N/A |
| 207 | 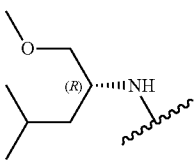 | Me | A1 | $C_{19}H_{24}N_4O_2S$ | 372.49 | (1R) |
| 208 | 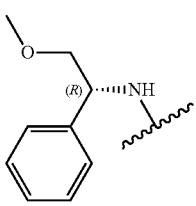 | Me | A2 | $C_{21}H_{20}N_4O_2S$ | 392.48 | (1R) |
| 209 | 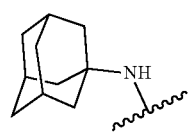 [SMILES: *NC12CC3CC(CC(C3)C1)C2] | Me | A1 | $C_{22}H_{24}N_4OS$ | 392.52 | N/A |
| 210 | 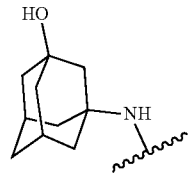 [SMILES: *NC12CC3CC(CC(O)(C3)C1)C2] | Me | A1 | $C_{22}H_{24}N_4O_2S$ | 408.52 | N/A |
| 211 | 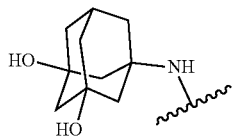 | H | A1 | $C_{21}H_{22}N_4O_3S$ | 410.49 | N/A |
| 212 | 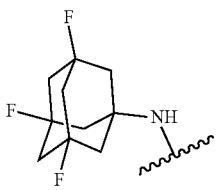 [SMILES: *NC12CC3(F)CC(F)(CC(F)(C3)C1)C2] | H | A1 | $C_{21}H_{19}F_3N_4OS$ | 432.47 | N/A |
| 213 | 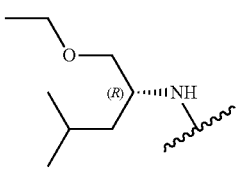 | H | A1 | $C_{19}H_{24}N_4OS$ | 372.49 | (1R) |

TABLE 2-continued

| # | Structure | | | Formula | MW | Config |
|---|---|---|---|---|---|---|
| 214 | (benzyl-O-CH2-CH(R)(NH)-CH2-CH(CH3)2) | H | A1 | $C_{24}H_{26}N_4O_2S$ | 434.56 | (1R) |
| 215 | (4-F-benzyl-O-CH2-CH(R)(NH)-CH2-CH(CH3)2) | H | A1 | $C_{24}H_{25}FN_4O_2S$ | 452.55 | (1R) |
| 216 | (cyclopropyl-O-CH2-CH(R)(NH)-CH2-CH(CH3)2) | H | A1 | $C_{20}H_{24}N_4O_2S$ | 384.50 | (1R) |

The below Table 3 describes the analytical and spectroscopic data of the compounds introduced in Table 2.

$^1$H NMR analyses (400 or 500 MHz) and $^{13}$C NMR spectra (101 MHz) were recorded with a Bruker ULTRASHIELD 500 or 400 spectrometer. Processing and analyses of the spectra were performed with MestReNova. Data appear in the following order: chemical shifts in ppm which were referenced to the internal solvent signal, multiplicity, number of protons, and coupling constant Jin Hertz.

Reversed-phase HPLC/MS analyses were carried out with a Waters Alliance 2795 HPLC equipped with an autosampler, an inline membrane degasser, a column oven (T=45° C.), a UV detector, and a ZQ quadrupole mass detector working in ionization electrospray mode. Compounds (0.1 to 0.3 mg) were solubilized in a minimum amount of DMSO completed with acetonitrile ($V_{total}$=1 mL). Standard analytical parameters: flow rate: 1 mL/min, $V_{inj.}$=5 µL.

Acidic conditions: Waters XSelect CSH C18 column (3.5 µm, 2.1×50 mm). Gradient: ($H_2O$+0.04% v/v HCOOH (10 mM))/ACN from 95/5 to 0/100 in 18.5 min.

Alkaline conditions: Waters Xbridge C18 column (3.5 µm, 2.1×50 mm). Gradient: ($H_2O$+0.06% v/v $NH_{3(aq)}$ (10 mM))/ACN from 95/5 to 0/100 in 18.5 min.

Enantiomers of racemic products (149), (169), (171) and (192) were separated by Reach Separations (Bio City, Pennyfoot St., Nottingham, NG1 1GF, UK. www.reachseparations.com) by preparative chiral SFC. Briefly: racemic products were solubilized in MeOH and purified by preparative SFC (conditions in Table 3). Combined fractions containing the first eluting enantiomer were then evaporated to near dryness using a rotary evaporator, transferred into final vessels with DCM which was removed on a Biotage V10 at 35° C. before being stored in a vacuum oven at 35° C. and 5 mbar until constant weight to afford the pure enantiomer. Fractions containing the second eluting enantiomer were combined, concentrated and repurified as described above. The optical purity of each enantiomer was controlled with respect to the racemate by analytical chiral SFC (conditions in Table 3). Chemical purity of each enantiomer was controlled by analytical UHPLC on an Acquity BEH C18 (1.7 µm, 50×2.1 mm) (60° C., 1 mL/min, inj. vol.=1 µL), gradient: ($H_2O$+0.1% v/v TFA)/ACN from 98/2 to 0/100 in 2.02 min.

TABLE 3

Spectroscopic and analytical characterization of compounds (1) to (216)

| Cpd N° | Structure | Formula | MW | HPLC | Description |
|---|---|---|---|---|---|
| 1 | 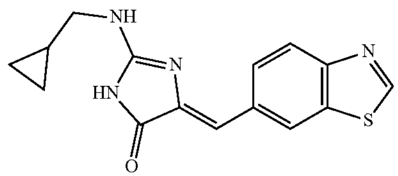 [SMILES: O=C1NC(NCC2CC2)=N/C1=C\c1ccc2ncsc2c1] | $C_{15}H_{14}N_4OS$ | 298.36 | >98% | Yellow solid. $^1$H NMR (400 MHz, DMSO-$d_6$, 300K) of major tautomer $\delta_H$ 10.66 (br s, 1H, NH, D$_2$O exchanged), 9.35 (s, 1H), 8.80 (s, 1H), 8.39-8.13 (m, 1H), 8.03 (d, J = 8.6 Hz, 1H), 7.56 (br s, 1H, NH, D$_2$O exchanged), 6.40 (s, 1H), 3.32-3.10 (m, 2H), 1.18-1.02 (m, 1H), 0.57-0.41 (m, 2H), 0.38-0.23 (m, 2H). MS (ESI$^+$): [M + H]$^+$ 299.2. |
| 2 | 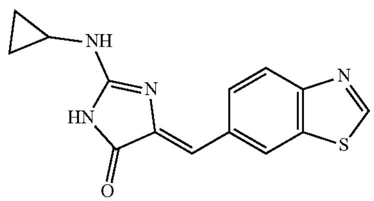 [SMILES: O=C1NC(NC2CC2)=N/C1=C\c1ccc2ncsc2c1] | $C_{14}H_{12}N_4OS$ | 284.34 | >98% | Yellow solid. $^1$H NMR (400 MHz, DMSO-$d_6$, 300K) of major tautomer $\delta_H$ 11.13 (br s, 1H, NH, D$_2$O exchanged), 9.35 (s, 1H), 8.83 (s, 1H), 8.26 (d, J = 8.6 Hz, 1H), 8.13 (br s, 1H, NH, D$_2$O exchanged), 8.03 (d, J = 8.6 Hz, 1H), 6.43 (s, 1H), 3.04-2.62 (m, 1H), 0.83-0.69 (m, 2H), 0.68-0.54 (m, 2H). MS (ESI$^+$): [M + H]$^+$ 285.1. |
| 3 | 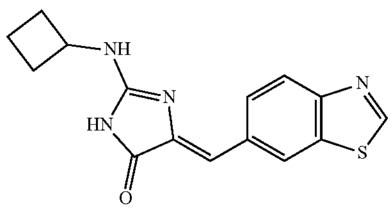 [SMILES: O=C1NC(NC2CCC2)=N/C1=C\c1ccc2ncsc2c1] | $C_{15}H_{14}N_4OS$ | 298.36 | >98% | Yellow solid. $^1$H NMR (400 MHz, DMSO-$d_6$, 300K) of major tautomer $\delta_H$ 10.72 (br s, 1H, NH, D$_2$O exchanged), 9.36 (s, 1H), 8.79 (s, 1H), 8.34-8.22 (m, 1H), 8.04 (d, J = 8.6 Hz, 1H), 7.83 (br s, 1H, NH, D$_2$O exchanged), 6.40 (s, 1H), 4.74-4.02 (m, 1H), 2.38-2.20 (m, 2H), 2.17-1.97 (m, 2H), 1.69 (s, 2H). MS (ESI$^+$): [M + H]$^+$ 299.2. |
| 4 | 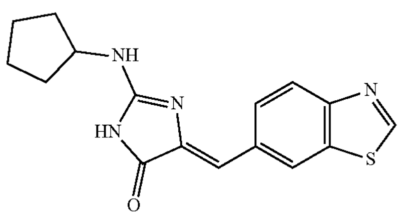 [SMILES: O=C1NC(NC2CCCC2)=N/C1=C\c1ccc2ncsc2c1] | $C_{16}H_{16}N_4OS$ | 312.39 | >98% | Yellow solid. $^1$H NMR (400 MHz, DMSO-$d_6$, 300K) of major tautomer $\delta_H$ 10.53 (br s, 1H, NH, D$_2$O exchanged), 9.36 (s, 1H), 8.76 (s, 1H), 8.22 (s, 1H), 8.04 (d, J = 8.0 Hz, 1H), 7.84 (br s, 1H, NH, D$_2$O exchanged), 6.41 (s, 1H), 4.43-4.05 (m, 1H), 2.04-1.92 (m, 2H), 1.76-1.67 (m, 2H), 1.56 (m, 2H), 1.40 (m, 2H). MS (ESI$^+$): [M + H]$^+$ 313.2. |

TABLE 3-continued

| | | | | |
|---|---|---|---|---|
| 5 | 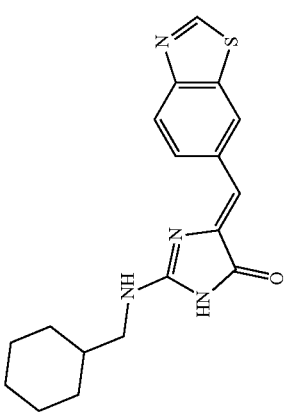 | $C_{18}H_{20}N_4OS$ | 340.45 | 97% | Yellow solid. $^1$H NMR (400 MHz, DMSO-d$_6$, 300K) of major tautomer δ$_H$ 10.57 (br s, 1H, NH, D$_2$O exchanged), 9.35 (s, 1H), 8.85 (s, 1H), 8.23 (d, J = 8.5 Hz, 1H), 8.03 (d, J = 8.5 Hz, 1H), 7.50 (br s, 1H, NH, D$_2$O exchanged), 6.38 (s, 1H), 3.28-3.00 (m, 2H), 1.83-1.49 (m, 6H), 1.35-1.09 (m, 3H), 1.08-0.82 (m, 2H). MS (ESI$^+$): [M + H]$^+$ 341.2. |
| 6 | 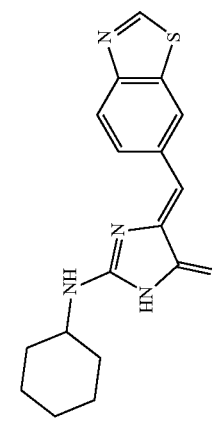 | $C_{17}H_{18}N_4OS$ | 326.42 | >98% | Yellow solid. $^1$H NMR (400 MHz, DMSO-d$_6$, 300K) of major tautomer δ$_H$ 10.62 (br s, 1H, NH, D$_2$O exchanged), 9.35 (s, 1H), 8.90-8.65 (m, 1H), 8.37-8.13 (m, 1H), 8.03 (d, J = 8.4 Hz, 1H), 7.49 (br s, 1H, NH, D$_2$O exchanged), 6.39 (s, 1H), 3.97-3.46 (m, 1H), 2.07-1.80 (m, 2H), 1.80-1.65 (m, 2H), 1.65-1.53 (m, 1H), 1.49-1.05 (m, 5H). MS (ESI$^+$): [M + H]$^+$ 327.2. |
| 7 | 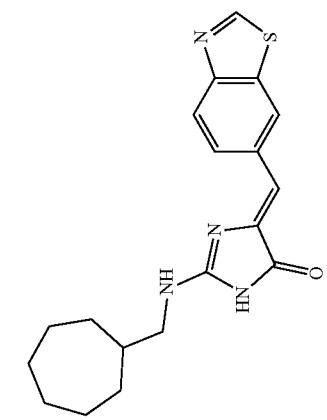 | $C_{19}H_{22}N_4OS$ | 354.47 | >98% | Yellow solid. $^1$H NMR (400 MHz, DMSO-d$_6$, 300K) of major tautomer δ$_H$ 10.61 (br s, 1H, NH, D$_2$O exchanged), 9.35 (s, 1H), 8.88 (s, 1H), 8.22 (d, J = 8.6 Hz, 1H), 8.03 (d, J = 8.5 Hz, 1H), 7.53 (br s, 1H, NH, D$_2$O exchanged), 6.39 (s, 1H), 3.29-3.02 (m, 2H), 1.95-1.36 (m, 11H), 1.33-1.12 (m, 2H). MS (ESI$^+$): [M + H]$^+$ 355.2. |
| 8 | 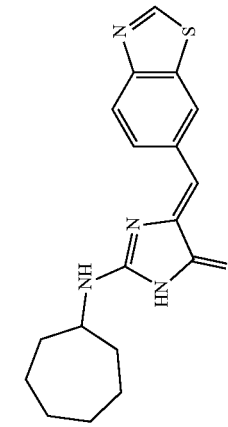 | $C_{18}H_{20}N_4OS$ | 340.45 | >98% | Yellow solid. $^1$H NMR (400 MHz, DMSO-d$_6$, 300K) of major tautomer δ$_H$ 10.40 (br s, 1H, NH, D$_2$O exchanged), 9.35 (s, 1H), 9.05-8.69 (m, 1H), 8.42-8.13 (m, 1H), 8.03 (d, J = 8.5 Hz, 1H), 7.54 (br s, 1H, NH, D$_2$O exchanged), 6.39 (s, 1H), 3.98 (s, 1H), 1.93 (s, 2H), 1.78-1.35 (m, 10H). MS (ESI$^+$): [M + H]$^+$ 342.2. |

TABLE 3-continued

| # | Structure | Formula | Purity | Description |
|---|---|---|---|---|
| 9 | (cyclooctyl-NH-imidazolone-benzothiazole structure) | C₁₉H₂₂N₄OS | >98% | Yellow solid. ¹H NMR (400 MHz, DMSO-d₆, 300K) of major tautomer δ_H 10.43 (br s, 1H, NH, D₂O exchanged), 9.35 (s, 1H), 8.98 (m, 1H), 8.18 (d, J = 8.6 Hz, 1H), 8.02 (d, J = 8.5 Hz, 1H), 7.56 (br s, 1H, NH, D₂O exchanged), 6.40 (s, 1H), 4.25-3.91 (m, 1H), 1.94-1.35 (m, 14H). MS (ESI⁺): [M + H]⁺ 355.2. |
| 10 | (HO-CH₂-C(CH₃)₂-CH₂-NH-imidazolone-benzothiazole structure) | C₁₆H₁₈N₄O₂S | >98% | Yellow solid. ¹H NMR (400 MHz, DMSO-d₆, 300K) of major tautomer δ_H 10.59 (br s, 1H, NH, D₂O exchanged), 9.37 (s, 1H), 8.82-8.62 (m, 1H), 8.22 (d, J = 8.6 Hz, 1H), 8.04 (d, J = 8.6 Hz, 1H), 7.45 (br s, 1H, NH, D₂O exchanged), 6.43 (br s, 1H, OH, D₂O exchanged), 5.02 (s, 1H), 3.33-3.24 (m, 2H), 3.22-3.11 (m, 2H), 1.09-0.65 (m, 6H). MS (ESI⁺): [M + H]⁺ 331.2. |
| 11 | (PhCH₂O-CH₂CH₂-NH-imidazolone-benzothiazole structure) | C₂₀H₁₈N₄O₂S | >98% | Yellow solid. ¹H NMR (500 MHz, DMSO-d₆, 300K) of major tautomer δ_H 10.62 (br s, 1H, NH, D₂O exchanged), 9.35 (s, 1H), 8.82 (s, 1H), 8.39-8.25 (m, 1H), 8.03 (d, J = 8.5 Hz, 1H), 7.27-7.42 (m, 1H), 7.40-7.20 (m, 5H), 6.42 (s, 1H), 4.61-4.50 (m, 2H), 3.88-3.47 (m, 4H). MS (ESI⁺): [M + H]⁺ 379.2. |
| 12 | (trans-(±) 2-methylcyclohexyl-NH-imidazolone-benzothiazole structure) trans-(±) | C₁₈H₂₀N₄OS | >98% | Yellow solid. ¹H NMR (400 MHz, DMSO-d₆, 300K) of major tautomer δ_H 10.49 (br s, 1H, NH, D₂O exchanged), 9.34 (s, 1H), 8.92-8.69 (m, 1H), 8.27-8.15 (m, 1H), 8.02 (d, J = 8.6 Hz, 1H), 7.42 (br s, 1H, NH, D₂O exchanged), 6.36 (s, 1H), 3.65-3.34 (m, 1H), 3.23-2.84 (m, 1H), 2.01-1.13 (m, 8H), 0.98-0.84 (m, 3H). MS (ESI⁺): [M + H]⁺ 341.2. |

TABLE 3-continued

| | | | | |
|---|---|---|---|---|
| 13 | 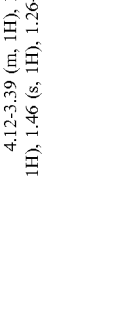 | C₁₉H₂₂N₄OS | 354.47 | >97% | Yellow solid. ¹H NMR (400 MHz, DMSO-d₆, 300K) of major tautomer δ_H 10.34 (br s, 1H, NH, D₂O exchanged), 9.34 (d, J = 1.4 Hz, 1H), 8.92-8.73 (m, 1H, NH, D₂O exchanged), 8.03 (d, J = 8.5 Hz, 1H), 7.37 (br s, 1H, NH, D₂O exchanged), 6.37 (s, 1H), 4.12-3.39 (m, 1H), 1.72 (d, J = 13.8 Hz, 4H), 1.65-1.57 (m, 1H), 1.46 (s, 1H), 1.26-0.96 (m, 8H). MS (ESI⁺): [M + H]⁺ 355.2. |
| 14 | 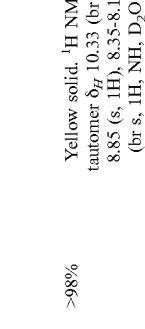 | C₂₂H₂₄N₄OS | 392.17 | >98% | Yellow solid. ¹H NMR (400 MHz, DMSO-d₆, 300K) of major tautomer δ_H 10.33 (br s, 1H, NH, D₂O exchanged), 9.35 (s, 1H), 8.85 (s, 1H), 8.35-8.14 (m, 1H), 8.03 (d, J = 8.5 Hz, 1H), 7.41 (br s, 1H, NH, D₂O exchanged), 6.38 (s, 1H), 3.25-2.80 (m, 2H), 1.96 (s, 3H), 1.72-1.43 (m, 12H). MS (ESI⁺): [M + H]⁺ 393.3. |
| 15 | 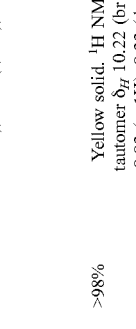 | C₂₃H₂₆N₄OS | 406.55 | >98% | Yellow solid. ¹H NMR (400 MHz, DMSO-d₆, 343K) of major tautomer δ_H 10.22 (br s, 1H, NH, D₂O exchanged), 9.30 (s, 1H), 8.82 (s, 1H), 8.22 (d, J = 8.8 Hz, 1H), 8.02 (d, J = 8.6 Hz, 1H), 7.14 (br s, 1H, NH, D₂O exchanged), 6.39 (s, 1H), 3.76-3.59 (m, 1H), 1.99 (s, 3H), 1.77-1.49 (m, 12H), 1.17-1.05 (m, 3H). MS (ESI⁺): [M + H]⁺ 407.3. |
| 16 | 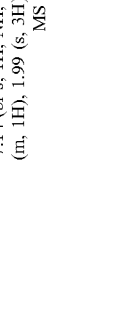 | C₂₁H₂₂N₄OS | 378.49 | 95% | Yellow solid. ¹H NMR (400 MHz, DMSO-d₆, 300K) of major tautomer δ_H 9.99 (br s, 1H, NH, D₂O exchanged), 9.35 (s, 1H), 9.02 (s, 1H), 8.17-8.13 (m, 1H), 8.03 (d, J = 8.5 Hz, 1H), 7.09 (br s, 1H, D₂O exchanged), 6.42 (s, 1H), 2.26-2.02 (m, 10H), 1.80-1.64 (m, 5H). MS (ESI⁺): [M + H]⁺ 379.2. |

TABLE 3-continued

| # | Structure | Formula | MW | Yield | Notes |
|---|---|---|---|---|---|
| 17 | (2-adamantyl-NH imidazolinone benzothiazole) | C₂₁H₂₂N₄OS | 378.49 | 93% | Yellow solid. ¹H NMR (400 MHz, DMSO-d₆, 343K) of major tautomer δ_H 10.06 (br s, 1H, D₂O exchanged), 9.31 (s, 1H), 8.87 (s, 1H), 8.20 (d, J = 8.7 Hz, 1H), 8.01 (d, J = 8.5 Hz, 1H), 7.35 (br s, 1H, D₂O exchanged), 6.44 (s, 1H), 4.15-3.95 (m, 1H), 2.13-1.56 (m, 14H). MS (ESI⁺): [M + H]⁺ 379.2. |
| 18 | (3,5-dimethyl-1-adamantyl-NH imidazolinone benzothiazole) | C₂₃H₂₆N₄OS | 406.55 | 97% | Yellow solid. ¹H NMR (400 MHz, DMSO-d₆, 300K) of major tautomer δ_H 10.04 (br s, 1H, NH, D₂O exchanged), 9.35 (s, 1H), 9.17 (s, 1H), 8.02 (s, 2H), 7.16 (br s, 1H, NH, D₂O exchanged), 6.41 (s, 1H), 2.23-2.13 (m, 1H), 2.02-1.70 (m, 6H), 1.49-1.28 (m, 4H), 1.25-1.14 (m, 2H), 0.98-0.85 (m, 6H). MS (ESI⁺): [M + H]⁺ 407.2. |
| 19 | (hydroxy-2-adamantyl-NH imidazolinone benzothiazole) | C₂₁H₂₂N₄O₂S | 394.49 | >98% | Yellow solid. ¹H NMR (400 MHz, DMSO-d₆, 300K) of major tautomer δ_H 9.93 (br s, 1H, NH, D₂O exchanged), 9.36 (s, 1H), 8.98-8.76 (m, 1H), 8.37-8.11 (m, 1H), 8.11-7.97 (m, 1H), 7.48 (br s, 1H, NH, D₂O exchanged), 6.42 (s, 1H), 4.57-4.36 (br s, 1H, OH, D₂O exchanged), 4.20-3.78 (m, 1H), 2.25-2.00 (m, 3H), 1.97-1.74 (m, 4H), 1.72-1.60 (m, 4H), 1.49-1.32 (m, 2H). MS (ESI⁺): [M + H]⁺ 395.2. |
| 20 | (3-hydroxy-1-adamantyl-NH imidazolinone benzothiazole) | C₂₁H₂₂N₄O₂S | 394.49 | 97% | Yellow solid. ¹H NMR (400 MHz, DMSO-d₆, 300K) of major tautomer δ_H 10.01 (br s, 1H, NH, D₂O exchanged), 9.35 (s, 1H), 9.00 (s, 1H), 8.15 (dd, J = 8.6, 1.6 Hz, 1H), 8.02 (d, J = 8.5 Hz, 1H), 7.17 (br s, 1H, NH, D₂O exchanged), 6.42 (s, 1H), 4.62 (br s, 1H, OH, D₂O exchanged), 2.28-2.17 (m, 2H), 2.12-2.01 (m, 5H), 1.99-1.91 (m, 1H), 1.69-1.45 (m, 6H). MS (ESI⁺): [M + H]⁺ 395.2. |

TABLE 3-continued

| | Structure | Formula | MW | Yield | Characterization |
|---|---|---|---|---|---|
| 21 | (1-methoxyadamantyl-NH-imidazolone-benzothiazole) | C₂₂H₂₄N₄O₂S | 408.52 | 96% | Yellow solid. ¹H NMR (400 MHz, DMSO-d₆, 300K) of major tautomer δ_H 10.08 (br s, 1H, NH, D₂O exchanged), 9.35 (s, 1H), 9.04 (s, 1H), 8.12 (d, J = 8.6 Hz, 1H), 8.02 (d, J = 8.6 Hz, 1H), 7.27 (br s, 1H, NH, D₂O exchanged), 6.43 (s, 1H), 3.18 (s, 3H), 2.38-1.91 (m, 8H), 1.83-1.47 (m, 6H).MS (ESI⁺): [M + H]⁺ 409.3. |
| 22 | ((R,R,S)-pinanyl-NH-imidazolone-benzothiazole) | C₂₁H₂₄N₄OS | 380.51 | 95% | Yellow solid. ¹H NMR (400 MHz, DMSO-d₆, 300K) of major tautomer δ_H 10.64 (br s, 1H, NH, D₂O exchanged), 9.34 (s, 1H), 9.12-8.81 (m, 1H), 8.17 (d, J = 8.6 Hz, 1H), 8.01 (d, J = 8.5 Hz, 1H), 7.71 (br s, 1H, NH, D₂O exchanged), 6.39 (s, 1H), 4.57-4.23 (m, 1H), 3.98-3.66 (m, 1H), 2.64-2.52 (m, 1H), 2.40-2.28 (m, 1H), 2.21-2.04 (m, 1H), 2.04-1.87 (m, 1H), 1.87-1.61 (m, 2H), 1.38-0.89 (m, 9H). MS (ESI⁺): [M + H]⁺ 381.2. |
| 23 | ((S,S,R)-pinanyl-NH-imidazolone-benzothiazole) | C₂₁H₂₄N₄OS | 380.51 | 95% | Yellow solid. ¹H NMR (400 MHz, DMSO-d₆, 300K) of major tautomer δ_H 10.64 (br s, 1H, NH, D₂O exchanged), 9.34 (s, 1H), 9.12-8.81 (m, 1H), 8.17 (d, J = 8.6 Hz, 1H), 8.01 (d, J = 8.5 Hz, 1H), 7.71 (br s, 1H, NH, D₂O exchanged), 6.39 (s, 1H), 4.57-4.23 (m, 1H), 3.98-3.66 (m, 1H), 2.64-2.52 (m, 1H), 2.40-2.28 (m, 1H), 2.21-2.04 (m, 1H), 2.04-1.87 (m, 1H), 1.87-1.61 (m, 2H), 1.38-0.89 (m, 9H). MS (ESI⁺): [M + H]⁺ 381.2. |
| 24 | (pinanylmethyl-NH-imidazolone-benzothiazole) | C₂₁H₂₄N₄OS | 380.51 | 94% | Yellow solid. ¹H NMR (400 MHz, DMSO-d₆, 343K) of major tautomer δ_H 10.51 (br s, 1H, NH, D₂O exchanged), 9.30 (s, 1H), 8.95 (s, 1H), 8.14 (d, J = 8.7 Hz, 1H), 7.99 (d, J = 8.5 Hz, 1H), 7.36 (br s, 1H, NH, D₂O exchanged), 6.40 (s, 1H), 3.54-3.35 (m, 2H), 2.42-2.29 (m, 2H), 2.09-1.80 (m, 5H), 1.72-1.58 (m, 1H), 1.20 (s, 6H), 0.92 (d, J = 9.5 Hz, 1H). MS (ESI⁺): [M + H]⁺ 381.2. |

TABLE 3-continued

| | | | | |
|---|---|---|---|---|
| 25 |  | $C_{19}H_{20}N_4OS$ | 352.46 | >98% | Yellow solid. $^1$H NMR (400 MHz, DMSO-$d_6$, 300K) of major tautomer $\delta_H$ 10.68 (br s, 1H, NH, D$_2$O exchanged), 9.35 (s, 1H), 9.14-8.80 (m, 1H), 8.16 (d, J = 8.6 Hz, 1H), 8.01 (d, J = 8.5 Hz, 1H), 7.67 (br s, 1H, NH, D$_2$O exchanged), 6.43 (s, 1H), 2.72-2.58 (m, 1H), 1.92-1.20 (m, 10H), 0.71 (dd, J = 7.9, 5.1 Hz, 1H), 0.55 (t, J = 4.7 Hz, 1H). MS (ESI$^+$): [M + H]$^+$ 353.2. |
| 26 | 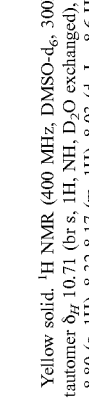 | $C_{18}H_{18}N_4OS$ | 338.43 | >98% | Yellow solid. $^1$H NMR (400 MHz, DMSO-$d_6$, 300K) of major tautomer $\delta_H$ 10.71 (br s, 1H, NH, D$_2$O exchanged), 9.35 (s, 1H), 8.80 (s, 1H), 8.32-8.17 (m, 1H), 8.03 (d, J = 8.6 Hz, 1H), 7.75 (br s, 1H, NH, D$_2$O exchanged), 6.39 (s, 1H), 4.61-3.67 (m, 2H), 2.45-2.32 (m, 2H), 2.16-1.99 (m, 3H), 1.99-1.88 (m, 2H), 1.87-1.74 (m, 2H). MS (ESI$^+$): [M + H]$^+$ 339.2. |
| 27 |  | $C_{21}H_{24}N_4OS$ | 380.51 | 96% | Yellow solid. $^1$H NMR (400 MHz, DMSO-$d_6$, 300K) of major tautomer $\delta_H$ 10.19 (br s, 1H, NH, D$_2$O exchanged), 9.34 (s, 1H), 8.92 (s, 1H), 8.19 (dd, J = 8.7, 1.6 Hz, 1H), 8.01 (d, J = 8.6 Hz, 1H), 7.58 (br s, 1H, NH, D$_2$O exchanged), 6.38 (s, 1H), 4.50-3.70 (m, 1H), 2.39-2.17 (m, 1H), 1.67 (s, 3H), 1.42-1.20 (m, 2H), 1.14-0.61 (m, 10H). MS (ESI$^+$): [M + H]$^+$ 381.2. |
| 28 | 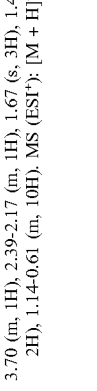 | $C_{18}H_{18}N_4OS$ | 338.43 | >98% | Yellow solid. $^1$H NMR (400 MHz, DMSO-$d_6$, 300K) of major tautomer $\delta_H$ 10.30 (br s, 1H, NH, D$_2$O exchanged), 9.35 (s, 1H), 8.97-8.71 (m, 1H), 8.40-8.20 (m, 1H), 8.04 (d, J = 8.6 Hz, 1H), 7.65 (br s, 1H, NH, D$_2$O exchanged), 6.40 (s, 1H), 4.30-3.71 (m, 1H), 2.47-2.34 (m, 1H), 2.27-2.12 (m, 1H), 2.08-1.86 (m, 1H), 1.74-1.25 (m, 6H), 1.18-1.02 (m, 1H). MS (ESI$^+$): [M + H]$^+$ 339.2 |

TABLE 3-continued

| | Structure | Formula | MW | Yield | Characterization |
|---|---|---|---|---|---|
| 29 | 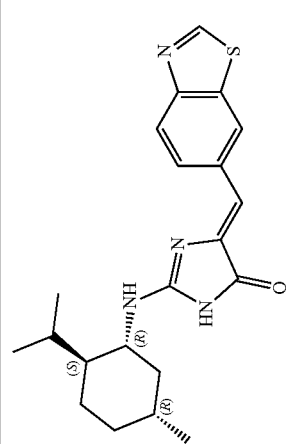 | C₂₁H₂₆N₄OS | 382.53 | 91% | Yellow solid. ¹H NMR (400 MHz, DMSO-d₆, 300K) of major tautomer δ_H 10.52 (br s, 1H, NH, D₂O exchanged), 9.34 (s, 1H), 8.84 (s, 1H), 8.27-8.15 (m, 1H), 8.01 (d, J = 8.6 Hz, 1H), 7.37 (br s, 1H, NH, D₂O exchanged), 6.36 (s, 1H), 3.97-3.66 (m, 1H), 2.11-1.20 (m, 7H), 1.19-0.58 (m, 11H). MS (ESI⁺): [M + H]⁺ 383.3. |
| 30 | 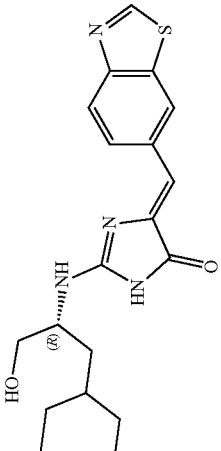 | C₂₀H₂₄N₄O₂S | 384.50 | 96% | Yellow solid. ¹H NMR (400 MHz, DMSO-d₆, 300K) of major tautomer δ_H 10.07 (br s, 1H, NH, D₂O exchanged), 9.28 (s, 1H), 9.03-8.63 (m, 1H), 8.35-8.04 (m, 1H), 8.04-7.90 (m, 1H), 6.90 (br s, 1H, NH, D₂O exchanged), 6.42 (s, 1H), 4.54 (br s, 1H, OH, D₂O exchanged), 4.14-3.93 (m, 1H), 3.66-3.44 (m, 2H), 1.95-0.90 (m, 13H). MS (ESI⁺): [M + H]⁺ 385.2. |
| 31 | 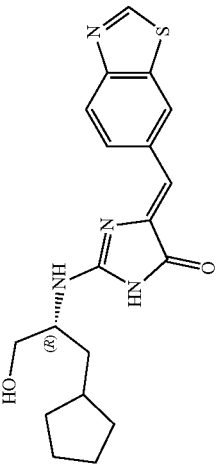 | C₁₉H₂₂N₄O₂S | 370.47 | >98% | Yellow solid. ¹H NMR (400 MHz, DMSO-d₆, 373K) of major tautomer δ_H 10.11 (br s, 1H, NH, D₂O exchanged), 9.28 (s, 1H), 9.03-8.85 (m, 1H), 8.28-8.09 (m, 1H), 8.07-7.95 (m, 1H), 6.91 (br s, 1H, NH, D₂O exchanged), 6.43 (s, 1H), 4.55 (br s, 1H, OH, D₂O exchanged), 4.08-3.86 (m, 1H), 3.66-3.44 (m, 2H), 1.99-1.08 (m, 11H). MS (ESI⁺): [M + H]⁺ 371.2. |
| 32 | 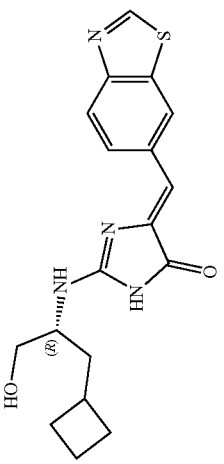 | C₁₈H₂₀N₄O₂S | 356.44 | >98% | Yellow solid. ¹H NMR (400 MHz, DMSO-d₆, 300K) of major tautomer δ_H 10.38 (br s, 1H, NH, D₂O exchanged), 9.35 (s, 1H), 9.03-8.72 (m, 1H), 8.19 (d, J = 8.7 Hz, 1H), 8.01 (d, J = 8.5 Hz, 1H), 7.22 (br s, 1H, NH, D₂O exchanged), 6.40 (s, 1H), 4.86 (br s, 1H, OH, D₂O exchanged), 4.14-3.75 (m, 1H), 3.71-3.39 (m, 2H), 2.44-2.30 (m, 1H), 2.18-1.92 (m 2H), 1.88-1.45 (m, 6H). MS (ESI⁺): [M + H]⁺ 357.2. |

TABLE 3-continued

| | | | | |
|---|---|---|---|---|
| 33 | [structure: benzothiazole-CH=imidazolone-NH-(R)-CH(CH2-cyclopropyl)-CH2OH] | C17H18N4O2S | 342.2 | >98% | Yellow solid. $^1$H NMR (400 MHz, DMSO-d$_6$, 323K) of major tautomer δ$_H$ 10.37 (br s, 1H, NH, D$_2$O exchanged), 9.33 (s, 1H), 8.98-8.72 (m, 1H), 8.34-8.12 (m, 1H), 8.02 (d, J = 8.5 Hz, 1H), 7.23 (br s, 1H, NH, D$_2$O exchanged), 6.41 (s, 1H), 4.77 (br s, 1H, NH, D$_2$O exchanged), 4.11-3.87 (m, 1H), 3.70-3.44 (m, 2H), 1.69-1.51 (m, 1H), 1.51-1.40 (m, 1H), 0.87-0.71 (m, 1H), 0.52-0.37 (m, 2H), 0.25-0.03 (m, 2H). MS (ESI$^+$): [M + H]$^+$ 343.1. |
| 34 | [structure: benzothiazole-CH=imidazolone-NH-(R)-CH(iBu)-CH2OH] | C17H22N4O2S | 344.43 | >98% | Yellow solid. $^1$H NMR (400 MHz, DMSO-d$_6$, 300K) of major tautomer δ$_H$ 10.42 (br s, 1H, NH, D$_2$O exchanged), 9.35 (s, 1H), 8.92 (s, 1H), 8.19 (d, J = 8.7 Hz, 1H), 8.01 (d, J = 8.6 Hz, 1H), 7.26 (br s, 1H, NH, D$_2$O exchanged), 6.40 (s, 1H), 4.87 (br s, 1H, OH, D$_2$O exchanged), 4.34-4.04 (m, 1H), 3.62-3.42 (m, 2H), 1.86-1.57 (m, 1H), 1.60-1.34 (m, 2H), 1.15-0.77 (m, 6H). MS (ESI$^+$): [M + H]$^+$ 345.2. |
| 35 | [structure: benzothiazole-CH=imidazolone-NH-(R)-CH(iBu)-CH2OMe] | C18H22N4O2S | 358.46 | >98% | Yellow solid. $^1$H NMR (400 MHz, DMSO-d$_6$, 373K) of major tautomer δ$_H$ 10.16 (br s, 1H, NH, D$_2$O exchanged), 9.27 (s, 1H), 8.89 (s, 1H), 8.15 (d, J = 8.6 Hz, 1H), 7.99 (d, J = 8.4 Hz, 1H), 7.01 (br s, 1H, NH, D$_2$O exchanged), 6.43 (s, 1H), 4.19 (s, 1H), 3.53-3.41 (m, 2H), 3.34 (s, 3H), 1.83-1.66 (m, 1H), 1.62-1.39 (m, 2H), 1.14-0.81 (m, 6H). MS (ESI$^+$): [M + H]$^+$ 359.2. |
| 36 | [structure: benzothiazole-CH=imidazolone-NH-(S)-CH(iBu)-CH2OH] | C17H22N4O2S | 344.43 | >98% | Yellow solid. $^1$H NMR (400 MHz, DMSO-d$_6$, 300K) of major tautomer δ$_H$ 10.42 (br s, 1H, NH, D$_2$O exchanged), 9.35 (s, 1H), 8.92 (s, 1H), 8.19 (d, J = 8.7 Hz, 1H), 8.01 (d, J = 8.6 Hz, 1H), 7.26 (br s, 1H, NH, D$_2$O exchanged), 6.40 (s, 1H), 4.87 (br s, 1H, OH, D$_2$O exchanged), 4.34-4.04 (m, 1H), 3.62-3.42 (m, 2H), 1.86-1.57 (m, 1H), 1.60-1.34 (m, 2H), 1.15-0.77 (m, 6H). MS (ESI$^+$): [M + H]$^+$ 345.2. |

TABLE 3-continued

| | Structure | Formula | MW | Purity | Data |
|---|---|---|---|---|---|
| 37 | (S)-methoxymethyl-isobutyl NH-imidazolone-benzothiazole | C₁₈H₂₂N₄O₂S | 358.46 | >98% | Yellow solid. ¹H NMR (400 MHz, DMSO-d₆, 373K) of major tautomer δ_H 10.16 (br s, 1H, NH, D₂O exchanged), 9.27 (s, 1H), 8.89 (s, 1H), 8.15 (d, J = 8.6 Hz, 1H), 7.99 (d, J = 8.4 Hz, 1H), 7.01 (br s, 1H, NH, D₂O exchanged), 6.43 (s, 1H), 4.19 (s, 1H), 3.53-3.41 (m, 2H), 3.34 (s, 3H), 1.83-1.66 (m, 1H), 1.62-1.39 (m, 2H), 1.14-0.81 (m, 6H). MS (ESI⁺): [M + H]⁺ 359.2. |
| 38 | (R)-hydroxymethyl-ethyl NH-imidazolone-benzothiazole | C₁₅H₁₆N₄O₂S | 316.38 | 88% | Yellow solid. ¹H NMR (400 MHz, DMSO-d₆, 333K) of major tautomer δ_H 10.41 (br s, 1H, NH, D₂O exchanged), 9.32 (s, 1H), 8.81 (s, 1H), 8.23 (d, J = 8.7 Hz, 1H), 8.02 (d, J = 8.7 Hz, 1H), 7.19 (br s, 1H, NH, D₂O exchanged), 6.41 (s, 1H), 4.89-4.62 (m, 1H, OH, D₂O exchanged), 3.81 (s, 1H), 3.53 (s, 2H), 1.76-1.62 (m, 1H), 1.62-1.45 (m, 1H), 1.00-0.87 (m, 3H). MS (ESI⁺): [M + H]⁺ 317.5. |
| 39 | (S)-hydroxymethyl-ethyl NH-imidazolone-benzothiazole | C₁₅H₁₆N₄O₂S | 316.38 | >96% | Yellow solid. ¹H NMR (400 MHz, DMSO-d₆, 333K) of major tautomer δ_H 10.41 (br s, 1H, NH, D₂O exchanged), 9.32 (s, 1H), 8.81 (s, 1H), 8.23 (d, J = 8.7 Hz, 1H), 8.02 (d, J = 8.7 Hz, 1H), 7.19 (br s, 1H, NH, D₂O exchanged), 6.41 (s, 1H), 4.86 (br s, 1H, OH, D₂O exchanged), 3.81 (s, 1H), 3.53 (s, 2H), 1.76-1.62 (m, 1H), 1.62-1.45 (m, 1H), 1.00-0.87 (m, 3H). MS (ESI⁺): [M + H]⁺ 317.5. |
| 40 | (±)-fluoromethyl-isobutyl NH-imidazolone-benzothiazole | C₁₇H₁₉FN₄OS | 346.42 | 91% | Yellow solid. ¹H NMR (400 MHz, DMSO-d₆, 373K) of major tautomer δ_H 10.28 (br s, 1H, NH, D₂O exchanged), 9.28 (s, 1H), 8.85 (s, 1H), 8.17 (d, J = 8.2 Hz, 1H), 8.00 (d, J = 8.5 Hz, 1H), 7.25 (br s, 1H, NH, D₂O exchanged), 6.46 (s, 1H), 4.64-4.52 (m, 1H), 4.50-4.40 (m, 1H), 4.37-4.22 (m, 1H), 1.84-1.71 (m, 1H), 1.65-1.55 (m, 1H), 1.52-1.41 (m, 1H), 1.04-0.81 (m, 6H). MS (ESI⁺): [M + H]⁺ 347.2. |

TABLE 3-continued

| | Structure | Formula | MW | Purity | Characterization |
|---|---|---|---|---|---|
| 41 | 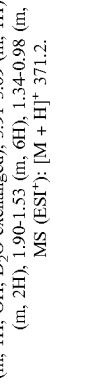 | $C_{19}H_{22}N_4O_2S$ | 370.47 | >98% | Yellow solid. $^1$H NMR (400 MHz, DMSO-$d_6$, 343K) of major tautomer $\delta_H$ 10.26 (br s, 1H, NH, D$_2$O exchanged), 9.31 (s, 1H), 8.84 (s, 1H), 8.20 (d, J = 8.7 Hz, 1H), 8.02 (d, J = 8.6 Hz, 1H), 7.11 (br s, 1H, NH, D$_2$O exchanged), 6.41 (s, 1H), 4.81-4.55 (m, 1H, OH, D$_2$O exchanged), 3.91-3.69 (m, 1H), 3.67-3.50 (m, 2H), 1.90-1.53 (m, 6H), 1.34-0.98 (m, 5H). MS (ESI$^+$): [M + H]$^+$ 371.2. |
| 42 | 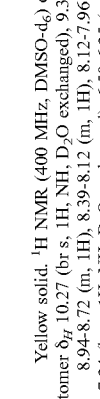 | $C_{20}H_{24}N_4O_2S$ | 384.0 | >98% | Yellow solid. $^1$H NMR (400 MHz, DMSO-$d_6$) of major tautomer $\delta_H$ 10.27 (br s, 1H, NH, D$_2$O exchanged), 9.38-9.24 (m, 1H), 8.94-8.72 (m, 1H), 8.39-8.12 (m, 1H), 8.12-7.96 (m, 1H), 7.24 (br s, 1H, NH, D$_2$O exchanged), 6.50-6.25 (m, 1H), 4.03-3.83 (m, 1H), 3.60-3.44 (m, 2H), 3.31 (s, 3H), 1.86-1.53 (m, 6H), 1.30-1.03 (m, 5H). MS (ESI$^+$): [M + H]$^+$ 385.2. |
| 43 | 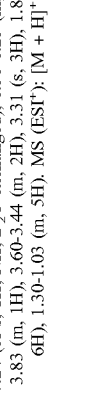 | $C_{19}H_{22}N_4O_2S$ | 370.47 | >98% | Yellow solid. $^1$H NMR (400 MHz, DMSO-$d_6$, 298K) of major tautomer $\delta_H$ 10.54 (br s, 1H, NH, D$_2$O exchanged), 9.35 (s, 1H), 8.94 (s, 1H), 8.29-8.09 (m, 1H), 8.01 (d, J = 8.6 Hz, 1H), 7.42 (br s, 1H, NH, D$_2$O exchanged), 6.41 (s, 1H), 4.95-4.72 (br s, 1H, OH, D$_2$O exchanged), 3.82-3.36 (m, 2H), 3.25-3.08 (m, 1H), 2.02-1.50 (m, 5H), 1.45-0.91 (m, 6H). MS (ESI$^+$): [M + H]$^+$ 371.3. |
| 44 | 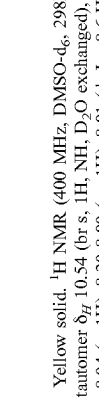 | $C_{20}H_{24}N_4O_2S$ | 384.50 | 97% | Yellow solid. $^1$H NMR (400 MHz, DMSO-$d_6$, 323K) of major tautomer $\delta_H$ 10.46 (br s, 1H, NH, D$_2$O exchanged), 9.33 (s, 1H), 8.96 (s, 1H), 8.15 (d, J = 8.7 Hz, 1H), 8.01 (d, J = 8.5 Hz, 1H), 7.42 (br s, 1H, NH, D$_2$O exchanged), 6.43 (s, 1H), 3.71-3.55 (m, 1H), 3.45-3.33 (m, 4H), 3.32-3.23 (m, 1H), 1.90-1.50 (m, 6H), 1.28-1.07 (m, 5H). MS (ESI$^+$): [M + H]$^+$ 385.2. |

TABLE 3-continued

| | Structure | Formula | MW | Purity | Notes |
|---|---|---|---|---|---|
| 45 | (benzothiazole-CH=imidazolone with (2-hydroxycyclopentyl)amino, cis-(±)) | C₁₆H₁₆N₄O₂S | 328.39 | >98% | Yellow solid. ¹H NMR (400 MHz, DMSO-d₆, 373K) of major tautomer δ_H 10.13 (br s, 1H, NH, D₂O exchanged), 9.28 (s, 1H), 8.87-8.67 (m, 1H), 8.41-8.13 (m, 1H), 8.09-7.94 (m, 1H), 6.73 (br s, 1H, NH, D₂O exchanged), 6.44 (s, 1H), 4.73 (br s, 1H, OH, D₂O exchanged), 4.22-3.96 (m, 2H), 2.11-1.51 (m, 6H). MS (ESI⁺): [M + H]⁺ 329.2. |
| 46 | (benzothiazole-CH=imidazolone with (2-hydroxycyclopentyl)amino, trans-(±)) | C₁₆H₁₆N₄O₂S | 328.39 | >98% | Yellow solid. ¹H NMR (400 MHz, DMSO-d₆, 323K) of major tautomer δ_H 10.53 (br s, 1H, NH, D₂O exchanged), 9.33 (s, 1H), 8.93-8.63 (m, 1H), 8.35-8.12 (m, 1H), 8.03 (d, J = 8.3 Hz, 1H), 7.61 (br s, 1H, NH, D₂O exchanged), 6.42 (s, 1H), 4.94 (br s, 1H, OH, D₂O exchanged), 4.10-3.75 (m, 2H), 2.18-2.03 (m, 1H), 1.98-1.82 (m, 1H), 1.79-1.42 (m, 4H). MS (ESI⁺): [M + H]⁺ 329.2. |
| 47 | (benzothiazole-CH=imidazolone with (2-methoxycyclopentyl)amino, cis-(±)) | C₁₇H₁₈N₄O₂S | 342.42 | 98% | Yellow solid. ¹H NMR (400 MHz, DMSO-d₆, 343K) of major tautomer δ_H 10.18 (br s, 1H, NH, D₂O exchanged), 9.31 (s, 1H), 8.79 (s, 1H), 8.44-8.15 (m, 1H), 8.15-7.97 (m, 1H), 6.96 (br s, 1H, NH, D₂O exchanged), 6.44 (s, 1H), 4.24 (s, 1H), 3.81 (s, 1H), 3.30 (s, 3H), 2.13-1.90 (m, 1H), 1.89-1.50 (m, 5H). MS (ESI⁺): [M + H]⁺ 343.2. |

TABLE 3-continued

| | Structure | Formula | MW | Purity | Characterization |
|---|---|---|---|---|---|
| 48 | trans-(±) methoxycyclopentyl-NH-imidazolone-benzothiazole | C₁₇H₁₈N₄O₂S | 342.42 | 97% | Yellow solid. ¹H NMR (400 MHz, DMSO-d₆, 343K) of major tautomer δ_H 10.12 (br s, 1H, NH, D₂O exchanged), 9.28 (s, 1H), 8.97-8.76 (m, 1H), 8.25-8.09 (m, 1H), 8.01 (d, J = 8.3 Hz, 1H), 7.28 (br s, 1H, NH, D₂O exchanged), 6.46 (s, 1H), 4.21-4.12 (m, 1H), 3.86-3.79 (m, 1H), 3.38 (s, 3H), 2.17-2.04 (m, 1H), 2.00-1.88 (m, 1H), 1.80-1.58 (m, 4H). MS (ESI⁺): [M + H]⁺ 343.2. |
| 49 | cis-(±) hydroxycyclohexyl-NH-imidazolone-benzothiazole | C₁₇H₁₈N₄O₂S | 342.42 | >98% | Yellow solid. ¹H NMR (400 MHz, DMSO-d₆, 343K) of major tautomer δ_H 10.18 (br s, 1H, NH, D₂O exchanged), 9.31 (s, 1H), 8.80 (s, 1H), 8.22 (d, J = 8.3 Hz, 1H), 8.02 (d, J = 8.6 Hz, 1H), 6.86 (br s, 1H, NH, D₂O exchanged), 6.42 (s, 1H), 4.77-4.63 (m, 1H, OH, D₂O exchanged), 4.02-3.74 (m, 2H), 1.88-1.47 (m, 6H), 1.46-1.25 (m, 2H). MS (ESI⁺): [M + H]⁺ 343.2. |
| 50 | trans-(±) hydroxycyclohexyl-NH-imidazolone-benzothiazole | C₁₇H₁₈N₄O₂S | 342.42 | >98% | Yellow solid. ¹H NMR (400 MHz, DMSO-d₆, 343K) of major tautomer δ_H 10.45 (br s, 1H, NH, D₂O exchanged), 9.30 (s, 1H), 8.83 (s, 1H), 8.31-8.09 (m, 1H), 8.09-7.96 (m, 1H), 7.35 (br s, 1H, NH, D₂O exchanged), 6.39 (s, 1H), 4.64 (br s, 1H, OH, D₂O exchanged), 3.59-3.31 (m, 2H), 2.13-1.84 (m, 2H), 1.78-1.58 (m, 2H), 1.48-1.11 (m, 4H). MS (ESI⁺): [M + H]⁺ 343.2. |

TABLE 3-continued

| | | | | |
|---|---|---|---|---|
| 51 | [structure: (S)-OH cyclohexyl, (R)-NH linked to imidazolone with benzothiazole methylidene] | $C_{17}H_{18}N_4O_2S$ | 342.42 | >98% | Yellow solid. $^1$H NMR (400 MHz, DMSO-d$_6$, 343K) of major tautomer δ$_H$ 10.18 (br s, 1H, NH, D$_2$O exchanged), 9.31 (s, 1H), 8.80 (s, 1H), (d, J = 8.3 Hz, 1H), 8.02 (d, J = 8.6 Hz, 1H), 6.86 (br s, 1H, NH, D$_2$O exchanged), 6.42 (s, 1H), 4.77-4.63 (m, 1H, OH, D$_2$O exchanged), 4.02-3.74 (m, 2H), 1.88-1.47 (m, 6H), 1.46-1.25 (m, 2H). MS (ESI$^+$): [M + H]$^+$ 343.2. |
| 52 | [structure: (R)-OH cyclohexyl, (S)-NH linked to imidazolone with benzothiazole methylidene] | $C_{17}H_{18}N_4O_2S$ | 342.42 | >98% | Yellow solid. $^1$H NMR (400 MHz, DMSO-d$_6$, 343K) of major tautomer δ$_H$ 10.18 (br s, 1H, NH, D$_2$O exchanged), 9.31 (s, 1H), 8.80 (s, 1H), 8.22 (d, J = 8.3 Hz, 1H), 8.02 (d, J = 8.06 Hz, 1H), 6.86 (br s, 1H, NH, D$_2$O exchanged), 6.42 (s, 1H), 4.77-4.63 (m, 1H, OH, D$_2$O exchanged), 4.02-3.74 (m, 2H), 1.88-1.47 (m, 6H), 1.46-1.25 (m, 2H). MS (ESI$^+$): [M + H]$^+$ 343.2. |
| 53 | [structure: (R)-OH cyclohexyl, (R)-NH linked to imidazolone with benzothiazole methylidene] | $C_{17}H_{18}N_4O_2S$ | 342.42 | 97% | Yellow solid. $^1$H NMR (400 MHz, DMSO-d$_6$, 343K) of major tautomer δ$_H$ 10.45 (br s, 1H, NH, D$_2$O exchanged), 9.30 (s, 1H), 8.83 (s, 1H), 8.31-8.09 (m, 1H), 8.09-7.96 (m, 1H), 7.35 (br s, 1H, NH, D$_2$O exchanged), 6.39 (s, 1H), 4.64 (br s, 1H, OH, D$_2$O exchanged), 3.59-3.31 (m, 2H), 2.13-1.84 (m, 2H), 1.78-1.58 (m, 2H), 1.48-1.11 (m, 4H). MS (ESI$^+$): [M + H]$^+$ 343.2. |
| 54 | [structure: (S)-OH cyclohexyl, (S)-NH linked to imidazolone with benzothiazole methylidene] | $C_{17}H_{18}N_4O_2S$ | 342.42 | >98% | Yellow solid. $^1$H NMR (400 MHz, DMSO-d$_6$, 343K) of major tautomer δ$_H$ 10.45 (br s, 1H, NH, D$_2$O exchanged), 9.30 (s, 1H), 8.83 (s, 1H), 8.31-8.09 (m, 1H), 8.09-7.96 (m, 1H), 7.35 (br s, 1H, NH, D$_2$O exchanged), 6.39 (s, 1H), 4.64 (br s, 1H, OH, D$_2$O exchanged), 3.59-3.31 (m, 2H), 2.13-1.84 (m, 2H), 1.78-1.58 (m, 2H), 1.48-1.11 (m, 4H). MS (ESI$^+$): [M + H]$^+$ 343.2. |

TABLE 3-continued

| | | | | |
|---|---|---|---|---|
| 55 | [structure: benzothiazole-methylene-imidazolone with cis-(±) 3-hydroxycyclohexylamine] cis-(±) | $C_{17}H_{18}N_4O_2S$ | 342.42 | >98% | Yellow solid. $^1$H NMR (400 MHz, DMSO-d$_6$, 373K) of major tautomer $\delta_H$ 10.24 (br s, 1H, NH, D$_2$O exchanged), 9.28 (s, 1H), 8.91-8.53 (m, 1H), 8.31-8.05 (m, 1H), 8.02 (d, J = 8.2 Hz, 1H), 7.24 (br s, 1H, NH, D$_2$O exchanged), 6.42 (s, 1H), 4.39 (br s, 1H, D$_2$O exchanged), 3.88-3.75 (m, 1H), 3.66-3.53 (m, 1H), 2.21-2.05 (m, 1H), 1.94-1.69 (m, 3H), 1.41-1.14 (m, 4H). MS (ESI$^+$): [M + H]$^+$ 343.2. |
| 56 | [structure: trans-(±) 3-hydroxycyclohexylamine analog] trans-(±) | $C_{17}H_{18}N_4O_2S$ | 342.42 | >98% | Yellow solid. $^1$H NMR (400 MHz, DMSO-d$_6$, 323K) of major tautomer $\delta_H$ 10.34 (br s, 1H, NH, D$_2$O exchanged), 9.33 (s, 1H), 8.97-8.55 (m, 1H), 8.37-8.09 (m, 1H), 8.03 (d, J = 8.4 Hz, 1H), 7.40 (br s, 1H, NH, D$_2$O exchanged), 6.40 (s, 1H), 4.53-4.32 (br s, 1H, OH, D$_2$O exchanged), 4.24-4.02 (m, 1H), 4.01-3.91 (m, 1H), 1.90-1.60 (m, 4H), 1.59-1.34 (m, 4H). MS (ESI$^+$): [M + H]$^+$ 343.1. |
| 57 | [structure: trans 4-hydroxycyclohexylamine analog] trans | $C_{17}H_{18}N_4O_2S$ | 342.42 | >98% | Yellow solid. $^1$H NMR (400 MHz, DMSO-d$_6$, 343K) of major tautomer $\delta_H$ 10.34 (br s, 1H, NH, D$_2$O exchanged), 9.31 (s, 1H), 9.05-8.54 (m, 1H), 8.41-8.08 (m, 1H), 8.02 (d, J = 8.4 Hz, 1H), 7.36 (br s, 1H, NH, D$_2$O exchanged), 6.41 (s, 1H), 4.36 (d, J = 4.4 Hz, 1H, OH, D$_2$O exchanged), 3.79-3.55 (m, 1H), 3.52-3.34 (m, 1H), 2.12-1.76 (m, 4H), 1.55-1.20 (m, 4H). MS (ESI$^+$): [M + H]$^+$ 343.2. |

TABLE 3-continued

| | | | | |
|---|---|---|---|---|
| 58 | [structure: cis-(±)] | $C_{18}H_{20}N_4O_2S$ | 356.44 | 98% | Yellow solid. $^1$H NMR (400 MHz, DMSO-d$_6$, 343K) of major tautomer $\delta_H$ 10.06 (br s, 1H, NH, D$_2$O exchanged), 9.31 (s, 1H), 8.81 (s, 1H), 8.23 (d, J = 8.1 Hz, 1H), 8.02 (d, J = 8.9 Hz, 1H), 6.96 (br s, 1H, NH, D$_2$O exchanged), 6.44 (s, 1H), 4.15-3.83 (m, 1H), 3.59-3.44 (m, 1H), 3.32 (s, 3H), 2.00-1.88 (m, 1H), 1.81-1.57 (m, 3H), 1.57-1.30 (m, 4H). MS (ESI$^+$): [M + H]$^+$ 357.2. |
| 59 | [structure: trans-(±)] | $C_{18}H_{20}N_4O_2S$ | 356.44 | >98% | Yellow solid. $^1$H NMR (400 MHz, DMSO-d$_6$, 323K) of major tautomer $\delta_H$ 10.62 (br s, 1H, NH, D$_2$O exchanged), 9.32 (s, 1H), 8.84 (s, 1H), 8.20 (d, J = 8.7 Hz, 1H), 8.01 (d, J = 8.6 Hz, 1H), 7.65 (br s, 1H, NH, D$_2$O exchanged), 6.39 (s, 1H), 3.82-3.53 (m, 1H), 3.31 (s, 3H), 3.25-3.12 (m, 1H), 2.15-1.90 (m, 2H), 1.76-1.59 (m, 2H), 1.47-1.15 (m, 4H). MS (ESI$^+$): [M + H]$^+$ 357.2. |
| 60 | [structure] | $C_{18}H_{20}N_4O_2S$ | 356.44 | >98% | Yellow solid. $^1$H NMR (400 MHz, DMSO-d$_6$, 343K) of major tautomer $\delta_H$ 10.51 (br s, 1H, NH, D$_2$O exchanged), 9.30 (s, 1H), 8.83 (s, 1H), 8.20 (d, J = 8.6 Hz, 1H), 8.02 (d, J = 8.6 Hz, 1H), 7.41 (br s, 1H, NH, D$_2$O exchanged), 6.41 (s, 1H), 3.82-3.62 (m, 1H), 3.27 (s, 3H), 3.22-3.12 (m, 1H), 2.10-1.93 (m, 4H), 1.50-1.36 (m, 2H), 1.36-1.22 (m, 2H). MS (ESI$^+$): [M + H]$^+$ 357.2. |

TABLE 3-continued

| # | | Formula | MW | Purity | Data |
|---|---|---|---|---|---|
| 61 | cis-(±) structure with benzothiazole, cycloheptane-OH, NH, imidazolone | $C_{18}H_{20}N_4O_2S$ | 356.44 | >98% | Yellow solid. $^1$H NMR (400 MHz, DMSO-d$_6$, 300K) of major tautomer $\delta_H$ 10.15 (br s, 1H, NH, D$_2$O exchanged), 9.35 (s, 1H), 8.90 (s, 1H), 8.22 (d, J = 9.0 Hz, 1H), 8.02 (d, J = 8.5 Hz, 1H), 7.07 (br s, 1H, NH, D$_2$O exchanged), 6.42 (s, 1H), 4.96 (br s, 1H, OH, D$_2$O exchanged), 4.08-3.77 (m, 2H), 1.98-1.29 (m, 10H). MS (ESI$^+$): [M + H]$^+$ 357.2. |
| 62 | trans-(±) structure | $C_{18}H_{20}N_4O_2S$ | 356.44 | >98% | Yellow solid. $^1$H NMR (400 MHz, DMSO-d$_6$, 323K) of major tautomer $\delta_H$ 10.46 (br s, 1H, NH, D$_2$O exchanged), 9.33 (s, 1H), 9.08-8.72 (m, 1H), 8.39-8.09 (m, 1H), 8.02 (d, J = 8.5 Hz, 1H), 7.45 (br s, 1H, NH, D$_2$O exchanged), 6.40 (s, 1H), 4.72 (br s, 1H, OH, D$_2$O exchanged), 3.89-3.53 (m, 2H), 2.03-1.37 (m, 10H). MS (ESI$^+$): [M + H]$^+$ 357.2. |
| 63 | (R,R) structure | $C_{18}H_{20}N_4O_2S$ | 356.44 | >98% | Yellow solid. $^1$H NMR (400 MHz, DMSO-d$_6$, 323K) of major tautomer $\delta_H$ 10.46 (br s, 1H, NH, D$_2$O exchanged), 9.33 (s, 1H), 9.08-8.72 (m, 1H), 8.39-8.09 (m, 1H), 8.02 (d, J = 8.5 Hz, 1H), 7.45 (br s, 1H, NH, D$_2$O exchanged), 6.40 (s, 1H), 4.76 (br s, 1H, OH, D$_2$O exchanged), 3.89-3.53 (m, 2H), 2.03-1.37 (m, 10H). MS (ESI$^+$): [M + H]$^+$ 357.2. |
| 64 | (S,S) structure | $C_{18}H_{20}N_4O_2S$ | 356.44 | 97% | Yellow solid. $^1$H NMR (400 MHz, DMSO-d$_6$, 323K) of major tautomer $\delta_H$ 10.46 (br s, 1H, NH, D$_2$O exchanged), 9.33 (s, 1H), 9.08-8.72 (m, 1H), 8.39-8.09 (m, 1H), 8.02 (d, J = 8.5 Hz, 1H), 7.45 (br s, 1H, NH, D$_2$O exchanged), 6.40 (s, 1H), 4.76 (br s, 1H, OH, D$_2$O exchanged), 3.89-3.53 (m, 2H), 2.03-1.37 (m, 10H). MS (ESI$^+$): [M + H]$^+$ 357.4. |

TABLE 3-continued

| | | | | |
|---|---|---|---|---|
| 65 | [structure: cis-(±) cycloheptane with OH and NH linked to imidazolinone with benzothiazole methylene] | C₁₈H₂₀N₄O₂S | 356.44 | >98% | Yellow solid. ¹H NMR (400 MHz, DMSO-d₆, 373K) of major tautomer δ_H 10.15 (br s, 1H, NH, D₂O exchanged), 9.28 (s, 1H), 8.99-8.54 (m, 1H), 8.28-8.06 (m, 1H), 8.02 (d, J = 7.8 Hz, 1H), 7.17 (br s, 1H, NH, D₂O exchanged), 6.43 (s, 1H), 4.23 (br s, 1H, OH, D₂O exchanged), 4.05-3.91 (m, 1H), 3.90-3.77 (m, 1H), 2.21-2.05 (m, 1H), 2.05-1.39 (m, 9H). MS (ESI⁺): [M + H]⁺ 357.2. |
| 66 | [structure: trans-(±) cycloheptane with OH and NH linked to imidazolinone with benzothiazole methylene] | C₁₈H₂₀N₄O₂S | 356.44 | >98% | Yellow solid. ¹H NMR (400 MHz, DMSO-d₆, 323K) of major tautomer δ_H 10.33 (br s, 1H, NH, D₂O exchanged), 9.33 (s, 1H), 8.99-8.65 (m, 1H), 8.34-8.07 (m, 1H), 8.02 (d, J = 8.4 Hz, 1H), 7.51 (br s, 1H, NH, D₂O exchanged), 6.41 (s, 1H), 4.47 (br s, 1H, OH, D₂O exchanged), 4.19-4.01 (m, 1H), 3.96-3.83 (m, s, 1H), 2.08-1.89 (m, 3H), 1.86-1.30 (m, 7H), MS (ESI⁺): [M + H]⁺ 357.2. |
| 67 | [structure: cis-(±) cycloheptane with OMe and NH linked to imidazolinone with benzothiazole methylene] | C₁₉H₂₂N₄O₂S | 370.47 | >98% | Yellow solid. ¹H NMR (400 MHz, DMSO-d₆, 300K) of major tautomer δ_H 10.04 (br s, 1H, NH, D₂O exchanged), 9.35 (s, 1H), 8.89 (s, 1H), 8.23 (d, J = 9.0 Hz, 1H), 8.02 (d, J = 8.5 Hz, 1H), 7.21 (br s, 1H, NH, D₂O exchanged), 6.43 (s, 1H), 4.25-3.85 (m, 1H), 3.74-3.49 (m, 1H), 3.31 (s, 3H), 2.03-1.86 (m, 10H). MS (ESI⁺): [M + H]⁺ 371.2. |

TABLE 3-continued

| | | | | |
|---|---|---|---|---|
| 68 | [structure: methoxycycloheptyl-NH substituted imidazolone with benzothiazole methylene; trans-(±)] | $C_{19}H_{22}N_4O_2S$ | 370.47 | 98% | Yellow solid. $^1$H NMR (400 MHz, DMSO-$d_6$, 343K) of major tautomer δ$_H$ 10.39 (br s, 1H, NH, D$_2$O exchanged), 9.30 (s, 1H), 8.90 (s, 1H), 8.18 (d, J = 8.6 Hz, 1H), 8.01 (d, J = 8.6 Hz, 1H), 7.47 (br s, 1H, NH, D$_2$O exchanged), 6.41 (s, 1H), 4.00-3.83 (m, 1H), 3.51-3.38 (m, 1H), 3.31 (s, 3H), 1.93-1.40 (m, 10H). MS (ESI$^+$): [M + H]$^+$ 371.2. |
| 69 | [structure: (S)-MeOOC-CH(iPr)-NH substituted imidazolone with benzothiazole methylene] | $C_{17}H_{18}N_4O_3S$ | 358.42 | 97% | Yellow solid. $^1$H NMR (400 MHz, DMSO-$d_6$, 300K) of major tautomer δ$_H$ 10.41 (br s, 1H, NH, D$_2$O exchanged), 9.38 (s, 1H), 8.83 (s, 1H), 8.39-7.36 (m, 2H + NH, D$_2$O exchanged), 6.48 (s, 1H), 4.50-4.26 (m, 1H), 3.73 (s, 3H), 2.29-2.16 (m, 1H), 1.16-0.80 (m, 6H). MS (ESI$^+$): [M + H]$^+$ 359.2. |
| 70 | [structure: (S)-MeOOC-CH(Me)-NH substituted imidazolone with benzothiazole methylene] | $C_{15}H_{14}N_4O_3S$ | 330.36 | 97% | Yellow solid. $^1$H NMR (400 MHz, DMSO-$d_6$, 300K) of major tautomer δ$_H$ 10.85 (br s, 1H, NH, D$_2$O exchanged), 9.37 (s, 1H), 8.83 (s, 1H), 8.19 (d, J = 8.5 Hz, 1H), 8.14 (br s, 1H, NH, D$_2$O exchanged), 8.03 (d, J = 8.6 Hz, 1H), 6.47 (s, 1H), 4.68-4.45 (m, 1H), 3.71 (s, 3H), 1.45 (d, J = 7.2 Hz, 3H). MS (ESI$^+$): [M + H]$^+$ 331.1. |
| 71 | [structure: (S)-MeOOC-CH(iBu)-NH substituted imidazolone with benzothiazole methylene] | $C_{18}H_{20}N_4O_3S$ | 372.44 | 91% | Yellow solid. $^1$H NMR (400 MHz, DMSO-$d_6$, 300K) of major tautomer δ$_H$ 10.75 (br s, 1H, NH, D$_2$O exchanged), 9.37 (s, 1H), 8.85 (s, 1H), 8.19 (d, J = 8.6 Hz, 1H), 8.09 (br s, 1H, NH, D$_2$O exchanged), 8.03 (d, J = 8.6 Hz, 1H), 6.47 (s, 1H), 4.70-4.41 (m, 1H), 3.71 (s, 3H), 1.84-1.57 (m, 3H), 1.07-0.77 (m, 6H). MS (ESI$^+$): [M + H]$^+$ 373.2. |

TABLE 3-continued

| | Structure | Formula | MW | Purity | Description |
|---|---|---|---|---|---|
| 72 | MeOOC—[(R)-iBu-CH-NH]—imidazolone=CH—benzothiazole | C₁₈H₂₀N₄O₃S | 372.44 | 98% | Yellow solid. ¹H NMR (400 MHz, DMSO-d₆, 300K) of major tautomer δ_H 10.75 (br s, 1H, NH, D₂O exchanged), 9.37 (s, 1H), 8.85 (s, 1H), 8.19 (d, J = 8.6 Hz, 1H), 8.09 (br s, 1H, NH, D₂O exchanged), 8.03 (d, J = 8.6 Hz, 1H), 6.47 (s, 1H), 4.70-4.41 (m, 1H), 3.71 (s, 3H), 1.84-1.57 (m, 3H), 1.07-0.77 (m, 6H). MS (ESI⁺): [M + H]⁺ 373.2. |
| 73 | MeOOC—[(S)-CH(CH(OH)Me)-NH]—imidazolone=CH—benzothiazole | C₁₆H₁₆N₄O₄S | 360.4 | >98% | Yellow solid. ¹H NMR (400 MHz, DMSO-d₆, 300K) of major tautomer δ_H 10.28 (br s, 1H, NH, D₂O exchanged), 9.37 (s, 1H), 8.78 (s, 1H), 8.21 (d, J = 8.5 Hz, 1H), 8.03 (d, J = 8.6 Hz, 1H), 7.58-7.34 (br s, 1H, NH, D₂O exchanged), 6.49 (s, 1H), 5.31 (br s, 1H, OH, D₂O exchanged), 4.66-4.49 (m, 1H), 4.35-4.16 (m, 1H), 3.72 (s, 3H), 1.20 (d, J = 6.3 Hz, 3H). MS (ESI⁺): [M + H]⁺ 361.2. |
| 74 | Bn-NH—imidazolone=CH—benzothiazole | C₁₈H₁₄N₄OS | 334.40 | 97% | Yellow solid. ¹H NMR (400 MHz, DMSO-d₆, 300K) of major tautomer δ_H 10.86 (br s, 1H, NH, D₂O exchanged), 9.36 (s, 1H), 8.84 (s, 1H), 8.26-8.20 (m, 1H), 8.19-8.06 (br s, 1H, NH, D₂O exchanged), 8.03 (d, J = 8.6 Hz, 1H), 7.55-7.20 (m, 5H), 6.43 (s, 1H), 4.67-4.48 (m, 2H). MS (ESI⁺): [M + H]⁺ 335.2. |
| 75 | Indanyl-NH—imidazolone=CH—benzothiazole | C₂₀H₁₆N₄OS | 360.44 | >98% | Yellow solid. ¹H NMR (400 MHz, DMSO-d₆, 300K) of major tautomer δ_H 10.55 (br s, 1H, NH, D₂O exchanged), 9.35 (s, 1H), 8.81 (s, 1H), 8.44-8.17 (m, 1H), 8.03 (d, J = 8.5 Hz, 1H), 7.92 (br s, 1H, NH, D₂O exchanged), 7.32-7.22 (m, 2H), 7.20-7.17 (m, 2H), 6.44 (s, 1H), 4.96-4.44 (m, 1H), 3.38-3.31 (m, 2H), 3.09-2.88 (m, 2H). MS (ESI⁺): [M + H]⁺ 361.1. |
| 76 | (3,4-diMe-Bn)-NH—imidazolone=CH—benzothiazole | C₂₀H₁₈N₄OS | 362.45 | >98% | Yellow solid. ¹H NMR (500 MHz, DMSO-d₆, 300K) of major tautomer δ_H 10.79 (br s, 1H, NH, D₂O exchanged), 9.36 (s, 1H), 8.86 (s, 1H), 8.24 (d, J = 8.6 Hz, 1H), 8.03 (d, J = 8.5 Hz, 1H), 7.99 (br s, 1H, NH, D₂O exchanged), 7.28-7.06 (m, 3H), 6.42 (s, 1H), 4.50 (s, 2H), 2.21 (s, 3H), 2.18 (s, 3H). MS (ESI⁺): [M + H]⁺ 363.2. |

TABLE 3-continued

| # | Structure | Formula | MW | Purity | Notes |
|---|---|---|---|---|---|
| 77 | 2,4-dimethylbenzyl-NH-imidazolone-CH=benzothiazole | C₂₀H₁₈N₄OS | 362.45 | >98% | Yellow solid. ¹H NMR (400 MHz, DMSO-d₆, 300K) of major tautomer δ$_H$ 10.69 (br s, 1H, NH, D₂O exchanged), 9.36 (s, 1H), 8.88 (s, 1H), 8.22 (d, J = 7.9 Hz, 1H), 8.15 (br s, 1H, NH, D₂O exchanged), 8.03 (d, J = 8.0 Hz, 1H), 7.29-7.17 (m, 1H), 7.14-7.03 (m, 1H), 7.03-6.89 (m, 1H), 6.43 (s, 1H), 4.54 (s, 2H), 2.36 (s, 3H), 2.25 (s, 3H). MS (ESI⁺): [M + H]⁺ 363.2. |
| 78 | 2-CF₃-benzyl-NH-imidazolone-CH=benzothiazole | C₁₉H₁₃F₃N₄OS | 402.40 | >98% | Yellow solid. ¹H NMR (400 MHz, DMSO-d₆, 300K) of major tautomer δ$_H$ 10.96 (br s, 1H, NH, D₂O exchanged), 9.34 (s, 1H), 8.87 (s, 1H), 8.23 (br s, 1H, NH, D₂O exchanged), 8.10-7.93 (m, 2H), 7.77 (d, J = 7.8 Hz, 1H), 7.74-7.62 (m, 2H), 7.55-7.43 (m, 1H), 6.44 (s, 1H), 4.80 (s, 2H). MS (ESI⁺): [M + H]⁺ 403.1. |
| 79 | 2-CF₃O-benzyl-NH-imidazolone-CH=benzothiazole | C₁₉H₁₃F₃N₄O₂S | 418.39 | 98% | Yellow solid. ¹H NMR (400 MHz, DMSO-d₆, 300K) of major tautomer δ$_H$ 10.93 (br s, 1H, NH, D₂O exchanged), 9.36 (s, 1H), 8.83 (s, 1H), 8.23 (d, J = 8.5 Hz, 1H), 8.14 (br s, 1H, NH, D₂O exchanged), 8.02 (d, J = 8.5 Hz, 1H), 7.57-7.36 (m, 3H), 7.27 (d, J = 7.6 Hz, 1H), 6.45 (s, 1H), 4.63 (s, 2H). MS (ESI⁺): [M + H]⁺ 419.2. |
| 80 | cis-(±) 2-hydroxyindanyl-NH-imidazolone-CH=benzothiazole | C₂₀H₁₆N₄O₂S | 376.43 | >98% | Yellow solid. ¹H NMR (400 MHz, DMSO-d₆, 323K) of major tautomer δ$_H$ 10.25 (br s, 1H, NH, D₂O exchanged), 9.31 (s, 1H), 8.80 (s, 1H), 8.30 (d, J = 8.7 Hz, 1H), 8.01 (d, J = 8.6 Hz, 1H), 7.55-7.07 (m, 4H + NH, D₂O exchanged), 6.51 (s, 1H), 5.54-5.40 (m, 1H), 5.34 (br s, 1H, OH, D₂O exchanged), 4.68-4.57 (m, 1H), 3.19-3.13 (m, 1H), 2.96-2.84 (m, 1H). MS (ESI⁺): [M + H]⁺ 377.2. |

TABLE 3-continued

| | | | | |
|---|---|---|---|---|
| 81 | [structure: trans-(±) indanol-OH linked via NH to imidazolinone with benzothiazole methylene] | $C_{20}H_{16}N_4O_2S$ | 376.43 | >98% | Yellow solid. $^1$H NMR (400 MHz, DMSO-d$_6$, 373K) of major tautomer $\delta_H$ 10.18 (br s, 1H, NH, D$_2$O exchanged), 9.27 (s, 1H), 8.87-8.56 (m, 1H), 8.27-8.06 (m, 1H), 8.01 (d, J = 8.4 Hz, 1H), 7.67 (br s, 1H, NH, D$_2$O exchanged), 7.39-7.11 (m, 4H), 6.49 (s, 1H), 5.55-4.90 (m, 1H + OH, D$_2$O exchanged), 4.49 (q, J = 6.7 Hz, 1H), 3.26 (dd, J = 15.7, 7.1 Hz, 1H), 2.82 (dd, J = 15.7, 6.9 Hz, 1H). MS (ESI$^+$): [M + H]$^+$ 377.2. |
| 82 | [structure: (1R,2R) indanol-OH linked via NH to imidazolinone with benzothiazole methylene] | $C_{20}H_{16}N_4O_2S$ | 376.43 | >98% | Yellow solid. $^1$H NMR (400 MHz, DMSO-d$_6$, 373K) of major tautomer $\delta_H$ 10.18 (br s, 1H, NH, D$_2$O exchanged), 9.27 (s, 1H), 8.87-8.56 (m, 1H), 8.27-8.06 (m, 1H), 8.01 (d, J = 8.4 Hz, 1H), 7.67 (br s, 1H, NH, D$_2$O exchanged), 7.39-7.11 (m, 4H), 6.49 (s, 1H), 5.55-4.90 (m, 1H + OH, D$_2$O exchanged), 4.49 (q, J = 6.7 Hz, 1H), 3.26 (dd, J = 15.7, 7.1 Hz, 1H), 2.82 (dd, J = 15.7, 6.9 Hz, 1H). MS (ESI$^+$): [M + H]$^+$ 377.1. |
| 83 | [structure: (1S,2S) indanol-OH linked via NH to imidazolinone with benzothiazole methylene] | $C_{20}H_{16}N_4O_2S$ | 376.43 | >98% | Yellow solid. $^1$H NMR (400 MHz, DMSO-d$_6$, 373K) of major tautomer $\delta_H$ 10.18 (br s, 1H, NH, D$_2$O exchanged), 9.27 (s, 1H), 8.87-8.56 (m, 1H), 8.27-8.06 (m, 1H), 8.01 (d, J = 8.4 Hz, 1H), 7.67 (br s, 1H, NH, D$_2$O exchanged), 7.39-7.11 (m, 4H), 6.49 (s, 1H), 5.55-4.90 (m, 1H + OH, D$_2$O exchanged), 4.49 (q, J = 6.7 Hz, 1H), 3.26 (dd, J = 15.7, 7.1 Hz, 1H), 2.82 (dd, J = 15.7, 6.9 Hz, 1H). MS (ESI$^+$): [M + H]$^+$ 377.1. |

TABLE 3-continued

| | | | | |
|---|---|---|---|---|
| 84 | cis-(±) structure with methoxy indane and benzothiazole | C₂₁H₁₈N₄O₂S | 390.46 | >98% | Yellow solid. ¹H NMR (400 MHz, DMSO-d₆, 300K) of major tautomer δ_H 10.22 (br s, 1H, NH, D₂O exchanged), 9.34 (s, 1H), 8.82 (s, 1H), 8.44-8.23 (m, 1H), 8.02 (d, J = 8.6 Hz, 1H), 7.51 (br s, 1H, NH, D₂O exchanged), 7.44-7.15 (m, 4H), 6.51 (s, 1H), 5.77-5.54 (m, 1H), 4.39-4.19 (m, 1H), 3.35 (s, 3H), 3.19-3.01 (m, 2H). MS (ESI⁺): [M + H]⁺ 391.2. |
| 85 | trans-(±) structure with methoxy indane and benzothiazole | C₂₁H₁₈N₄O₂S | 390.46 | >98% | Yellow solid. ¹H NMR (400 MHz, DMSO-d₆, 300K) of major tautomer δ_H 10.73 (b r s, 1H, NH, D₂O exchanged), 9.35 (s, 1H), 8.82 (s, 1H), 8.23 (dd, J = 8.6, 1.6 Hz, 1H), 8.12 (br s, 1H, NH, D₂O exchanged), 8.01 (d, J = 8.6 Hz, 1H), 7.44-7.10 (m, 4H), 6.48 (s, 1H), 5.60-5.22 (m, 1H), 4.30-4.13 (m, 1H), 3.46 (s, 3H), 3.41-3.33 (m, 1H), 2.93-2.74 (m, 1H). MS (ESI⁺): [M + H]⁺ 391.2. |
| 86 | (S) MeOOC phenethyl structure with benzothiazole | C₂₁H₁₈N₄O₃S | 406.46 | >98% | Yellow solid. ¹H NMR (400 MHz, DMSO-d₆, 300K) of major tautomer δ_H 10.68 (br s, 1H, D₂O exchanged), 9.38 (s, 1H), 8.82 (s, 1H), 8.19 (d, J = 8.6 Hz, 1H), 8.03 (d, J = 8.5 Hz, 1H), 8.00 (br s, 1H, NH, D₂O exchanged), 7.39-7.18 (m, 5H), 6.47 (s, 1H), 4.82-4.66 (m, 1H), 3.68 (s, 3H), 3.26-3.09 (m, 2H). MS (ESI⁺): [M + H]⁺ 407.2. |
| 87 | (R) MeOOC phenethyl structure with benzothiazole | C₂₁H₁₈N₄O₃S | 406.46 | >98% | Yellow solid. ¹H NMR (400 MHz, DMSO-d₆, 300K) of major tautomer δ_H 10.68 (br s, 1H, D₂O exchanged), 9.38 (s, 1H), 8.82 (s, 1H), 8.19 (d, J = 8.6 Hz, 1H), 8.03 (d, J = 8.5 Hz, 1H), 8.00 (br s, 1H, NH, D₂O exchanged), 7.39-7.18 (m, 5H), 6.47 (s, 1H), 4.82-4.66 (m, 1H), 3.68 (s, 3H), 3.26-3.09 (m, 2H). MS (ESI⁺): [M + H]⁺ 407.1. |

TABLE 3-continued

| # | Structure | Formula | MW | Yield | Characterization |
|---|---|---|---|---|---|
| 88 | (benzothiazolylmethylene-imidazolone with NH-CH(Ph)-CH2F substituent, (±)) | $C_{19}H_{15}FN_4OS$ | 366.41 | 94% | Yellow solid. $^1$H NMR (400 MHz, DMSO-$d_6$, 300K) of major tautomer $\delta_H$ 10.76 (br s, 1H, NH, D$_2$O exchanged), 9.37 (s, 1H), 8.83 (s, 1H), 8.45 (br s, 1H, NH, D$_2$O exchanged), 8.19 (d, J = 8.6 Hz, 1H), 8.03 (d, J = 8.6 Hz, 1H), 7.58-7.16 (m, 5H), 6.44 (s, 1H), 5.58-5.22 (m, 1H), 4.96-4.52 (m, 2H). MS (ESI$^+$): [M + H]$^+$ 367.1. |
| 89 | (benzothiazolylmethylene-imidazolone with NH-CH(Ph)-CH2NH2 substituent, (±)) ·2HCl | $C_{19}H_{19}Cl_2N_5OS$ | 436.36 | >98% | Yellow solid. $^1$H NMR (400 MHz, DMSO-$d_6$, 323K) of major tautomer $\delta_H$ 9.38 (s, 1H), 8.88-8.73 (m, 1H), 8.28 (br s, 3H, NH, D$_2$O exchanged), 8.14-8.02 (m, 2H), 7.53 (d, J = 7.3 Hz, 2H), 7.44 (t, J = 7.6 Hz, 2H), 7.35 (t, J = 7.3 Hz, 1H), 6.55 (s, 1H), 5.53-5.35 (m, 1H), 4.45 (br s, 3H, NH, D$_2$O exchanged), 3.50-3.37 (m, 1H), 3.34-3.22 (m, 1H). MS (ESI$^+$): [M + H]$^+$ 364.1 (+2HCl). |
| 90 | (benzothiazolylmethylene-imidazolone with NH-CH(Ph)-CH2NHMe substituent, (±)) ·2HCl | $C_{20}H_{21}Cl_2N_5OS$ | 450.38 | 84% | Yellow solid. $^1$H NMR (400 MHz, DMSO-$d_6$ + D$_2$O, 300K) of major tautomer $\delta_H$ 9.39 (s, 1H), 8.82 (s, 1H), 8.18 (s, 1H), 8.06 (d, J = 8.3 Hz, 1H), 7.73-7.28 (m, 5H), 6.52 (s, 1H), 5.61-5.43 (m, 1H), 3.43-3.33 (m, 1H), 3.14-3.04 (m, 1H), 2.66 (s, 3H). MS (ESI$^+$): [M + H]$^+$ 378.2 (+2HCl). |
| 91 | (benzothiazolylmethylene-imidazolone with NH-CH(Ph)-CH2NMe2 substituent, (±)) | $C_{21}H_{21}N_5OS$ | 391.49 | >98% | Yellow solid. $^1$H NMR (400 MHz, DMSO-$d_6$, 323K) of major tautomer $\delta_H$ 10.56 (br s, 1H, NH, D$_2$O exchanged), 9.34 (s, 1H), 8.86-8.66 (m, 1H), 8.15-7.96 (m, 2H), 7.83 (br s, 1H, NH, D$_2$O exchanged), 7.51-7.21 (m, 5H), 6.40 (s, 1H), 5.17-4.80 (m, 1H), 2.81 (dd, J = 12.5, 9.4 Hz, 1H), 2.49-2.42 (m, 1H), 2.26 (s, 6H). MS (ESI$^+$): [M + H]$^+$ 392.1. |

TABLE 3-continued

| | | | | |
|---|---|---|---|---|
| 92 | 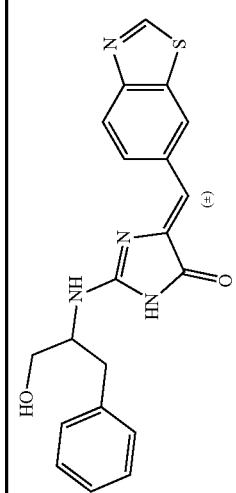 | C<sub>20</sub>H<sub>18</sub>N<sub>4</sub>O<sub>2</sub>S | 378.45 | >98% | Yellow solid. $^1$H NMR (400 MHz, DMSO-d$_6$, 300K) of major tautomer δ$_H$ 10.45 (br s, 1H, NH, D$_2$O exchanged), 9.38 (s, 1H), 9.04-8.83 (m, 1H), 8.31-8.10 (m, 1H), 8.05 (d, J = 8.4 Hz, 1H), 7.46 (br s, 1H, NH, D$_2$O exchanged), 7.42-7.26 (m, 4H), 7.26-7.10 (m, 1H), 6.41 (s, 1H), 5.33-4.75 (m, 1H, OH, D$_2$O exchanged), 4.30-3.84 (m, 1H), 3.68-3.39 (m, 2H), 3.11-2.70 (m, 2H). MS (ESI$^+$): [M + H]$^+$ 379.2. |
| 93 | 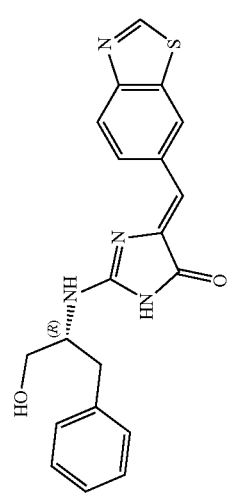 | C<sub>20</sub>H<sub>18</sub>N<sub>4</sub>O<sub>2</sub>S | 378.45 | >98% | Yellow solid. $^1$H NMR (400 MHz, DMSO-d$_6$, 300K) of major tautomer δ$_H$ 10.45 (br s, 1H, NH, D$_2$O exchanged), 9.38 (s, 1H), 9.04-8.83 (m, 1H), 8.31-8.10 (m, 1H), 8.05 (d, J = 8.4 Hz, 1H), 7.46 (br s, 1H, NH, D$_2$O exchanged), 7.42-7.26 (m, 4H), 7.26-7.10 (m, 1H), 6.41 (s, 1H), 5.33-4.75 (m, 1H, OH, D$_2$O exchanged), 4.30-3.84 (m, 1H), 3.68-3.39 (m, 2H), 3.11-2.70 (m, 2H). MS (ESI$^+$): [M + H]$^+$ 379.2. |
| 94 | 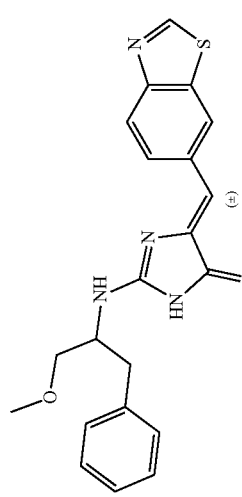 | C<sub>21</sub>H<sub>20</sub>N<sub>4</sub>O<sub>2</sub>S | 392.48 | 96% | Yellow solid. $^1$H NMR (400 MHz, DMSO-d$_6$, 373K) of major tautomer δ$_H$ 10.09 (br s, 1H, NH, D$_2$O exchanged), 9.29 (s, 1H), 8.96-8.72 (m, 1H), 8.33-8.07 (m, 1H), 8.03 (d, J = 8.0 Hz, 1H), 7.39-7.26 (m, 4H), 7.25-7.18 (m, 1H), 7.12 (br s, 1H, NH, D$_2$O exchanged), 6.44 (s, 1H), 4.38-4.26 (m, 1H), 3.57-3.44 (m, 2H), 3.35 (s, 3H), 3.05-2.90 (m, 2H). MS (ESI$^+$): [M + H]$^+$ 393.2. |
| 95 | 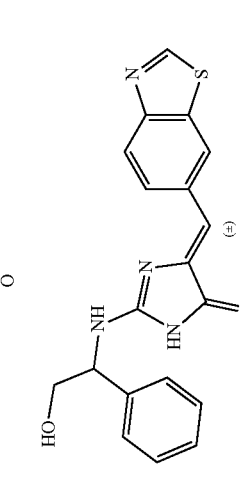 | C<sub>19</sub>H<sub>16</sub>N<sub>4</sub>O<sub>2</sub>S | 364.42 | >98% | Yellow solid. $^1$H NMR (400 MHz, DMSO-d$_6$, 323K) of major tautomer δ$_H$ 10.50 (br s, 1H, NH, D$_2$O exchanged), 9.34 (s, 1H), 9.00-8.63 (m, 1H), 8.25-8.07 (m, 1H), 8.07-7.97 (m, 1H), 7.92 (br s, 1H, NH, D$_2$O exchanged), 7.51-7.43 (m, 2H), 7.37 (t, J = 7.6 Hz, 2H), 7.26 (t, J = 7.3 Hz, 1H), 6.40 (s, 1H), 5.25-4.77 (m, 1H + OH, D$_2$O exchanged), 3.75 (d, J = 6.1 Hz, 2H). MS (ESI$^+$): [M + H]$^+$ 365.2. |

TABLE 3-continued

| | Structure | Formula | MW | Purity | Characterization |
|---|---|---|---|---|---|
| 96 | (R)-HOCH2CH(Ph)NH- benzothiazolylmethylene imidazolone | C19H16N4O2S | 364.42 | >98% | Yellow solid. $^1$H NMR (400 MHz, DMSO-d$_6$, 323K) of major tautomer $\delta_H$ 10.50 (br s, 1H, NH, D$_2$O exchanged), 9.34 (s, 1H), 9.00-8.63 (m, 1H), 8.25-8.07 (m, 1H, NH, D$_2$O exchanged), 8.07-7.97 (m, 1H), 7.92 (br ss, 1H, NH, D$_2$O exchanged), 7.51-7.43 (m, 2H), 7.37 (t, J = 7.6 Hz, 2H), 7.26 (t, J = 7.3 Hz, 1H), 6.40 (s, 1H), 5.25-4.77 (m, 1H + D$_2$O exchanged), 3.75 (d, J = 6.1 Hz, 2H). MS (ESI$^+$): [M + H]$^+$ 365.2. |
| 97 | (S)-HOCH2CH(Ph)NH- benzothiazolylmethylene imidazolone | C19H16N4O2S | 364.42 | >98% | Yellow solid. $^1$H NMR (400 MHz, DMSO-d$_6$, 323K) of major tautomer $\delta_H$ 10.50 (br s, 1H, NH, D$_2$O exchanged), 9.34 (s, 1H), 9.00-8.63 (m, 1H), 8.25-8.07 (m, 1H, NH, D$_2$O exchanged), 8.07-7.97 (m, 1H), 7.92 (br s, 1H, NH, D$_2$O exchanged), 7.51-7.43 (m, 2H), 7.37 (t, J = 7.6 Hz, 2H), 7.26 (t, J = 7.3 Hz, 1H), 6.40 (s, 1H), 5.25-4.77 (m, 1H + OH, D$_2$O exchanged), 3.75 (d, J = 6.1 Hz, 2H). MS (ESI$^+$): [M + H]$^+$ 365.2. |
| 98 | MeO-CH2CH(Ph)NH- benzothiazolylmethylene imidazolone (±) | C20H18N4O2S | 378.45 | >98% | Yellow solid. $^1$H NMR (400 MHz, DMSO-d$_6$, 323K) of major tautomer $\delta_H$ 10.55 (br s, 1H, NH, D$_2$O exchanged), 9.34 (s, 1H), 8.82 (s, 1H), 8.29-7.92 (m, 2H + NH, D$_2$O exchanged), 7.48 (d, J = 7.6 Hz, 2H), 7.39 (t, J = 7.5 Hz, 2H), 7.28 (t, J = 7.3 Hz, 1H), 6.41 (s, 1H), 5.35-5.11 (m, 1H), 3.88-3.58 (m, 2H), 3.34 (s, 3H). MS (ESI$^+$): [M + H]$^+$ 379.2. |
| 99 | HO-CH(Ph)CH2NH- benzothiazolylmethylene imidazolone (±) | C19H16N4O2S | 364.42 | >98% | Yellow solid. $^1$H NMR (400 MHz, DMSO-d$_6$, 300K) of major tautomer $\delta_H$ 10.57 (br s, 1H, NH, D$_2$O exchanged), 9.37 (s, 1H), 9.05-8.80 (m, 1H), 8.30-8.13 (m, 1H), 8.05 (d, J = 8.5 Hz, 1H), 7.57 (br s, 1H, NH, D$_2$O exchanged), 7.53-7.23 (m, 5H), 6.44 (s, 1H), 5.69 (br s, 1H, OH, D$_2$O exchanged), 5.19-4.67 (m, 1H), 3.85-3.50 (m, 1H), 3.48-3.33 (m, 1H). MS (ESI$^+$): [M + H]$^+$ 365.2. |

TABLE 3-continued

| | Structure | Formula | MW | Yield | Characterization |
|---|---|---|---|---|---|
| 100 | 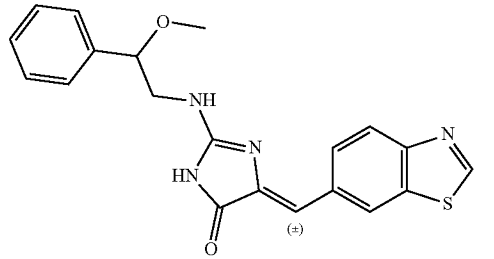 [SMILES: COC(CNC1=N/C(=C\c2ccc3ncsc3c2)C(=O)N1)c1ccccc1] | C₂₀H₁₈N₄O₂S | 378.45 | 98% | Yellow solid. ¹H NMR (400 MHz, DMSO-d₆, 300K) of major tautomer δ_H 10.57 (br s, 1H, NH, D₂O exchanged), 9.37 (s, 1H), 8.94 (s, 1H), 8.20 (dd, J = 8.6, 1.6 Hz, 1H), 8.04 (d, J = 8.5 Hz, 1H), 7.67 (br s, 1H, NH, D₂O exchanged), 7.53-7.26 (m, 5H), 6.45 (s, 1H), 4.73-4.41 (m, 1H), 3.80-3.42 (m, 2H), 3.21 (s, 3H). MS (ESI⁺): [M + H]⁺ 379.2. |
| 101 | 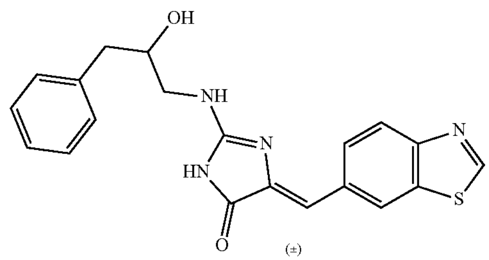 [SMILES: O=C1NC(NCC(O)Cc2ccccc2)=N/C1=C\c1ccc2ncsc2c1] | C₂₀H₁₈N₄O₂S | 378.45 | 98% | Yellow solid. ¹H NMR (400 MHz, DMSO-d₆, 373K) of major tautomer δ_H 10.13 (br s, 1H, NH, D₂O exchanged), 9.29 (s, 1H), 8.75-8.59 (m, 1H), 8.21-8.05 (m, 1H), 8.01 (d, J = 8.1 Hz, 1H), 7.35-7.15 (m, 5H), 7.14-6.92 (br s, 1H, NH, D₂O exchanged), 6.44 (s, 1H), 5.12-4.60 (m, 1H, OH, D₂O exchanged), 4.12-3.86 (m, 1H), 3.54 (dd, J = 13.4, 3.8 Hz, 1H), 3.34 (dd, J = 13.3, 7.0 Hz, 1H), 2.89-2.72 (m, 2H). MS (ESI⁺): [M + H]⁺ 379.2. |
| 102 | 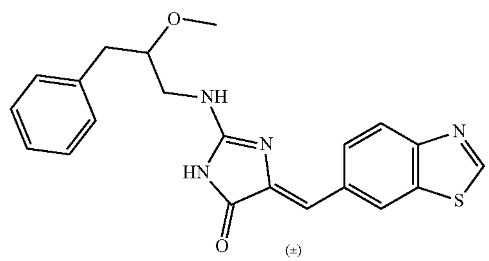 [SMILES: COC(CNC1=N/C(=C\c2ccc3ncsc3c2)C(=O)N1)Cc1ccccc1] | C₂₁H₂₀N₄O₂S | 392.48 | 96% | Yellow solid. ¹H NMR (400 MHz, DMSO-d₆, 323K) of major tautomer δ_H 10.44 (br, s, 1H, NH, D₂O exchanged), 9.34 (s, 1H), 8.94-8.73 (m, 1H), 8.36-8.10 (m, 1H), 8.00 (d, J = 8.6 Hz, 1H), 7.41 (br s, 1H, NH, D₂O exchanged), 7.36-7.17 (m, 5H), 6.43 (s, 1H), 3.77-3.66 (m, 1H), 3.60-3.41 (m, 2H), 3.35 (s, 3H), 2.91-2.78 (m, 2H). MS (ESI⁺): [M + H]⁺ 393.2. |
| 103 | 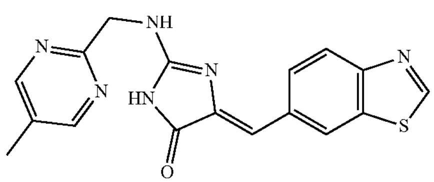 [SMILES: Cc1cnc(CNC2=N/C(=C\c3ccc4ncsc4c3)C(=O)N2)nc1] | C₁₇H₁₄N₆OS | 350.41 | 97% | Yellow solid. ¹H NMR (500 MHz, Methanol-d₄, 300K) of major tautomer δ_H 9.24 (s, 1H), 8.89-8.56 (m, 2H), 8.52 (s, 1H), 8.22-7.78 (m, 2H), 6.65 (s, 1H), 4.81 (s, 2H), 2.54 (s, 3H). MS (ESI⁺): [M + H]⁺ 351.2. |

TABLE 3-continued

| 104 | ![structure] | C₁₇H₁₃N₅OS | 335.39 | >98% | Yellow solid. ¹H NMR (500 MHz, DMSO-d₆, 300K) of major tautomer δ_H 10.84 (br s, 1H, NH, D₂O exchanged), 9.35 (s, 1H), 8.79 (s, 1H), 8.57 (d, J = 4.9 Hz, 1H), 8.21 (d, J = 8.6 Hz, 1H), 8.12 (br s, 1H, NH, D₂O exchanged), 8.01 (d, J = 8.5 Hz, 1H), 7.81 (td, J = 7.7, 1.9 Hz, 1H), 7.51-7.43 (m, 1H), 7.34-7.26 (m, 1H), 6.44 (s, 1H), 4.72-4.48 (m, 2H). MS (ESI⁺): [M + H]⁺ 336.2. |
| --- | --- | --- | --- | --- | --- |
| 105 | ![structure] | C₁₇H₁₃N₅OS | 335.39 | >98% | Yellow solid. ¹H NMR (400 MHz, DMSO-d₆, 300K) of major tautomer δ_H 10.95 (br s, 1H, NH, D₂O exchanged), 9.35 (s, 1H), 8.91-8.75 (m, 1H), 8.73-8.57 (m, 1H), 8.47 (dd, J = 4.8, 1.7 Hz, 1H), 8.30-8.20 (m, 1H), 8.15 (br s, 1H, NH, D₂O exchanged), 8.03 (d, J = 8.5 Hz, 1H), 7.89-7.78 (m, 1H), 7.39 (dd, J = 7.8, 4.8 Hz, 1H), 6.45 (s, 1H), 4.72-4.48 (m, 2H). MS (ESI⁺): [M + H]⁺ 336.2. |
| 106 | ![structure] | C₁₇H₁₃N₅OS | 335.39 | >98% | Yellow solid. ¹H NMR (400 MHz, DMSO-d₆, 300K) of major tautomer δ_H 11.04 (br s, 1H, NH, D₂O exchanged), 9.36 (s, 1H), 8.79 (s, 1H), 8.55 (d, J = 5.9 Hz, 2H), 8.20 (d, J = 8.4 Hz, 1H), 8.15 (br s, 1H, NH, D₂O exchanged), 8.02 (d, J = 8.6 Hz, 1H), 7.41 (d, J = 4.6 Hz, 2H), 6.45 (s, 1H), 4.72-4.54 (m, 2H). MS (ESI⁺): [M + H]⁺ 336.2. |
| 107 | ![structure] | C₁₇H₁₄N₄O₂S | 338.39 | >98% | Yellow solid. ¹H NMR (400 MHz, DMSO-d₆, 300K) of major tautomer δ_H 10.77 (br s, 1H, NH, D₂O exchanged), 9.36 (s, 1H), 8.86 (s, 1H), 8.27 (d, J = 8.6 Hz, 1H), 8.04 (d, J = 8.6 Hz, 1H), 7.99 (br s, 1H, NH, D₂O exchanged), 6.45 (s, 1H), 6.26 (d, J = 3.1 Hz, 1H), 6.02 (dd, J = 3.0, 1.3 Hz, 1H), 4.53 (s, 2H), 2.25 (s, 3H). MS (ESI⁺): [M + H]⁺ 339.2. |

| | | | | |
|---|---|---|---|---|
| 108 | 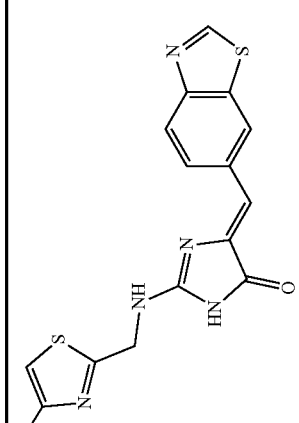 | $C_{16}H_{13}N_5OS_2$ | 355.43 | >98% | Yellow solid. $^1$H NMR (500 MHz, DMSO-d$_6$, 300K) of major tautomer δ$_H$ 11.01 (br s, 1H, NH, D$_2$O exchanged), 9.36 (s, 1H), 8.88 (s, 1H), 8.33 (br s, 1H, NH, D$_2$O exchanged), 8.22 (d, J = 8.5 Hz, 1H), 8.02 (d, J = 8.6 Hz, 1H), 7.18 (s, 1H), 6.49 (s, 1H), 4.84 (s, 2H), 2.36 (s, 3H). MS (ESI$^+$): [M + H]$^+$ 356.2. |
| 109 | 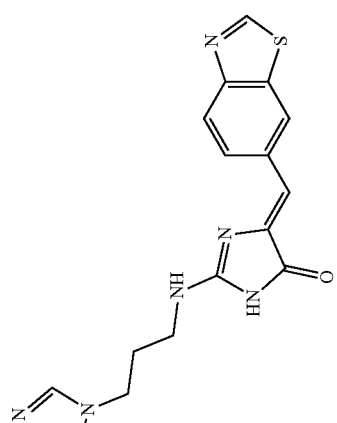 | $C_{17}H_{16}N_6OS$ | 352.42 | >98% | Yellow solid. $^1$H NMR (500 MHz, DMSO-d$_6$, 300K) of major tautomer δ$_H$ 10.86 (br s, 1H, NH, D$_2$O exchanged), 9.36 (s, 1H), 8.86-8.71 (m, 1H), 8.39-8.20 (m, 1H), 8.05 (d, J = 8.6 Hz, 1H), 7.74 (s, 1H), 7.65 (br s, 1H, NH, D$_2$O exchanged), 7.26 (s, 1H), 6.95 (s, 1H), 6.42 (s, 1H), 4.08 (t, J = 7.0 Hz, 2H), 3.45-3.28 (m, 2H), 2.12-1.97 (m, 2H). MS (ESI$^+$): [M + H]$^+$ 353.2. |
| 110 | 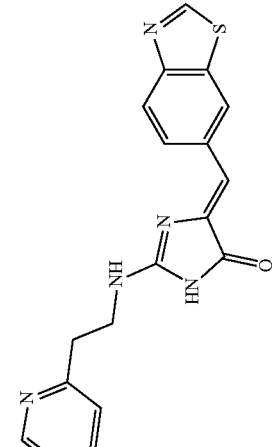 | $C_{18}H_{15}N_5OS$ | 349.41 | 95% | Yellow solid. $^1$H NMR (500 MHz, DMSO-d$_6$, 300K) of major tautomer δ$_H$ 10.67 (br s, 1H, NH, D$_2$O exchanged), 9.36 (s, 1H), 8.87 (s, 1H), 8.54 (d, J = 4.9 Hz, 1H), 8.30-8.18 (m, 1H), 8.04 (d, J = 8.6 Hz, 1H), 7.75 (td, J = 7.6, 1.9 Hz, 1H), 7.53 (br s, 1H, NH, D$_2$O exchanged verifier), 7.35 (d, J = 7.8 Hz, 1H), 7.27-7.22 (m, 1H), 6.41 (s, 1H), 3.85-3.68 (m, 2H), 3.16-3.03 (m, 2H). MS (ESI$^+$): [M + H]$^+$ 350.1. |

TABLE 3-continued

| | | | | |
|---|---|---|---|---|
| 111 | 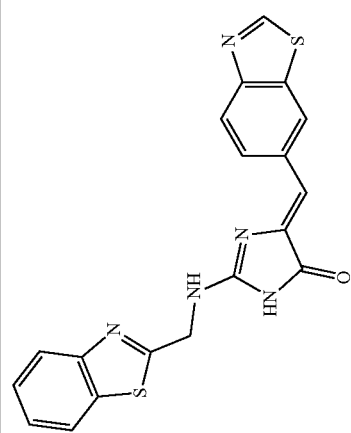 | $C_{19}H_{13}N_5OS_2$ | 391.47 | 98% | Yellow solid. $^1$H NMR (500 MHz, DMSO-d$_6$, 300K) of major tautomer $\delta_H$ 11.13 (br s, 1H, NH, D$_2$O exchanged), 9.35 (s, 1H), 8.86 (s, 1H), 8.47 (br s, 1H, NH, D$_2$O exchanged), 8.19 (d, J = 8.5 Hz, 1H), 8.06 (d, J = 8.1 Hz, 1H), 8.00 (t, J = 9.0 Hz, 2H), 7.51 (t, J = 7.6 Hz, 1H), 7.41 (t, J = 7.6 Hz, 1H), 6.50 (s, 1H), 5.12-4.91 (m, 2H). MS (ESI$^+$): [M + H]$^+$ 392.2. |
| 112 | 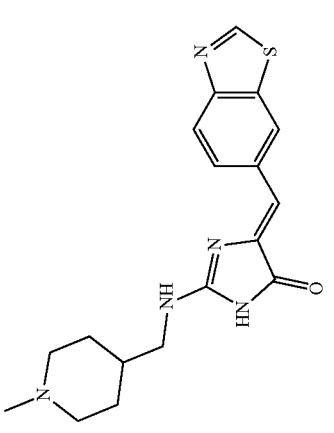 | $C_{18}H_{21}N_5OS$ | 355.46 | 92% | Yellow solid. $^1$H NMR (500 MHz, Methanol-d$_4$, 300K) of major tautomer $\delta_H$ 9.24 (s, 1H), 8.81-7.74 (m, 3H), 6.65 (s, 1H), 3.59-3.36 (m, 2H), 3.28-3.14 (m 2H), 2.73-2.42 (m, 5H), 2.09-1.76 (m, 3H), 1.63-1.38 (m, 2H). MS (ESI$^+$): [M + H]$^+$ 356.2. |
| 113 | 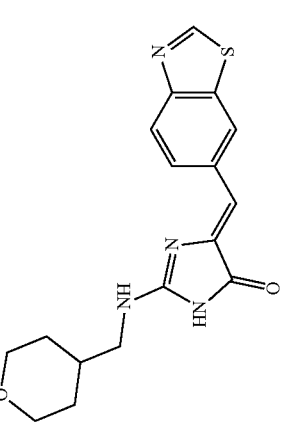 | $C_{17}H_{18}N_4O_2S$ | 342.42 | 97% | Yellow solid. $^1$H NMR (500 MHz, DMSO-d$_6$, 300K) of major tautomer $\delta_H$ 10.64 (br s, 1H, NH, D$_2$O exchanged), 9.35 (s, 1H), 8.83 (s, 1H), 8.36-8.18 (m, 1H), 8.03 (d, J = 8.5 Hz, 1H), 7.56 (br s, 1H, NH, D$_2$O exchanged), 6.40 (s, 1H), 3.97-3.78 (m, 2H), 3.31-3.11 (m, 3H), 2.03-1.74 (m, 1H), 1.63 (d, J = 13.1 Hz, 2H), 1.43-1.10 (m, 3H). MS (ESI$^+$): [M + H]$^+$ 343.3. |

TABLE 3-continued

| | | | | |
|---|---|---|---|---|
| 114 | [structure] | $C_{22}H_{27}N_5O_3S$ | 441.55 | >98% | Yellow solid. $^1$H NMR (400 MHz, DMSO-$d_6$, 300K) of major tautomer $\delta_H$ 10.64 (br s, 1H, NH, D$_2$O exchanged), 9.35 (s, 1H), 8.83 (s, 1H), 8.38-8.17 (m, 1H), 8.02 (d, J = 8.5 Hz, 1H), 7.56 (br s, 1H, NH, D$_2$O exchanged), 6.40 (s, 1H), 4.15-3.81 (m, 2H), 3.31-3.01 (m, 2H), 2.90-2.57 (m, 2H), 1.96-1.60 (m, 3H), 1.39 (s, 9H), 1.19-0.94 (m, 2H).. MS (ESI$^+$): [M + H]$^+$ 442.3. |
| 115 | [structure] | $C_{20}H_{23}N_5OS$ | 381.5 | 90% | Yellow solid. $^1$H NMR (400 MHz, DMSO-$d_6$, 300K) of major tautomer $\delta_H$ 10.22 (br s, 1H, NH, D$_2$O exchanged), 9.33 (s, 1H), 8.93-8.64 (m, 1H), 8.33-8.09 (m, 1H + NH, D$_2$O exchanged), 8.02 (d, J = 8.1 Hz, 1H), 6.39 (s, 1H), 4.45-4.14 (m, 1H), 2.33-2.16 (m, 4H), 2.11 (s, 3H), 1.95-1.74 (m, 3H), 1.65-1.45 (m, 5H). MS (ESI$^+$): [M + H]$^+$ 382.3. |
| 116 | [structure] | $C_{18}H_{13}FN_4OS$ | 352.39 | >98% | Yellow solid. $^1$H NMR (500 MHz, DMSO-$d_6$, 300K) of major tautomer $\delta_H$ 10.89 (s, 1H, NH, D$_2$O exchanged), 10.08 (br s, 1H, NH, D$_2$O exchanged), 9.42 (s, 1H), 8.95 (s, 1H), 8.25 (d, J = 7.0 Hz, 1H), 8.09 (d, J = 8.5 Hz, 1H), 7.92 (d, J = 12.9 Hz, 1H), 7.38 (d, J = 8.2 Hz, 1H), 7.29 (t, J = 8.5 Hz, 1H), 6.68 (s, 1H), 2.23 (s, 3H). MS (ESI$^+$): [M + H]$^+$ 353.1. |
| 117 | [structure] | $C_{17}H_{11}FN_4OS$ | 338.37 | >98% | Yellow solid. $^1$H NMR (500 MHz, DMSO-$d_6$, 300K) of major tautomer $\delta_H$ 10.87 (br s, 1H, NH, D$_2$O exchanged), 9.97 (br s, 1H, NH, D$_2$O exchanged), 9.41 (s, 1H), 8.81 (s, 1H), 8.36 (d, J = 8.9 Hz, 1H), 8.10 (d, J = 8.6 Hz, 1H), 7.91-7.76 (m, 2H), 7.26 (t, J = 8.8 Hz, 2H), 6.65 (s, 1H). MS (ESI$^+$): [M + H]$^+$ 339.1. |

TABLE 3-continued

| # | Structure | Formula | MW | Purity | Characterization |
|---|---|---|---|---|---|
| 118 | (4-hexylphenyl-NH imidazolinone benzothiazole) | C₂₃H₂₄N₄OS | 404.53 | >98% | Yellow solid. ¹H NMR (400 MHz, DMSO-d₆, 300K) of major tautomer δ_H 10.76 (br s, 1H, NH, D₂O exchanged), 9.85 (br s, 1H, NH, D₂O exchanged), 9.41 (s, 1H), 8.85 (s, 1H), 8.49-8.24 (m, 1H), 8.22-8.02 (m, 1H), 7.90-7.54 (m, 2H), 7.37-7.11 (m, 2H), 6.63 (s, 1H), 2.67-2.53 (m, 2H), 1.72-1.47 (m, 2H), 1.29 (s, 6H), 0.87 (s, 3H). MS (ESI⁺): [M + H]⁺ 405.3. |
| 119 | (4-(4-methylpiperazin-1-yl)phenyl-NH imidazolinone benzothiazole) | C₂₂H₂₂N₆OS | 418.52 | 97% | Yellow solid. ¹H NMR (400 MHz, DMSO-d₆, 300K) of major tautomer δ_H 10.73 (br s, 1H, NH, D₂O exchanged), 9.73 (br s, 1H, NH, D₂O exchanged), 9.39 (s, 1H), 8.88-8.77 (m, 1H), 8.43-8.30 (m, 1H), 8.09 (d, J = 8.5 Hz, 1H), 7.73-7.53 (m, 2H), 6.99 (d, J = 8.5 Hz, 2H), 6.57 (s, 1H), 3.18-3.10 (m, 4H), 2.48-2.44 (m, 4H), 2.23 (s, 3H). MS (ESI⁺): [M + H]⁺ 419.2. |
| 120 | (3-difluoromethoxyphenyl-NH imidazolinone benzothiazole) | C₁₈H₁₂F₂N₄O₂S | 386.37 | 96% | Yellow solid. ¹H NMR (500 MHz, DMSO-d₆, 300K) of major tautomer δ_H 10.87 (br s, 1H, NH, D₂O exchanged), 10.19 (br s, 1H, NH, D₂O exchanged), 9.42 (s, 1H), 8.88 (s, 1H), 8.37-8.27 (m, 1H), 8.17 (s, 1H), 8.06 (d, J = 8.5 Hz, 1H), 7.49-7.30 (m, 3H), 6.98-6.86 (m, 1H), 6.71 (s, 1H). MS (ESI⁺): [M + H]⁺ 387.1. |
| 121 | (1-acetyl-indolin-6-yl-NH imidazolinone benzothiazole) | C₂₁H₁₇N₅O₂S | 403.47 | 98% | Yellow solid. ¹H NMR (400 MHz, DMSO-d₆, 300K) of major tautomer δ_H 10.57 (br s, 1H, NH, D₂O exchanged), 9.89 (br s, 1H, NH, D₂O exchanged), 9.39 (s, 1H), 9.27-9.00 (m, 2H), 8.32-8.00 (m, 2H), 7.36-7.06 (m, 2H), 6.64 (s, 1H), 4.31-4.04 (m, 2H), 3.20-3.06 (m, 2H), 2.31 (s, 3H). MS (ESI⁺): [M + H]⁺ 404.2. |

TABLE 3-continued

| | Structure | Formula | MW | Yield | Notes |
|---|---|---|---|---|---|
| 122 | (3-CF3-phenyl)NH-imidazolone-benzothiazole | C18H11F3N4OS | 388.37 | 95% | Yellow solid. 1H NMR (500 MHz, DMSO-d6, 300K) of major tautomer δH 11.02 (br s, 1H, NH, D2O exchanged), 10.34 (br s, 1H, NH, D2O exchanged), 9.42 (s, 1H), 8.96 (s, 1H), 8.85 (s, 1H), 8.24 (d, J = 8.5 Hz, 1H), 8.05 (d, J = 8.5 Hz, 1H), 7.75 (d, J = 8.3 Hz, 1H), 7.62 (t, J = 7.8 Hz, 1H), 7.46 (d, J = 7.6 Hz, 1H), 6.74 (s, 1H). MS (ESI+): [M + H]+ 389.1. |
| 123 | (indanyl)NH-imidazolone-benzothiazole | C20H16N4OS | 360.44 | >98% | Yellow solid. 1H NMR (500 MHz, DMSO-d6, 300K) of major tautomer δH 10.72 (br s, 1H, NH, D2O exchanged), 9.83 (br s, 1H, NH, D2O exchanged), 9.40 (s, 1H), 9.03 (s, 1H), 8.21 (d, J = 8.5 Hz, 1H), 8.08 (d, J = 8.5 Hz, 1H), 7.93 (s, 1H), 7.38 (d, J = 8.1 Hz, 1H), 7.23 (d, J = 8.1 Hz, 1H), 6.62 (s, 1H), 2.96 (t, J = 7.3 Hz, 2H), 2.86 (t, J = 7.3 Hz, 2H), 2.08 (p, J = 7.4 Hz, 2H). MS (ESI+): [M + H]+ 361.1. |
| 124 | (4-morpholinophenyl)NH-imidazolone-benzothiazole | C21H19N5O2S | 405.48 | >98% | Yellow solid. 1H NMR (500 MHz, DMSO-d6, 300K) of major tautomer δH 10.72 (br s, 1H, NH, D2O exchanged), 9.73 (br s, 1H, NH, D2O exchanged), 9.39 (s, 1H), 8.83 (s, 1H), 8.35 (d, J = 8.7 Hz, 1H), 8.09 (d, J = 8.5 Hz, 1H), 7.66 (d, J = 8.2 Hz, 2H), 7.01 (d, J = 8.6 Hz, 2H), 6.58 (s, 1H), 3.81-3.72 (m, 4H), 3.15-3.06 (m, 4H). MS (ESI+): [M + H]+ 406.2. |
| 125 | (1-methylindazol-7-yl)NH-imidazolone-benzothiazole | C19H14N6OS | 374.42 | 97% | Yellow solid. 1H NMR (500 MHz, DMSO-d6, 300K) of major tautomer δH 11.21 (br s, 1H, NH, D2O exchanged), 10.40 (br s, 1H, NH, D2O exchanged), 9.39 (s, 1H), 8.74-8.59 (m, 1H), 8.16-7.91 (m, 3H), 7.72-7.41 (m, 1H), 7.27-6.88 (m, 2H), 6.50 (s, 1H), 4.19 (s, 3H). MS (ESI+): [M + H]+ 375.1. |

TABLE 3-continued

| # | Structure | Formula | MW | Purity | Notes |
|---|---|---|---|---|---|
| 126 | (pyrimidin-2-ylamino benzothiazole methylene imidazolone) | C₁₅H₁₀N₆OS | 322.35 | 98% | Yellow solid. ¹H NMR (400 MHz, DMSO-d₆, 300K) of major tautomer δ_H 11.56 (br s, 1H, NH, D₂O exchanged), 11.37 (br s, 1H, NH, D₂O exchanged), 9.44 (s, 1H), 9.12-8.84 (m, 1H), 8.65 (d, J = 4.9 Hz, 2H), 8.42-8.25 (m, 1H), 8.12 (d, J = 8.5 Hz, 1H), 7.38-7.06 (m, 1H), 6.81 (s, 1H). MS (ESI⁺): [M + H]⁺ 323.2. |
| 127 | (pyridin-2-ylamino benzothiazole methylene imidazolone) | C₁₆H₁₁N₅OS | 321.36 | 96% | Yellow solid. ¹H NMR (400 MHz, DMSO-d₆, 300K) of major tautomer δ_H 11.20 (br s, 1H, NH, D₂O exchanged), 10.97 (br s, 1H, NH, D₂O exchanged), 9.43 (s, 1H), 8.88 (s, 1H), 8.49-8.26 (m, 2H), 8.12 (d, J = 8.6 Hz, 1H), 7.84 (t, J = 8.0 Hz, 1H), 7.66-7.33 (m, 1H), 7.23-6.98 (m, 1H), 6.76 (s, 1H). MS (ESI⁺): [M + H]⁺ 322.2. |
| 128 | (1-methylpyrazol-3-ylamino benzothiazole methylene imidazolone) | C₁₅H₁₂N₆OS | 324.37 | >98% | Pale yellow solid. ¹H NMR (400 MHz, DMSO-d₆, 300K) of major tautomer δ_H 10.58 (br s, 2H, NH, D₂O exchanged), 9.40 (s, 1H), 8.81 (s, 1H), 8.48-8.03 (m, 2H), 7.80-7.63 (m, 1H), 6.61 (s, 1H), 6.49-6.23 (m, 1H), 3.80 (s, 3H). MS (ESI⁺): [M + H]⁺ 325.1. |
| 129 | (2-methoxy-6-methylpyridin-3-ylamino benzothiazole methylene imidazolone) | C₁₈H₁₇N₅O₂S | 365.41 | 98% | Yellow solid. ¹H NMR (500 MHz, DMSO-d₆, 300K) of major tautomer δ_H 10.30 (br s, 1H, NH, D₂O exchanged), 9.42 (s, 1H), 9.06 (br s, 1H, NH, D₂O exchanged), 8.90-8.72 (m, 1H), 8.72-8.54 (m, 1H), 8.44-8.23 (m, 1H), 8.11 (d, J = 8.5 Hz, 1H), 6.99 (d, J = 7.7 Hz, 1H), 6.69 (s, 1H), 3.99 (s, 3H), 2.41 (s, 3H). MS (ESI⁺): [M + H]⁺ 366.2. |

TABLE 3-continued

| | | | | |
|---|---|---|---|---|
| 130 | [structure] | $C_{15}H_{10}N_6OS$ | 322.35 | >98% | Yellow solid. $^1$H NMR (500 MHz, DMSO-d$_6$, 300K) of major tautomer δ$_H$ 11.30 (br s, 1H, NH, D$_2$O exchanged), 10.37 (br s, 1H, NH, D$_2$O exchanged), 9.42 (s, 1H), 9.41-9.02 (m, 2H), 8.92 (s, 1H), 8.88-8.69 (m, 1H), 8.45-8.17 (m, 1H), 8.10 (d, J = 8.5 Hz, 1H), 6.93-6.49 (m, 1H). MS (ESI$^+$): [M + H]$^+$ 323.1. |
| 131 | [structure] | $C_{16}H_{11}N_5OS$ | 321.36 | >98% | Yellow solid. $^1$H NMR (400 MHz, DMSO-d$_6$, 300K) of major tautomer δ$_H$ 11.03 (br s, 1H, NH, D$_2$O exchanged), 10.16 (br s, 1H, NH, D$_2$O exchanged), 9.42 (s, 1H), 9.06-8.90 (m, 1H), 8.87-8.78 (m, 1H), 8.44-8.21 (m, 3H), 8.11 (d, J = 8.5 Hz, 1H), 7.49-7.41 (m, 1H), 6.70 (s, 1H). MS (ESI$^+$): [M + H]$^+$ 322.2. |
| 132 | [structure] | $C_{13}H_8N_6OS_2$ | 328.37 | 95% | Yellow solid. $^1$H NMR (400 MHz, DMSO-d$_6$, 300K) of major tautomer δ$_H$ 12.52 (br s, 1H, NH, D$_2$O exchanged), 11.38 (br s, 1H, NH, D$_2$O exchanged), 9.44 (s, 1H), 9.18-9.03 (m 1H), 8.87-8.71 (m, 1H), 8.53-8.24 (m, 1H), 8.15 (d, J = 8.4 Hz, 1H), 6.76 (s, 1H). MS (ESI$^+$): [M + H]$^+$ 329.2. |
| 133 | [structure] | $C_{21}H_{21}N_7OS$ | 419.51 | 95% | Yellow solid. $^1$H NMR (400 MHz, DMSO-d$_6$, 300K) of major tautomer δ$_H$ 11.02 (br s, 1H, NH, D$_2$O exchanged), 10.78 (br s, 1H, NH, D$_2$O exchanged), 9.42 (s, 1H), 8.99-8.65 (m, 1H), 8.47-8.22 (m, 1H), 8.20-8.06 (m, 1H), 8.01 (s, 1H), 7.60-7.49 (m, 1H), 7.48-7.22 (m, 1H), 6.67 (s, 1H), 3.23-3.06 (m, 4H), 2.62-2.52 (m, 4H), 2.28 (s, 3H). MS (ESI$^+$): [M + H]$^+$ 420.3. |

TABLE 3-continued

| # | Structure | Formula | MW | Purity | Data |
|---|---|---|---|---|---|
| 134 | [structure] | C₂₁H₂₁N₇OS | 419.51 | >98% | Yellow solid. ¹H NMR (400 MHz, DMSO-d₆, 300K) of major tautomer δ_H 10.92 (br s, 1H, NH, D₂O exchanged), 9.79 (br s, 1H, NH, D₂O exchanged), 9.39 (s, 1H), 8.87-8.72 (m, 1H), 8.50-8.37 (m, 1H), 8.36-8.23 (m, 1H), 8.08 (d, J = 8.5 Hz, 1H), 8.04-7.90 (m, 1H), 6.92 (d, J = 9.1 Hz, 1H), 6.57 (s, 1H), 3.53-3.43 (m, 4H), 2.45-2.39 (m, 4H), 2.23 (s, 3H). MS (ESI⁺): [M + H]⁺ 420.3. |
| 135 | [structure] | C₂₀H₂₀N₈OS | 420.50 | >98% | Yellow solid. ¹H NMR (400 MHz, DMSO-d₆, 300K) of major tautomer δ_H 11.12 (br s, 1H, NH, D₂O exchanged), 9.79 (br s, 1H, NH, D₂O exchanged), 9.39 (s, 1H), 8.93-8.52 (m, 3H), 8.32-8.16 (m, 1H), 8.06 (d, J = 8.6 Hz, 1H), 6.58 (s, 1H), 3.86-3.65 (m, 4H), 2.48-2.36 (m, 4H), 2.26 (s, 3H). MS (ESI⁺): [M + H]⁺ 421.2. |
| 136 | [structure] | C₂₀H₂₀N₈OS | 420.50 | >98% | Yellow solid. ¹H NMR (400 MHz, DMSO-d₆, 373K) of major tautomer δ_H 11.00 (br s, 2H, NH, D₂O exchanged), 9.35 (s, 1H), 8.79 (s, 1H), 8.38 (s, 2H), 8.25-7.98 (m, 2H), 6.72 (s, 1H), 3.26-3.17 (m, 4H) 2.54-2.51 (m, 4H), 2.27 (s, 3H). MS (ESI⁺): [M + H]⁺ 421.2. |
| 137 | [structure] | C₂₀H₂₀N₈OS | 420.50 | >98% | Yellow solid. ¹H NMR (400 MHz, DMSO-d₆, 300K) of major tautomer δ_H 11.35 (br s, 1H, NH, D₂O exchanged), 10.82 (br s, 1H, NH, D₂O exchanged), 9.42 (s, 1H), 9.01-7.83 (m, 5H), 6.64 (s, 1H), 3.60-3.44 (m, 4H), 2.48-2.41 (m, 4H), 2.24 (s, 3H). MS (ESI⁺): [M + H]⁺ 421.2. |

TABLE 3-continued

| # | Structure | Formula | MW | Purity | Notes |
|---|---|---|---|---|---|
| 138 | 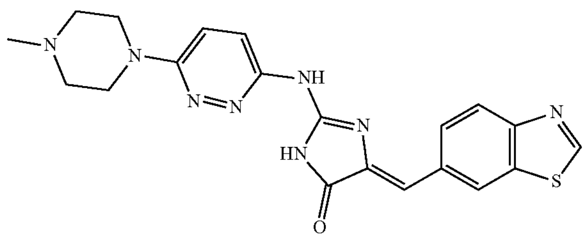 [SMILES: CN1CCN(c2ccc(NC3=N/C(=C\c4ccc5ncsc5c4)C(=O)N3)nn2)CC1] | $C_{20}H_{20}N_8OS$ | 420.50 | >98% | Yellow solid. $^1$H NMR (400 MHz, DMSO-d$_6$, 323K) of major tautomer δ$_H$ 10.99 (m, 1H), 8.76-8.59 (m, 2H, NH, D$_2$O exchanged), 9.40 (s, 1H), 7.47 (d, J = 9.7 Hz, 1H), 6.68 (s, 1H), 3.60-3.48 (m, 4H), 2.48-2.42 (m, 4H), 2.25 (s, 3H). MS (ESI$^+$): [M + H]$^+$ 421.2. |
| 139 | 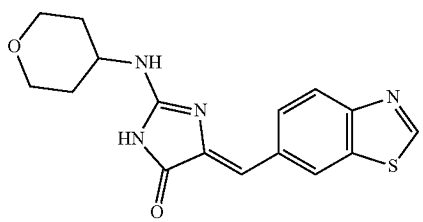 [SMILES: O=C1NC(NC2CCOCC2)=N/C1=C\c1ccc2ncsc2c1] | $C_{16}H_{16}N_4O_2S$ | 328.40 | 95% | Yellow solid. $^1$H NMR (500 MHz, DMSO-d$_6$, 300K) of major tautomer δ$_H$ 10.68 (br s, 1H, NH, D$_2$O exchanged), 9.35 (s, 1H), 8.81 (s, 1H), 8.37-8.21 (m, 1H), 8.03 (d, J = 8.7 Hz, 1H), 7.66 (br s, 1H, NH, D$_2$O exchanged), 6.41 (s, 1H), 4.21-3.70 (m, 3H), 3.55-3.33 (m, 2H), 2.00-1.79 (m, 2H), 1.67-1.50 (m, 2H). MS (ESI$^+$): [M + H]$^+$ 329.2. |
| 140 | 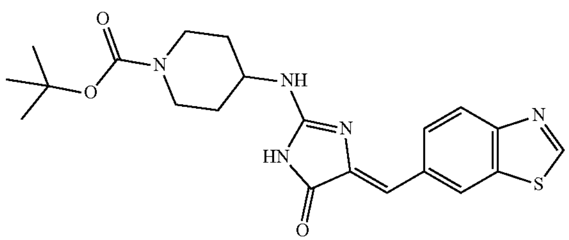 [SMILES: CC(C)(C)OC(=O)N1CCC(NC2=N/C(=C\c3ccc4ncsc4c3)C(=O)N2)CC1] | $C_{21}H_{25}N_5O_3S$ | 427.52 | >98% | Yellow solid. $^1$H NMR (500 MHz, DMSO-d$_6$, 300K) of major tautomer δ$_H$ 10.66 (br s, 1H, NH, D$_2$O exchanged), 9.35 (s, 1H), 8.81 (s, 1H), 8.32-8.13 (m, 1H), 8.02 (d, J = 8.6 Hz, 1H), 7.62 (br s, 1H, NH, D$_2$O exchanged), 6.42 (s, 1H), 4.22-3.66 (m, 3H), 3.08-2.73 (m, 2H), 2.00-1.79 (m, 2H), 1.54-1.30 (m, 11H). MS (ESI$^+$): [M + H]$^+$ 428.3. |
| 141 | 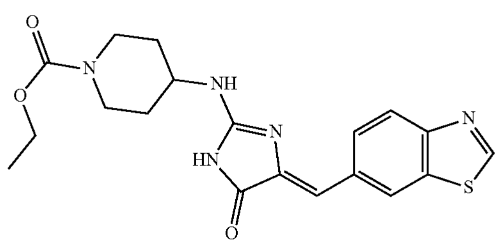 [SMILES: CCOC(=O)N1CCC(NC2=N/C(=C\c3ccc4ncsc4c3)C(=O)N2)CC1] | $C_{19}H_{21}N_5O_3S$ | 399.47 | >98% | Yellow solid. $^1$H NMR (500 MHz, DMSO-d$_6$, 300K) of major tautomer δ$_H$ 10.79 (br s, 1H, NH, D$_2$O exchanged), 9.36 (s, 1H), 8.81 (s, 1H), 8.45-8.16 (m, 1H), 8.13-7.95 (m, 1H), 7.68 (br s, 1H, NH, D$_2$O exchanged), 6.42 (s, 1H), 4.19-3.77 (m, 5H), 3.17-2.82 (m, 2H), 2.12-1.79 (m, 2H), 1.60-1.33 (m, 2H), 1.20 (t, J = 6.8 Hz, 3H). MS (ESI$^+$): [M + H]$^+$ 400.2. |

TABLE 3-continued

| | | | | |
|---|---|---|---|---|
| 142 | 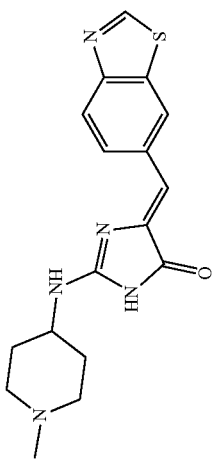 | $C_{17}H_{19}N_5OS$ | 341.43 | 96% | Yellow solid. ¹H NMR (400 MHz, DMSO-d₆, 300K) of major tautomer δ_H 9.74 (br s, 1H, NH, D₂O exchanged), 9.34 (s, 1H), 8.82-8.66 (m, 1H), 8.36-8.09 (m, 1H), 8.03 (d, J = 8.4 Hz, 1H), 7.78 (br s, 1H, NH, D₂O exchanged), 6.40 (s, 1H), 3.89-3.56 (m, 1H), 2.81-2.62 (m, 2H), 2.16 (s, 3H), 2.01 (s, 2H), 1.94-1.82 (m, 2H), 1.64-1.50 (m, 2H). MS (ESI⁺): [M + H]⁺ 342.2. |
| 143 | 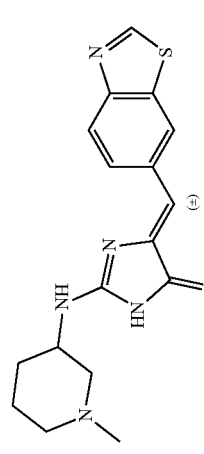 | $C_{17}H_{19}N_5OS$ | 341.43 | >98% | Yellow solid. ¹H NMR (400 MHz, DMSO-d₆, 300K) of major tautomer δ_H 10.59 (br s, 1H, NH, D₂O exchanged), 9.36 (s, 1H), 8.80 (s, 1H), 8.43-8.18 (m, 1H), 8.04 (d, J = 8.5 Hz, 1H), 7.68 (br s, 1H, NH, D₂O exchanged), 6.44 (s, 1H), 4.40-3.95 (m, 1H), 3.15-2.96 (m, 2H), 2.47-2.28 (m, 3H), 1.94-1.43 (m, 4H), 1.18 (t, J = 7.3 Hz, 2H). MS (ESI⁺): [M + H]⁺ 342.2. |
| 144 | 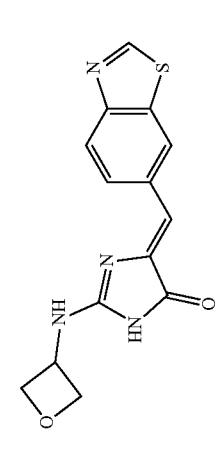 | $C_{14}H_{12}N_4O_2S$ | 300.34 | >98% | Yellow solid. ¹H NMR (400 MHz, DMSO-d₆, 302K) of major tautomer δ_H 10.92 (br s, 1H, NH, D₂O exchanged), 9.37 (s, 1H), 8.92-8.73 (m, 1H), 8.44 (br s, 1H, NH, D₂O exchanged), 8.31-8.16 (m, 1H), 8.04 (d, J = 8.5 Hz, 1H), 6.46 (s, 1H), 5.19-4.93 (m, 1H), 4.90-4.73 (m, 2H), 4.72-4.54 (m, 2H). MS (ESI⁺): [M + H]⁺ 301.1. |
| 145 | 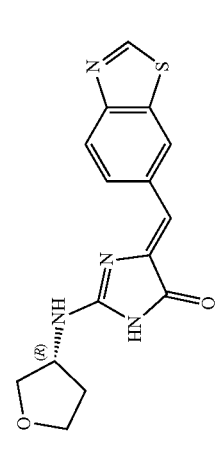 | $C_{15}H_{14}N_4O_2S$ | 314.36 | >98% | Yellow solid. ¹H NMR (400 MHz, DMSO-d₆, 300K) of major tautomer δ_H 10.71 (br s, 1H, NH, D₂O exchanged), 9.36 (s, 1H), 8.81 (s, 1H), 8.28 (d, J = 8.7 Hz, 1H), 8.04 (d, J = 8.6 Hz, 1H), 7.97 (br s, 1H, NH, D₂O exchanged), 6.44 (s, 1H), 4.48 (s, 1H), 4.00-3.80 (m, 2H), 3.80-3.69 (m, 1H), 3.69-3.59 (m, 1H), 2.30-2.17 (m, 1H), 2.01-1.85 (m, 1H). MS (ESI⁺): [M + H]⁺ 315.2. |
| 146 | 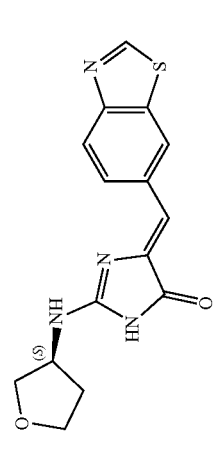 | $C_{15}H_{14}N_4O_2S$ | 314.36 | >98% | Yellow solid. ¹H NMR (400 MHz, DMSO-d₆, 300K) of major tautomer δ_H 10.71 (br s, 1H, NH, D₂O exchanged), 9.36 (s, 1H), 8.81 (s, 1H), 8.28 (d, J = 8.7 Hz, 1H), 8.04 (d, J = 8.6 Hz, 1H), 7.97 (br s, 1H, NH, D₂O exchanged), 6.44 (s, 1H), 4.48 (s, 1H), 4.00-3.80 (m, 2H), 3.80-3.69 (m, 1H), 3.69-3.59 (m, 1H), 2.30-2.17 (m, 1H), 2.01-1.85 (m, 1H). MS (ESI⁺): [M + H]⁺ 315.2. |

TABLE 3-continued

| | | | | |
|---|---|---|---|---|
| 147 | -tetrahydropyran-NH-imidazolone-benzothiazole | C₁₆H₁₆N₄O₂S | 328.39 | >98% | Yellow solid. ¹H NMR (400 MHz, DMSO-d₆, 300K) of major tautomer δ_H 10.45 (br s, 1H, NH, D₂O exchanged), 9.36 (s, 1H), 8.77 (s, 1H), 8.28 (s, 1H), 8.04 (d, J = 8.6 Hz, 1H), 7.62 (br s, 1H, NH, D₂O exchanged), 6.43 (s, 1H), 4.18-3.36 (m, 5H), 2.09-1.88 (m, 1H), 1.81-1.46 (m, 3H). MS (ESI⁺): [M + H]⁺ 329.2. |
| 148 | -tetrahydropyran-NH-imidazolone-benzothiazole | C₁₆H₁₆N₄O₂S | 328.39 | >98% | Yellow solid. ¹H NMR (400 MHz, DMSO-d₆, 300K) of major tautomer δ_H 10.45 (br s, 1H, NH, D₂O exchanged), 9.36 (s, 1H), 8.77 (s, 1H), 8.28 (s, 1H), 8.04 (d, J = 8.6 Hz, 1H), 7.62 (br s, 1H, NH, D₂O exchanged), 6.43 (s, 1H), 4.18-3.36 (m, 5H), 2.09-1.88 (m, 1H), 1.81-1.46 (m, 3H). MS (ESI⁺): [M + H]⁺ 329.2. |
| 149 | -dimethyl-tetrahydropyran-NH-imidazolone-benzothiazole | C₁₈H₂₀N₄O₂S | 356.44 | >98% | Yellow solid. ¹H NMR (400 MHz, DMSO-d₆, 373K) of major tautomer δ_H 10.20 (br s, 1H, NH, D₂O exchanged), 9.28 (s, 1H), 8.89-8.64 (m, 1H), 8.33-8.11 (m, 1H), 8.02 (d, J = 8.4 Hz, 1H), 7.14 (br s, 1H, NH, D₂O exchanged), 6.45 (s, 1H), 3.95-3.72 (m, 2H), 3.62-3.49 (m, 1H), 2.01-1.76 (m, 2H), 1.73-1.60 (m, 1H), 1.58-1.46 (m, 1H), 1.29-1.15 (m, 6H). MS (ESI⁺): [M + H]⁺ 357.2. Anal chiral SFC: Amy-C (4.6 mm × 250 mm, 5 um) (40° C., 4 mL/min, 210-400 nm, inj. vol.: 1 µL; isocratic conditions: 1/1 (MeOH/CO₂ (0.2% v/v NH₃)), t_R(149A): 1.21 min, t_R(149B): 1.52 min. |
| 149A | ![structure](R or S)-dimethyl-tetrahydropyran-NH-imidazolone-benzothiazole | C₁₈H₂₀N₄O₂S | 356.44 | >98% | Yellow solid. ¹H NMR (400 MHz, DMSO-d₆, 373K) of major tautomer δ_H 10.20 (br s, 1H, NH, D₂O exchanged), 9.28 (s, 1H), 8.89-8.64 (m, 1H), 8.33-8.11 (m, 1H), 8.02 (d, J = 8.4 Hz, 1H), 7.14 (br s, 1H, NH, D₂O exchanged), 6.45 (s, 1H), 3.95-3.72 (m, 2H), 3.62-3.49 (m, 1H), 2.01-1.76 (m, 2H), 1.73-1.60 (m, 1H), 1.58-1.46 (m, 1H), 1.29-1.15 (m, 6H). MS (ESI⁺): [M + H]⁺ 357.2. Prep. chiral SFC from 149: Lux A1 (21.2 mm × 250 mm, 5 um) (40° C., 50 mL/min, 210 nm, inj. vol.: 1300 µL (19.5 mg); isocratic conditions: 1/1 (MeOH/CO₂). Anal. chiral SFC: same conditions as 149. t_R(149A): 1.21 min, ee = >99%. |

TABLE 3-continued

| | Structure | Formula | MW | Purity | Characterization |
|---|---|---|---|---|---|
| 149B | (tetrahydropyran-4-yl with gem-dimethyl, NH (R or S), linked to aminoimidazolone with benzothiazole methylidene) | C₁₈H₂₀N₄O₂S | 356.44 | >98% | Yellow solid. ¹H NMR (400 MHz, DMSO-d₆, 373K) of major tautomer δ_H 10.20 (br s, 1H, NH, D₂O exchanged), 9.28 (s, 1H), 8.89-8.64 (m, 1H), 8.33-8.11 (m, 1H), 8.02 (d, J = 8.4 Hz, 1H), 7.14 (br s, 1H, NH, D₂O exchanged), 6.46 (s, 1H), 3.95-3.72 (m, 2H), 3.62-3.49 (m, 1H), 2.01-1.76 (m, 2H), 1.73-1.60 (m, 1H), 1.58-1.46 (m, 1H), 1.29-1.15 (m, 6H). MS (ESI⁺): [M + H]⁺ 357.2. Prep. chiral SFC from 149: Lux A1 (21.2 mm × 250 mm, 5 um); isocratic conditions: 1/1 (MeOH/CO₂). Anal. chiral SFC: same conditions as 149. t_R(149B): 1.51 min, ee = >99%. |
| 150 | (4-hydroxy-tetrahydropyran-3-yl (R), NH, linked to aminoimidazolone with benzothiazole methylidene) | C₁₆H₁₆N₄O₃S | 344.39 | 97% | Yellow solid. ¹H NMR (400 MHz, DMSO-d₆, 343K) of major tautomer δ_H 10.12 (br s, 1H, NH, D₂O exchanged), 9.32 (s, 1H), 8.89-8.54 (m, 1H), 8.34-8.08 (m, 1H), 8.04 (d, J = 8.4 Hz, 1H), 7.36 (br s, 1H, NH, D₂O exchanged), 6.45 (s, 1H), 4.96 (br s, 1H, OH, D₂O exchanged), 4.01 (d, J = 11.2 Hz, 1H), 3.93-3.79 (m, 1H), 3.78-3.58 (m, 2H), 3.41 (t, J = 10.7 Hz, 1H), 3.33-3.20 (m, 1H), 1.94 (d, J = 13.3 Hz, 1H), 1.63-1.47 (m, 1H). MS (ESI⁺): [M + H]⁺ 345.2. |
| 151 | (oxepan-3-yl amino (±), linked to aminoimidazolone with benzothiazole methylidene) | C₁₇H₁₈N₄O₂S | 342.42 | >98% | Yellow solid. ¹H NMR (400 MHz, DMSO-d₆, 300K) of major tautomer δ_H 10.31 (br s, 1H, NH, D₂O exchanged), 9.35 (s, 1H), 8.79 (s, 1H), 8.35-8.17 (m, 1H), 8.03 (d, J = 8.6 Hz, 1H), 7.51 (br s, 1H, NH, D₂O exchanged), 6.42 (s, 1H), 4.32-3.99 (m, 1H), 3.89-3.53 (m, 4H), 1.96-1.50 (m, 6H). MS (ESI⁺): [M + H]⁺ 343.2. |
| 152 | (2-oxo-piperidin-3-yl amino (±), linked to aminoimidazolone with benzothiazole methylidene) | C₁₆H₁₅N₅O₂S | 341.39 | >98% | Yellow solid. ¹H NMR (400 MHz, DMSO-d₆, 300K) of major tautomer δ_H 10.75 (br s, 1H, NH, D₂O exchanged), 9.36 (s, 1H), 8.84 (s, 1H), 8.23 (d, J = 8.6 Hz, 1H), 8.03 (d, J = 8.5 Hz, 1H), 7.78 (br s, 2H, NH, D₂O exchanged), 6.43 (s, 1H), 4.49-4.16 (m, 1H), 3.28-3.12 (m, 2H), 2.30-2.09 (m, 1H), 1.88 (s, 3H). MS (ESI⁺): [M + H]⁺ 342.2. |

TABLE 3-continued

| | | | | |
|---|---|---|---|---|
| 153 | [structure] | $C_{16}H_{15}N_5O_2S$ | 341.39 | >98% | Yellow solid. $^1$H NMR (400 MHz, DMSO-$d_6$, 300K) of major tautomer $\delta_H$ 10.75 (br s, 1H, NH, D$_2$O exchanged), 9.36 (s, 1H), 8.84 (s, 1H), 8.23 (d, J = 8.6 Hz, 1H), 8.03 (d, J = 8.5 Hz, 1H), 7.78 (br s, 2H, NH, D$_2$O exchanged), 6.43 (s, 1H), 4.49-4.16 (m, 1H), 3.28-3.12 (m, 2H), 2.30-2.09 (m, 1H), 1.88 (s, 3H). MS (ESI$^+$): [M + H]$^+$ 342.2. |
| 154 | [structure] | $C_{16}H_{15}N_5O_2S$ | 341.39 | >98% | Yellow solid. $^1$H NMR (400 MHz, DMSO-$d_6$, 300K) of major tautomer $\delta_H$ 10.76 (br s, 1H, NH, D$_2$O exchanged), 9.36 (s, 1H), 8.82 (s, 1H), 8.40-8.20 (m, 1H), 8.09-8.00 (m, 1H), 7.79 (br s, 1H, NH, D$_2$O exchanged), 7.52 (br s, 1H, NH, D$_2$O exchanged), 6.44 (s, 1H), 4.38-3.73 (m, 1H), 3.58-3.39 (m, 2H), 2.36-1.78 (m, 4H). MS (ESI$^+$): [M + H]$^+$ 342.2. |
| 155 | [structure] | $C_{16}H_{14}F_2N_4OS$ | 348.37 | >98% | Yellow solid. $^1$H NMR (400 MHz, DMSO-$d_6$, 323K) of major tautomer $\delta_H$ 10.69 (br s, 1H, NH, D$_2$O exchanged), 9.34 (s, 1H), 8.91-8.66 (m, 1H), 8.35-8.11 (m, 1H), 8.03 (d, J = 8.5 Hz, 1H), 7.81 (br s, 1H, NH, D$_2$O exchanged), 6.46 (s, 1H), 4.54-4.31 (m, 1H), 2.70-2.53 (m, 1H), 2.38-2.03 (m, 4H), 1.97-1.83 (m, 1H). MS (ESI$^+$): [M + H]$^+$ 349.2. |
| 156 | [structure] | $C_{17}H_{16}F_2N_4OS$ | 362.40 | >98% | Yellow solid. $^1$H NMR (400 MHz, DMSO-$d_6$, 323K) of major tautomer $\delta_H$ 10.67 (br s, 1H, NH, D$_2$O exchanged), 9.34 (s, 1H), 8.97-8.65 (m, 1H), 8.42-8.16 (m, 1H), 8.03 (d, J = 8.5 Hz, 1H), 7.67 (br s, 1H, NH, D$_2$O exchanged), 6.44 (s, 1H), 4.02-3.80 (m, 1H), 2.19-1.85 (m, 6H), 1.82-1.63 (m, 2H). MS (ESI$^+$): [M + H]$^+$ 363.1. |

| | | | | |
|---|---|---|---|---|
| 157 | [structure: benzothiazole-CH=imidazolinone-NH-3,3-difluorocyclohexyl, (±)] | C₁₇H₁₆F₂N₄OS | 362.40 | >98% | Yellow solid. ¹H NMR (400 MHz, DMSO-d₆, 300K) of major tautomer δ_H 10.76 (br s, 1H, NH, D₂O exchanged), 9.36 (s, 1H), 8.98-8.75 (m, 1H), 8.37-8.12 (m, 1H), 8.03 (d, J = 8.5 Hz, 1H), 7.70 (br s, 1H, NH, D₂O exchanged), 6.45 (s, 1H), 4.21-3.82 (m, 1H), 2.48-2.28 (m, 1H), 2.09-1.68 (m, 5H), 1.61-1.36 (m, 2H). MS (ESI⁺): [M + H]⁺ 363.1. |
| 158 | [structure: benzothiazole-CH=imidazolinone-NH-2,2-difluorocyclohexyl, (±)] | C₁₇H₁₆F₂N₄OS | 362.40 | >98% | Yellow solid. ¹H NMR (400 MHz, DMSO-d₆, 323K) of major tautomer δ_H 10.46 (br s, 1H, NH, D₂O exchanged), 9.35 (s, 1H), 8.93-8.67 (m, 1H), 8.43-8.14 (m, 1H), 8.04 (d, J = 8.4 Hz, 1H), 7.80 (br s, 1H, NH, D₂O exchanged), 6.48 (s, 1H), 4.43-4.12 (m, 1H), 2.21-2.08 (m, 1H), 2.05-1.38 (m, 7H) MS (ESI⁺): [M + H]⁺ 363.2. |
| 159 | [structure: benzothiazole-CH=imidazolinone-NH-3,3-difluorocycloheptyl, (±)] | C₁₈H₁₈F₂N₄OS | 376.43 | >98% | Yellow solid. ¹H NMR (400 MHz, DMSO-d₆, 323K) of major tautomer δ_H 10.52 (br s, 1H, NH, D₂O exchanged), 9.33 (s, 1H), 9.11-8.85 (m, 1H), 8.30-8.09 (m, 1H), 8.01 (d, J = 8.5 Hz, 1H), 7.54 (br s, 1H, NH, D₂O exchanged), 6.46 (s, 1H), 4.19-3.99 (m, 1H), 2.70-2.52 (m, 1H), 2.45-2.26 (m, 1H), 2.25-1.96 (m, 3H), 1.85-1.50 (m, 5H). MS (ESI⁺): [M + H]⁺ 377.2. |
| 160 | [structure: benzothiazole-CH=imidazolinone-NH-CH₂-(R)-CH(iBu)-CH₂F] | C₁₇H₁₉FN₄OS | 346.42 | 95% | Yellow solid. ¹H NMR (400 MHz, DMSO-d₆, 373K) of major tautomer δ_H 10.28 (br s, 1H, NH, D₂O exchanged), 9.28 (s, 1H), 8.85 (s, 1H), 8.17 (d, J = 8.2 Hz, 1H), 8.00 (d, J = 8.5 Hz, 1H), 7.25 (br s, 1H, NH, D₂O exchanged), 6.46 (s, 1H), 4.64-4.52 (m, 1H), 4.50-4.40 (m, 1H), 4.37-4.22 (m, 1H), 1.84-1.71 (m, 1H), 1.65-1.55 (m, 1H), 1.52-1.41 (m, 1H), 1.04-0.81 (m, 6H). MS (ESI⁺): [M + H]⁺ 347.2. |

TABLE 3-continued

| | | | | |
|---|---|---|---|---|
| 161 | (structure) | $C_{17}H_{19}FN_4OS$ | 346.42 | >98% | Yellow solid. $^1$H NMR (400 MHz, DMSO-d$_6$, 373K) of major tautomer $\delta_H$ 10.28 (br s, 1H, NH, D$_2$O exchanged), 9.28 (s, 1H), 8.85 (s, 1H), 8.17 (d, J = 8.2 Hz, 1H), 8.00 (d, J = 8.5 Hz, 1H), 7.25 (br s, 1H, NH, D$_2$O exchanged), 6.46 (s, 1H), 4.64-4.52 (m, 1H), 4.50-4.40 (m, 1H), 4.37-4.22 (m, 1H), 1.84-1.71 (m, 1H), 1.65-1.55 (m, 1H), 1.52-1.41 (m, 1H), 1.04-0.81 (m, 6H). MS (ESI$^+$): [M + H]$^+$ 347.2. |
| 162 | (structure) | $C_{23}H_{24}N_4O_3S$ | 436.53 | 97% | Yellow solid. $^1$H NMR (400 MHz, DMSO-d$_6$, 300K) of major tautomer $\delta_H$ 10.09 (br s, 1H, NH, D$_2$O exchanged), 9.34 (s, 1H), 9.03 (s, 1H), 8.13 (d, J = 8.5 Hz, 1H), 8.03 (d, J = 8.5 Hz, 1H), 7.29 (br s, 1H, NH, D$_2$O exchanged), 6.43 (s, 1H), 2.67 (s, 2H), 2.35-2.00 (m, 8H), 1.99-1.88 (m, 5H), 1.66-1.54 (m, 2H). MS (ESI$^+$): [M + H]$^+$ 437.3. |
| 163 | (structure) | $C_{26}H_{30}N_4O_3S$ | 478.61 | 98% | Yellow solid. $^1$H NMR (400 MHz, DMSO-d$_6$, 373K) of major tautomer $\delta_H$ 9.84 (br s, 1H, NH, D$_2$O exchanged), 9.31 (s, 1H), 9.01 (s, 1H), 8.12 (dd, J = 8.7, 1.7 Hz, 1H), 8.01 (d, J = 8.5 Hz, 1H), 7.00 (br s, 1H, NH, D$_2$O exchanged), 6.45 (s, 1H), 2.68 (s, 2H), 2.39-1.90 (m, 10H), 1.69-1.58 (m, 2H), 1.12 (s, 9H). MS (ESI$^+$): [M + H]$^+$ 479.4. |
| 164 | (structure) | $C_{17}H_{18}N_4O_2S$ | 342.42 | >98% | Yellow solid. $^1$H NMR (400 MHz, DMSO-d$_6$, 343K) of major tautomer $\delta_H$ 10.12 (br s, 1H, NH, D$_2$O exchanged), 9.28 (s, 1H), 8.97-8.76 (m, 1H), 8.25-8.09 (m, 1H), 8.01 (d, J = 8.3 Hz, 1H), 7.28 (br s, 1H, NH, D$_2$O exchanged), 6.46 (s, 1H), 4.21-4.12 (m, 1H), 3.86-3.79 (m, 1H), 3.38 (s, 3H), 2.17-2.04 (m, 1H), 2.00-1.88 (m, 1H), 1.80-1.58 (m, 4H). MS (ESI$^+$): [M + H]$^+$ 343.2. |

TABLE 3-continued

| | | | | |
|---|---|---|---|---|
| 165 | [structure: (1S,2S)-2-methoxycyclopentyl-NH-imidazolinone-benzothiazole] | C17H18N4O2S | 342.42 | >98% | Yellow solid. $^1$H NMR (400 MHz, DMSO-d$_6$, 343K) of major tautomer δ$_H$ 10.12 (br s, 1H, NH, D$_2$O exchanged), 9.28 (s, 1H), 8.97-8.76 (m, 1H), 8.25-8.09 (m, 1H), 8.01 (d, J = 8.3 Hz, 1H), 7.28 (br s, 1H, NH, D$_2$O exchanged), 6.46 (s, 1H), 4.21-4.12 (m, 1H), 3.86-3.79 (m, 1H), 3.38 (s, 3H), 2.17-2.04 (m, 1H), 2.00-1.88 (m, 1H), 1.80-1.58 (m, 4H). MS (ESI$^+$): [M + H]$^+$ 343.2. |
| 166 | [structure: (1R,2R)-2-methoxycyclohexyl-NH-imidazolinone-benzothiazole] | C18H20N4O2S | 356.44 | >98% | Yellow solid. $^1$H NMR (400 MHz, DMSO-d$_6$, 323K) of major tautomer δ$_H$ 10.62 (br s, 1H, NH, D$_2$O exchanged), 9.32 (s, 1H), 8.84 (s, 1H), 8.20 (d, J = 8.7 Hz, 1H), 8.01 (d, J = 8.6 Hz, 1H), 7.65 (br s, 1H, NH, D$_2$O exchanged), 6.39 (s, 1H), 3.82-3.53 (m, 1H), 3.31 (s, 3H), 3.25-3.12 (m, 1H), 2.15-1.90 (m, 4H), 1.76-1.59 (m, 2H), 1.47-1.15 (m, 4H). MS (ESI$^+$): [M + H]$^+$ 357.2. |
| 167 | [structure: (1S,2R)-2-methoxycyclohexyl-NH-imidazolinone-benzothiazole] | C18H20N4O2S | 356.44 | >98% | Yellow solid. $^1$H NMR (400 MHz, DMSO-d$_6$, 323K) of major tautomer δ$_H$ 10.62 (br s, 1H, NH, D$_2$O exchanged), 9.32 (s, 1H), 8.84 (s, 1H), 8.20 (d, J = 8.7 Hz, 1H), 8.01 (d, J = 8.6 Hz, 1H), 7.65 (br s, 1H, NH, D$_2$O exchanged), 6.39 (s, 1H), 3.82-3.53 (m, 1H), 3.31 (s, 3H), 3.25-3.12 (m, 1H), 2.15-1.90 (m, 4H), 1.76-1.59 (m, 2H), 1.47-1.15 (m, 4H). MS (ESI$^+$): [M + H]$^+$ 357.2. |

TABLE 3-continued

| | | | | |
|---|---|---|---|---|
| 168 | [structure, cis-(±)] | $C_{18}H_{20}N_4O_2S$ | 356.44 | >98% | Yellow solid. $^1$H NMR (400 MHz, DMSO-d$_6$, 373K) of major tautomer δ$_H$ 10.29 (br s, 1H, NH, D$_2$O exchanged), 9.28 (s, 1H), 9.00-8.58 (m, 1H), 8.34-8.07 (m, 1H), 8.02 (d, J = 8.2 Hz, 1H), 7.19 (br s, 1H, NH, D$_2$O exchanged), 6.43 (s, 1H), 3.87-3.74 (m, 1H), 3.36-3.22 (m, 4H), 2.39-2.24 (m, 1H), 1.99-1.72 (m, 3H), 1.41-1.15 (m, 4H). MS (ESI$^+$): [M + H]$^+$ 357.2. |
| 169 | [structure, trans-(±)] | $C_{18}H_{20}N_4O_2S$ | 356.44 | >98% | Yellow solid. $^1$H NMR (400 MHz, DMSO-d$_6$, 323K) of major tautomer δ$_H$ 10.40 (br s, 1H, NH, D$_2$O exchanged), 9.33 (s, 1H), 8.99-8.76 (m, 1H), 8.31-8.11 (m, 1H), 8.02 (d, J = 8.5 Hz, 1H), 7.39 (br s, 1H, NH, D$_2$O exchanged), 6.41 (s, 1H), 4.14-3.91 (m, 1H), 3.65-3.53 (m, 1H), 3.35 (s, 3H), 2.34-2.04 (m, 1H), 1.93-1.81 (m, 1H), 1.76-1.35 (m, 6H). MS (ESI$^+$): [M + H]$^+$ 357.2. Anal. chiral SFC: Lux A2 (4.6 mm × 250 mm, 5 um), (40° C., 4 mL/min, 210-400 nm, inj. vol.: 1 μL; isocratic conditions: 25/75 (MeOH/CO$_2$ (0.2% v/v NH$_3$)), t$_R$(169A): 5.06 min, t$_R$(169B): 6.27 min. |
| 169A | [structure, (R,R) or (S,S)] | $C_{18}H_{20}N_4O_2S$ | 356.44 | >98% | Yellow solid. $^1$H NMR (400 MHz, DMSO-d$_6$, 323K) of major tautomer δ$_H$ 10.40 (br s, 1H, NH, D$_2$O exchanged), 9.33 (s, 1H), 8.99-8.75 (m, 1H), 8.31-8.11 (m, 1H), 8.02 (d, J = 8.5 Hz, 1H), 7.39 (br s, 1H, NH, D$_2$O exchanged), 6.41 (s, 1H), 4.14-3.91 (m, 1H), 3.65-3.53 (m, 1H), 3.35 (s, 3H), 2.34-2.04 (m, 1H), 1.93-1.81 (m, 1H), 1.76-1.35 (m, 6H). MS (ESI$^+$): [M + H]$^+$ 357.2. Prep. chiral SFC from 169: Lux A2 (21.2 mm × 250 mm, 5 um), (40° C., 50 mL/min, 218 nm, inj. vol.: 500 μL (10 mg); isocratic conditions: 27/75 (MeOH/CO$_2$). Anal. chiral SFC: same conditions as 169; t$_R$(169A): 5.04 min, ee = >99%. |

TABLE 3-continued

| | | | | |
|---|---|---|---|---|
| 169B | 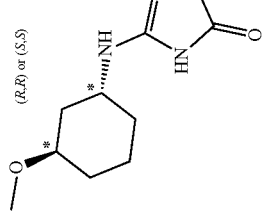 (R,R) or (S,S) | $C_{18}H_{20}N_4O_2S$ | 356.44 | >98% | Yellow solid. $^1$H NMR (400 MHz, DMSO-$d_6$, 323K) of major tautomer $\delta_H$ 10.40 (br s, 1H, NH, D$_2$O exchanged), 9.33 (s, 1H), 8.99-8.76 (m, 1H), 8.31-8.11 (m, 1H, NH, D$_2$O exchanged), 8.02 (d, J = 8.5 Hz, 1H), 7.39 (br s, 1H, NH, D$_2$O exchanged), 6.41 (s, 1H), 4.14-3.91 (m, 1H), 3.65-3.53 (m, 1H), 3.35 (s, 3H), 2.34-2.04 (m, 1H), 1.93-1.81 (m, 1H), 1.76-1.35 (m, 6H). MS (ESI$^+$): [M + H]$^+$ 357.2. Prep. chiral SFC from 169: Lux A2 (21.2 mm × 250 mm, 5 um), (40° C., 50 mL/min, 218 nm, inj. vol.: 500 μL (10 mg); isocratic conditions: 25/75 (MeOH/CO$_2$). Anal. chiral SFC: same conditions as 169. $t_R$(169B): 6.25 min, ee = >98%. |
| 170 | 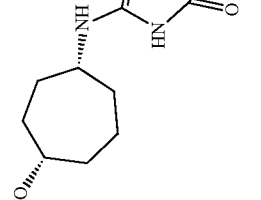 cis-(±) | $C_{18}H_{20}N_4O_2S$ | 356.44 | >98% | Yellow solid. $^1$H NMR (400 MHz, DMSO-$d_6$, 323K) of major tautomer $\delta_H$ 10.37 (br s, 1H, NH, D$_2$O exchanged), 9.33 (s, 1H), 8.97-8.59 (m, 1H), 8.36-8.08 (m, 1H, NH, D$_2$O exchanged), 8.02 (d, J = 8.4 Hz, 1H), 7.56 (br s, 1H, NH, D$_2$O exchanged), 6.40 (s, 1H), 4.46-4.23 (m, 1H, OH, D$_2$O exchanged), 4.09-3.83 (m, 1H), 3.83-3.69 (m, 1H), 2.01-1.53 (m, 8H), 1.53-1.39 (m, 1H), 1.38-1.21 (m, 1H). MS (ESI$^+$): [M + H]$^+$ 357.2. |
| 171 | 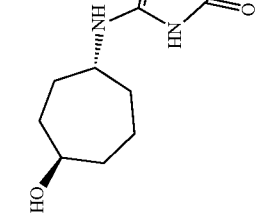 trans-(±) | $C_{18}H_{20}N_4O_2S$ | 356.44 | >98% | Yellow solid. $^1$H NMR (400 MHz, DMSO-$d_6$, 373K) of major tautomer $\delta_H$ 10.36 (br s, 1H, NH, D$_2$O exchanged), 9.31 (s, 1H), 8.85 (s, 1H), 8.20 (d, J = 8.6 Hz, 1H), 8.01 (d, J = 8.6 Hz, 1H), 7.35 (br s, 1H, NH, D$_2$O exchanged), 6.40 (s, 1H), 4.23 (d, J = 4.2 Hz, 1H, OH, D$_2$O exchanged), 4.04-3.82 (m, 1H), 3.79-3.64 (m, 1H), 2.05-1.72 (m, 4H), 1.69-1.39 (m, 6H). MS (ESI$^+$): [M + H]$^+$ 357.2. Anal. chiral SFC: Chiralpak IG (4.6 mm × 250 mm, 5 um), (40° C., 4 mL/min, 210-400 nm, inj. vol.: 1 μL; isocratic conditions: 1/1 (MeOH/CO$_2$ (0.2% v/v NH$_3$)), $t_R$(171A): 1.79 min, $t_R$(171B): 2.34 min. |
| 171A | 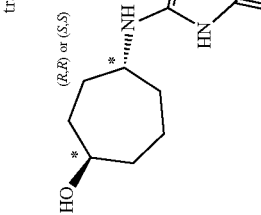 (R,R) or (S,S) | $C_{18}H_{20}N_4O_2S$ | 345.44 | >98% | Yellow solid. $^1$H NMR (400 MHz, DMSO-$d_6$, 373K) of major tautomer $\delta_H$ 10.36 (br s, 1H, NH, D$_2$O exchanged), 9.31 (s, 1H), 8.85 (s, 1H), 8.20 (d, J = 8.6 Hz, 1H), 8.01 (d, J = 8.6 Hz, 1H), 7.35 (br s, 1H, NH, D$_2$O exchanged), 6.40 (s, 1H), 4.23 (d, J = 4.2 Hz, 1H, OH, D$_2$O exchanged), 4.04-3.82 (m, 1H), 3.79-3.64 (m, 1H), 2.05-1.72 (m, 4H), 1.69-1.39 (m, 6H). MS (ESI$^+$): [M + H]$^+$ 357.2. Prep. chiral SFC from 171: Chiral pak IG (20 mm × 250 mm, 5 um), (40° C., 50 mL/min, 218 nm, inj. vol.: 500 μL (8 mg); isocratic conditions: 4/6 (MeOH/CO$_2$). Anal. chiral SFC: same conditions as 171. $t_R$(171A): 1.80 min, ee = >99%. |

TABLE 3-continued

| | | | | |
|---|---|---|---|---|
| 171B | (structure: benzothiazole-CH= imidazolinone with trans-4-hydroxycycloheptyl-NH, (R,R) or (S,S)) | $C_{18}H_{20}N_4O_2S$ | 356.44 | >98% | Yellow solid. $^1$H NMR (400 MHz, DMSO-d$_6$, 373K) of major tautomer δ$_H$ 10.36 (br s, 1H, NH, D$_2$O exchanged), 9.31 (s, 1H), 8.85 (s, 1H), 8.20 (d, J = 8.6 Hz, 1H), 8.01 (d, J = 8.6 Hz, 1H), 7.35 (br s, 1H, NH, D$_2$O exchanged), 6.40 (s, 1H), 4.23 (d, J = 4.2 Hz, 1H, OH, D$_2$O exchanged), 4.04-3.82 (m, 1H), 3.79-3.64 (m, 1H), 2.05-1.72 (m, 4H), 1.69-1.39 (m, 6H). MS (ESI$^+$): [M + H]$^+$ 357.2. MS (ESI$^+$): [M + H]$^+$ 357.2. Prep. chiral SFC from 171: Chiralpak IG (20 mm × 250 mm, 5 μm), (40° C., 50 mL/min, 218 nm, inj. vol.: 500 μL (8 mg; isocratic conditions: 4/6 (MeOH/CO$_2$). Anal. chiral SFC: same conditions as 171. t$_R$(171B): 2.36 min, ee = >97.8%. |
| 172 | (structure: benzothiazole-CH= imidazolinone with cis-(±) methoxycycloheptyl-NH) | $C_{19}H_{22}N_4O_2S$ | 370.47 | >98% | Yellow solid. $^1$H NMR (400 MHz, DMSO-d$_6$, 323K) of major tautomer δ$_H$ 10.50 (br s, 1H, NH, D$_2$O exchanged), 9.33 (s, 1H), 8.90 (s, 1H), 8.27-8.13 (m, 1H), 8.02 (d, J = 8.5 Hz, 1H), 7.45 (br s, 1H, NH, D$_2$O exchanged), 6.42 (s, 1H), 4.14-3.78 (m, 1H), 3.55-3.36 (m, 1H), 3.26 (s, 3H), 2.39-2.14 (m, 1H), 2.04-1.80 (m, 2H), 1.81-1.38 (m, 7H). MS (ESI$^+$): [M + H]$^+$ 371.1. |
| 173 | (structure: benzothiazole-CH= imidazolinone with trans-(±) methoxycycloheptyl-NH) | $C_{19}H_{22}N_4O_2S$ | 370.47 | 98% | Yellow solid. $^1$H NMR (400 MHz, DMSO-d$_6$, 323K) of major tautomer δ$_H$ 10.44 (br s, 1H, NH, D$_2$O exchanged), 9.32 (s, 1H), 8.90 (s, 1H), 8.19 (d, J = 8.7 Hz, 1H), 8.01 (d, J = 8.5 Hz, 1H), 7.48 (br s, 1H, NH, D$_2$O exchanged), 6.41 (s, 1H), 4.21-3.96 (m, 1H), 3.57-3.45 (m, 1H), 3.28 (s, 3H), 2.23-2.06 (m, 1H), 2.05-1.78 (m, 3H), 1.78-1.33 (m, 6H). MS (ESI$^+$): [M + H]$^+$ 371.2. |

| # | Structure | Formula | MW | Purity | Data |
|---|---|---|---|---|---|
| 174 | cis-(±) | C₁₉H₂₂N₄O₂S | 370.47 | >98% | Yellow solid. ¹H NMR (400 MHz, DMSO-d₆, 323K) of major tautomer δ_H 10.46 (br s, 1H, NH, D₂O exchanged), 9.33 (s, 1H), 8.92-8.75 (m, 1H), 8.28-8.16 (m, 1H), 8.02 (d, J = 8.4 Hz, 1H), 7.51 (br s, 1H, NH, D₂O exchanged), 6.40 (s, 1H), 4.08-3.79 (m, 1H), 3.45-3.34 (m, 1H), 3.23 (s, 3H), 2.01-1.48 (m, 9H), 1.42-1.29 (m, 1H). MS (ESI⁺): [M + H]⁺ 371.2. |
| 175 | trans-(±) | C₁₉H₂₂N₄O₂S | 370.47 | >98% | Yellow solid. ¹H NMR (400 MHz, DMSO-d₆, 323K) of major tautomer δ_H 10.46 (br s, 1H, NH, D₂O exchanged), 9.33 (s, 1H), 9.03-8.63 (m, 1H), 8.31-8.09 (m, 1H), 8.02 (d, J = 8.4 Hz, 1H), 7.51 (br s, 1H, NH, D₂O exchanged), 6.40 (s, 1H), 4.09-3.81 (m, 1H), 3.43-3.31 (m, 1H), 3.24 (s, 3H), 2.08-1.88 (m, 3H), 1.86-1.74 (m, 1H), 1.73-1.44 (m, 6H). MS (ESI⁺): [M + H]⁺ 371.2. |
| 176 | (R) | C₂₀H₁₈N₄O₂S | 378.45 | >98% | Yellow solid. ¹H NMR (400 MHz, DMSO-d₆, 323K) of major tautomer δ_H 10.55 (br s, 1H, NH, D₂O exchanged), 9.34 (s, 1H), 8.82 (s, 1H), 8.29-7.92 (m, 2H + NH, D₂O exchanged), 7.48 (d, J = 7.6 Hz, 2H), 7.38 (t, J = 7.5 Hz, 2H), 7.28 (t, J = 7.3 Hz, 1H), 6.42 (s, 1H), 5.35-5.11 (m, 1H), 3.88-3.58 (m, 2H), 3.34 (s, 3H). MS (ESI⁺): [M + H]⁺ 379.2. |
| 177 | (S) | C₂₀H₁₈N₄O₂S | 378.45 | >98% | Yellow solid. ¹H NMR (400 MHz, DMSO-d₆, 323K) of major tautomer δ_H 10.55 (br s, 1H, NH, D₂O exchanged), 9.34 (s, 1H), 8.82 (s, 1H), 8.29-7.92 (m, 2H + NH, D₂O exchanged), 7.48 (d, J = 7.6 Hz, 2H), 7.38 (t, J = 7.5 Hz, 2H), 7.28 (t, J = 7.3 Hz, 1H), 6.42 (s, 1H), 5.35-5.11 (m, 1H), 3.88-3.58 (m, 2H), 3.34 (s, 3H). MS (ESI⁺): [M + H]⁺ 379.2. |

TABLE 3-continued

| | Structure | Formula | MW | Purity | Characterization |
|---|---|---|---|---|---|
| 178 | (R)-benzothiazole imidazolone with OH-phenethylamine | C₁₉H₁₆N₄O₂S | 364.42 | >98% | Yellow solid. ¹H NMR (400 MHz, DMSO-d₆, 300K) of major tautomer δ_H 10.57 (br s, 1H, NH, D₂O exchanged), 9.37 (s, 1H), 9.05-8.80 (m, 1H), 8.30-8.13 (m, 1H), 8.05 (d, J = 8.5 Hz, 1H), 7.57 (br s, 1H, NH, D₂O exchanged), 7.53-7.23 (m, 5H), 6.44 (s, 1H), 5.69 (br s, 1H, OH, D₂O exchanged), 5.19-4.67 (m, 1H), 3.85-3.50 (m, 1H), 3.48-3.33 (m, 1H). MS (ESI⁺): [M + H]⁺ 365.1. |
| 179 | (R)-benzothiazole imidazolone with OH-phenethylamine | C₁₉H₁₆N₄O₂S | 364.42 | >98% | Yellow solid. ¹H NMR (400 MHz, DMSO-d₆, 300K) of major tautomer δ_H 10.57 (br s, 1H, NH, D₂O exchanged), 9.37 (s, 1H), 9.05-8.80 (m, 1H), 8.30-8.13 (m, 1H), 8.05 (d, J = 8.5 Hz, 1H), 7.57 (br s, 1H, NH, D₂O exchanged), 7.53-7.23 (m, 5H), 6.44 (s, 1H), 5.69 (br s, 1H, OH, D₂O exchanged), 5.19-4.67 (m, 1H), 3.85-3.50 (m, 1H), 3.48-3.33 (m, 1H). MS (ESI⁺): [M + H]⁺ 365.1. |
| 180 | (R)-benzothiazole imidazolone with NH₂-phenethylamine ·2HCl | C₁₉H₁₉Cl₂N₅OS | 436.36 | 98% | Yellow solid. ¹H NMR (400 MHz, DMSO-d₆, 323K) of major tautomer δ_H 9.38 (s, 1H), 8.88-8.73 (m, 1H), 8.28 (br s, 3H, NH, D₂O exchanged), 8.14-8.02 (m, 2H), 7.53 (d, J = 7.3 Hz, 2H), 7.44 (t, J = 7.6 Hz, 2H), 7.35 (t, J = 7.3 Hz, 1H), 6.55 (s, 1H), 5.53-5.35 (m, 1H), 4.45 (br s, 3H, NH, D₂O exchanged), 3.50-3.37 (m, 1H), 3.34-3.22 (m, 1H). MS (ESI⁺): [M + H]⁺ 364.1 (+2HCl). |
| 181 | (S)-benzothiazole imidazolone with NH₂-phenethylamine ·2HCl | C₁₉H₁₉Cl₂N₅OS | 436.36 | 97% | Yellow solid. ¹H NMR (400 MHz, DMSO-d₆, 323K) of major tautomer δ_H 9.38 (s, 1H), 8.88-8.73 (m, 1H), 8.28 (br s, 3H, NH, D₂O exchanged), 8.14-8.02 (m, 2H), 7.53 (d, J = 7.3 Hz, 2H), 7.44 (t, J = 7.6 Hz, 2H), 7.35 (t, J = 7.3 Hz, 1H), 6.55 (s, 1H), 5.53-5.35 (m, 1H), 4.45 (br s, 3H, NH, D₂O exchanged), 3.50-3.37 (m, 1H), 3.34-3.22 (m, 1H). MS (ESI⁺): [M + H]⁺ 364.1 (+2HCl). |

TABLE 3-continued

| | | | | |
|---|---|---|---|---|
| 182 | [structure: benzothiazole-imidazolone with (R)-quinuclidinyl amine] | $C_{18}H_{19}N_5OS$ | 353.44 | 97% | Yellow solid. $^1$H NMR (400 MHz, DMSO-$d_6$, 373K) of major tautomer $\delta_H$ 10.52 (br s, 1H, NH, D$_2$O exchanged), 9.31 (s, 1H), 8.88-8.66 (m, 1H), 8.33-8.09 (m, 1H), 8.03 (d, J = 8.4 Hz, 1H), 7.89 (br s, 1H, NH, D$_2$O exchanged), 6.47 (s, 1H), 4.21-4.05 (m, 1H), 3.61-3.43 (m, 1H), 3.18-2.81 (m, 5H), 2.23-2.08 (m, 1H), 2.01-1.72 (m, 3H), 1.67-1.53 (s, 1H). MS (ESI$^+$): [M + H]$^+$ 354.2. |
| 183 | [structure: benzothiazole-imidazolone with (S)-quinuclidinyl amine] | $C_{18}H_{19}N_5OS$ | 353.44 | >98% | Yellow solid. $^1$H NMR (400 MHz, DMSO-$d_6$, 373K) of major tautomer $\delta_H$ 10.52 (br s, 1H, NH, D$_2$O exchanged), 9.31 (s, 1H), 8.88-8.66 (m, 1H), 8.33-8.09 (m, 1H), 8.03 (d, J = 8.4 Hz, 1H), 7.89 (br s, 1H, NH, D$_2$O exchanged), 6.47 (s, 1H), 4.21-4.05 (m, 1H), 3.61-3.43 (m, 1H), 3.18-2.81 (m, 5H), 2.23-2.08 (m, 1H), 2.01-1.72 (m, 3H), 1.67-1.53 (s, 1H). MS (ESI$^+$): [M + H]$^+$ 354.2. |
| 184 | [structure: benzothiazole-imidazolone with (±)-thiopyranyl amine] | $C_{16}H_{16}N_4OS_2$ | 344.45 | >98% | Yellow solid. $^1$H NMR (400 MHz, DMSO-$d_6$, 373K) of major tautomer $\delta_H$ 10.20 (br s, 1H, NH, D$_2$O exchanged), 9.29 (s, 1H), 8.95-8.61 (m, 1H), 8.36-8.08 (m, 1H), 8.03 (d, J = 8.2 Hz, 1H), 7.24 (br s, 1H, NH, D$_2$O exchanged), 6.46 (s, 1H), 4.16-3.99 (m, 1H), 2.95-2.88 (m, 1H), 2.66 (dd, J = 13.0, 8.9 Hz, 1H), 2.60-2.52 (m, 2H), 2.16-1.89 (m, 2H), 1.88-1.75 (m, 1H), 1.69-1.57 (m, 1H). MS (ESI$^+$): [M + H]$^+$ 345.1. |
| 185 | [structure: benzothiazole-imidazolone with dioxepanyl amine] | $C_{16}H_{16}N_4O_3S$ | 344.39 | >98% | Yellow solid. $^1$H NMR (400 MHz, DMSO-$d_6$, 343K) of major tautomer $\delta_H$ 10.41 (br s, 1H, NH, D$_2$O exchanged), 9.32 (s, 1H), 8.97-8.65 (m, 1H), 8.39-8.11 (m, 1H), 8.04 (d, J = 8.4 Hz, 1H), 7.36 (br s, 1H, NH, D$_2$O exchanged), 6.45 (s, 1H), 3.92-3.71 (m, 3H), 3.71-3.57 (m, 2H), 3.56-3.29 (m, 4H). MS (ESI$^+$): [M + H]$^+$ 345.2. |

TABLE 3-continued

| | | | | |
|---|---|---|---|---|
| 186 | 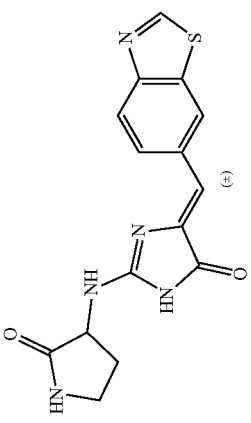 | $C_{15}H_{13}N_5O_2S$ | 327.36 | >98% | Yellow solid. $^1$H NMR (400 MHz, DMSO-$d_6$, 323K) of major tautomer $\delta_H$ 10.65 (br s, 1H, NH, D$_2$O exchanged), 9.34 (s, 1H), 8.90-8.70 (m, 1H), 8.34-8.16 (m, 1H), 8.03 (d, J = 8.5 Hz, 1H), 7.90 (br s, 1H, NH, D$_2$O exchanged), 7.71 (br s, 1H, NH, D$_2$O exchanged), 6.46 (s, 1H), 4.58-4.40 (m, 1H), 3.39-3.23 (m, 2H), 2.59-2.51 (m, 1H), 2.20-2.04 (m, 1H), MS (ESI$^+$): [M + H]$^+$ 328.1. |
| 187 | 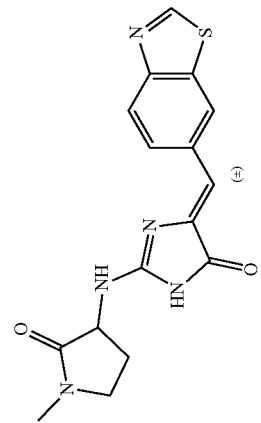 | $C_{16}H_{15}N_5O_2S$ | 341.39 | >98% | Yellow solid. $^1$H NMR (400 MHz, DMSO-$d_6$, 323K) of major tautomer $\delta_H$ 10.72 (br s, 1H, NH, D$_2$O exchanged), 9.34 (s, 1H), 8.79 (s, 1H), 8.22 (d, J = 8.6 Hz, 1H), 8.03 (d, J = 8.6 Hz, 1H), 7.77 (br s, 1H, NH, D$_2$O exchanged), 6.46 (s, 1H), 4.66-4.43 (m, 1H), 3.48-3.32 (m, 2H), 3.20 (s, 3H), 2.49-2.42 (m, 1H), 2.19-2.01 (m, 1H), MS (ESI$^+$): [M + H]$^+$ 342.2. |
| 188 | 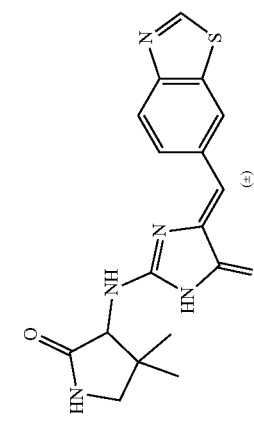 | $C_{17}H_{17}N_5O_2S$ | 355.42 | >98% | Yellow solid. $^1$H NMR (400 MHz, DMSO-$d_6$, 323K) of major tautomer $\delta_H$ 10.51 (br s, 1H, NH, D$_2$O exchanged), 9.34 (s, 1H), 9.00-8.66 (m, 1H), 8.32-8.10 (m, 1H), 8.02 (d, J = 8.4 Hz, 1H), 7.87 (br s, 1H, NH, D$_2$O exchanged), 7.65 (br s, 1H, NH, D$_2$O exchanged), 6.47 (s, 1H), 4.62-4.37 (m, 1H), 3.19-3.13 (m, 1H), 3.00 (d, J = 9.7 Hz, 1H), 1.30 (s, 3H), 0.99 (s, 3H). MS (ESI$^+$): [M + H]$^+$ 356.1. |
| 189 | 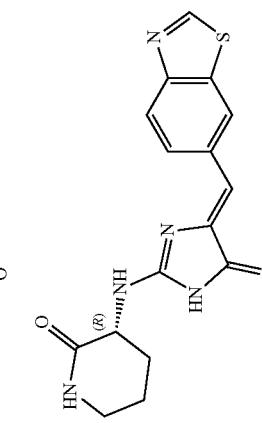 | $C_{16}H_{15}N_5O_2S$ | 341.39 | >98% | Yellow solid. $^1$H NMR (400 MHz, DMSO-$d_6$, 300K) of major tautomer $\delta_H$ 10.75 (br s, 1H, NH, D$_2$O exchanged), 9.36 (s, 1H), 8.84 (s, 1H), 8.23 (d, J = 8.6 Hz, 1H), 8.03 (d, J = 8.5 Hz, 1H), 7.78 (br s, 2H, NH, D$_2$O exchanged), 6.43 (s, 1H), 4.49-4.16 (m, 1H), 3.28-3.12 (m, 2H), 2.30-2.09 (m, 1H), 1.88 (s, 3H). MS (ESI$^+$): [M + H]$^+$ 342.1. |

TABLE 3-continued

| | Structure | Formula | MW | Purity | Characterization |
|---|---|---|---|---|---|
| 190 | 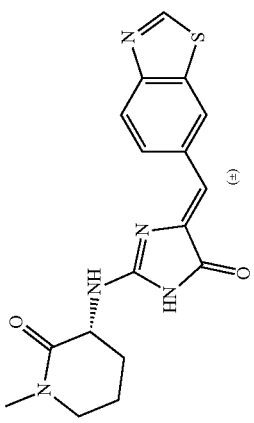 | C₁₇H₁₇N₅O₂S | 355.42 | >98% | Yellow solid. ¹H NMR (400 MHz, DMSO-d₆, 323K) of major tautomer δ_H 10.65 (br s, 1H, NH, D₂O exchanged), 9.34 (s, 1H), 8.91-8.70 (m, 1H), 8.34-8.12 (m, 1H), 8.03 (d, J = 8.5 Hz, 1H), 7.67 (br s, 1H, NH, D₂O exchanged), 6.45 (s, 1H), 4.41-4.22 (m, 1H), 3.46-3.27 (m, 2H), 2.89 (s, 3H), 2.35-2.17 (m, 1H), 2.10-1.86 (m, 3H). MS (ESI⁺): [M + H]⁺ 356.1. |
| 191 | 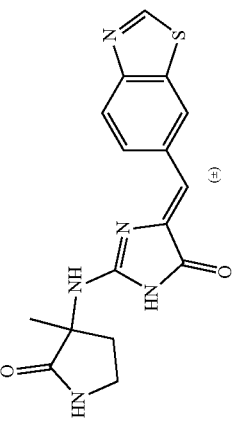 | C₁₆H₁₅N₅O₂S | 341.39 | >98% | Yellow solid. ¹H NMR (400 MHz, DMSO-d₆, 323K) of major tautomer δ_H 10.10 (br s, 1H, NH, D₂O exchanged), 9.35 (s, 1H), 8.80 (s, 1H), 8.26 (d, J = 8.7 Hz, 1H), 8.05 (d, J = 8.6 Hz, 1H), 7.94 (br s, 1H, NH, D₂O exchanged), 7.33 (br s, 1H, NH, D₂O exchanged), 6.48 (s, 1H), 3.46-3.25 (m, 2H), 2.85-2.70 (m, 1H), 2.30 (dd, J = 12.8 and 7.2 Hz, 1H), 1.46 (s, 3H). MS (ESI⁺): [M + H]⁺ 342.1. |
| 192 | 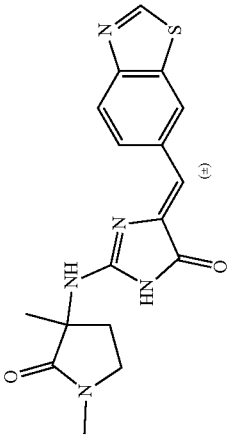 | C₁₇H₁₇N₅O₂S | 355.42 | >98% | Yellow solid. ¹H NMR (400 MHz, DMSO-d₆, 300K) of major tautomer δ_H 10.33 (br s, 1H, NH, D₂O exchanged), 9.37 (s, 1H), 8.75 (s, 1H), 8.18 (dd, J = 8.6, 1.6 Hz, 1H), 8.04 (d, J = 8.6 Hz, 1H), 7.70 (br s, 1H, NH, D₂O exchanged), 6.46 (s, 1H), 3.56-3.41 (m, 2H), 2.89 (s, 3H), 2.83-2.71 (m, 1H), 2.18-2.06 (m, 1H), 1.40 (s, 3H). MS (ESI⁺): [M + H]⁺ 356.2. Anal. chiral SFC: Amy-C (4.6 mm × 250 mm, 5 um), (40° C., 4 mL/min, 210-400 nm, inj. vol.: 1 µL; isocratic conditions: 4/6 (MeOH/CO₂ (0.2% v/v NH₃)), t_R(192A): 1.95 min, t_R(192B): 2.53 min. |
| 192A | 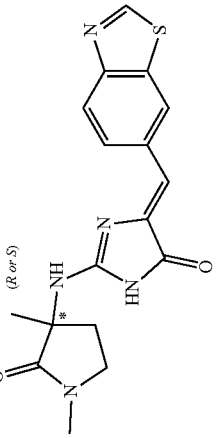 | C₁₇H₁₇N₅O₂S | 355.42 | >98% | Yellow solid. ¹H NMR (400 MHz, DMSO-d₆, 300K) of major tautomer δ_H 10.33 (br s, 1H, NH, D₂O exchanged), 9.37 (s, 1H), 8.75 (s, 1H), 8.18 (dd, J = 8.6, 1.6 Hz, 1H), 8.04 (d, J = 8.6 Hz, 1H), 7.70 (br s, 1H, NH, D₂O exchanged), 6.46 (s, 1H), 3.56-3.41 (m, 2H), 2.89 (s, 3H), 2.83-2.71 (m, 1H), 2.18-2.06 (m, 1H), 1.40 (s, 3H). MS (ESI⁺): [M + H]⁺ 356.1. ee = >99%. Prep. chiral SFC from 192: Lux A1 (21.2 mm × 250 mm, 5 um) (40° C., 50 mL/min, 210 nm, inj. vol.: 1000 µL (19 mg); isocratic conditions: 4/6 (MeOH/CO₂). Anal. chiral SFC: same conditions as 192. t_R(192A): 1.96 min, ee = >99%. |

TABLE 3-continued

| | Structure | Formula | MW | Purity | Notes |
|---|---|---|---|---|---|
| 192B | (structure with pyrrolidinone, R or S center) | C₁₇H₁₇N₅O₂S | 355.42 | >98% | Yellow solid. ¹H NMR (400 MHz, DMSO-d₆, 300K) of major tautomer δ_H 10.33 (br s, 1H, NH, D₂O exchanged), 9.37 (s, 1H), 8.75 (s, 1H), 8.18 (dd, J = 8.6, 1.6 Hz, 1H) 8.04 (d, J = 8.6 Hz, 1H), 7.70 (br s, 1H, NH, D₂O exchanged), 6.46 (s, 1H), 3.56-3.41 (m, 2H), 2.89 (s, 3H), 2.83-2.71 (m, 1H), 2.18-2.06 (m, 1H), 1.40 (s, 3H). MS (ESI⁺): [M + H]⁺ 356.1. ee = >99%. Prep. chiral SFC from 192: Lux A1 (21.2 mm × 250 mm, 5 um); (40° C., 50 mL/min, 210 nm, inj. vol.: 1000 μL (19 mg); isocratic conditions: 4/6 (MeOH/CO₂). Anal. chiral SFC: same conditions as 192. t_R(192B): 2.51 min, ee = >99%. |
| 193 | (tetrahydropyran with OH, stereochemistry S,S) | C₁₆H₁₆N₄O₃S | 344.39 | >98% | Yellow solid. ¹H NMR (400 MHz, DMSO-d₆, 343K) of major tautomer δ_H 10.12 (br s, 1H, NH, D₂O exchanged), 9.32 (s, 1H), 8.89-8.54 (m, 1H), 8.34-8.08 (m, 1H), 8.04 (d, J = 8.4 Hz, 1H), 7.36 (br s, 1H, NH, D₂O exchanged), 6.45 (s, 1H), 4.96 (br s, 1H, OH, D₂O exchanged), 4.01 (d, J = 11.2 Hz, 1H), 3.93-3.79 (m, 1H), 3.78-3.58 (m, 2H), 3.41 (t, J = 10.7 Hz, 1H), 3.33-3.20 (m, 1H), 1.94 (d, J = 13.3 Hz, 1H), 1.63-1.47 (m, 1H). MS (ESI⁺): [M + H]⁺ 345.2. |
| 194 | (adamantyl) | C₂₀H₂₀N₄OS | 364.47 | >98% | Yellow solid. ¹H NMR (400 MHz, DMSO-d₆, 343K) of major tautomer δ_H 9.95 (br s, 1H, NH, D₂O exchanged), 9.30 (s, 1H), 8.99 (s, 1H), 8.12 (dd, J = 8.6, 1.6 Hz, 1H), 7.99 (d, J = 8.5 Hz, 1H), 7.29 (br s, 1H, NH, D₂O exchanged), 6.43 (s, 1H), 2.72 (t, J = 6.7 Hz, 1H), 2.37-2.26 (m, 4H), 2.22-2.12 (m, 2H), 2.03-1.94 (m, 2H), 1.74-1.53 (m, 4H). MS (ESI⁺): [M + H]⁺ 365.2. |

TABLE 3-continued

| # | Structure | Formula | MW | Yield | Characterization |
|---|---|---|---|---|---|
| 195 | 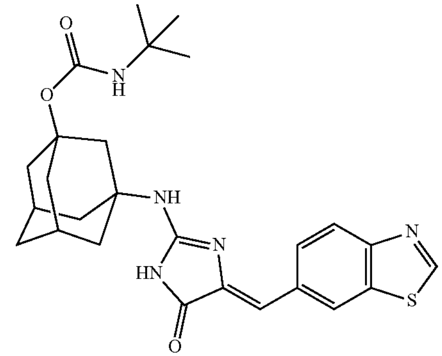 [SMILES: CC(C)(C)NC(=O)OC12CC3CC(CC(NC4=N/C(=C\c5ccc6ncsc6c5)C(=O)N4)(C3)C1)C2] | C₂₆H₃₁N₅O₃S | 493.63 | 92% (NMR) | Yellow solid. ¹H NMR (400 MHz, DMSO-d₆, 343K) of major tautomer δ_H 9.81 (br s, 1H, NH, D₂O exchanged), 9.31 (s, 1H), 8.95 (s, 1H), 8.17 (d, J = 8.6 Hz, 1H), 8.03 (d, J = 8.5 Hz, 1H), 6.98 (br s, 1H, NH, D₂O exchanged), 6.44 (s, 1H), 6.20 (br s, 1H, NH, D₂O exchanged), 2.60 (s, 1H), 2.40-1.93 (m, 9H), 1.68-1.39 (m, 4H), 1.31-1.09 (m, 9H). MS (ESI⁺): [M + H]⁺ 494.3 |
| 196 | 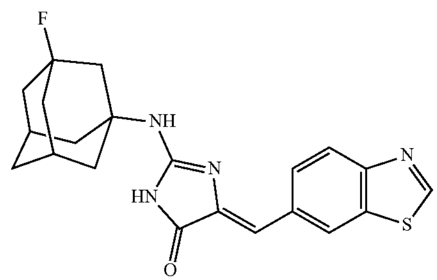 [SMILES: O=C1NC(NC23CC4CC(CC(F)(C4)C2)C3)=N/C1=C\c1ccc2ncsc2c1] | C₂₁H₂₁FN₄OS | 396.48 | 98% | Yellow solid. ¹H NMR (400 MHz, DMSO-d₆, 343K) of major tautomer δ_H 9.89 (br s, 1H, NH, D₂O exchanged), 9.31 (s, 1H), 8.97 (s, 1H), 8.13 (d, J = 8.6 Hz, 1H), 8.02 (d, J = 8.5 Hz, 1H), 7.04 (br s, 1H, NH, D₂O exchanged), 6.46 (s, 1H), 2.44-2.25 (m, 4H), 2.23-1.98 (m, 4H), 1.96-1.83 (m, 4H), 1.67-1.53 (m, 2H). (ESI⁺): [M + H]⁺ 397.2. |
| 197 | 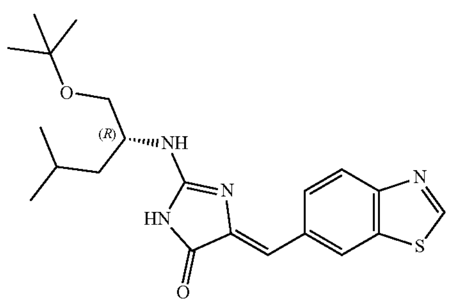 | C₂₁H₂₈N₄O₂S | 400.54 | 95% | Yellow solid. ¹H NMR (400 MHz, DMSO-d₆, 343K) of major tautomer δ_H 10.31 (br s, 1H, NH, D₂O exchanged), 9.30 (s, 1H), 8.92 (s, 1H), 8.16 (d, J = 8.5 Hz, 1H), 7.99 (d, J = 8.5 Hz, 1H), 7.02 (br s, 1H, NH, D₂O exchanged), 6.42 (s, 1H), 4.21-3.92 (m, 1H), 3.60-3.32 (m, 2H), 1.81-1.62 (m, 1H), 1.61-1.40 (m, 2H), 1.18 (s, 9H), 0.97 (t, J = 7.4 Hz, 6H). MS (ESI⁺): [M + H]⁺ 401.3. |

TABLE 3-continued

| | | | | |
|---|---|---|---|---|
| 198 | [structure] | $C_{23}H_{24}N_4O_2S$ | 420.53 | >98% | Yellow solid. $^1$H NMR (400 MHz, DMSO-d$_6$, 343K) of major tautomer δ$_H$ 10.39 (br s, 1H, NH, D$_2$O exchanged), 9.32 (s, 1H), 8.82 (s, 1H), 8.13 (d, J = 8.6 Hz, 1H), 8.00 (d, J = 8.5 Hz, 1H), 7.66 (br s, 1H, NH, D$_2$O exchanged), 7.55-7.19 (m, 5H), 6.42 (s, 1H), 5.16-4.96 (m, 1H), 3.81-3.58 (m, 2H), 1.16 (s, 9H). MS (ESI$^+$): [M + H]$^+$ 421.3. |
| 199 | [structure] | $C_{23}H_{25}N_5O_2S$ | 435.55 | >98% | Yellow solid. $^1$H NMR (400 MHz, DMSO-d$_6$, 323K) of major tautomer δ$_H$ 9.87 (br s, 1H, NH, D$_2$O exchanged), 9.32 (s, 1H), 9.00 (s, 1H), 8.15 (d, J = 8.7 Hz, 1H), 8.03 (d, J = 8.5 Hz, 1H), 7.36 (br s, 1H, NH, D$_2$O exchanged), 6.99 (br s, 1H, NH, D$_2$O exchanged), 6.43 (s, 1H), 2.49-2.43 (m, 2H), 2.35-2.11 (m, 4H), 2.10-1.85 (m, 6H), 1.76 (s, 3H), 1.68-1.55 (m, 2H). MS (ESI$^+$): [M + H]$^+$ 436.2. |
| 200 | [structure] | $C_{25}H_{27}N_5O_2S$ | 461.58 | >98% | Yellow solid. $^1$H NMR (400 MHz, DMSO-d$_6$, 323K) of major tautomer δ$_H$ 9.87 (br s, 1H, D$_2$O exchanged), 9.32 (s, 1H), 8.99 (s, 1H), 8.15 (d, J = 8.6 Hz, 1H), 8.03 (d, J = 8.6 Hz, 1H), 7.58 (br s, 1H, NH, D$_2$O exchanged), 7.01 (br s, 1H, NH, D$_2$O exchanged), 6.43 (s, 1H), 2.49-2.44 (m, 2H), 2.38-2.11 (m, 4H), 2.11-1.84 (m, 6H), 1.70-1.51 (m, 3H), 0.75-0.44 (m, 4H). MS (ESI$^+$): [M + H]$^+$ 462.2. |

TABLE 3-continued

| | | | |
|---|---|---|---|
| 201 | [structure: methanesulfonamide-adamantyl-NH-imidazolone-benzothiazole] | C$_{22}$H$_{25}$N$_5$O$_3$S$_2$ 471.59 >98% | Yellow solid. $^1$H NMR (400 MHz, DMSO-d$_6$, 323K) of major tautomer δ$_H$ 9.90 (br s, 1H, NH, D$_2$O exchanged), 9.32 (s, 1H), 8.94 (s, 1H), 8.17 (d, J = 8.6 Hz, 1H), 8.02 (d, J = 8.5 Hz, 1H), 7.04 (br s, 1H, NH, D$_2$O exchanged), 6.93 (br s, 1H, NH, D$_2$O exchanged), 6.43 (s, 1H), 2.97 (s, 3H), 2.43 (s, 2H), 2.29-1.84 (m, 10H), 1.68-1.54 (m, 2H). MS (ESI$^+$): [M + H]$^+$ 472.1. |
| 202 | [structure: cyclopropylsulfonamide-adamantyl-NH-imidazolone-benzothiazole] | C$_{24}$H$_{27}$N$_5$O$_3$S$_2$ 497.63 >98% | Yellow solid. $^1$H NMR (400 MHz, DMSO-d$_6$, 323K) of major tautomer δ$_H$ 9.89 (br s, 1H, NH, D$_2$O exchanged), 9.32 (s, 1H), 8.93 (s, 1H), 8.18 (d, J = 8.6 Hz, 1H), 8.02 (d, J = 8.6 Hz, 1H), 7.03 (br s, 1H, NH, D$_2$O exchanged), 6.91 (br s, 1H, NH, D$_2$O exchanged), 6.44 (s, 1H), 2.58-2.51 (m, 1H), 2.43 (s, 2H), 2.30-1.87 (m, 10H), 1.69-1.48 (m, 2H), 0.99-0.85 (m, 4H). MS (ESI$^+$): [M + H]$^+$ 498.1. |
| 203 | [structure: dimethylamino-adamantyl-NH-imidazolone-benzothiazole] | C$_{23}$H$_{27}$N$_5$OS 421.56 97% | Yellow solid. $^1$H NMR (400 MHz, DMSO-d$_6$, 373K) of major tautomer δ$_H$ 9.61 (s, 1H, NH, D$_2$O exchanged), 9.28 (s, 1H), 9.10-8.85 (m, 1H), 8.26-8.06 (m, 1H), 8.00 (d, J = 7.9 Hz, 1H), 6.71 (br s, 1H, NH, D$_2$O exchanged), 6.44 (s, 1H), 2.27 (s, 6H), 2.26-1.93 (m, 8H), 1.79-1.53 (m, 6H). MS (ESI$^+$): [M + H]$^+$ 422.1. |

TABLE 3-continued

| | Structure | Formula | MW | Purity | Characterization |
|---|---|---|---|---|---|
| 204 | (adamantyl-COOMe-NH-imidazolone-CH=benzothiazole) | C₂₃H₂₄N₄O₃S | 436.53 | 85% (NMR) | Yellow solid. ¹H NMR (400 MHz, DMSO-d₆, 323K) of major tautomer δ_H 9.91 (br s, 1H, NH, D₂O exchanged), 9.34 (s, 1H), 8.95 (s, 1H), 8.05 (d, J = 8.8 Hz, 1H), 8.00 (d, J = 8.5 Hz, 1H), 7.46 (br s, 1H, NH, D₂O exchanged), 6.46 (s, 1H), 3.63 (s, 3H), 2.70-2.58 (m, 2H), 2.19-2.00 (m, 4H), 1.91-1.58 (m, 8H). MS (ESI⁺): [M + H]⁺ 437.0. |
| 205 | (cyclohexyl-NH-imidazolone-CH=2-methylbenzothiazole) | C₁₈H₂₀N₄OS | 340.45 | >98% | Yellow solid. ¹H NMR (400 MHz, DMSO-d₆, 343K) of major tautomer δ_H 10.14 (br s, 1H, NH, D₂O exchanged), 8.78-8.51 (m, 1H), 8.20-7.95 (m, 1H), 7.84 (d, J = 8.5 Hz, 1H), 7.33 (br s, 1H, NH, D₂O exchanged), 6.37 (s, 1H), 3.79-3.66 (m, 1H), 2.79 (s, 3H), 2.01-1.87 (m, 2H), 1.80-1.69 (m, 2H), 1.65-1.56 (m, 1H), 1.43-1.15 (m, 5H). MS (ESI⁺): [M + H]⁺ 341.2. |
| 206 | (cycloheptyl-NH-imidazolone-CH=2-methylbenzothiazole) | C₁₉H₂₂N₄OS | 354.47 | >98% | Yellow solid. ¹H NMR (400 MHz, DMSO-d₆, 343K) of major tautomer δ_H 10.29 (br s, 1H, NH, D₂O exchanged), 8.93-8.59 (m, 1H), 8.26-7.98 (m, 1H), 7.84 (d, J = 8.4 Hz, 1H), 7.31 (br s, 1H, NH, D₂O exchanged), 6.38 (s, 1H), 4.03-3.83 (m, 1H), 2.79 (s, 3H), 2.06-1.88 (m, 2H), 1.81-1.40 (m, 10H). MS (ESI⁺): [M + H]⁺ 355.2. |
| 207 | ((R)-methoxymethyl-isobutyl-NH-imidazolone-CH=2-methylbenzothiazole) | C₁₉H₂₄N₄O₂S | 372.49 | >98% | Yellow solid. ¹H NMR (400 MHz, DMSO-d₆, 343K) of major tautomer δ_H 10.29 (br s, 1H, NH, D₂O exchanged), 8.92-8.59 (m, 1H), 8.18-7.95 (m, 1H), 7.83 (d, J = 8.4 Hz, 1H), 7.18 (br s, 1H, NH, D₂O exchanged), 6.39 (s, 1H), 4.27-4.05 (m, 1H), 3.52-3.37 (m, 2H), 3.32 (s, 3H), 2.79 (s, 3H), 1.80-1.64 (m, 1H), 1.59-1.47 (m, 1H), 1.47-1.36 (m, 1H), 1.02-0.90 (m, 6H). MS (ESI⁺): [M + H]⁺ 373.3. |

TABLE 3-continued

| | | | | |
|---|---|---|---|---|
| 208 | 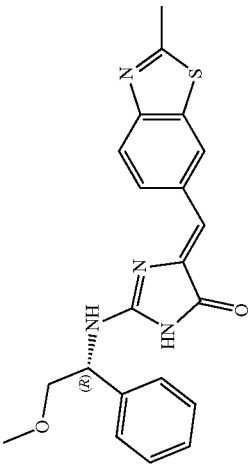 | C₂₁H₂₀N₄O₂S | 392.48 | >98% | Yellow solid. ¹H NMR (400 MHz, DMSO-d₆, 343K) of major tautomer δ_H 10.37 (br s, 1H, NH, D₂O exchanged), 8.79-8.57 (m, 1H), 8.06-7.99 (m, 1H), 7.95-7.83 (br s, 1H, NH, D₂O exchanged) 7.83 (d, J = 8.4 Hz, 1H), 7.47 (d, J = 7.6 Hz, 2H), 7.38 (t, J = 7.5 Hz, 2H), 7.28 (t, J = 7.3 Hz, 1H), 6.39 (s, 1H), 5.26-5.12 (m, 1H), 3.79-3.72 (m, 1H), 3.66 (dd, J = 10.1, 5.1 Hz, 1H), 3.34 (s, 3H), 2.80 (s, 3H). MS (ESI⁺): [M + H]⁺ 393.2. |
| 209 | 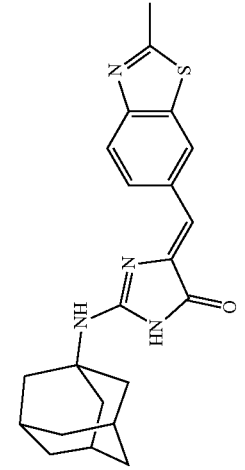 | C₂₂H₂₄N₄OS | 392.52 | >98% | Yellow solid. ¹H NMR (400 MHz, DMSO-d₆, 300K) of major tautomer δ_H 9.95 (br s, 1H, NH, D₂O exchanged), 8.94 (s, 1H), 8.03 (d, J = 8.5 Hz, 1H), 7.84 (d, J = 8.6 Hz, 1H), 7.05 (br s, 1H, NH, D₂O exchanged), 6.39 (s, 1H), 2.80 (s, 3H), 2.36-1.98 (m, 9H), 1.90-1.56 (m, 6H). MS (ESI⁺): [M + H]⁺ 393.3. |
| 210 | 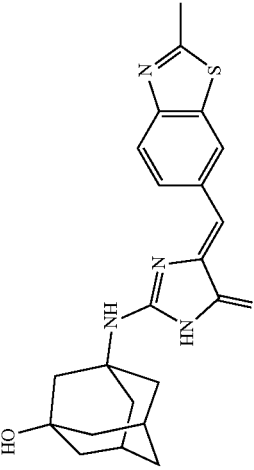 | C₂₂H₂₄N₄O₂S | 408.52 | >98% | Yellow solid. ¹H NMR (400 MHz, DMSO-d₆, 343K) of major tautomer δ_H 9.73 (br s, 1H, NH, D₂O exchanged), 8.88 (s, 1H), 8.02 (d, J = 8.5 Hz, 1H), 7.83 (d, J = 8.5 Hz, 1H), 6.81 (br s, 1H, NH, D₂O exchanged), 6.40 (s, 1H), 4.39 (br s, 1H, OH, D₂O exchanged), 2.80 (s, 3H), 2.28-2.19 (m, 2H), 2.15-1.90 (m, 6H), 1.74-1.47 (m, 6H). MS (ESI⁺): [M + H]⁺ 409.3. |
| 211 | 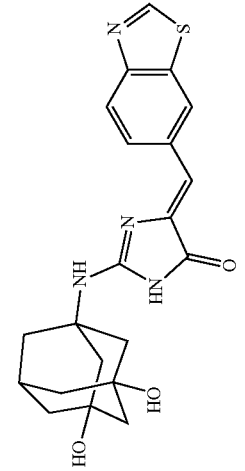 | C₂₁H₂₂N₄O₃S | 410.49 | >80% | Yellow solid. ¹H NMR (400 MHz, DMSO-d₆, 343K) of major tautomer δ_H 10.04 (br s, 1H, NH, D₂O exchanged), 9.35 (s, 1H), 8.98 (s, 1H), 8.15 (d, J = 8.7 Hz, 1H), 8.02 (d, J = 8.6 Hz, 1H), 7.24 (br s, 1H, NH, D₂O exchanged), 6.42 (s, 1H), 4.71 (s, 2H, OH, D₂O exchanged), 2.30-2.20 (m, 1H), 2.03-1.78 (m, 6H), 1.65-1.37 (m, 6H). MS (ESI⁺): [M + H]⁺ 411.1. |

TABLE 3-continued

| | Structure | Formula | MW | Purity | Characterization |
|---|---|---|---|---|---|
| 212 | 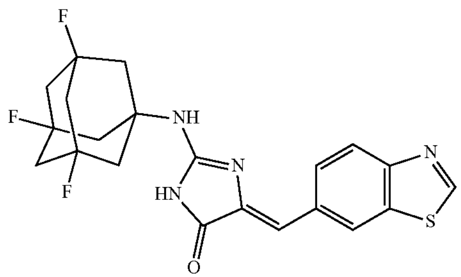 [SMILES: O=C1NC(NC23CC4(F)CC(F)(CC(F)(C4)C2)C3)=N/C1=C\c1ccc2ncsc2c1] | C$_{21}$H$_{19}$F$_3$N$_4$OS | 432.47 | >98% | Yellow solid. $^1$H NMR (400 MHz, DMSO-d$_6$, 343K) of major tautomer δ$_H$ 10.12 (br s, 1H, NH, D$_2$O exchanged), 9.34 (s, 1H), 9.15-8.77 (m, 1H), 8.31-7.93 (m, 2H), 7.50 (br s, 1H, NH, D$_2$O exchanged), 6.52 (s, 1H), 2.48-2.05 (m, 12H). MS (ESI$^+$): [M + H]$^+$ 433.2. |
| 213 | 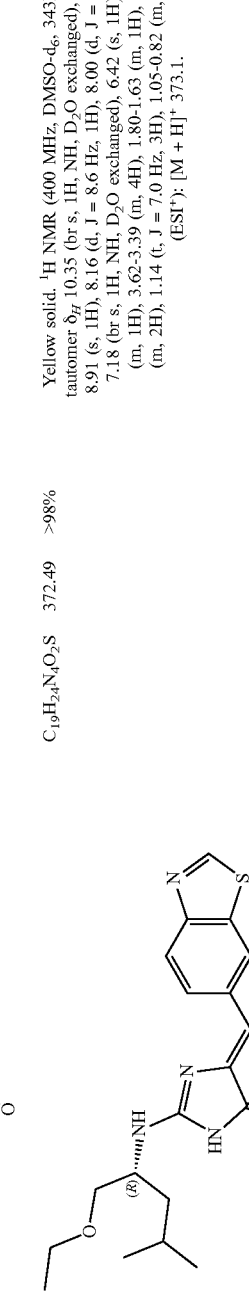 | C$_{19}$H$_{24}$N$_4$O$_2$S | 372.49 | >98% | Yellow solid. $^1$H NMR (400 MHz, DMSO-d$_6$, 343K) of major tautomer δ$_H$ 10.35 (br s, 1H, NH, D$_2$O exchanged), 9.30 (s, 1H), 8.91 (s, 1H), 8.16 (d, J = 8.6 Hz, 1H), 8.00 (d, J = 8.6 Hz, 1H), 7.18 (br s, 1H, NH, D$_2$O exchanged), 6.42 (s, 1H), 4.24-4.06 (m, 1H), 3.62-3.39 (m, 4H), 1.80-1.63 (m, 1H), 1.59-1.38 (m, 2H), 1.14 (t, J = 7.0 Hz, 3H), 1.05-0.82 (m, 6H). MS (ESI$^+$): [M + H]$^+$ 373.1. |
| 214 | 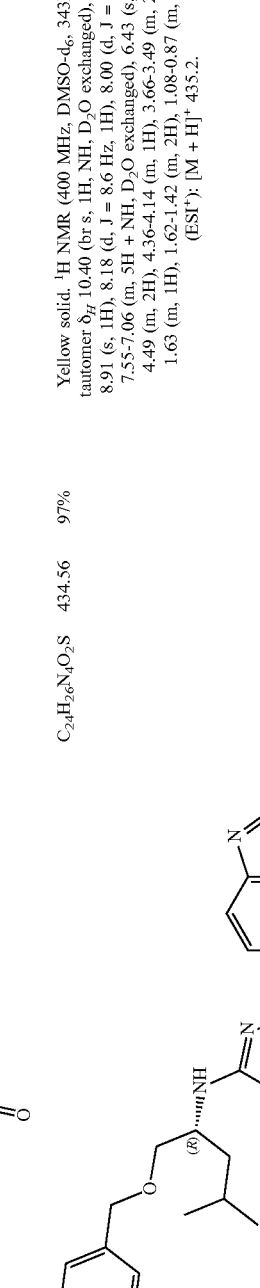 | C$_{24}$H$_{26}$N$_4$O$_2$S | 434.56 | 97% | Yellow solid. $^1$H NMR (400 MHz, DMSO-d$_6$, 343K) of major tautomer δ$_H$ 10.40 (br s, 1H, NH, D$_2$O exchanged), 9.30 (s, 1H), 8.91 (s, 1H), 8.18 (d, J = 8.6 Hz, 1H), 8.00 (d, J = 8.6 Hz, 1H), 7.55-7.06 (m, 5H + NH, D$_2$O exchanged), 6.43 (s, 1H), 4.66-4.49 (m, 2H), 4.36-4.14 (m, 1H), 3.66-3.49 (m, 2H), 1.81-1.63 (m, 1H), 1.62-1.42 (m, 2H), 1.08-0.87 (m, 6H). MS (ESI$^+$): [M + H]$^+$ 435.2. |

TABLE 3-continued

| | | | | |
|---|---|---|---|---|
| 215 | 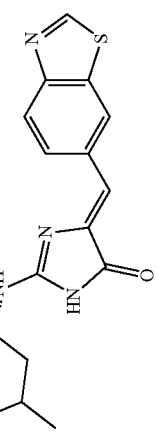 | C_{24}H_{25}FN_4O_2S | 452.55 | >98% | Yellow solid. $^1$H NMR (400 MHz, DMSO-d$_6$, 343K) of major tautomer δ$_H$ 10.39 (br s, 1H, NH, D$_2$O exchanged), 9.30 (s, 1H), 8.89 (s, 1H), 8.17 (dd, J = 8.6, 1.6 Hz, 1H), 8.00 (d, J = 8.6 Hz, 1H), 7.37 (dd, J = 8.5, 5.7 Hz, 2H), 7.24 (br s, 1H, NH, D$_2$O exchanged), 7.10 (t, J = 8.9 Hz, 2H), 6.42 (s, 1H), 4.61-4.47 (m, 2H), 4.31-3.12 (m, 1H), 3.56 (d, J = 5.4 Hz, 2H), 1.78-1.64 (m, 1H), 1.61-1.40 (m, 2H), 1.05-0.84 (m, 6H). MS (ESI$^+$): [M + H]$^+$ 453.1. |
| 216 | 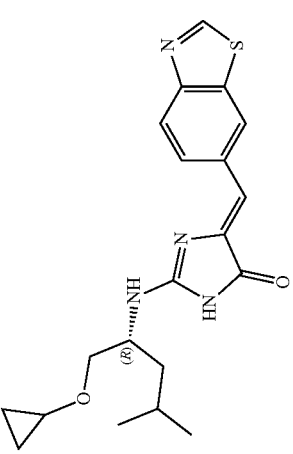 | C_{20}H_{24}N_4O_2S | 384.50 | >98% | Yellow solid. $^1$H NMR (400 MHz, DMSO-d$_6$, 343K) of major tautomer δ$_H$ 10.34 (br s, 1H, NH, D$_2$O exchanged), 9.30 (s, 1H), 8.91 (s, 1H), 8.16 (d, J = 8.5 Hz, 1H), 8.00 (d, J = 8.5 Hz, 1H), 7.18 (br s, 1H, NH, D$_2$O exchanged), 6.42 (s, 1H), 4.28-4.05 (m, 1H), 3.63-3.47 (m, 2H), 3.42-3.31 (m, 1H), 1.79-1.60 (m, 1H), 1.57-1.34 (m, 2H), 1.04-0.83 (m, 6H), 0.57-0.37 (m, 4H). MS (ESI$^+$): [M + H]$^+$ 385.1. |

Pathologies

The compounds of formula (I) may be useful in the treatment and/or in the prevention of a disease selected from cognitive deficits associated with Down syndrome (Trisomy 21); Alzheimer's disease and related diseases; dementia; tauopathies; and other neurodegenerative diseases (Parkinson's disease; Pick disease, including Niemann-Pick Type C Disease); CDKL5 Deficiency Disorder; McDermid syndrome; autism; type 1 and type 2 diabetes; abnormal folate and methionine metabolism; osteoarthritis, in particular knee osteoarthritis; Duchenne muscular dystrophy; several cancers, such as brain cancer, including glioblastoma, leukemia, including megakaryoblastic leukemia, acute lymphoblastic leukemia, head and neck squamous cell carcinoma, pancreatic cancer, including pancreatic ductal adenocarcinoma, prostate cancer, gastrointestinal cancer, breast cancer, such as Triple-negative breast cancer (TNBC), tissue cancer, including liposarcoma, Hedgehog/GLI-dependent cancer, liver cancer, including Hepatocellular carcinoma and viral infections, such as caused by Human immunodeficiency virus type 1 (HIV-1), Human cytomegalovirus (HCMV), Influenza A, Herpes virus, rhesus macaque cytomegalovirus, varicella-zoster virus, herpes simplex virus (HSV), Hepatitis C virus, Chikungunya virus, Dengue virus, Influenza virus and Severe acute respiratory syndrome (SARS) coronavirus, Cytomegalovirus and Human papillomavirus; neuroinflammation; anemia; infections caused by unicellular parasites, such as malaria, Leishmaniasis, Chagas and sleeping sickness (*Trypanosoma* sp.), and cattle diseases due to unicellular pathogens and for regulating body temperature.

According to a particular embodiment, the compounds of formula (I) of the present invention may be useful in the treatment and/or in the prevention of a disease selected from cognitive deficits associated with Down syndrome (Trisomy 21); Alzheimer's disease and related diseases; dementia; tauopathies; other neurodegenerative diseases (Parkinson's disease; Pick disease, including Niemann-Pick Type C Disease); CDKL5 Deficiency Disorder; type 1 and type 2 diabetes; abnormal folate and methionine metabolism; osteoarthritis, in particular knee osteoarthritis; Duchenne muscular dystrophy; several cancers, such as brain cancer, including glioblastoma, leukemia, including megakaryoblastic leukemia and acute lymphoblastic leukemia, head and neck squamous cell carcinoma, pancreatic cancer, including pancreatic ductal adenocarcinoma, prostate cancer, gastrointerstinal cancer and breast cancer, such as Triple-negative breast cancer (TNBC) and viral infections, such as caused by Human immunodeficiency virus type 1 (HIV-1), Human cytomegalovirus (HCMV), Influenza A, Herpes virus, rhesus macaque cytomegalovirus, varicella-zoster virus and herpes simplex virus (HSV) and for regulating body temperature. Said diseases are more particularly associated with the abnormalities in DYRK1A and/or CLK1 dosage.

Still according to this particular embodiment, the compounds of formula (I) of the present invention may be useful in the treatment and/or prevention of a disease selected from Down syndrome, Alzheimer's disease, dementia, tauopathies, Parkinson's disease, Niemann-Pick Type C Disease, CDKL5 Deficiency Disorder and Phelan-McDermid syndrome and their associated cognitive and motor conditions, more particularly due to high expression and activity of DYRK1A.

Still according to this particular embodiment, the compounds of formula (I) of the present invention may be useful in the treatment and/or prevention of a disease selected from Down syndrome, Alzheimer's disease and related Tauopathies, Parkinson's disease, the cognitive/motor disorders associated therewith, or one or more symptoms of such diseases. As a typical symptom of such diseases is a decline in learning and memory and social interactions.

Still according to this particular embodiment, the compounds of formula (I) of the present invention may be useful in combatting cognitive decline associated with Down syndrome (Trisomy 21), in learning and memory, in particular associated with the cognitive or neurodegenerative disorders as mentioned above.

Still according to this particular embodiment, the compounds of formula (I) of the present invention may be useful in the treatment and/or prevention of type 1 and type 2 diabetes.

The compounds of formula (I) of the present invention may be useful in the treatment and/or prevention of type 1 and type 2 diabetes either by direct treatment of the diabetic patient or by treating pancreatic islets or 3-cells prior to transplantation into diabetic patients.

Still according to this particular embodiment, the compounds of formula (I) of the present invention may be useful in the treatment and/or prevention of viral infections, in particular caused by such as caused by Human immunodeficiency virus type 1 (HIV-1), Human cytomegalovirus (HCMV), Influenza A, Herpes virus, rhesus macaque cytomegalovirus, varicella-zoster virus and herpes simplex virus (HSV), and in particular by Herpes, Coronaviruses, Cytomegaloviruses and Influenzas. These infections may be associated with high expression and activity of DYRK1A and/or CLK1, and optionally additionally with dual inhibitors of CLKs/DYRKS.

Acute respiratory disease has recently been caused by a new coronavirus (SARS-CoV-2, previously known as 2019-nCoV), also known here as coronavirus 2019 (COVID-19), which belongs to Coronaviridae. The compounds of formula (I) according to the present invention can also treat said infection caused by SARS-CoV-2 virus.

Still according to this particular embodiment, the compounds of formula (I) of the present invention may be useful in the treatment and/or prevention of cancers, such as brain cancer, including glioblastoma, leukemia, including megakaryoblastic leukemia and acute lymphoblastic leukemia, head and neck squamous cell carcinoma, pancreatic cancer, including pancreatic ductal adenocarcinoma, prostate cancer, gastrointerstinal cancer and breast cancer, such as Triple-negative breast cancer (TNBC). These cancers may be associated with high expression and activity of DYRK1A and/or CLK1, and optionally additionally with dual inhibitors of CLKs/DYRKS.

Still according to this particular embodiment, the compounds of formula (I) of the present invention may be useful in the treatment and/or prevention of osteoarthritis. Osteoarthritis may be associated with high expression and activity of DYRK1A and/or CLK2.

Still according to this particular embodiment, the compounds of formula (I) of the present invention may be useful in the treatment and/or prevention of infections caused by unicellular parasites, such as such as malaria, Leishmaniasis, Chagas and sleeping sickness (*Trypanosoma* sp.), and cattle diseases due to unicellular pathogens Said parasitic infections may be associated with expression and activity of DYRKs/CLKs.

Still according to this particular embodiment, the compounds of formula (I) of the present invention may be useful in the regulation of the body temperature. Said body temperature regulation may be associated with expression and activity of CLKs.

According to another particular embodiment, the compounds of formula (I) of the present invention may be useful in the treatment and/or in the prevention of a disease selected from Phelan-McDermid syndrome; autism; further viral infections, such as caused by Hepatitis C virus, Chikungunya virus, Dengue virus, Influenza virus and Severe acute respiratory syndrome (SARS) coronavirus, Cytomegalovirus and Human papillomavirus; further cancers, such as tissue cancer, including liposarcoma, Hedgehog/GLI-dependent cancer, liver cancer, including Hepatocellular carcinoma, neuroinflammation, anemia, infections caused by unicellular parasites, such as such as malaria, Leishmaniasis, Chagas and sleeping sickness (*Trypanosoma* sp.), and cattle diseases due to unicellular pathogens. Said diseases are more particularly associated with the abnormalities in other DYRKs (DYR1B, 2, 3, 4) and the closely related further cdc2-like kinases (CLKs) (CLK 2, 3, 4).

The following examples are provided as illustrations and in no way limit the scope of this invention.

The following examples illustrate in detail the preparation of some compounds according to the invention. The structures of the products obtained have been confirmed by NMR analyses and mass spectroscopy.

Example 1: General Protocol 1—Synthesis of (5Z)-5-heteroaryl-2-thioxo-imidazolidin-4-ones

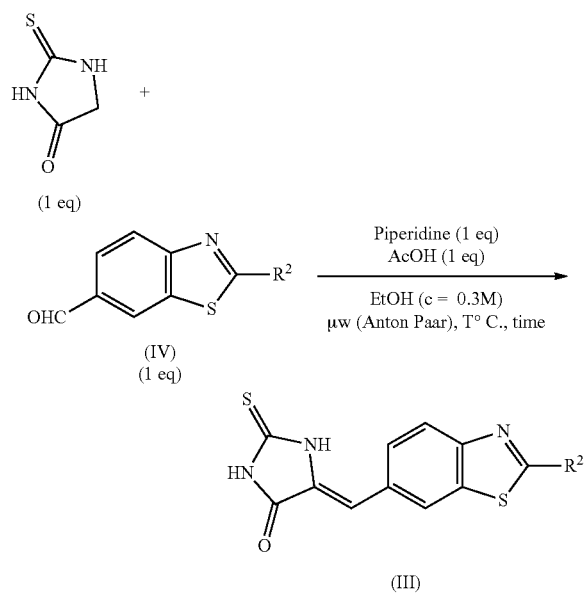

In the above scheme, $R^2$ represents a hydrogen atom or a ($C_1$-$C_3$)alkyl group, in particular $R^2$ represents a hydrogen atom or a methyl group.

GP1: a stirred solution of 2-thiohydantoin (1 eq), the appropriate heteroarylcarbaldehyde (1 eq), piperidine (1 eq) and AcOH (1 eq) in EtOH (c=0.3 M) was heated in a sealed tube in a microwave oven (Anton Paar) for the appropriate time, at the indicated temperature. Upon completion (followed by consumption of the aldehyde on TLC), the reaction medium was cooled down and added dropwise onto water. The precipitated solid was stirred for 30 min, filtered off on a fritted glass funnel, thoroughly dried, and could be used in the next step without further purification. When necessary, a final trituration in EtOH may help remove trace impurities without significant yield loss.

Example 1.1: Synthesis of (5Z)-5-(1,3-benzothiazol-6-ylmethylene)-2-thioxo-imidazolidin-4-one (1.1)

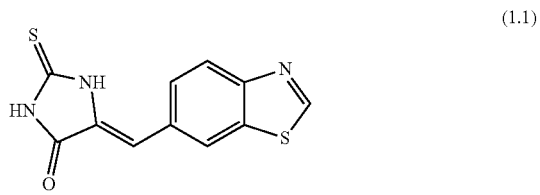 [SMILES: O=C1NC(=S)N/C1=C\c1ccc2ncsc2c1]

Compound (1.1) was synthesized according to GP1: reaction was carried out on a 4.2 mmol scale of 2-thiohydantoin, benzothiazole-6-carbaldehyde, AcOH and piperidine. Reaction temperature: 110° C., time: 90 min. The yellow solid was triturated in EtOH after filtration. Yellow solid, 89% (978 mg). $^1$H NMR (400 MHz, DMSO-d$_6$) $\delta_H$ 12.44 (br s, 1H, NH, D$_2$O exchanged), 12.25 (br s, 1H, NH, D$_2$O exchanged), 9.47 (s, 1H), 8.61 (d, J=1.8 Hz, 1H), 8.09 (d, J=8.5 Hz, 1H), 7.84 (dd, J=8.6, 1.8 Hz, 1H), 6.64 (s, 1H). $^{13}$C NMR (101 MHz, DMSO-d$_6$) $\delta_C$ 179.3, 165.7, 158.0, 153.1, 134.4, 129.8, 128.9, 128.1, 123.7, 123.1, 110.9. MS (ESI$^+$): [M+H]$^+$ 262.1.

Example 1.2: Synthesis of (5Z)-5-[(2-methyl-1,3-benzothiazol-6-yl)methylene]-2-thioxo-imidazolidin-4-one (1.2)

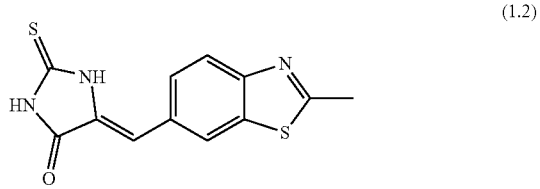 [SMILES: Cc1nc2ccc(/C=C3\NC(=S)NC3=O)cc2s1]

Compound (1.2) was synthesized according to GP1: reaction was carried out on a 7.34 mmol scale of 2-thiohydantoin, 2-methyl-1,3-benzothiazole-6-carbaldehyde, AcOH and piperidine. Reaction temperature: 110° C., time: 90 min. The yellow solid was triturated in EtOH after filtration. Yellow solid, 94% (1.898 g). $^1$H NMR (400 MHz, DMSO-d$_6$) $\delta_H$ 12.42 (br s, 1H, NH, D$_2$O exchanged), 12.21 (br s, 1H, NH, D$_2$O exchanged), 8.48 (s, 1H), 7.91 (d, J=8.4 Hz, 1H), 7.77 (d, J=8.5 Hz, 1H), 6.60 (s, 1H), 2.82 (s, 3H). $^{13}$C NMR (101 MHz, DMSO-d$_6$) $\delta_C$ 179.2, 169.1, 165.7, 153.1, 136.0, 129.0, 128.8, 127.7, 123.0, 122.0, 111.1, 20.0. MS (ESI$^+$): [M+H]$^+$ 275.9.

Example 2: General Protocol 2—S-Alkylation of (5Z)-5-heteroaryl-2-thioxo-imidazolidin-4-ones

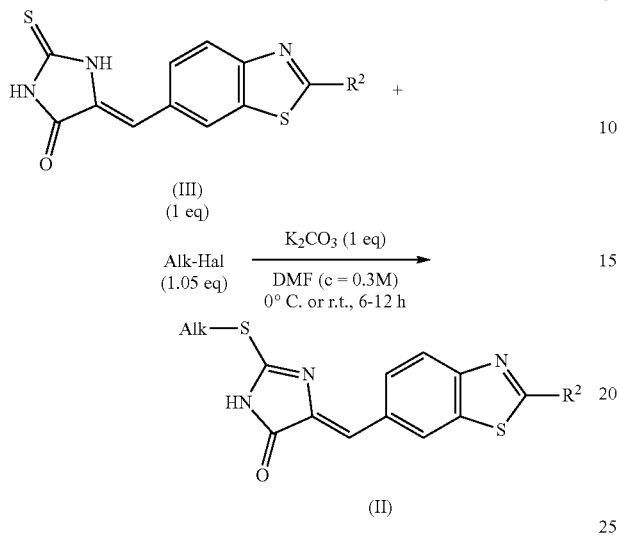

In the above scheme, Hal represents a halogen atom, in particular selected from an iodine and a bromine atom, Alk is a ($C_1$-$C_5$) alkyl and $R^2$ represents a hydrogen atom or a ($C_1$-$C_3$)alkyl group, in particular $R^2$ represents a hydrogen atom or a methyl group.

GP2: The appropriate alkyliodide (1.05 eq) was added dropwise to a stirred solution of (5Z)-5-heteroaryl-2-thioxo-imidazolidin-4-one (1 eq) and $K_2CO_3$ (1 eq) in DMF (c=0.3 M) at the appropriate temperature. The resulting mixture was stirred at the indicated temperature, for the appropriate time. Upon completion (TLC), the mixture was poured into water. The precipitated solid was stirred for 30 min and filtered off on a fritted glass funnel, thoroughly dried, and could be used in the next step without further purification. Trace impurities resulting from the double alkylation may be removed by FC: elution: cyclohexane/AcOEt 7/3 to 3/7 or trituration.

Example 2.1: Synthesis of (4Z)-4-(1,3-benzothiazol-6-ylmethylene)-2-ethylsulfanyl-1H-imidazol-5-one (2.1)

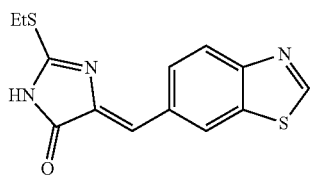

Compound (2.1) was synthesized according to GP2: reaction was carried out with (5Z)-5-(1,3-benzothiazol-6-ylmethylene)-2-thioxo-imidazolidin-4-one (7.69 mmol) and EtI, at room temperature, for 12 h. Yellow solid, 89% (978 mg). $^1$H NMR (400 MHz, DMSO-$d_6$) $\delta_H$ 11.85 (br s, 1H, NH, $D_2O$ exchanged), 9.46 (s, 1H), 8.90 (s, 1H), 8.45 (d, J=8.6 Hz, 1H), 8.12 (d, J=8.6 Hz, 1H), 6.88 (s, 1H), 3.70-3.17 (m, 2H), 1.44 (t, J=7.3 Hz, 3H). $^{13}$C NMR (101 MHz, DMSO-$d_6$) $\delta_C$ 170.5, 165.0, 157.8, 153.2, 139.5, 134.1, 132.0, 129.2, 125.4, 123.0, 119.9, 24.4, 14.5. MS (ESI$^+$): [M+H]$^+$ 289.9.

Example 2.2: Synthesis of (4Z)-4-(1,3-benzothiazol-6-ylmethylene)-2-methylsulfanyl-1H-imidazol-5-one (2.2)

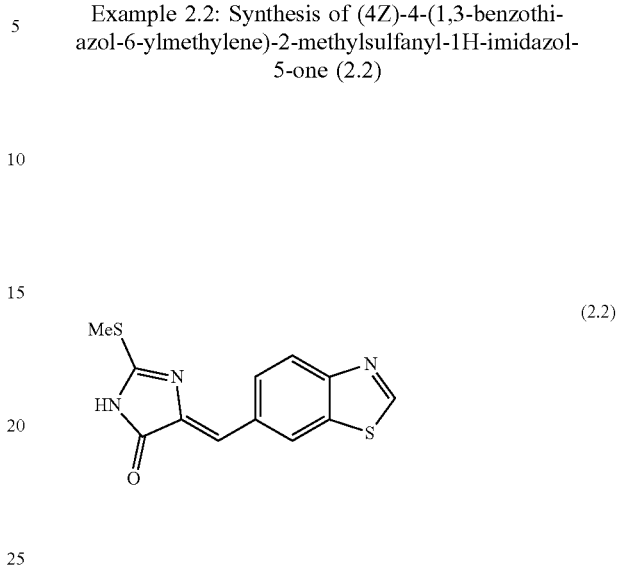

Compound (2.2) was synthesized according to GP2: reaction was carried out with (5Z)-5-(1,3-benzothiazol-6-ylmethylene)-2-thioxo-imidazolidin-4-one (3.83 mmol) and MeI, at 0° C., for 6 h. The yellow solid was triturated in DCM after filtration. Yellow solid, 83% (879 mg). $^1$H NMR (400 MHz, DMSO-$d_6$) $\delta_H$ 11.89 (br s, 1H, NH, $D_2O$ exchanged), 9.46 (s, 1H), 8.92 (d, J=1.6 Hz, 1H), 8.45 (d, J=8.6 Hz, 1H), 8.12 (d, J=8.6 Hz, 1H), 6.88 (s, 1H), 2.72 (s, 3H). $^{13}$C NMR (101 MHz, DMSO-$d_6$) $\delta$ 171.1, 166.1, 158.3, 153.7, 140.0, 134.6, 132.4, 129.8, 125.9, 123.5, 120.4, 12.8. MS (ESI$^+$): [M+H]$^+$ 275.9.

Example 2.3: Synthesis of (4Z)-2-ethylsulfanyl-4-[(2-methyl-1,3-benzothiazol-6-yl)methylene]-1H-imidazol-5-one (2.3)

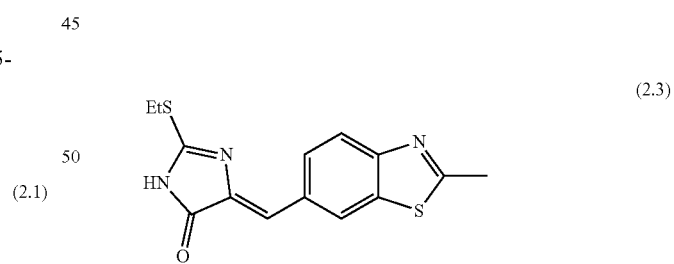

Compound (2.3) was synthesized according to GP2: reaction was carried out with (5Z)-5-[(2-methyl-1,3-benzothiazol-6-yl)methylene]-2-thioxo-imidazolidin-4-one (1.45 mmol) and EtI, at room temperature, for 12 h. Yellow solid, 84% (368 mg). $^1$H NMR (400 MHz, DMSO-$d_6$) $\delta_H$ 11.82 (br s, 1H, NH, $D_2O$ exchanged), 8.75 (s, 1H), 8.39 (d, J=8.5 Hz, 1H), 7.94 (d, J=8.6 Hz, 1H), 6.85 (s, 1H), 3.43-3.21 (m, 2H), 2.82 (s, 3H), 1.44 (t, J=7.3 Hz, 3H). $^{13}$C NMR (101 MHz, DMSO-$d_6$) $\delta_C$ 170.5, 169.0, 164.6, 153.3, 139.2, 135.7, 131.2, 129.1, 124.8, 122.0, 120.1, 24.3, 19.9, 14.5. MS (ESI$^+$): [M+H]$^+$ 303.9.

Example 2.4: Synthesis of (4Z)-4-[(2-methyl-1,3-benzothiazol-6-yl)methylene]-2-methylsulfanyl-1H-imidazol-5-one (2.4)

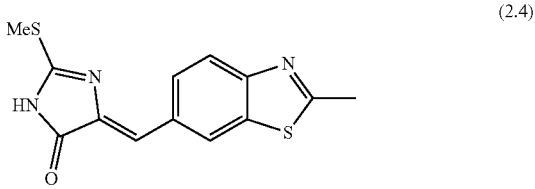 [SMILES: CSC1=N/C(=C\c2ccc3nc(C)sc3c2)C(=O)N1]

(2.4)

Compound (2.4) was synthesized according to GP2: reaction was carried out with (5Z)-5-[(2-methyl-1,3-benzothiazol-6-yl)methylene]-2-thioxo-imidazolidin-4-one (3.63 mmol) and MeI, at room temperature, for 6 h. The yellow solid was triturated in DCM after filtration. Yellow solid, 92% (962 mg). $^1$H NMR (400 MHz, DMSO-$d_6$) $\delta_H$ 11.86 (br s, 1H, NH, $D_2O$ exchanged), 8.77 (s, 1H), 8.39 (d, J=8.6 Hz, 1H), 7.94 (d, J=8.6 Hz, 1H), 6.85 (s, 1H), 2.82 (s, 3H), 2.71 (s, 3H). $^{13}$C NMR (101 MHz, DMSO-$d_6$)$^6$c 170.6, 169.0, 165.3, 153.3, 139.2, 135.7, 131.2, 129.3, 124.9, 121.9, 120.2, 19.9, 12.3. MS (ESI$^+$): [M+H]$^+$ 290.1.

Example 3: General Protocol 3—Addition of Aliphatic and Aromatic amines on (4Z)-4-(1,3-benzothiazol-6-ylmethylene)-2-alkylsulfanyl-1H-imidazol-5-ones

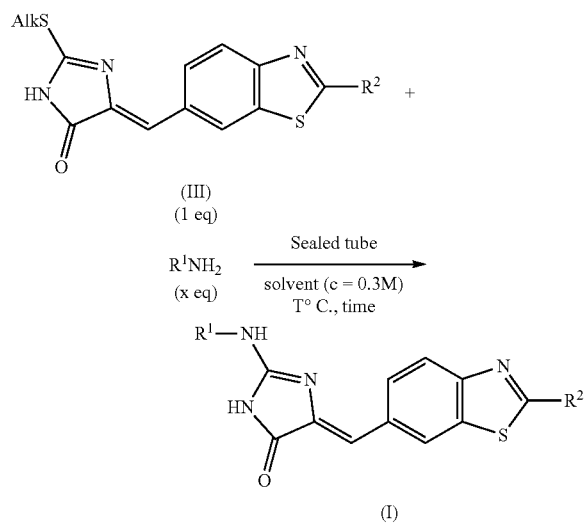

In the above scheme, Alk is a ($C_1$-$C_5$) alkyl and $R^2$ represents a hydrogen atom or a ($C_1$-$C_3$)alkyl group, in particular $R^2$ represents a hydrogen atom or a methyl group.

The appropriate amine$^{(a)}$ (x eq) was added to a stirred suspension of (4Z)-4-heteroaryl-2-alkylsulfanyl-1H-imidazol-5-one(b) (1 eq) in the appropriate solvent mixture (c=0.3 M) in a sealed tube (heating block or pw). The mixture was thoroughly purged with vacuum/argon cycles and heated (pw or heating block) at the appropriate temperature for the indicated time. Upon completion (followed by consumption of the isothiourea on TLC), the mixture was brought back to room temperature.

GP3-A: direct precipitation of the desired product: The reaction medium was stirred 1 h at 0° C. The precipitated solid was filtered off on a fritted-glass funnel. High purity may be achieved after filtration by washing, reprecipitation, trituration, or recrystallization.

GP3-B: the product failed to precipitate: the reaction mixture was concentrated in vacuo, adsorbed on silica, and purified by FC. High purity may be achieved after filtration by reprecipitation, trituration, or recrystallization.

GP3-C: the product failed to precipitate: the reaction mixture was concentrated in vacuo. The resulting crude was triturated in EtOH (at r.t. or reflux), filtered off on a fritted-glass funnel. High purity may be achieved after filtration by purification, reprecipitation, trituration, or recrystallization.

(a) When amine hydrochlorides were used, they were quenched in situ with TEA or DIPEA.
(b) May require activation with AcOH, depending on the amine.

Selected Examples from Sub-Group A1

Example 3.1: Synthesis of (4Z)-4-(1,3-benzothiazol-6-ylmethylene)-2-(cyclohexylamino)-1H-imidazol-5-one (6)

Reaction was carried out according to GP3-A, in THF (0.3 M), on a 2.73 mmol scale of (2.1), with 4 eq of cyclohexylamine at 110° C. (sealed tube, heating block), for 12 h. The product directly precipitated in the reaction medium: it was isolated after filtration, washing with cold THF, then pentane. Isolated yield: 34%.

Example 3.2: Synthesis of (4Z)-4-(1,3-benzothiazol-6-ylmethylene)-2-(cycloheptylmethylamino)-1H-imidazol-5-one (7)

Reaction was carried out according to GP3-B, in THF (0.3 M), on a 1.01 mmol scale of (2.1), with 4 eq of cycloheptylmethylamine at 110° C. (sealed tube, heating block), for 12 h. Purification by FC (elution: DCM/MeOH: 99/1 to 93/7). The final product required a reprecipitation from DCM/pentane at 0° C. Isolated yield: 23%.

Example 3.3: Synthesis of (4Z)-4-(1,3-benzothiazol-6-ylmethylene)-2-(cycloheptylamino)-1H-imidazol-5-one (8)

Reaction was carried out according to GP3-A, in THF (0.3 M), on a 4.84 mmol scale of (2.1), with 4 eq of cycloheptylamine at 110° C. (sealed tube, heating block), for 12 h. The product directly precipitated in the reaction medium: it was isolated after filtration, washing with cold THF, then pentane. Isolated yield: 49%.

Example 3.4: Synthesis of (4Z)-4-(1,3-benzothiazol-6-ylmethylene)-2-(cyclooctylamino)-1H-imidazol-5-one (9)

Reaction was carried out according to GP3-A, in THF (0.3 M), on a 2.73 mmol scale of (2.1) and 4 eq of cyclooctylamine at 110° C. (sealed tube, heating block), for 12 h. The product directly precipitated in the reaction medium it was isolated after filtration, washing with cold THF, then pentane. Isolated yield: 58%.

Example 3.5: Synthesis of (4Z)-2-(1-adamantylamino)-4-(1,3-benzothiazol-6-ylmethylene)-1H-imidazol-5-one (16)

Reaction was carried out according to GP3-B, in THF (0.3 M), on a 2.54 mmol scale of (2.2), with 3 eq of 1-adamantylamine and 15 eq of AcOH, at 160° C. (sealed tube, heating block), for 24 h. Purification by FC (elution: DCM/MeOH: 99/1 to 93/7). The final product required two successive triturations in refluxing EtOH. Isolated yield: 61%.

Example 3.6: Synthesis of (4Z)-2-(2-adamantylamino)-4-(1,3-benzothiazol-6-ylmethylene)-1H-imidazol-5-one (17)

Reaction was carried out according to GP3-B, in THF (0.3 M), on a 746 µmol scale of (2.2), with 4 eq of 2-adamantylamine and 15 eq of AcOH, at 170° C. (sealed tube, heating block), for 12 h. Purification by FC (elution: DCM/MeOH: 99/1 to 93/7). The final product required trituration in EtOH at 0° C. Isolated yield: 44%.

Example 3.7: Synthesis of (4Z)-4-(1,3-benzothiazol-6-ylmethylene)-2-[(trans-5-hydroxy-2-adamantyl)amino]-1H-imidazol-5-one (19)

Reaction was carried out according to GP3-B, in THF (0.3 M), on a 746 µmol scale of (2.2), with 4 eq of trans-4-aminoadamantan-1-ol and 15 eq of AcOH, at 170° C. (sealed tube, heating block), for 12 h. Purification by FC (elution: DCM/MeOH: 99/1 to 93/7). The final product required trituration in EtOH at 0° C. Isolated yield: 27%.

Example 3.8: Synthesis of (4Z)-4-(1,3-benzothiazol-6-ylmethylene)-2-[(3-hydroxy-1-adamantyl)amino]-1H-imidazol-5-one (20)

Reaction was carried out according to GP3-B, in THF (0.3 M), on a 746 µmol scale of (2.2), with 4 eq of 3-amino-1-adamantanol and 15 eq of AcOH, at 160° C. (sealed tube, heating block), for 12 h. Purification by FC (elution: DCM/MeOH: 99/1 to 93/7). The final product required trituration in EtOH at 0° C. Isolated yield: 59%.

Example 3.9: Synthesis of (4Z)-4-(1,3-benzothiazol-6-ylmethylene)-2-[[(1R,2R,3R,5S)-2,6,6-trimethylnorpinan-3-yl]amino]-1H-imidazol-5-one (22)

Reaction was carried out according to GP3-B, in THF (0.3 M), on a 746 µmol scale of (2.1), with 4 eq of (1R,2R,3R,5S)-3-pinanamine, at 120° C. (sealed tube, heating block), for 12 h. Purification by FC (elution: DCM/MeOH: 99/1 to 93/7). The final product required a reprecipitation from DCM/pentane at 0° C. Isolated yield: 60%.

Example 3.10: Synthesis of (±)-(4Z)-4-(1,3-benzothiazol-6-ylmethylene)-2-(spiro[2.5]octan-2-ylamino)-1H-imidazol-5-one (25)

Reaction was carried out according to GP3-B, in THF (0.3 M), on a 773 µmol scale of (2.1), with 2 eq of (±)-spiro[2.5]octan-2-amine hydrochloride and 2 eq of TEA, at 110° C. (sealed tube, heating block), for 12 h. Purification by FC (elution: DCM/MeOH: 99/1 to 93/7). The final product required a reprecipitation from DCM/pentane at 0° C. Isolated yield: 61%.

Example 3.11: Synthesis of (4Z)-4-(1,3-benzothiazol-6-ylmethylene)-2-[[(2R)-1,7,7-trimethylnorbornan-2-yl]amino]-1H-imidazol-5-one (27)

Reaction was carried out according to GP3-B, in THF (0.3 M) on a 746 µmol scale of (2.1), with 3 eq of (R)-(+)-bornylamine, at 150° C. (sealed tube, heating block), for 8 h. Purification by FC (elution: DCM/MeOH: 99/1 to 93/7). The final product required a reprecipitation from DCM/pentane at 0° C. Isolated yield: 34%.

Example 3.12: Synthesis of (4Z)-4-(1,3-benzothiazol-6-ylmethylene)-2-[[(1R)-1-(hydroxymethyl)-3-methyl-butyl]amino]-1H-imidazol-5-one (34)

Reaction was carried out according to GP3-B, in THF (0.3 M) on a 746 µmol scale of (2.1), with 4 eq of D-leucinol, at 110° C. (sealed tube, heating block), for 12 h. Purification by FC (elution: DCM/MeOH: 99/1 to 93/7). The final product required a reprecipitation from DCM/pentane at 0° C. Isolated yield: 39%.

Example 3.13: Synthesis of (4Z)-4-(1,3-benzothiazol-6-ylmethylene)-2-[[(1R)-1-(methoxymethyl)-3-methyl-butyl]amino]-1H-imidazol-5-one (35)

Reaction was carried out according to GP3-B, in THF (0.3 M) on a 2.91 mmol scale of (2.2), with 2.5 eq of (2R)-1-methoxy-4-methyl-pentan-2-amine, at 120° C. (sealed tube, heating block), for 12 h. Purification by FC (elution: DCM/MeOH: 99/1 to 93/7). The final product required a reprecipitation from DCM/pentane at 0° C. Isolated yield: 74%.

Example 3.14: Synthesis of (4Z)-4-(1,3-Benzothiazol-6-ylmethylene)-2-[[(1S)-1-(hydroxymethyl)-3-methyl-butyl]amino]-1H-imidazol-5-one (36)

Reaction was carried out according to GP3-B, in THF (0.3 M) on a 746 µmol scale of (2.1), with 4 eq of L-leucinol, at 110° C. (sealed tube, heating block), for 12 h. Purification by FC (elution: DCM/MeOH: 99/1 to 93/7). The final product required a reprecipitation from DCM/pentane at 0° C. Isolated yield: 39%.

Example 3.15: Synthesis of (4Z)-4-(1,3-benzothiazol-6-ylmethylene)-2-[[1-(fluoromethyl)-3-methyl-butyl]amino]-1H-imidazol-5-one (40)

Reaction was carried out according to GP3-B, in THF (0.3 M) on a 908 µmol scale of (2.2), with 1.2 eq of (±)-1-fluoro-4-methyl-pentan-2-amine, at 150° C. (sealed tube, heating block), for 96 h. Purification by FC (elution: DCM/MeOH: 99/1 to 93/7) then PTLC. Isolated yield: 8%.

Example 3.16: Synthesis of (±)-(4Z)-4-(1,3-benzothiazol-6-ylmethylene)-2-[[trans-2-methoxycyclopentyl]amino]-1H-imidazol-5-one (48)

Reaction was carried out according to GP3-B, in THF (0.3 M) on a 272 µmol scale of (2.2), with 3 eq of (±)-trans-2-methoxycyclopentanamine hydrochloride and 4 eq of DIPEA, at 120° C. (sealed tube, heating block), for 7 h. Purification by FC (elution: DCM/MeOH: 99/1 to 93/7). The final product required a trituration in refluxing EtOH. Isolated yield: 81%.

Example 3.17: Synthesis of (±)-(4Z)-4-(1,3-benzo-thiazol-6-ylmethylene)-2-[[cis-3-hydroxycyclohexyl]amino]-1H-imidazol-5-one (55)

Reaction was carried out according to GP3-B, in THF (0.3 M) on a 272 µmol scale of (2.2), with 3 eq of (±)-cis-3-aminocyclohexanol hydrochloride and 4 eq of DIPEA, at 120° C. (sealed tube, heating block) for 24 h. Purification by FC (elution: DCM/MeOH: 99/1 to 93/7). Isolated yield: 82%.

Example 3.18: Synthesis of (±)-(4Z)-4-(1,3-benzo-thiazol-6-ylmethylene)-2-[[trans-3-hydroxycyclohexyl]amino]-1H-imidazol-5-one (56)

Reaction was carried out according to GP3-B, in THF (0.3 M) on a 272 µmol scale of (2.2), with 3 eq of (±)-trans-3-aminocyclohexanol hydrochloride and 4 eq of DIPEA, at 120° C. (sealed tube, heating block) for 24 h. Purification by FC (elution: DCM/MeOH: 99/1 to 93/7) then PTLC. Isolated yield: 82%.

Example 3.19: Synthesis of (±)-(4Z)-4-(1,3-benzo-thiazol-6-ylmethylene)-2-[[trans-2-methoxycyclohexyl]amino]-1H-imidazol-5-one (59)

Reaction was carried out according to GP3-B, in THF (0.3 M) on a 272 µmol scale of (2.2), with 3 eq of (±)-trans-2-methoxycyclohexanamine hydrochloride and 4 eq of DIPEA, at 120° C. (sealed tube, heating block) for 28 h. Purification by FC (elution: DCM/MeOH: 99/1 to 93/7). Isolated yield: 82%.

Example 3.20: Synthesis of (±)-(4Z)-4-(1,3-benzo-thiazol-6-ylmethylene)-2-[[cis-2-hydroxycycloheptyl]amino]-1H-imidazol-5-one (61)

Reaction was carried out according to GP3-B, in THF (0.3 M) on a 272 µmol scale of (2.2), with 3 eq of (±)-cis-2-aminocycloheptanol hydrochloride and 4 eq of DIPEA, at 120° C. (sealed tube, heating block), for 28 h. Purification by FC (elution: DCM/MeOH: 99/1 to 93/7). The final product required a trituration in refluxing EtOH. Isolated yield: 56%.

Example 3.21: Synthesis of (±)-(4Z)-4-(1,3-benzo-thiazol-6-ylmethylene)-2-[[trans-2-hydroxycycloheptyl]amino]-1H-imidazol-5-one (62)

Reaction was carried out according to GP3-B, in THF (0.3 M) on a 272 µmol scale of (2.2), with 3 eq of (±)-trans-2-aminocycloheptanol, at 120° C. (sealed tube, heating block), for 6 h. Purification by FC (elution: DCM/MeOH: 99/1 to 93/7). The final product required a trituration in refluxing EtOH. Isolated yield: 31%.

Example 3.22: Synthesis of (4Z)-4-(1,3-benzothi-azol-6-ylmethylene)-2-[[(1R,2R)-2-hydroxycycloheptyl]amino]-1H-imidazol-5-one (63)

Reaction was carried out according to GP3-B, in THF (0.3 M) on a 746 µmol scale of (2.1), with 3 eq of (1R,2R)-2-aminocycloheptanol, at 110° C. (sealed tube, heating block) for 12 h. Purification by FC (elution: DCM/MeOH: 99/1 to 93/7). The final product required a reprecipitation from DCM/pentane at 0° C. Isolated yield: 49%.

Example 3.23: Synthesis of (±)-(4Z)-4-(1,3-benzo-thiazol-6-ylmethylene)-2-[[cis-3-hydroxycycloheptyl]amino]-1H-imidazol-5-one (65)

Reaction was carried out according to GP3-B, in THF (0.3 M) on a 218 µmol scale of (2.2), with 3 eq of (±)-cis-3-aminocycloheptanol hydrochloride and 4 eq of DIPEA, at 150° C. (sealed tube, pw) for 6 h. Purification by FC (elution: DCM/MeOH: 99/1 to 93/7). Isolated yield: 46%.

Example 3.24: Synthesis of (±)-(4Z)-4-(1,3-benzo-thiazol-6-ylmethylene)-2-[[trans-3-hydroxycycloheptyl]amino]-1H-imidazol-5-one (66)

Reaction was carried out according to GP3-B, in THF (0.3 M) on a 272 µmol scale of (2.2), with 3 eq of (±)-trans-3-aminocycloheptanol hydrochloride and 4 eq of DIPEA, at 120° C. (sealed tube, heating block) for 31 h. Purification by FC (elution: DCM/MeOH: 99/1 to 93/7) then PTLC. Isolated yield: 67%.

Example 3.25: Synthesis of (±)-(4Z)-4-(1,3-benzo-thiazol-6-ylmethylene)-2-[[trans-2-methoxycycloheptyl]amino]-1H-imidazol-5-one (68)

Reaction was carried out according to GP3-B, in THF (0.3 M) on a 272 µmol scale of (2.2), with 3 eq of (±)-trans-2-methoxycycloheptanamine, at 120° C. (sealed tube, heating block) for 24 h. Purification by FC (elution: DCM/MeOH: 99/1 to 93/7). Isolated yield: 79%.

Selected Examples from Sub-Group A2

Example 3.26: Synthesis of (4Z)-4-(1,3-benzothi-azol-6-ylmethylene)-2-(benzylamino)-1H-imidazol-5-one (74)

Reaction was carried out according to GP3-A, in THF (0.3 M), on a 1.38 mmol scale of (2.1), with 4 eq of benzylamine at 110° C. (sealed tube, heating block) for 12 h. The product directly precipitated in the reaction medium: it was isolated after filtration, washing with cold THF, then pentane. Isolated yield: 80%.

Example 3.27: Synthesis of (4Z)-4-(1,3-benzothi-azol-6-ylmethylene)-2-[[2-(trifluoromethyl)phenyl]methylamino]-1H-imidazol-5-one (78)

Reaction was carried out according to GP3-A, in THF (0.3 M), on a 272 µmol scale of (2.2), with 3 eq of [2-(trifluoromethyl)phenyl]methanamine at 120° C. (sealed tube, heating block) for 24 h. The product directly precipitated in the reaction medium: it was isolated after filtration, washing with cold THF. The final product required a trituration in refluxing EtOH. Isolated yield: 72%.

Example 3.28: Synthesis of (±)-(4Z)-4-(1,3-benzo-thiazol-6-ylmethylene)-2-[[trans-2-hydroxyindan-1-yl]amino]-1H-imidazol-5-one (81)

Reaction carried out according to GP3-A, in THF (0.3 M), on a 272 µmol scale of (2.2), with 3 eq of (±)-trans-1-aminoindan-2-ol at 120° C. (sealed tube, heating block) for 30 h. The product directly precipitated in the reaction medium: it was isolated after filtration, washing with cold THF. The final product required a trituration in EtOH at r.t. Isolated yield: 56%.

Example 3.29: Synthesis of (4Z)-4-(1,3-benzothiazol-6-ylmethylene)-2-[[(1S,2S)-2-hydroxyindan-1-yl]amino]-1H-imidazol-5-one (83)

Reaction carried out according to GP3-A, in THF (0.3 M), on a 272 µmol scale of (2.2), with 3 eq of (1S,2S)-1-aminoindan-2-ol at 120° C. (sealed tube, heating block) for 40 h. The product directly precipitated in the reaction medium: it was isolated after filtration, washing with cold THF. The final product required a trituration in EtOH at r.t. Isolated yield: 62%.

Example 3.30: Synthesis of (±)-(4Z)-2-[(2-amino-1-phenyl-ethyl)amino]-4-(1,3-benzothiazol-6-ylmethylene)-1H-imidazol-5-one dihydrochloride (89)

Reaction carried out according to GP3-B, in THF (0.3 M), on a 363 µmol scale of (2.2), with 3 eq of (±)-tert-butyl N-(2-amino-2-phenyl-ethyl)carbamate at 120° C. (sealed tube, heating block) for 48 h. Purification by FC (elution: DCM/MeOH: 99/1 to 93/7) followed by deprotection with HCl (4M in dioxane). Isolated yield: 63%.

Example 3.31: Synthesis of (±)-(4Z)-4-(1,3-benzothiazol-6-ylmethylene)-2-[(2-hydroxy-1-phenyl-ethyl)amino]-1H-imidazol-5-one (95)

Reaction carried out according to GP3-B, in THF (0.3 M), on a 272 µmol scale of (2.2), with 3 eq of (±)-2-phenylglycinol at 150° C. (sealed tube, heating block) for 8 h. Purification by FC (elution: DCM/MeOH: 99/1 to 93/7). The final product required a trituration in refluxing EtOH. Isolated yield: 37%.

Example 3.32: Synthesis of (±)-(4Z)-4-(1,3-benzothiazol-6-ylmethylene)-2-[(2-methoxy-1-phenyl-ethyl)amino]-1H-imidazol-5-one (98)

Reaction carried out according to GP3-B, in THF (0.3 M), on a 272 µmol scale of (2.2), with 3 eq of (±)-2-methoxy-1-phenyl-ethanamine at 120° C. (sealed tube, heating block) for 48 h. Purification by FC (elution: DCM/MeOH: 99/1 to 93/7). The final product required a trituration in refluxing EtOH. Isolated yield: 41%.

Example 3.33: Synthesis of (±)-(4Z)-4-(1,3-benzothiazol-6-ylmethylene)-2-[(2-hydroxy-1-phenyl-ethyl)amino]-1H-imidazol-5-one (99)

Reaction carried out according to GP3-B, in THF (0.3 M), on a 272 µmol scale of (2.2), with 3 eq of (±)-2-amino-1-phenyl-ethanol hydrochloride and 4 eq of DIPEA, at 120° C. (sealed tube, heating block) for 2.5 h. Purification by FC (elution: DCM/MeOH: 99/1 to 93/7). The final product required a trituration in refluxing EtOH. Isolated yield: 41%.

Example 3.34: Synthesis of (4Z)-4-(1,3-benzothiazol-6-ylmethylene)-2-[[(1R)-2-methoxy-1-phenyl-ethyl]amino]-1H-imidazol-5-one (176)

Reaction carried out according to GP3-A, in THF (0.3 M), on a 12.71 mmol scale of (2.2), with 3 eq of (1R)-2-methoxy-1-phenyl-ethanamine at 140° C. (sealed tube, heating block) for 24 h. The product directly precipitated in the reaction medium: it was isolated after filtration, washing with cold THF. The final product required a trituration in refluxing EtOH. Isolated yield: 51%.

Selected Examples from Sub-Group A3

Example 3.35: Synthesis of (4Z)-4-(1,3-benzothiazol-6-ylmethylene)-2-[(5-methylpyrazin-2-yl)methylamino]-1H-imidazol-5-one (103)

Reaction carried out according to GP3-B, in THF (0.3 M), on a 182 µmol scale of (2.2), with 3 eq of (5-methylpyrazin-2-yl)methanamine, at 80° C. (sealed tube, heating block) for 16 h. Purification by FC (elution: DCM/MeOH: 99/1 to 93/7). Isolated yield: 47%.

Example 3.36: Synthesis of (4Z)-4-(1,3-benzothiazol-6-ylmethylene)-2-[(4-methylthiazol-2-yl)methylamino]-1H-imidazol-5-one (108)

Reaction carried out according to GP3-B, in THF (0.3 M), on a 182 µmol scale of (2.2), with 3 eq of (4-methylthiazol-2-yl)methanamine, at 120° C. (sealed tube, heating block) for 24 h. Purification by FC (elution: DCM/MeOH: 99/1 to 93/7). The final product required a trituration in refluxing EtOH. Isolated yield: 40%.

Selected Examples from Sub-Group A4

Example 3.37: Synthesis of (4Z)-4-(1,3-benzothiazol-6-ylmethylene)-2-(tetrahydropyran-4-ylmethylamino)-1H-imidazol-5-one (113)

Reaction carried out according to GP3-B, in THF (0.3 M), on a 182 µmol scale of (2.2), with 3 eq of tetrahydropyran-4-ylmethanamine, at 120° C. (sealed tube, heating block) for 2 h. Purification by FC (elution: DCM/MeOH: 99/1 to 93/7). Isolated yield: 51%.

Selected Examples from Sub-Group A5

Example 3.38: Synthesis of (4Z)-4-(1,3-benzothiazol-6-ylmethylene)-2-[4-(4-methylpiperazin-1-yl)anilino]-1H-imidazol-5-one (119)

Reaction carried out according to GP3-A, in THF (0.3 M), on a 182 µmol scale of (2.1), with 5 eq of 4-(4-methylpiperazin-1-yl)aniline, at 150° C. (sealed tube, pw) for 3 h. The product directly precipitated in the reaction medium: it was isolated after filtration. The final product required two successive triturations in refluxing EtOH. Isolated yield: 65%.

Example 3.39: Synthesis of (4Z)-4-(1,3-benzothiazol-6-ylmethylene)-2-[(1-methylindazol-7-yl)amino]-1H-imidazol-5-one (125)

Reaction carried out according to GP3-A, in THF (0.3 M), on a 182 µmol scale of (2.2), with 5 eq of 1-methylindazol-7-amine and 15 eq AcOH, at 130° C. (sealed tube, heating block) for 5 h. The product directly precipitated in the reaction medium: it was isolated after filtration. The final product required a trituration in EtOH at r.t. Isolated yield: 52%.

Selected Examples from Sub-Group A6

Example 3.40: Synthesis of (4Z)-4-(1,3-benzothiazol-6-ylmethylene)-2-(2-pyridylamino)-1H-imidazol-5-one (127)

Reaction carried out according to GP3-A, in THF (0.3 M), on a 1.05 mmol scale of (2.2), with 5 eq of pyridine-2-amine and 15 eq AcOH, at 150° C. (sealed tube, pw) for 2 h. The product directly precipitated in the reaction medium: it was isolated after filtration. The final product required a trituration in refluxing EtOH. Isolated yield: 41%.

Example 3.41: Synthesis of (4Z)-4-(1,3-benzothiazol-6-ylmethylene)-2-[(1-methylpyrazol-3-yl)amino]-1H-imidazol-5-one (128)

Reaction carried out according to GP3-A, in THF (0.3 M), on a 182 μmol scale of (2.2), with 5 eq of 1-methylpyrazol-3-amine, at 150° C. (sealed tube, pw) for 3 h. The product directly precipitated in the reaction medium: it was isolated after filtration. The final product required a trituration in EtOH at r.t. Isolated yield: 71%.

Selected Examples from Sub-Group A7

Example 3.42: Synthesis of (4Z)-4-(1,3-benzothiazol-6-ylmethylene)-2-[[(3S)-tetrahydrofuran-3-yl]amino]-1H-imidazol-5-one (146)

Reaction carried out according to GP3-B, in THF (0.3 M), on a 746 μmol scale of (2.2), with 3 eq of (3S)-tetrahydrofuran-3-amine, at 120° C. (sealed tube, heating block) for 12 h. The product directly precipitated in the reaction medium: it was isolated after filtration. Purification by FC (elution: DCM/MeOH: 99/1 to 93/7). The final product required a reprecipitation from DCM/pentane at 0° C. Isolated yield: 51%.

Example 3.43: Synthesis of (4Z)-4-(1,3-benzothiazol-6-ylmethylene)-2-[[(3R)-tetrahydropyran-3-yl]amino]-1H-imidazol-5-one (147)

Reaction carried out according to GP3-B, in THF (0.3 M), on a 1.04 mmol scale of (2.1), with 4 eq of (3R)-tetrahydropyran-3-amine hydrochloride and 6 eq of TEA, at 110° C. (sealed tube, heating block) for 12 h. Purification by FC (elution: DCM/MeOH: 99/1 to 93/7). The final product required a reprecipitation from DCM/pentane at 0° C. Isolated yield: 60%.

Example 3.44: Synthesis of (4Z)-4-(1,3-benzothiazol-6-ylmethylene)-2-[[(3S)-tetrahydropyran-3-yl]amino]-1H-imidazol-5-one (148)

Reaction carried out according to GP3-B, in THF (0.3 M), on a 746 μmol scale of (2.2), with 3 eq of (3S)-tetrahydropyran-3-amine hydrochloride and 4 eq of DIPEA, at 130° C. (sealed tube, heating block) for 12 h. Purification by FC (elution: DCM/MeOH: 99/1 to 93/7). The final product required a reprecipitation from DCM/pentane at 0° C. Isolated yield: 62%.

Example 3.45: Synthesis of (4Z)-4-(1,3-benzothiazol-6-ylmethylene)-2-[[(3R,4R)-4-hydroxytetrahydropyran-3-yl]amino]-1H-imidazol-5-one (150)

Reaction carried out according to GP3-B, in THF (0.3 M), on a 746 μmol scale of (2.2), with 3 eq of (3R,4R)-3-aminotetrahydropyran-4-ol, at 130° C. (sealed tube, heating block) for 12 h. Purification by FC (elution: DCM/MeOH: 99/1 to 93/7). The final product required a reprecipitation from DCM/pentane at 0° C. Isolated yield: 35%.

Example 3.46: Synthesis of (±)-(4Z)-4-(1,3-benzothiazol-6-ylmethylene)-2-(oxepan-3-ylamino)-1H-imidazol-5-one (151)

Reaction carried out according to GP3-B, in THF (0.3 M), on a 272 μmol scale of (2.2), with 1.2 eq of (±)-oxepan-3-amine, at 130° C. (sealed tube, heating block) for 12 h. Purification by FC (elution: DCM/MeOH: 99/1 to 93/7). Isolated yield: 33%.

Example 4: Biological Activity

Material and Methods
Protein Kinase Assays
1. Overview

Assays were performed by ProQinase GmbH (Engesserstr. 4, D-79108 Freiburg, Germany. www.proqinase.com) (Now Reaction Biology; https://www.reactionbiology.com/). The $IC_{50}$ profile of all compounds was determined using 12 protein kinases (CDK5/p25, CK1ε, CLK1, 2, 3, 4, DYRK1A, 1B, 2, 3, 4, GSK3β). $IC_{50}$ values were measured by testing 10 concentrations (10 μM to 30 nM) of each compound in singlicate.

2. Test Compounds

The compounds were provided as 1 μM stock solutions in 100% DMSO. Prior to testing, the 1 μM stock solutions were subjected to a serial, semi-logarithmic dilution using 100% DMSO as a solvent. This resulted in 10 distinct concentrations, with a dilution endpoint of 3×10 nM/100% DMSO, with 100% DMSO as controls. In the process, 90 μL $H_2O$ were added to each well of each compound dilution plate. To minimize potential precipitation, the $H_2O$ was added to each plate only a few minutes before the transfer of the compound solutions into the assay plates. The plate was shaken thoroughly, resulting in a compound dilution plate/10% DMSO.

For the assays (see below), 5 μL solution from each well of the compound dilution plates/10% DMSO were transferred into the assay plates. The final volume of the assay was 50 μL. All compounds were tested at 10 final assay concentrations in the range from 10 μM to 30 nM. The final DMSO concentration in the reaction cocktails was 1% in all cases.

3. Recombinant Protein Kinases

All protein kinases provided by ProQinase were expressed in Sf9 insect cells or in E. coli as recombinant GST-fusion proteins or His-tagged proteins, either as full-length or enzymatically active fragments. All kinases were produced from human cDNAs and purified by either GSH-affinity chromatography or immobilized metal. Affinity tags were removed from a number of kinases during purification. The purity of the protein kinases was examined by SDS-PAGE/Coomassie staining, the identity was checked by mass spectroscopy.

4. Protein Kinase Assay

A radiometric protein kinase assay (33PanQinase® Activity Assay) was used for measuring the kinase activity of the 12 protein kinases. All kinase assays were performed in 96-well FlashPlates™ from PerkinElmer (Boston, MA, USA) in a 50 μL reaction volume. The reaction cocktail was pipetted in four steps in the following order:
  25 μL of assay buffer (standard buffer/[γ-$^{33}$P]-ATP),
  10 μL of ATP solution (in $H_2O$), 5 µL of test compound (in 10% DMSO),
10 µL of enzyme/substrate mixture.

The assay for all protein kinases contained 70 mM HEPES-NaOH pH 7.5, 3 mM $MgCl_2$, 3 mM $MnCl_2$, 3 µM Na-orthovanadate, 1.2 mM DTT, 50 µg/ml PEG20000, ATP (variable concentrations, corresponding to the apparent ATP-Km of the respective kinase), [γ-$^{33}$P]-ATP (approx. 6.5×10-05 cpm per well), protein kinase (variable amounts), and substrate (variable amounts). The reaction cocktails were incubated at 30° C. for 60 minutes. The reaction was stopped with 50 µL of 2% (v/v) $H_3PO_4$, plates were aspirated and washed two times with 200 µL 0.9% (w/v) NaCl. Incorporation of $^{33}$Pi was determined with a microplate scintillation counter (Microbeta, Wallac). The $IC_{50}$ values for all compounds were calculated from the dose response curves 5. Quality Controls As a parameter for assay quality, the Z'-factor (Zhang et al., J. Biomol. Screen. 2: 67-73, 1999) for the low and high controls of each assay plate (n=8) was used. ProQinase's criterion for repetition of an assay plate is a Z'-factor below 0.4 (Iversen et al., J. Biomol. Screen. 3: 247-252, 2006).

Their activity has been classified according to two criteria, kinase inhibition potency and kinase selectivity.

The kinase inhibition potency classification was done according to the following ranges of $IC_{50}$ values:

Some compounds have an $IC_{50}$ activity varying from above 0.050 PM. These compounds correspond to the above-reported class E. Some compounds have an $IC_{50}$ activity varying from 0.025 to 0.050 µM. These compounds correspond to the above-reported class D. Some compounds of the invention have an $IC_{50}$ activity varying from 0.010 to 0.025 µM. These compounds correspond to the above-reported class C. Further some particular compounds have an $IC_{50}$ activity varying from 0.005 to 0.010 PM. These compounds correspond to the above-reported class B. Even preferred are compounds of the invention that have an $IC_{50}$ activity of less than 0.005 µM. These compounds correspond to the above-reported class A. This classification was applied to CLK1 and DYRK1A. Said letters A to E were used to quote the activity/efficacy of the compounds of the invention in the following Table 4, 4A and 4B.

The kinase selectivity classification was based on comparing the $IC_{50}$ values of DYRK1A with that of CLK1 or with that of DYRK1B. The classification was done according to the following ranges of values: I: ratio of $IC_{50}$ on CLK1 or DYRK1B over $IC_{50}$ on DYRK1A ≥10 fold (most DYRK1A-selective compounds); II: ratio between 2 and 10 fold; III: ratio between 0.5 and 2 fold; IV: ratio between 0.1 and 0.5 fold; V: ratio >0.1 fold (most CLK1- or DYRK1B-selective compounds). Said numbers I to V were used to quote the relative selectivity of the compounds of the invention in the following Tables.

TABLE 4

Kinase inhibitory activities of compounds (1) to (216), tested on 12 kinases. $IC_{50}$ values were calculated from dose-response curves. Compounds were further classified in terms of efficacy on CLK1 or DYRK1A (decreasing efficacy range: A to E) and in terms of relative selectivity (decreasing selectivity range: I to V).

| Cpd No | Potency Class CLK1 | Potency Class DYRK1A | Selectivity Class DYRK1A vs. CLK1 | Selectivity Class DYRK1A vs. DYRK1B | Cpd No | Potency Class CLK1 | Potency Class DYRK1A | Selectivity Class DYRK1A vs. CLK1 | Selectivity Class DYRK1A vs. DYRK1B |
|---|---|---|---|---|---|---|---|---|---|
| 1 | D | E | IV | III | 22 | C | A | I | II |
| 2 | E | E | IV | III | 23 | C | E | IV | IV |
| 3 | E | E | IV | III | 24 | D | C | III | III |
| 4 | D | E | III | III | 25 | C | A | II | II |
| 5 | D | E | IV | III | 26 | C | E | V | V |
| 6 | C | D | IV | III | 27 | C | A | II | II |
| 7 | C | D | IV | III | 28 | C | D | IV | I |
| 8 | C | C | III | III | 29 | E | E | II | II |
| 9 | B | B | III | III | 30 | D | E | III | III |
| 10 | C | E | V | IV | 31 | C | D | IV | III |
| 11 | E | E | IV | III | 32 | D | C | III | III |
| 12 | C | C | III | II | 33 | C | E | V | IV |
| 13 | D | E | IV | II | 34 | C | A | II | III |
| 14 | C | C | III | II | 35 | B | A | II | II |
| 15 | E | E | III | II | 36 | D | C | II | II |
| 16 | B | A | II | III | 37 | E | E | IV | II |
| 17 | C | B | II | II | 38 | D | D | III | III |
| 18 | E | E | II | III | 39 | E | E | III | III |
| 19 | A | A | II | II | 40 | C | B | II | II |
| 20 | B | A | I | II | 41 | D | D | III | III |
| 21 | B | A | II | II | 42 | E | E | III | I |
| 43 | C | C | III | II | 70 | C | E | IV | III |
| 44 | C | C | III | II | 71 | C | E | IV | II |
| 45 | E | E | III | II | 72 | E | E | III | III |
| 46 | C | D | IV | II | 73 | B | E | IV | III |
| 47 | E | E | III | III | 74 | C | D | IV | III |
| 48 | B | A | III | II | 75 | E | E | IV | II |
| 49 | D | D | III | II | 76 | C | E | IV | II |
| 50 | E | E | III | II | 77 | C | D | IV | II |
| 51 | C | C | III | II | 78 | B | B | III | II |
| 52 | E | E | III | II | 79 | D | E | V | III |
| 53 | D | D | III | II | 80 | D | D | III | II |
| 54 | E | E | III | II | 81 | B | A | II | III |
| 55 | C | C | III | II | 82 | D | E | V | IV |
| 56 | D | C | III | II | 83 | C | B | II | IV |
| 57 | D | C | III | II | 84 | E | E | III | II |
| 58 | E | E | IV | III | 85 | C | C | III | II |

TABLE 4-continued

Kinase inhibitory activities of compounds (1) to (216), tested on 12 kinases. $IC_{50}$ values were calculated from dose-response curves. Compounds were further classified in terms of efficacy on CLK1 or DYRK1A (decreasing efficacy range: A to E) and in terms of relative selectivity (decreasing selectivity range: I to V).

| Cpd No | Potency Class CLK1 | Potency Class DYRK1A | Selectivity Class DYRK1A vs. CLK1 | Selectivity Class DYRK1A vs. DYRK1B | Cpd No | Potency Class CLK1 | Potency Class DYRK1A | Selectivity Class DYRK1A vs. CLK1 | Selectivity Class DYRK1A vs. DYRK1B |
|---|---|---|---|---|---|---|---|---|---|
| 59 | C | C | III | II | 86 | D | D | III | II |
| 60 | E | E | III | II | 87 | E | E | III | II |
| 61 | B | A | II | II | 88 | C | E | IV | IV |
| 62 | C | C | III | II | 89 | C | B | II | II |
| 63 | C | C | III | II | 90 | D | D | III | II |
| 64 | D | C | III | II | 91 | E | E | IV | III |
| 65 | C | A | II | II | 92 | C | D | III | III |
| 66 | C | A | II | II | 93 | D | D | III | II |
| 67 | C | D | IV | II | 94 | D | E | IV | III |
| 68 | C | C | III | III | 95 | B | A | II | II |
| 69 | C | D | IV | III | 96 | B | A | II | II |
| 97 | C | B | II | II | 124 | E | E | — | — |
| 98 | C | C | III | II | 125 | E | D | II | III |
| 99 | C | B | III | II | 126 | E | E | IV | III |
| 100 | C | E | IV | IV | 127 | C | E | IV | |
| 101 | C | E | IV | III | 128 | D | E | III | III |
| 102 | C | E | V | III | 129 | E | E | IV | II |
| 103 | E | E | IV | III | 130 | C | E | IV | III |
| 104 | C | E | IV | III | 131 | C | E | IV | III |
| 105 | C | E | V | III | 132 | E | E | IV | III |
| 106 | C | E | IV | III | 133 | n.t. | n.t. | n.t. | n.t. |
| 107 | E | E | IV | III | 134 | n.t. | n.t. | n.t. | n.t. |
| 108 | C | D | III | III | 135 | D | E | III | IV |
| 109 | D | E | IV | III | 136 | E | E | III | II |
| 110 | E | E | III | III | 137 | E | E | IV | III |
| 111 | E | E | IV | II | 138 | n.t. | n.t. | n.t. | n.t. |
| 112 | E | E | IV | III | 139 | C | E | IV | III |
| 113 | D | E | IV | III | 140 | E | E | IV | III |
| 114 | E | E | — | III | 141 | D | E | IV | II |
| 115 | E | E | V | IV | 142 | E | E | IV | III |
| 116 | E | E | III | I | 143 | E | E | IV | III |
| 117 | D | E | IV | III | 144 | E | E | IV | II |
| 118 | E | E | — | — | 145 | E | E | IV | III |
| 119 | C | C | III | III | 146 | D | D | III | II |
| 120 | E | E | IV | I | 147 | D | E | III | III |
| 121 | E | E | III | II | 148 | D | C | II | I |
| 122 | E | E | IV | II | 149 | D | C | III | II |
| 123 | E | E | V | IV | 150 | D | D | III | II |
| 151 | C | C | III | III | 172 | C | B | II | I |
| 152 | E | E | IV | II | 173 | C | B | III | I |
| 153 | E | E | IV | II | 174 | D | C | II | I |
| 154 | E | E | III | II | 175 | D | B | II | I |
| 149A | D | D | III | II | 176 | B | A | III | II |
| 149B | D | D | III | III | 177 | E | E | IV | II |
| 155 | B | C | III | III | 178 | C | C | III | I |
| 156 | C | E | III | | 179 | C | C | III | III |
| 157 | C | C | III | III | 180 | C | C | III | III |
| 158 | C | B | III | II | 181 | D | C | III | II |
| 159 | B | A | II | II | 182 | C | D | III | II |
| 160 | B | A | II | II | 183 | D | E | III | II |
| 161 | B | D | IV | III | 184 | B | A | II | II |
| 162 | D | B | II | III | 185 | C | C | III | I |
| 163 | D | E | III | II | 186 | E | E | IV | II |
| 164 | C | C | III | II | 187 | E | E | IV | II |
| 165 | C | C | III | III | 188 | E | E | III | II |
| 166 | D | E | III | II | 189 | E | E | III | II |
| 167 | C | C | III | II | 190 | E | E | III | I |
| 168 | C | C | III | I | 191 | C | D | III | I |
| 169 | B | B | III | I | 192 | C | C | III | II |
| 169A | B | C | III | II | 192A | C | D | IV | II |
| 169B | C | C | III | II | 192B | C | E | II | II |
| 170 | C | C | III | I | 193 | E | E | III | III |
| 171 | C | C | III | I | 194 | C | A | I | III |
| 171A | B | C | III | III | 195 | C | B | III | III |
| 171B | C | C | III | III | 196 | B | A | I | III |
| 197 | E | E | III | II | | | | | |
| 198 | C | D | II | II | | | | | |
| 199 | B | A | II | II | | | | | |
| 200 | B | A | II | II | | | | | |
| 201 | B | A | II | III | | | | | |
| 202 | B | A | II | III | | | | | |

TABLE 4-continued

Kinase inhibitory activities of compounds (1) to (216), tested on 12 kinases. $IC_{50}$ values were calculated from dose-response curves. Compounds were further classified in terms of efficacy on CLK1 or DYRK1A (decreasing efficacy range: A to E) and in terms of relative selectivity (decreasing selectivity range: I to V).

| Cpd No | Potency Class CLK1 | Potency Class DYRK1A | Selectivity Class DYRK1A vs. CLK1 | Selectivity Class DYRK1A vs. DYRK1B | Cpd No | Potency Class CLK1 | Potency Class DYRK1A | Selectivity Class DYRK1A vs. CLK1 | Selectivity Class DYRK1A vs. DYRK1B |
|---|---|---|---|---|---|---|---|---|---|
| 203 | B | A | II | III | | | | | |
| 204 | E | C | I | III | | | | | |
| 205 | E | E | II | II | | | | | |
| 206 | E | E | III | III | | | | | |
| 207 | E | C | II | II | | | | | |
| 208 | E | D | III | II | | | | | |
| 209 | E | C | II | II | | | | | |
| 210 | B | A | II | II | | | | | |
| 211 | n.t. | n.t. | n.t. | n.t. | | | | | |
| 212 | n.t. | n.t. | n.t. | n.t. | | | | | |
| 214 | n.t. | n.t. | n.t. | n.t. | | | | | |
| 215 | n.t. | n.t. | n.t. | n.t. | | | | | |
| 216 | n.t. | n.t. | n.t. | n.t. | | | | | |

TABLE 4A

Most potent CLK1 inhibitors ($IC_{50}$ ≤ 10 nM). Kinase inhibition potency classes: $IC_{50}$ values: A ≤0.005 μM; B ≤0.010 μM; C ≤0.025 μM; D ≤0.050 μM; E >0.050 μM. Kinase selectivity classes based on DYRK1A: class I (>10 fold selectivity), class II (2-10 fold selectivity), class III (0.5-2 fold selectivity = equipotency). Some compounds display a better selectivity for CLK1 or DYRK1B compared to DYRK1A. These compounds correspond to the above-reported class IV (2-10-fold selectivity) or class V (>10-fold selectivity).

| Cpd No | Potency Class CLK1 | Potency Class DYRK1A | Selectivity Class DYRK1A vs. CLK1 |
|---|---|---|---|
| 19 | A | A | II |
| 73 | B | E | IV |
| 78 | B | B | III |
| 20 | B | A | I |
| 21 | B | A | II |
| 61 | B | A | II |
| 95 | B | A | II |
| 16 | B | A | II |
| 35 | B | A | II |
| 48 | B | A | III |
| 81 | B | A | II |
| 96 | B | A | II |
| 9 | B | B | III |
| 155 | B | C | III |
| 159 | B | A | II |
| 160 | B | A | II |
| 161 | B | D | IV |
| 169 | B | B | III |
| 169A | B | C | III |
| 171A | B | C | III |
| 176 | B | A | III |
| 184 | B | A | II |
| 196 | B | A | I |
| 199 | B | A | II |
| 200 | B | A | II |
| 201 | B | A | II |
| 202 | B | A | II |
| 203 | B | A | II |
| 210 | B | A | II |

The most potent CLK2 inhibitors, with an $IC_{50}$ lower or equal to 10 nM are compounds (9), (16), (20), (21), (22), (24), (25), (81), (83), (89), (95), (96), (159), (181), (194), (196), (199), (200), (201), (202) and (203).

The most potent CLK3 inhibitors, with an $IC_{50}$ lower or equal to 100 nM are compounds (48), (89) (90), (159), (164), (165), (169), (169B), (178) and (181).

The most potent CLK4 inhibitors, with an $IC_{50}$ lower or equal to 10 nM are compounds (7), (8), (9), (10), (12), (16), (17), (19), (20), (21), (23), (25), (26), (28), (32), (33), (34), (35), (40), (41), (43), (44), (46), (48), (51), (55), (56), (57), (59), (61), (62), (63), (65), (66), (67), (68), (69), (70), (73), (77), (78), (81), (83), (88), (89), (90), (95), (96), (97), (98), (99), (100), (101), (102), (104), (105), (106), (117), (119), (127), (131), (139), (148), (149), (149B), (151), (155), (156), (157), (158), (159), (160), (161), (164), (165), (167), (169), (169A), (169B), (170), (171), (171A), (171B), (172), (173), (176), (178), (179), (180), (181), (184), (185), (191), (192), (192A), (194), (196), (198), (199), (200), (201), (202), (203) and (210).

TABLE 4B

Most potent DYRK1A inhibitors ($IC_{50}$ ≤ 10 nM). Kinase Inhibition Efficacy Classes and Kinase Selectivity Classes as described in Table 4A.

| Cpd No | Potency Class CLK1 | Potency Class DYRK1A | Selectivity Class DYRK1A vs. CLK1 | Selectivity Class DYRK1A vs. DYRK1B |
|---|---|---|---|---|
| 20 | B | A | I | II |
| 16 | B | A | II | III |
| 19 | A | A | II | II |
| 27 | C | A | II | II |
| 21 | B | A | II | II |
| 22 | C | A | I | II |
| 81 | B | A | II | III |
| 61 | B | A | II | II |
| 35 | B | A | II | II |
| 95 | B | A | II | II |
| 96 | B | A | II | II |
| 65 | C | A | II | II |
| 66 | C | A | II | II |
| 34 | C | A | II | III |
| 25 | C | A | II | II |
| 48 | B | A | III | II |
| 159 | B | A | II | II |
| 160 | B | A | II | II |
| 176 | B | A | III | II |
| 184 | B | A | II | II |
| 196 | B | A | I | III |
| 194 | C | A | I | III |
| 199 | B | A | II | II |
| 200 | B | A | II | II |
| 201 | B | A | II | II |
| 202 | B | A | II | III |
| 203 | B | A | II | II |

TABLE 4B-continued

Most potent DYRK1A inhibitors (IC$_{50}$ ≤ 10 nM). Kinase Inhibition Efficacy Classes and Kinase Selectivity Classes as described in Table 4A.

| Cpd No | Potency Class CLK1 | Potency Class DYRK1A | Selectivity Class DYRK1A vs. CLK1 | Selectivity Class DYRK1A vs. DYRK1B |
|---|---|---|---|---|
| 210 | B | A | II | II |
| 83 | C | B | II | IV |
| 40 | C | B | II | II |
| 9 | B | B | III | III |
| 89 | C | B | II | II |
| 17 | C | B | II | II |
| 78 | B | B | III | II |
| 97 | C | B | II | II |
| 99 | C | B | III | II |
| 169 | B | B | III | I |
| 158 | C | B | III | II |
| 172 | C | B | II | I |
| 173 | C | B | III | I |
| 195 | C | B | III | III |
| 162 | D | B | II | III |
| 175 | D | B | II | I |

The most potent DYRK1B inhibitors, with an IC$_{50}$ lower or equal to 10 nM are compounds (20), (16), (83), (81), (34), (95), (21), (22), (27), (35), (61), (9), (96), (159), (160), (162), (176), (194), (196), (199), (200), (201), (202), (203) and (210).

The most potent DYRK2 inhibitors, with an IC$_{50}$ lower or equal to 100 nM are compounds (16), (20), (21), (48), (89), (90), (99), (119), (158), (159), (169), (179), (194), (196), (199), (200), (201), (203) and (210).

The most potent DYRK3 inhibitors, with an IC$_{50}$ lower or equal to 100 nM are compounds (16), (20), (21), (89), (90), (119), (162), (159), (181), (194), (196), (199), (200), (201) and (203).

The most potent DYRK4 inhibitors, with an IC$_{50}$ lower or equal to 100 nM are compounds (20) and (48), (164), (194) and (196).

TABLE 4C

Most DYRK1A selective inhibitors compared to CLK1. Kinase Selectivity Classes as described in Table 4A.

| Cpd No | Selectivity Class DYRK1A vs. CLK1 | Cpd No | Selectivity Class DYRK1A vs. CLK1 |
|---|---|---|---|
| 20 | I | 66 | II |
| 22 | I | 83 | II |
| 194 | I | 18 | II |
| 196 | I | 29 | II |
| 204 | I | 125 | II |
| 16 | II | 36 | II |
| 17 | II | 159 | II |
| 21 | II | 160 | II |
| 61 | II | 162 | II |
| 27 | II | 172 | II |
| 35 | II | 174 | II |
| 95 | II | 175 | II |
| 96 | II | 184 | II |
| 97 | II | 192B | II |
| 89 | II | 199 | II |
| 19 | II | 200 | II |
| 81 | II | 201 | II |
| 148 | II | 202 | II |
| 65 | II | 203 | II |
| 34 | II | 205 | II |
| 40 | II | 209 | II |
| 25 | II | 210 | II |

TABLE 4D

Most CLK1 selective inhibitors compared to DYRK1A. Kinase Selectivity Classes as described in Table 4A.

| Cpd No | Selectivity Class DYRK1A vs. CLK1 |
|---|---|
| 79 | V |
| 115 | V |
| 123 | V |
| 82 | V |
| 10 | V |
| 33 | V |
| 102 | V |
| 26 | V |
| 105 | V |

TABLE 4E

Most DYRK1A selective inhibitors compared to DYRK1B. Kinase Selectivity Classes as described in Table 4A.

| Cpd No | Selectivity Class DYRK1A vs. DYRK1B | Cpd No | Selectivity Class DYRK1A vs. DYRK1B |
|---|---|---|---|
| 28 | I | 45 | II |
| 120 | I | 12 | II |
| 116 | I | 56 | II |
| 42 | I | 149 | II |
| 148 | I | 50 | II |
| 168 | I | 150 | II |
| 169 | I | 121 | II |
| 170 | I | 55 | II |
| 171 | I | 146 | II |
| 172 | I | 44 | II |
| 173 | I | 93 | II |
| 174 | I | 51 | II |
| 175 | I | 52 | II |
| 178 | I | 53 | II |
| 185 | I | 54 | II |
| 190 | I | 57 | II |
| 191 | I | 78 | II |
| 76 | II | 64 | II |
| 111 | II | 60 | II |
| 75 | II | 154 | II |
| 122 | II | 14 | II |
| 46 | II | 87 | II |
| 71 | II | 84 | II |
| 67 | II | 17 | II |
| 129 | II | 61 | II |
| 144 | II | 27 | II |
| 141 | II | 35 | II |
| 37 | II | 95 | II |
| 153 | II | 96 | II |
| 13 | II | 97 | II |
| 152 | II | 89 | II |
| 77 | II | 19 | II |
| 15 | II | 65 | II |
| 136 | II | 40 | II |
| 48 | II | 25 | II |
| 85 | II | 66 | II |
| 49 | II | 29 | II |
| 62 | II | 36 | II |
| 59 | II | 20 | II |
| 90 | II | 21 | II |
| 43 | II | 22 | II |
| 99 | II | 149A | II |
| 63 | II | 158 | II |
| 80 | II | 159 | II |
| 98 | II | 160 | II |
| 86 | II | 163 | II |
| 164 | II | 189 | II |
| 166 | II | 192 | II |
| 167 | II | 192A | II |
| 169A | II | 192B | II |
| 169B | II | 197 | II |
| 176 | II | 198 | II |
| 177 | II | 199 | II |
| 181 | II | 200 | II |

TABLE 4E-continued

Most DYRK1A selective inhibitors compared to DYRK1B.
Kinase Selectivity Classes as described in Table 4A.

| Cpd No | Selectivity Class DYRK1A vs. DYRK1B | Cpd No | Selectivity Class DYRK1A vs. DYRK1B |
|---|---|---|---|
| 182 | II | 205 | II |
| 183 | II | 207 | II |
| 184 | II | 208 | II |
| 186 | II | 209 | II |
| 187 | II | 210 | II |
| 188 | II | | |

TABLE 4F

Most DYRK1B selective inhibitors compared to DYRK1A.
Kinase Selectivity Classes as described in Table 4A.

| Cpd No | Selectivity Class DYRK1A vs. DYRK1B |
|---|---|
| 26 | V |
| 115 | IV |
| 123 | IV |
| 82 | IV |
| 10 | IV |
| 33 | IV |
| 88 | IV |
| 23 | IV |
| 100 | IV |
| 135 | IV |
| 83 | IV |

Results

Most compounds of the present invention present an $IC_{50}$ activity of less than 2 µM on CLKs or DYRKs. All the compounds were inhibitors of DYRK1A and CLK1 (Table 4).

Compounds were preferably inhibitory on CLK1 (Table 4A), CLK4, DYRK1A (Table 4B) and DYRK1B.

Some are most selective for DYRK1A vs. CLK1 (Table 4C), DYRK1A vs. DYRK1B (Table 4E), DYRK1B vs. DYRK1A (Table 4F) or CLK1 vs. DYRK1A (Table 4D). Some compounds display a better selectivity for DYRK1A compared to CLK1 or DYRK1B. These compounds correspond to the above-reported class I (>10-fold selectivity) or class II (2 to 10-fold selectivity). Some compounds are equipotent. These compounds correspond to the above-reported class III (0.5 to 2-fold selectivity). Some compounds display a better selectivity for CLK1 or DYRK1B compared to DYRK1A. These compounds correspond to the above-reported class IV (2 to 10-fold selectivity) or class V (>10-fold selectivity).

CONCLUSION

Based on the previous results, it can be concluded that the compounds of formula (I) are suitable chemical compounds in the prevention and/or treatment of cognitive deficits associated with Down syndrome (Trisomy 21); Alzheimer's disease and related diseases; dementia; tauopathies; other neurodegenerative diseases (Parkinson's disease; Pick disease, including Niemann-Pick Type C Disease); CDKL5 Deficiency Disorder; type 1 and type 2 diabetes; abnormal folate and methionine metabolism; osteoarthritis, in particular knee osteoarthritis; Duchenne muscular dystrophy; several cancers, such as brain cancer, including glioblastoma, leukemia, including megakaryoblastic leukemia and acute lymphoblastic leukemia, head and neck squamous cell carcinoma, pancreatic cancer, including pancreatic ductal adenocarcinoma, prostate cancer, gastrointerstinal cancer and breast cancer, such as Triple-negative breast cancer (TNBC), malaria, Leishmaniasis, Chagas and sleeping sickness (*Trypanosoma* sp.), and cattle diseases due to unicellular pathogens, viral infections, such as caused by Human immunodeficiency virus type 1 (HIV-1), Human cytomegalovirus (HCMV), Influenza A, Herpes virus, rhesus macaque cytomegalovirus, varicella-zoster virus and herpes simplex virus (HSV) and in the regulation of body temperature.

It may further be concluded that some compounds of formula (I) are further suitable for treating and/or preventing Phelan-McDermid syndrome; autism; further viral infections, such as caused by Hepatitis C virus, Chikungunya virus, Dengue virus, Influenza virus and Severe acute respiratory syndrome (SARS) coronavirus, Cytomegalovirus and Human papillomavirus; further cancers, such as tissue cancer, including liposarcoma, Hedgehog/GLI-dependent cancer, liver cancer, including Hepatocellular carcinoma, neuroinflammation, anemia, infections caused by unicellular parasites, such as malaria, Leishmaniasis, Chagas and sleeping sickness (*Trypanosoma* sp.), and cattle diseases due to unicellular pathogens.

Leucettinibs display much increased efficacy (down to sub-micromolar and single-digit micromolar $IC_{50}$ values) compared to reference compounds. They also display a large range of selectivity towards DYRK1A or CLK1. And some products being equipotent on CLKs and DYRKs may also find applications as dual-specificity inhibitors.

The present invention further relates to a pharmaceutical composition comprising at least one compound of formula (I) as defined above or any of its pharmaceutically acceptable salts or at least any of compounds (1) to (216) as defined above or any of its pharmaceutically acceptable salts and also at least one pharmaceutically acceptable excipient.

Pharmaceutical compositions of the invention can contain one or more compound(s) of the invention in any form described herein.

Still a further object of the present invention consists of the use of at least one compound of formula (I) as defined above, and compounds (1) to (216) as defined above, or one of their pharmaceutically acceptable salts according to the present invention for preparing a drug for preventing and/or treating a disease selected from cognitive deficits associated with Down syndrome (Trisomy 21); Alzheimer's disease and related diseases; dementia; tauopathies; and other neurodegenerative diseases (Parkinson's disease; Pick disease, including Niemann-Pick Type C Disease); CDKL5 Deficiency Disorder; McDermid syndrome; autism; type 1 and type 2 diabetes; regulation of folate and methionine metabolism; osteoarthritis, in particular knee osteoarthritis; Duchenne muscular dystrophy; several cancers, such as brain cancer, including glioblastoma, leukemia, including megakaryoblastic leukemia, head and neck squamous cell carcinoma, pancreatic cancer, including pancreatic ductal adenocarcinoma, prostate cancer, gastrointerstinal cancer, breast cancer, such as Triple-negative breast cancer (TNBC), tissue cancer, including liposarcoma, Hedgehog/GLI-dependent cancer, liver cancer, including Hepatocellular carcinoma and viral infections, such as caused by Human immunodeficiency virus type 1 (HIV-1), Human cytomegalovirus (HCMV), Influenza A, Herpes virus, rhesus macaque cytomegalovirus, varicella-zoster virus, herpes simplex virus (HSV), Hepatitis C virus, Chikungunya virus, Dengue virus, Influenza virus and Severe acute respiratory syndrome (SARS) coronavirus, Cytomegalovirus and Human papillomavirus; neuroinflammation; anemia; infections caused by unicellular parasites, such malaria, Leishmaniasis, Chagas and sleeping sickness (*Trypanosoma* sp.), and cattle diseases due to unicellular pathogens, and for regulating body temperature.

Still a further object of the present invention consists of the use of at least one compound of formula (I) as defined above, and compounds (1) to (216) as defined above, or one of their pharmaceutically acceptable salts according to the present invention for preparing a drug for preventing and/or treating a disease selected from cognitive deficits associated with Down syndrome (Trisomy 21); Alzheimer's disease and related diseases; dementia; tauopathies; other neurodegenerative diseases (Parkinson's disease; Pick disease, including Niemann-Pick Type C Disease); CDKL5 Deficiency Disorder; type 1 and type 2 diabetes; regulation of folate and methionine metabolism; osteoarthritis, in particular knee osteoarthritis; Duchenne muscular dystrophy; several cancers, such as brain cancer, including glioblastoma, leukemia, including megakaryoblastic leukemia, head and neck squamous cell carcinoma, pancreatic cancer, including pancreatic ductal adenocarcinoma, prostate cancer, gastrointerstinal cancer and breast cancer, such as Triple-negative breast cancer (TNBC), infections caused by unicellular parasites, such malaria, Leishmaniasis, Chagas and sleeping sickness (*Trypanosoma* sp.), and cattle diseases due to unicellular pathogens, and viral infections, such as caused by Human immunodeficiency virus type 1 (HIV-1), Human cytomegalovirus (HCMV), Influenza A, Herpes virus, rhesus macaque cytomegalovirus, varicella-zoster virus and herpes simplex virus (HSV) and for regulating body temperature.

Still a further object of the present invention consists of the use of at least one compound of formula (I), as defined above, and compounds (1) to (216) as defined above, or one of their pharmaceutically acceptable salts according to the present invention for preparing a drug for combatting a disease selected from type 1 and type 2 diabetes, viral infections, in particular as mentioned above, osteoarthritis, cancers, in particular as mentioned above, infections caused by unicellular parasites, such malaria, Leishmaniasis, Chagas and sleeping sickness (*Trypanosoma* sp.), and cattle diseases due to unicellular pathogens, and to regulate body temperature.

According to a particular embodiment, the treatment is continuous or non-continuous.

A "continuous treatment" means a long-term treatment which can be implemented with various administration frequencies, such as once every day, every three days, once a week, or once every two weeks or once every month or by transdermal patch delivery.

According to one embodiment, the compound of formula (I), or any of its pharmaceutically acceptable salts, is administered at a dose varying from 0.1 to 1000 mg. in particular varying from 1 to 500 mg, or for example varying from 5 to 100 mg.

Another object of the invention relates to a therapeutic method for the treatment and/or for the prevention of a disease selected from cognitive deficits associated with Down syndrome (Trisomy 21); Alzheimer's disease and related diseases; dementia; tauopathies; and other neurodegenerative diseases (Parkinson's disease; Pick disease, including Niemann-Pick Type C Disease); CDKL5 Deficiency Disorder; McDermid syndrome; autism; type 1 and type 2 diabetes; regulation of folate and methionine metabolism; osteoarthritis, in particular knee osteoarthritis; Duchenne muscular dystrophy; several cancers, such as brain cancer, including glioblastoma, leukemia, including megakaryoblastic leukemia, head and neck squamous cell carcinoma, pancreatic cancer, including pancreatic ductal adenocarcinoma, prostate cancer, gastrointerstinal cancer, breast cancer, such as Triple-negative breast cancer (TNBC), tissue cancer, including liposarcoma, Hedgehog/GLI-dependent cancer, liver cancer, including Hepatocellular carcinoma and viral infections, such as caused by Human immunodeficiency virus type 1 (HIV-1), Human cytomegalovirus (HCMV), Influenza A, Herpes virus, rhesus macaque cytomegalovirus, varicella-zoster virus, herpes simplex virus (HSV), Hepatitis C virus, Chikungunya virus, Dengue virus, Influenza virus and Severe acute respiratory syndrome (SARS) coronavirus, Cytomegalovirus and Human papillomavirus; neuroinflammation; anemia; infections caused by unicellular parasites, such malaria, Leishmaniasis, Chagas and sleeping sickness (*Trypanosoma* sp.), and cattle diseases due to unicellular pathogens, and for the regulation of the body temperature, in a patient in need thereof, comprising at least a step of administering a therapeutically effective amount of a compound of formula (I) or of compounds (1) to (216), as defined above. or one of their acceptable salts.

In a specific embodiment, the invention provides a use of a compound of formula (I) according to the invention or a pharmaceutically acceptable salt thereof or a pharmaceutically active derivative thereof or a method according to the invention wherein the compound of formula (I) is to be administered in combination with a co-agent useful in anyone of the hereabove mentioned diseases.

The compounds can be administered through any mode of administration such as, for example, intramuscular, intravenous, intranasal or oral route, transdermal patch, etc.

The inventive composition can further include one or more additives such as diluents, excipients, stabilizers and preservatives. Such additives are well known to those skilled in the art and are described notably in "*Ullmann's Encyclopedia of Industrial Chemistry, 6$^{th}$ Ed.*" (various editors, 1989-1998, Marcel Dekker) and in "*Pharmaceutical Dosage Forms and Drug Delivery Systems*" (ANSEL et al, 1994, WILLIAMS & WILKINS).

The aforementioned excipients are selected according to the dosage form and the desired mode of administration.

Compositions of this invention may be administered in any manner, including, but not limited to, orally, parenterally, sublingually, transdermally, vaginally, rectally, transmucosally, topically, intranasally via inhalation, via buccal or intranasal administration, or combinations thereof. Parenteral administration includes, but is not limited to, intravenous, intra-arterial, intra-peritoneal, subcutaneous, intramuscular, intra-thecal, and intra-articular. The compositions of this invention may also be administered in the form of an implant, which allows slow release of the compositions as well as a slow controlled i.v. infusion.

For example, a compound of formula (I) can be present in any pharmaceutical form which is suitable for enteral or parenteral administration, in association with appropriate excipients, for example in the form of plain or coated tablets, hard gelatine, soft shell capsules and other capsules, suppositories, or drinkable, such as suspensions, syrups, or injectable solutions or suspensions.

In a particular embodiment, a compound of formula (I) according to the invention is administered orally.

Oral route of administration is in particular preferred in the prophylaxis or treatment aspect of the invention.

The invention claimed is:
1. A compound of formula (I)

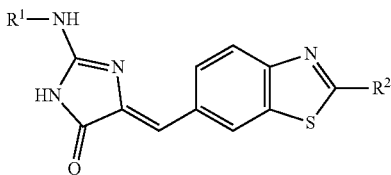

wherein R¹ represents:
(i). a $(C_1-C_6)$ alkyl group substituted by one or two groups selected from a —COOR$^a$ group, a hydroxy group, a halogen atom, a $(C_1-C_4)$ alkoxy group and a benzyloxy group, said benzyloxy being optionally substituted on its phenyl group by one to three halogen atoms,
(ii). a spiro$(C_5-C_{11})$ bicyclic ring,
(iii). a fused phenyl group, chosen from phenyl groups fused with a cyclopentyl or a heterocyclopentyl selected from acetylindolinyl, methylindazolyl, and indazolyl which cyclopentyl group optionally comprises an insaturation and is optionally substituted by a $(C_1-C_4)$ alkyl group, a hydroxy group, a halogen atom, a $(C_1-C_3)$ alkoxy group or a —COR$^a$ group,
(iv). a phenyl group, substituted by one or two groups selected from a $(C_1-C_8)$ alkyl, a $(C_1-C_3)$ fluoroalkyl, a fluoro $(C_1-C_4)$ alkoxy group, a fluor atom, a bromine atom, an iodine atom, and a $(C_4-C_7)$ heterocycloalkyl group, said $(C_4-C_7)$ heterocycloalkyl group being itself optionally substituted by a $(C_1-C_4)$ alkyl group, or
(v.1.A). a R'-L- group, wherein
L is either a single bond or a $(C_2-C_3)$ alkanediyl group, optionally substituted by a group selected from a hydroxy group and a $(C_1-C_3)$ alkoxy group, and
R' represents a $(C_3-C_8)$ cycloalkyl group, optionally substituted by one, two or three groups selected from a $(C_1-C_4)$ alkyl group, a hydroxy group, a halogen atom and a $(C_1-C_3)$ alkoxy group, or
(v.1.B). a R'-L- group, wherein
L is a $(C_1)$ alkanediyl group, optionally substituted by a group selected from a hydroxy group and a $(C_1-C_3)$ alkoxy group, and
R' represents:
a $(C_4-C_8)$ cycloalkyl group, optionally substituted by one, two or three groups selected from a $(C_1-C_4)$ alkyl group, a hydroxy group, a halogen atom and a $(C_1-C_3)$ alkoxy group, or
(v.2) a R'-L- group, wherein
L is either a single bond or a $(C_1-C_3)$ alkanediyl group, optionally substituted by a group selected from a hydroxy group and a $(C_1-C_3)$ alkoxy group, and
R' represents:
a bridged $(C_6-C_{10})$ cycloalkyl group, optionally substituted by one to three groups selected from a $(C_1-C_4)$ alkyl group, a $(C_1-C_4)$ alkoxy group, a halogen atom, a hydroxy group, a —O—C(O)—R$^d$ group, a —O—C(O)—NHR$^d$ group, a —NH—C(O)—R$^d$ group, a —SO$_2$—R$^d$ group, a —N(R$^e$)$_2$ group and a —COOR$^a$ group, or (v.3) a R'-L- group, wherein
L is either a single bond or a $(C_1-C_3)$ alkanediyl group, optionally substituted by a group selected from a hydroxy group and a $(C_1-C_3)$ alkoxy group, and
R' represents:
a $(C_3-C_8)$ heterocycloalkyl group selected from a tetrahydropyranyl, an oxetanyl, a tetrahydrofuranyl, an oxepanyl, a tetrahydrothiopyranyl, a pyrrolidinyl, a dioxepanyl and a piperidinyl, said group being optionally substituted by one to three groups selected from a —COOR$^a$ group, a hydroxy group, a halogen atom, a $(C_1-C_4)$ alkyl group and an oxo group or
(v.4) a 1,3-benzothiazol-2-ylmethyl group or R'-L- group, wherein
L is either a single bond or a $(C_1-C_3)$ alkanediyl group, optionally substituted by a group selected from a hydroxy group and a $(C_1-C_3)$ alkoxy group, and
R' represents:
a monocyclic $(C_5-C_8)$ heteroaryl group, optionally substituted by one to three groups selected from a halogen atom, a $(C_1-C_4)$ alkyl group, a $(C_1-C_4)$ alkoxy group and a N-methylpiperazinyl group, or
(v.5) a R'-L- group, wherein
L is either a single bond or a $(C_1-C_3)$ alkanediyl group, optionally substituted by a group selected from a hydroxy group and a $(C_1-C_3)$ alkoxy group, and
R' represents a bridged $(C_6-C_{10})$ heterocycloalkyl group, or
(vi.1). a R'-L- group wherein
L is a $(C_1-C_3)$ alkanediyl group, and
R' is a phenyl group, substituted by one to three groups selected from the group consisting of $(C_1-C_6)$ alkyl group, a fluoro $(C_1-C_4)$ alkyl group and a fluoro $(C_1-C_4)$ alkoxy group, a halogen atom and a hydroxy group, or
(vi.2) a R'-L- group wherein
L is a $(C_1-C_3)$ alkanediyl group, optionally substituted by a group selected from a —NR$^b$R$^c$ group, a $(C_1-C_4)$ alkoxy group, a hydroxy group, a —COOR$^a$ group and a halogen atom, and
R' is a phenyl group, optionally substituted by one to three groups selected from the group consisting of $(C_1-C_6)$ alkyl group, a fluoro $(C_1-C_4)$ alkyl group and a fluoro $(C_1-C_4)$ alkoxy group, a halogen atom and a hydroxy group, and
R$^a$ represents a $(C_1-C_4)$ alkyl group or a hydrogen atom,
R$^b$ and R$^c$ independently represent a $(C_1-C_6)$ alkyl group or a hydrogen atom,
R$^d$ represents a $(C_1-C_4)$ alkyl group or a cyclopropyl group,
R$^e$ represents a $(C_1-C_3)$ alkyl group, and
R$^2$ represents a hydrogen atom or a $(C_1-C_3)$ alkyl group, or any of its pharmaceutically acceptable salt.
2. A compound of formula (I) according to claim 1, wherein R¹ represents:
(i). a $(C_2-C_6)$ alkyl group substituted by one or two groups selected from a —COOR$^a$ group, a hydroxy group, a halogen atom, a $(C_1-C_4)$ alkoxy group and a benzyloxy group, said benzyloxy being optionally substituted on its phenyl group by one to three halogen atoms,
(ii) a spiro$(C_7-C_9)$ bicyclic ring,
(iii). a fused phenyl group, chosen from phenyl groups fused with a cyclopentyl or a heterocyclopentyl selected from acetylindolinyl, methylindazolyl, and indazolyl which cyclopentyl group optionally comprises an insaturation and is optionally substituted by a $(C_1-C_4)$ alkyl group, a hydroxy group, a halogen atom, a $(C_1-C_3)$ alkoxy group or a —COR$^a$ group, (iv). a phenyl group, substituted by one or two groups selected from ($C_1$-$C_8$) alkyl, a ($C_1$-$C_3$) fluoroalkyl, a fluoro ($C_1$-$C_4$) alkoxy group, a fluor atom, a bromine atom, an iodine atom, and a ($C_4$-$C_7$) heterocycloalkyl group, said ($C_4$-$C_7$) heterocycloalkyl group being itself optionally substituted by a ($C_1$-$C_4$) alkyl group, or (v.1.A). a R'-L- group, wherein L is either a single bond or a ($C_2$-$C_3$) alkanediyl group, optionally substituted by a group selected from a hydroxy group and a ($C_1$-$C_3$) alkoxy group, and R' represents a ($C_3$-$C_8$) cycloalkyl group, optionally substituted by one, two or three groups selected from a ($C_1$-$C_4$) alkyl group, a hydroxy group, a halogen atom and a ($C_1$-$C_3$) alkoxy group, or (v.1.B). a R'-L- group, wherein L is a ($C_1$) alkanediyl group, optionally substituted by a group selected from a hydroxy group and a ($C_1$-$C_3$) alkoxy group, and R' represents:

a ($C_4$-$C_8$) cycloalkyl group, optionally substituted by one, two or three groups selected from a ($C_1$-$C_4$) alkyl group, a hydroxy group, a halogen atom and a ($C_1$-$C_3$) alkoxy group, or (v.2) a R'-L- group, wherein L is either a single bond or a ($C_1$-$C_3$) alkanediyl group, optionally substituted by a group selected from a hydroxy group and a ($C_1$-$C_3$) alkoxy group, and R' represents:

a bridged ($C_7$-$C_{10}$) cycloalkyl group, optionally substituted by one to three groups selected from a ($C_1$-$C_4$) alkyl group, a ($C_1$-$C_4$) alkoxy group, a hydroxy group, a halogen atom, a —O—C(O)—$R^d$ group, a —O—C(O)—NH$R^d$ group, a —NH—C(O)—$R^d$ group, a —SO$_2$—$R^d$ group, a —N($R^e$)$_2$ group and a —COO$R^a$ group, or (v.3) a R'-L- group, wherein L is either a single bond or a ($C_1$-$C_3$) alkanediyl group, optionally substituted by a group selected from a hydroxy group and a ($C_1$-$C_3$) alkoxy group, and R' represents:

a ($C_3$-$C_8$) heterocycloalkyl group, selected from a tetrahydropyranyl, an oxetanyl, a tetrahydrofuranyl, an oxepanyl, a tetrahydrothiopyranyl, a pyrrolidinyl, a dioxepanyl or a piperidinyl, said group being optionally substituted by one to three groups selected from a —COO$R^a$ group, a hydroxy group, a halogen atom, a ($C_1$-$C_4$) alkyl group and a oxo group, or (v.4) a 1,3-benzothiazol-2-ylmethyl group or R'-L- group, wherein L is either a single bond or a ($C_1$-$C_3$) alkanediyl group, optionally substituted by a group selected from a hydroxy group and a ($C_1$-$C_3$) alkoxy group, and R' represents:

a monocyclic ($C_5$-$C_8$) heteroaryl group, optionally substituted by one to three groups selected from a halogen atom, ($C_1$-$C_4$) alkyl group, a ($C_1$-$C_4$) alkoxy group, a N-methylpiperazinyl group, or (v.5) a R'-L- group, wherein L is either a single bond or a ($C_1$-$C_3$) alkanediyl group, optionally substituted by a group selected from a hydroxy group and a ($C_1$-$C_3$) alkoxy group, and R' represents a bridged ($C_6$-$C_{10}$) heterocycloalkyl group, or (vi.1) a R'-L- group wherein L is a ($C_1$-$C_3$) alkanediyl group, and R' is a phenyl group, substituted by one to three groups selected from the group consisting of ($C_1$-$C_6$) alkyl group, a fluoro ($C_1$-$C_4$) alkyl group and a fluoro ($C_1$-$C_4$) alkoxy group, a hydroxy group and a halogen atom, or (vi.2) a R'-L- group wherein L is a ($C_1$-$C_3$) alkanediyl group, substituted by a group selected from a —NR$^b$R$^c$ group, a ($C_1$-$C_4$) alkoxy group, a hydroxy group, a —COOR$^a$ group and a halogen atom, and R' is a phenyl group, optionally substituted by one to three groups selected from the group consisting of ($C_1$-$C_6$) alkyl group, a fluoro ($C_1$-$C_4$) alkyl group and a fluoro ($C_1$-$C_4$) alkoxy group, a hydroxy group and a halogen atom, $R^a$ represents a ($C_1$-$C_4$) alkyl group or a hydrogen atom, $R^b$ and $R^c$ independently represent a ($C_1$-$C_6$) alkyl group or a hydrogen atom, $R^d$ represents a ($C_1$-$C_4$) alkyl group or a cyclopropyl group, $R^e$ represents a ($C_1$-$C_3$) alkyl group, and $R^2$ represents a hydrogen atom or a ($C_1$-$C_3$) alkyl group, or any of its pharmaceutically acceptable salt.

3. A compound of formula (I) according to claim 1, wherein $R^1$ represents:

(i). a ($C_2$-$C_6$) alkyl group substituted by one or two groups selected from a —COOCH$_3$ group, a hydroxy group, a fluorine atom, a methoxy group, an ethoxy group, a tert-butoxy group, a cyclopropoxy group and a benzyloxy group, said benzyloxy being optionally substituted on its phenyl group by a fluorine atom, (ii). a spiro($C_7$-$C_8$) bicyclic ring, in particular a spiro[3.3]heptyl, a spiro [2.5]octanyl or a 7-azaspiro [3.5]nonyl, (iii). a fused phenyl group, chosen from phenyl groups fused with a cyclopentyl or a heterocyclopentyl selected from acetylindolinyl, methylindazolyl and indazolyl which cyclopentyl group optionally comprise an insaturation and is optionally substituted by a methyl, a hydroxy group, a methoxy group and a —COCH$_3$ group, (iv). a phenyl group, substituted by one or two groups selected from a methyl, a hexyl, a trifluoromethyl, a difluoromethoxy group, a fluor atom, a bromine atom, an iodine atom, in particular a morpholino group and a N-methylpiperazinyl group, or (v.1.A). a R'-L- group, wherein L is either a single bond or a ($C_2$-$C_3$) alkanediyl group, optionally substituted by a group selected from a hydroxy group and a ($C_1$-$C_3$) alkoxy group, and R' represents a ($C_3$-$C_8$) cycloalkyl group in particular a cyclopropyl, a cyclobutyl, a cyclopentyl, a cyclohexyl, a cycloheptyl or a cyclooctyl, optionally substituted by one, two or three groups selected from a methyl, an isopropyl, a hydroxy group and a methoxy group, or (v.1.B). a R'-L- group, wherein L is a ($C_1$) alkanediyl group, optionally substituted by a group selected from a hydroxy group and a ($C_1$-$C_3$) alkoxy group, and R' represents:

a ($C_4$-$C_8$) cycloalkyl group in particular a cyclobutyl, a cyclopentyl, a cyclohexyl, a cycloheptyl or a cyclooctyl, optionally substituted by one, two or three groups selected from a methyl, an isopropyl, a hydroxy group and a methoxy group, or (v.2) a R'-L- group, wherein L is either a single bond or a ($C_1$-$C_3$) alkanediyl group, optionally substituted by a group selected from a hydroxy group and a ($C_1$-$C_3$) alkoxy group, and R' represents:

a bridged ($C_7$-$C_{10}$) cycloalkyl group, in particular an adamantyl or a bicyclo[3.1.1]heptyl, optionally substituted by one to three groups selected from a methyl group, a methoxy group, a hydroxy group, a fluorine atom, a —O—C(O)—$CH_3$ group, a —O—C(O)—C($CH_3$)$_3$ group, a —O—C(O)—NH—C($CH_3$)$_3$ group, a —NH—C(O)—$CH_3$ group, a —NH—C(O)-cyclopropyl group, a —S(O)$_2$—$CH_3$ group, a —S(O)$_2$-cyclopropyl group, a —N($CH_3$)$_2$ group and a —C(O)—O—$CH_3$ group, (v.3). a R'-L- group, wherein L is either a single bond or a ($C_1$-$C_3$) alkanediyl group, optionally substituted by a group selected from a hydroxy group and a ($C_1$-$C_3$) alkoxy group, and R' represents:

a ($C_5$-$C_8$) heterocycloalkyl group, selected from a tetrahydropyranyl, an oxetanyl, a tetrahydrofuranyl, an oxepanyl, a tetrahydrothiopyranyl, a pyrrolidinyl, a dioxepanyl or a piperidinyl, said group being optionally substituted by one, two or three group(s) selected from a —COOR$^a$ group, a hydroxy group, a methyl group and an oxo group, wherein R$^a$ represents either an ethyl or an isopropyl group, or (v.4) a 1,3-benzothiazol-2-ylmethyl group or R'-L- group, wherein L is either a single bond or a ($C_1$-$C_3$) alkanediyl group, optionally substituted by a group selected from a hydroxy group and a ($C_1$-$C_3$) alkoxy group, and R' represents:

a monocyclic ($C_5$-$C_8$) heteroaryl group, in particular a pyrimidinyl, a pyridinyl, a thiazolyl, a imidazolyl, a pyrazolyl, a thiadiazolyl, a pyridazinyl, a pyrazinyl, a furyl, optionally substituted by one to three groups selected from methyl group, a methoxy group and a N-methylpiperazinyl group, or (v.5). a R'-L- group, wherein L is either a single bond or a ($C_1$-$C_3$) alkanediyl group, optionally substituted by a group selected from a hydroxy group and a ($C_1$-$C_3$) alkoxy group, and R' represents a bridged ($C_7$-$C_{10}$) heterocycloalkyl group, in particular a quinuclidine-3-yl, or (vi.1). a R'-L- group wherein L is a ($C_1$-$C_3$) alkanediyl group, and R' is a phenyl group, substituted by one or two groups selected from the group consisting of methyl group, a trifluoromethyl group and a trifluromethoxy group, or (vi.2) a R'-L- group wherein L is a ($C_1$-$C_3$) alkanediyl group, substituted by a group selected from a —NR$^b$R$^c$ group, a ($C_1$-$C_4$) alkoxy group, a hydroxy group, a —COOR$^a$ group and a halogen atom, and R' is a phenyl group, optionally substituted by one or two groups selected from the group consisting of methyl group, a trifluoromethyl group and a trifluromethoxy group, R$^a$ representing a ($C_1$-$C_3$) alkyl group, R$^b$ and R$^c$ are independently chosen from a methyl group or a hydrogen atom, and R$^2$ represents a hydrogen atom or a ($C_1$-$C_3$) alkyl group, or any of its pharmaceutically acceptable salts.

4. A compound of formula (I) according to claim 1, wherein L is selected from a group consisting of a —$CH_2$— group, a —CH($CH_3$)— group, a —CH($CH_2OH$)—$CH_2$— group, a —CH($CH_2OH$)— group, a —CH($CH_2OCH_3$)— group, a —CH(OH)—$CH_2$— group, a —$CH_2$—CH($CH_2OCH_3$)— group, a —CH($OCH_3$)—$CH_2$— group, a —$CH_2$—CH($COOCH_3$)— group, a —CH($CH_2F$)— group, a —CH($CH_2NH_2$)— group, a —CH($CH_2NHCH_3$)— group, a —CH($CH_2N$($CH_3$)$_2$)— group, a —$CH_2$—CH($CH_2OH$)— group, a —CH($OCH_3$)—$CH_2$— group, a —$CH_2$—CH($OCH_3$)— group, a —$CH_2$—CH(OH)—$CH_2$— group, a —$CH_2$—CH($OCH_3$)—$CH_2$ group, a —($CH_2$)$_3$— group, a —($CH_2$)$_2$— group and a —CH($CH_2OC$($CH_3$)$_3$) group, or any of its pharmaceutically acceptable salts.

5. A compound of formula (I) according to claim 1, wherein:

(v.1.A). when R' is a ($C_4$-$C_8$) cycloalkyl group, L is selected from the group consisting of a single bond, a —$CH_2$— group, a —CH($CH_3$)— group, a —CH($CH_2OH$)—$CH_2$— group, a —CH($CH_2OH$)— group, a —CH($CH_2OCH_3$)— group and a —CH(OH)—$CH_2$— group and a —CH($OCH_3$)—$CH_2$— group, (v.1.B). when R' is a cyclopropyl, L is selected from the group consisting of a single bond, a —CH($CH_3$)— group, a —CH($CH_2OH$)—$CH_2$— group, a —CH($CH_2OH$)— group, a —CH($CH_2OCH_3$)— group and a —CH(OH)—$CH_2$— group and a —CH($OCH_3$)—$CH_2$— group, (v.2). when R' is a bridged ($C_7$-$C_{10}$) cycloalkyl group, L is a single bond, a —$CH_2$— group or a —CH($CH_3$)— group, (v.3). when R' is a ($C_5$-$C_8$) heterocycloalkyl group including spiro($C_3$-$C_8$) heterocycloalkyls, L is a single bond or a —$CH_2$— group, (v.4). when R' is a phenyl, L is selected from the group consisting of a single bond, a —$CH_2$—CH($COOCH_3$)— group, a —CH($CH_2F$)— group, a —CH($CH_2NH_2$)— group, a —CH($CH_2NHCH_3$)— group, a —CH($CH_2N$($CH_3$)$_2$)— group, a —$CH_2$—CH($CH_2OH$)— group, a —CH($CH_2OH$)— group, a —CH($CH_2OCH_3$)— group, a —CH(OH)—$CH_2$— group, a —$CH_2$—CH($CH_2OCH_3$)— group, a —$CH_2$—CH(OH)—$CH_2$— group and a —$CH_2$—CH($OCH_3$)—$CH_2$ group, (v.5). when R' is a monocyclic heteroaryl group, L is selected from the group comprising a single bond, a —$CH_2$— group, a —($CH_2$)$_3$— group and a —($CH_2$)$_2$— group, and (v.6). when R' is a bridged ($C_7$-$C_{10}$) heterocycloalkyl group, L is a single bond, or any of its pharmaceutically acceptable salts.

6. A compound of formula (I) according to claim 1, wherein R$^1$ represents:

an adamantyl group, optionally substituted by one to three groups, and in particular substituted by one group, selected from a methyl group, a methoxy group, a hydroxy group, a fluorine atom, a —O—C(O)—$CH_3$ group, a —O—C(O)—C($CH_3$)$_3$ group, a —O—C(O)—NH—C($CH_3$)$_3$ group, a —NH—C(O)—$CH_3$ group, a —NH—C(O)-cyclopropyl group, a —S(O)$_2$—$CH_3$ group, a —S(O)$_2$-cyclopropyl group, a —N($CH_3$)$_2$ group and a —C(O)—O—$CH_3$ group, the adamantyl group being preferably unsubstituted; or a R"—O—$CH_2$CH(R''')— group, wherein:

R" is a ($C_1$-$C_4$) alkyl group, preferably a methyl or ethyl group, and

R''' is a ($C_1$-$C_4$) alkyl group, in particular a ($C_3$-$C_4$) alkyl group, and preferably an isopropylmethyl group, or R''' is a phenyl group, optionally substituted by one to three groups and in particular substituted by one group, selected from the group consisting of a ($C_1$-$C_6$) alkyl group, a fluoro ($C_1$-$C_4$) alkyl group, a fluoro ($C_1$-$C_4$) alkoxy group, a halogen atom and a hydroxy group, the phenyl group being preferably unsubstituted, or any of its pharmaceutically acceptable salts.

7. A compound of formula (I) according to claim 1, wherein $R^1$ represents:
a $(C_1-C_6)$ alkyl group substituted by one or two groups selected from a —COOR$^a$ group, a hydroxy group, a fluorine atom, a $(C_1-C_4)$ alkoxy group and a benzyloxy group, said benzyloxy being optionally substituted on its phenyl group by a halogen atom,
a spiro$(C_5-C_{11})$ bicyclic ring,
a R'-L- group, wherein
L is either a single bond or a $(C_2-C_3)$ alkanediyl group, optionally substituted by a group chosen from a hydroxy group and a $(C_1-C_3)$ alkoxy group, and
R' represents a $(C_3-C_8)$ cycloalkyl group, optionally substituted by one, two or three groups selected from a $(C_1-C_4)$ alkyl group, a hydroxy group, a halogen atom and a $(C_1-C_3)$ alkoxy group, or
a R'-L- group, wherein
L is a $(C_1)$ alkanediyl group, optionally substituted by a group chosen from a hydroxy group and a $(C_1-C_3)$ alkoxy group, and
R' represents:
a $(C_4-C_8)$ cycloalkyl group, optionally substituted by one, two or three groups selected from a $(C_1-C_4)$ alkyl group, a hydroxy group, a halogen atom and a $(C_1-C_3)$ alkoxy group, or
a R'-L- group, wherein
L is either a single bond or a $(C_1-C_3)$ alkanediyl group, optionally substituted by a group chosen from a hydroxy group and a $(C_1-C_3)$ alkoxy group, and
R' represents:
a bridged $(C_6-C_{10})$ cycloalkyl group, optionally substituted by one to three groups selected from a $(C_1-C_4)$ alkyl group, a $(C_1-C_4)$ alkoxy group, a halogen atom, a hydroxy group, a —O—C(O)—R$^d$ group, a —O—C(O)—NHR$^d$ group, a —NH—C(O)—R$^d$ group, a —SO$_2$—R$^d$ group, a —N(R$^e$)$_2$ group and a —COOR$^a$ group,
R$^a$ representing a $(C_1-C_4)$ alkyl group, R$^d$ representing a $(C_1-C_4)$ alkyl group or a cyclopropyl group and R$^e$ representing a $(C_1-C_3)$ alkyl group, and
wherein $R^2$ represents a hydrogen atom or a $(C_1-C_3)$ alkyl group,
or any of its pharmaceutically acceptable salt.

8. A compound of formula (I) according to claim 1, wherein $R^1$ represents:
a fused phenyl group, chosen from phenyl groups fused with a $(C_5-C_6)$ cycloalkyl or $(C_5-C_6)$ heterocycloalkyl selected from acetylindolinyl, methylindazolyl and indazolyl, which $(C_5-C_6)$ cycloalkyl group optionally comprises an insaturation and is optionally substituted by a $(C_1-C_4)$ alkyl group, a hydroxy group, a halogen atom, a $(C_1-C_3)$ alkoxy group and a —COR$^a$ group,
a phenyl group, substituted by one or two groups selected from $(C_1-C_8)$ alkyl, a $(C_1-C_3)$ fluoroalkyl, a fluoro $(C_1-C_4)$ alkoxy group a fluorine atom, a bromine atom, an iodine atom and a $(C_4-C_7)$ heterocycloalkyl group said $(C_4-C_7)$ heterocycloalkyl group being itself optionally substituted by a $(C_1-C_4)$ alkyl group, of
a R'-L- group wherein
L is a $(C_1-C_3)$ alkanediyl group, and
R' is a phenyl group, substituted by one to three groups selected from the group consisting of $(C_1-C_6)$ alkyl group, a fluoro $(C_1-C_4)$ alkyl group and a fluoro $(C_1-C_4)$ alkoxy group, a halogen atom and a hydroxy group, or a R'-L- group wherein
L is a $(C_1-C_3)$ alkanediyl group, optionally substituted by a group chosen from a hydroxy group, a $(C_1-C_4)$ alkoxy group, a —NR$^b$R$^c$ group, a —COOR$^a$ group and a halogen atom, and
R' is a phenyl group, optionally substituted by one to three groups selected from the group consisting of $(C_1-C_6)$ alkyl group, a fluoro $(C_1-C_4)$ alkyl group and a fluoro $(C_1-C_4)$ alkoxy group, a halogen atom and a hydroxy group, and
wherein $R^2$ represents a hydrogen atom or a $(C_1-C_3)$ alkyl group,
or any pharmaceutically acceptable salt thereof.

9. A compound of formula (I) according to claim 1, wherein $R^2$ represents a hydrogen atom or a methyl group.

10. A compound of formula (I) according to claim 1, wherein $R^1$ represents a R'-L- group wherein
R' is a monocyclic $(C_5-C_8)$ heteroaryl group, optionally substituted by one to three groups selected from a halogen atom, a $(C_1-C_4)$ alkyl group, a $(C_1-C_4)$ alkoxy group and a N-methylpiperazinyl group, and
L is a $(C_1-C_3)$ alkanediyl or a single bond, and
wherein $R^2$ represents a hydrogen atom,
or any pharmaceutically acceptable salt thereof.

11. A compound of formula (I) according to claim 1, wherein $R^1$ represents a R'-L- group wherein
R' is a $(C_3-C_5)$ heterocycloalkyl group, optionally substituted by one to three groups selected from a hydroxy group, a $(C_1-C_4)$ alkyl group, an oxo group and a —COOR$^a$ group wherein R$^a$ is as defined in claim 1, and
L is a methylene or a single bond, and
wherein $R^2$ represents a hydrogen atom,
or any pharmaceutically acceptable salt thereof.

12. A compound of formula (I) according to claim 1 selected from:
(2) (4Z)-4-(1,3-Benzothiazol-6-ylmethylene)-2-(cyclopropylamino)-1H-imidazol-5-one,
(3) (4Z)-4-(1,3-Benzothiazol-6-ylmethylene)-2-(cyclobutylamino)-1H-imidazol-5-one,
(4) (4Z)-4-(1,3-Benzothiazol-6-ylmethylene)-2-(cyclopentylamino)-1H-imidazol-5-one,
(5) (4Z)-4-(1,3-Benzothiazol-6-ylmethylene)-2-(cyclohexylmethylamino)-1H-imidazol-5-one,
(6) (4Z)-4-(1,3-Benzothiazol-6-ylmethylene)-2-(cyclohexylamino)-1H-imidazol-5-one,
(7) (4Z)-4-(1,3-Benzothiazol-6-ylmethylene)-2-(cycloheptylmethylamino)-1H-imidazol-5-one,
(8) (4Z)-4-(1,3-Benzothiazol-6-ylmethylene)-2-(cycloheptylamino)-1H-imidazol-5-one,
(9) (4Z)-4-(1,3-Benzothiazol-6-ylmethylene)-2-(cyclooctylamino)-1H-imidazol-5-one,
(10) (4Z)-4-(1,3-Benzothiazol-6-ylmethylene)-2-[(3-hydroxy-2,2-dimethyl-propyl) amino]-1H-imidazol-5-one,
(11) (4Z)-4-(1,3-Benzothiazol-6-ylmethylene)-2-(2-benzyloxyethylamino)-1H-imidazol-5-one,
(12) (+)-(4Z)-4-(1,3-Benzothiazol-6-ylmethylene)-2-[[cis-2-methylcyclohexyl]amino]-1H-imidazol-5-one,
(13) (4Z)-4-(1,3-Benzothiazol-6-ylmethylene)-2-[[(1R)-1-cyclohexylethyl]amino]-1H-imidazol-5-one,
(14) (4Z)-2-(1-Adamantylmethylamino)-4-(1,3-benzothiazol-6-ylmethylene)-1H-imidazol-5-one,
(15) (+)-(4Z)-2-[1-(1-Adamantyl) ethylamino]-4-(1,3-benzothiazol-6-ylmethylene)-1H-imidazol-5-one,
(16) (4Z)-2-(1-Adamantylamino)-4-(1,3-benzothiazol-6-ylmethylene)-1H-imidazol-5-one,

(17) (4Z)-2-(2-Adamantylamino)-4-(1,3-benzothiazol-6-ylmethylene)-1H-imidazol-5-one,
(18) (4Z)-4-(1,3-Benzothiazol-6-ylmethylene)-2-[[3,5-dimethyl-1-adamantyl]amino]-1H-imidazol-5-one,
(19) (4Z)-4-(1,3-Benzothiazol-6-ylmethylene)-2-[(trans-5-hydroxy-2-adamantyl) amino]-1H-imidazol-5-one,
(20) (4Z)-4-(1,3-Benzothiazol-6-ylmethylene)-2-[(3-hydroxy-1-adamantyl) amino]-1H-imidazol-5-one,
(21) (4Z)-4-(1,3-Benzothiazol-6-ylmethylene)-2-[(3-methoxy-1-adamantyl) amino]-1H-imidazol-5-one,
(22) (4Z)-4-(1,3-Benzothiazol-6-ylmethylene)-2-[[(1R,2R,3R,5S)-2,6,6-trimethylnorpinan-3-yl]amino]-1H-imidazol-5-one,
(23) (4Z)-4-(1,3-Benzothiazol-6-ylmethylene)-2-[[(1S,2S,3S,5R)-2,6,6-trimethylnorpinan-3-yl]amino]-1H-imidazol-5-one,
(24) (4Z)-4-(1,3-Benzothiazol-6-ylmethylene)-2-[[(1R,2R,5R)-6,6-dimethylnorpinan-2-yl]methylamino]-1H-imidazol-5-one,
(25) (+)-(4Z)-4-(1,3-Benzothiazol-6-ylmethylene)-2-(spiro[2.5]octan-2-ylamino)-1H-imidazol-5-one,
(26) (4Z)-4-(1,3-Benzothiazol-6-ylmethylene)-2-(spiro[3.3]heptan-2-ylamino)-1H-imidazol-5-one,
(27) (4Z)-4-(1,3-Benzothiazol-6-ylmethylene)-2-[[(2R)-1,7,7-trimethylnorbornan-2-yl]amino]-1H-imidazol-5-one,
(28) (+)-(4Z)-4-(1,3-Benzothiazol-6-ylmethylene)-2-(norbornan-2-ylamino)-1H-imidazol-5-one,
(29) (4Z)-4-(1,3-Benzothiazol-6-ylmethylene)-2-[[(1R,2S,5R)-2-isopropyl-5-methyl-cyclohexyl]amino]-1H-imidazol-5-one,
(30) (4Z)-4-(1,3-Benzothiazol-6-ylmethylene)-2-[[(1R)-1-(cyclohexylmethyl)-2-hydroxy-ethyl]amino]-1H-imidazol-5-one,
(31) (4Z)-4-(1,3-Benzothiazol-6-ylmethylene)-2-[(1R)-1-(cyclopentylmethyl)-2-hydroxy-ethyl]amino]-1H-imidazol-5-one,
(32) (4Z)-4-(1,3-Benzothiazol-6-ylmethylene)-2-[[(1R)-1-(cyclobutylmethyl)-2-hydroxy-ethyl]amino]-1H-imidazol-5-one,
(33) (4Z)-4-(1,3-Benzothiazol-6-ylmethylene)-2-[(1R)-1-(cyclopropylmethyl)-2-hydroxy-ethyl]amino]-1H-imidazol-5-one,
(34) (4Z)-4-(1,3-Benzothiazol-6-ylmethylene)-2-[[(1R)-1-(hydroxymethyl)-3-methyl-butyl]amino]-1H-imidazol-5-one,
(35) (4Z)-4-(1,3-Benzothiazol-6-ylmethylene)-2-[[(1R)-1-(methoxymethyl)-3-methyl-butyl]amino]-1H-imidazol-5-one,
(36) (4Z)-4-(1,3-Benzothiazol-6-ylmethylene)-2-[[(1S)-1-(hydroxymethyl)-3-methyl-butyl]amino]-1H-imidazol-5-one,
(37) (4Z)-4-(1,3-Benzothiazol-6-ylmethylene)-2-[[(1S)-1-(methoxymethyl)-3-methyl-butyl]amino]-1H-imidazol-5-one,
(38) (4Z)-4-(1,3-Benzothiazol-6-ylmethylene)-2-[(1R)-1-(hydroxymethyl) propyl]amino]-1H-imidazol-5-one,
(39) (4Z)-4-(1,3-Benzothiazol-6-ylmethylene)-2-[[(1S)-1-(hydroxymethyl) propyl]amino]-1H-imidazol-5-one,
(40) (+)-(4Z)-4-(1,3-Benzothiazol-6-ylmethylene)-2-[1-(fluoromethyl)-3-methyl-butyl]amino]-1H-imidazol-5-one,
(41) (+)-(4Z)-4-(1,3-Benzothiazol-6-ylmethylene)-2-[(1-cyclohexyl-2-hydroxy-ethyl) amino]-1H-imidazol-5-one,
(42) (+)-(4Z)-4-(1,3-Benzothiazol-6-ylmethylene)-2-[(1-cyclohexyl-2-methoxy-ethyl) amino]-1H-imidazol-5-one,
(43) (+)-(4Z)-4-(1,3-Benzothiazol-6-ylmethylene)-2-[(2-cyclohexyl-2-hydroxy-ethyl) amino]-1H-imidazol-5-one,
(44) (+)-(4Z)-4-(1,3-Benzothiazol-6-ylmethylene)-2-[(2-cyclohexyl-2-methoxy-ethyl) amino]-1H-imidazol-5-one,
(45) (+)-(4Z)-4-(1,3-Benzothiazol-6-ylmethylene)-2-[[cis-2-hydroxycyclopentyl]amino]-1H-imidazol-5-one,
(46) (+)-(4Z)-4-(1,3-Benzothiazol-6-ylmethylene)-2-[[trans-2-hydroxycyclopentyl]amino]-1H-imidazol-5-one,
(47) (+)-(4Z)-4-(1,3-Benzothiazol-6-ylmethylene)-2-[cis-2-methoxycyclopentyl]amino]-1H-imidazol-5-one,
(48) (+)-(4Z)-4-(1,3-Benzothiazol-6-ylmethylene)-2-[[trans-2-methoxycyclopentyl]amino]-1H-imidazol-5-one,
(49) (+)-(4Z)-4-(1,3-Benzothiazol-6-ylmethylene)-2-[cis-2-hydroxycyclohexyl]amino]-1H-imidazol-5-one,
(50) (+)-(4Z)-4-(1,3-Benzothiazol-6-ylmethylene)-2-hydroxycyclohexyl]amino]-1H-imidazol-5-one,
(51) (4Z)-4-(1,3-Benzothiazol-6-ylmethylene)-2-[[(1R,2S)-2-hydroxycyclohexyl]amino]-1H-imidazol-5-one,
(52) (4Z)-4-(1,3-Benzothiazol-6-ylmethylene)-2-[[(1S,2R)-2-hydroxycyclohexyl]amino]-1H-imidazol-5-one,
(53) (4Z)-4-(1,3-Benzothiazol-6-ylmethylene)-2-[[(1R,2R)-2-hydroxycyclohexyl]amino]-1H-imidazol-5-one,
(54) (4Z)-4-(1,3-Benzothiazol-6-ylmethylene)-2-[[(1S,2S)-2-hydroxycyclohexyl]amino]-1H-imidazol-5-one,
(55) (+)-(4Z)-4-(1,3-Benzothiazol-6-ylmethylene)-2-[[cis-3-hydroxycyclohexyl]amino]-1H-imidazol-5-one,
(56) (+)-(4Z)-4-(1,3-Benzothiazol-6-ylmethylene)-2-[trans-3-hydroxycyclohexyl]amino]-1H-imidazol-5-one,
(57) (4Z)-4-(1,3-Benzothiazol-6-ylmethylene)-2-[(trans-4-hydroxycyclohexyl) amino]-1H-imidazol-5-one,
(58) (+)-(4Z)-4-(1,3-Benzothiazol-6-ylmethylene)-2-[[cis-2-methoxycyclohexyl]amino]-1H-imidazol-5-one,
(59) (+)-(4Z)-4-(1,3-Benzothiazol-6-ylmethylene)-2-[trans-2-methoxycyclohexyl]amino]-1H-imidazol-5-one,
(60) (4Z)-4-(1,3-Benzothiazol-6-ylmethylene)-2-[(trans-4-methoxycyclohexyl) amino]-1H-imidazol-5-one,
(61) (+)-(4Z)-4-(1,3-Benzothiazol-6-ylmethylene)-2-[[cis-2-hydroxycycloheptyl]amino]-1H-imidazol-5-one,
(62) (+)-(4Z)-4-(1,3-Benzothiazol-6-ylmethylene)-2-[[trans-2-hydroxycycloheptyl]amino]-1H-imidazol-5-one,
(63) (4Z)-4-(1,3-Benzothiazol-6-ylmethylene)-2-[[(1R,2R)-2-hydroxycycloheptyl]amino]-1H-imidazol-5-one,
(64) (4Z)-4-(1,3-Benzothiazol-6-ylmethylene)-2-[[(1S,2S)-2-hydroxycycloheptyl]amino]-1H-imidazol-5-one,
(65) (+)-(4Z)-4-(1,3-Benzothiazol-6-ylmethylene)-2-[[cis-3-hydroxycycloheptyl]amino]-1H-imidazol-5-one,
(66) (+)-(4Z)-4-(1,3-Benzothiazol-6-ylmethylene)-2-[[trans-3-hydroxycycloheptyl]amino]-1H-imidazol-5-one,

(67) (+)-(4Z)-4-(1,3-Benzothiazol-6-ylmethylene)-2-[[cis-2-methoxycycloheptyl]amino]-1H-imidazol-5-one,
(68) (+)-(4Z)-4-(1,3-Benzothiazol-6-ylmethylene)-2-[[trans-2-methoxycycloheptyl]amino]-1H-imidazol-5-one,
(69) Methyl (2S)-2-[[(4Z)-4-(1,3-benzothiazol-6-ylmethylene)-5-oxo-1H-imidazol-2-yl]amino]-3-methyl-butanoate,
(70) Methyl (2S)-2-[[(4Z)-4-(1,3-benzothiazol-6-ylmethylene)-5-oxo-1H-imidazol-2-yl]amino]propanoate,
(71) Methyl (2S)-2-[[(4Z)-4-(1,3-benzothiazol-6-ylmethylene)-5-oxo-1H-imidazol-2-yl]amino]-4-methyl-pentanoate,
(72) Methyl (2R)-2-[[(4Z)-4-(1,3-benzothiazol-6-ylmethylene)-5-oxo-1H-imidazol-2-yl]amino]-4-methyl-pentanoate,
(73) Methyl (2S)-2-[[(4Z)-4-(1,3-benzothiazol-6-ylmethylene)-5-oxo-1H-imidazol-2-yl]amino]-3-hydroxy-butanoate,
(75) (4Z)-4-(1,3-Benzothiazol-6-ylmethylene)-2-(indan-2-ylamino)-1H-imidazol-5-one,
(76) (4Z)-4-(1,3-Benzothiazol-6-ylmethylene)-2-[(3,4-dimethylphenyl) methylamino]-1H-imidazol-5-one,
(77) (4Z)-4-(1,3-Benzothiazol-6-ylmethylene)-2-[(2,4-dimethylphenyl) methylamino]-1H-imidazol-5-one,
(78) (4Z)-4-(1,3-Benzothiazol-6-ylmethylene)-2-[[2-(trifluoromethyl) phenyl]methylamino]-1H-imidazol-5-one,
(79) (4Z)-4-(1,3-Benzothiazol-6-ylmethylene)-2-[[2-(trifluoromethoxy) phenyl]methylamino]-1H-imidazol-5-one,
(80) (+)-(4Z)-4-(1,3-Benzothiazol-6-ylmethylene)-2-[[cis-2-hydroxyindan-1-yl]amino]-1H-imidazol-5-one,
(81) (+)-(4Z)-4-(1,3-Benzothiazol-6-ylmethylene)-2-[[trans-2-hydroxyindan-1-yl]amino]-1H-imidazol-5-one,
(82) (4Z)-4-(1,3-Benzothiazol-6-ylmethylene)-2-[[(1R,2R)-2-hydroxyindan-1-yl]amino]-1H-imidazol-5-one,
(83) (4Z)-4-(1,3-Benzothiazol-6-ylmethylene)-2-[[(1S,2S)-2-hydroxyindan-1-yl]amino]-1H-imidazol-5-one,
(84) (+)-(4Z)-4-(1,3-Benzothiazol-6-ylmethylene)-2-[[cis-2-methoxyindan-1-yl]amino]-1H-imidazol-5-one,
(85) (+)-(4Z)-4-(1,3-Benzothiazol-6-ylmethylene)-2-[[trans-2-methoxyindan-1-yl]amino]-1H-imidazol-5-one,
(86) Methyl (2S)-2-[[(4Z)-4-(1,3-benzothiazol-6-ylmethylene)-5-oxo-1H-imidazol-2-yl]amino]-3-phenyl-propanoate,
(87) Methyl (2R)-2-[[(4Z)-4-(1,3-benzothiazol-6-ylmethylene)-5-oxo-1H-imidazol-2-yl]amino]-3-phenyl-propanoate,
(88) (+)-(4Z)-4-(1,3-Benzothiazol-6-ylmethylene)-2-[(2-fluoro-1-phenyl-ethyl) amino]-1H-imidazol-5-one,
(89) (+)-(4Z)-2-[(2-Amino-1-phenyl-ethyl) amino]-4-(1,3-benzothiazol-6-ylmethylene)-1H-imidazol-5-one dihydrochloride,
(90) (+)-(4Z)-4-(1,3-Benzothiazol-6-ylmethylene)-2-[[2-(methylamino)-1-phenyl-ethyl]amino]-1H-imidazol-5-one dihydrochloride,
(91) (+)-(4Z)-4-(1,3-Benzothiazol-6-ylmethylene)-2-[[2-(dimethylamino)-1-phenyl-ethyl]amino]-1H-imidazol-5-one,
(92) (+)-(4Z)-4-(1,3-Benzothiazol-6-ylmethylene)-2-[(1-benzyl-2-hydroxy-ethyl) amino]-1H-imidazol-5-one,
(93) (4Z)-4-(1,3-Benzothiazol-6-ylmethylene)-2-[[(1R)-1-benzyl-2-hydroxy-ethyl]amino]-1H-imidazol-5-one,
(94) (+)-(4Z)-4-(1,3-Benzothiazol-6-ylmethylene)-2-[(1-benzyl-2-methoxy-ethyl) amino]-1H-imidazol-5-one,
(95) (+)-(4Z)-4-(1,3-Benzothiazol-6-ylmethylene)-2-[(2-hydroxy-1-phenyl-ethyl) amino]-1H-imidazol-5-one,
(96) (4Z)-4-(1,3-Benzothiazol-6-ylmethylene)-2-[[(1R)-2-hydroxy-1-phenyl-ethyl]amino]-1H-imidazol-5-one,
(97) (4Z)-4-(1,3-Benzothiazol-6-ylmethylene)-2-[[(1S)-2-hydroxy-1-phenyl-ethyl]amino]-1H-imidazol-5-one,
(98) (+)-(4Z)-4-(1,3-Benzothiazol-6-ylmethylene)-2-[(2-methoxy-1-phenyl-ethyl) amino]-1H-imidazol-5-one,
(99) (+)-(4Z)-4-(1,3-Benzothiazol-6-ylmethylene)-2-[(2-hydroxy-2-phenyl-ethyl) amino]-1H-imidazol-5-one,
(100) (+)-(4Z)-4-(1,3-Benzothiazol-6-ylmethylene)-2-[(2-methoxy-2-phenyl-ethyl) amino]-1H-imidazol-5-one,
(101) (+)-(4Z)-4-(1,3-Benzothiazol-6-ylmethylene)-2-[(2-hydroxy-3-phenyl-propyl) amino]-1H-imidazol-5-one,
(102) (+)-(4Z)-4-(1,3-Benzothiazol-6-ylmethylene)-2-[(2-methoxy-3-phenyl-propyl) amino]-1H-imidazol-5-one,
(103) (4Z)-4-(1,3-Benzothiazol-6-ylmethylene)-2-[(5-methylpyrazin-2-yl) methylamino]-1H-imidazol-5-one,
(104) (4Z)-4-(1,3-Benzothiazol-6-ylmethylene)-2-(2-pyridylmethylamino)-1H-imidazol-5-one,
(105) (4Z)-4-(1,3-Benzothiazol-6-ylmethylene)-2-(3-pyridylmethylamino)-1H-imidazol-5-one,
(106) (4Z)-4-(1,3-Benzothiazol-6-ylmethylene)-2-(4-pyridylmethylamino)-1H-imidazol-5-one,
(107) (4Z)-4-(1,3-Benzothiazol-6-ylmethylene)-2-[(5-methyl-2-furyl) methylamino]-1H-imidazol-5-one,
(108) (4Z)-4-(1,3-Benzothiazol-6-ylmethylene)-2-[(4-methylthiazol-2-yl) methylamino]-1H-imidazol-5-one,
(109) (4Z)-4-(1,3-Benzothiazol-6-ylmethylene)-2-(3-imidazol-1-ylpropylamino)-1H-imidazol-5-one,
(110) (4Z)-4-(1,3-Benzothiazol-6-ylmethylene)-2-[2-(2-pyridyl) ethylamino]-1H-imidazol-5-one,
(111) (4Z)-2-(1,3-Benzothiazol-2-ylmethylamino)-4-(1,3-benzothiazol-6-ylmethylene)-1H-imidazol-5-one,
(112) (4Z)-4-(1,3-Benzothiazol-6-ylmethylene)-2-[(1-methyl-4-piperidyl) methylamino]-1H-imidazol-5-one,
(113) (4Z)-4-(1,3-Benzothiazol-6-ylmethylene)-2-(tetrahydropyran-4-ylmethylamino)-1H-imidazol-5-one,
(114) Tert-butyl 4-[[[(4Z)-4-(1,3-benzothiazol-6-ylmethylene)-5-oxo-1H-imidazol-2-yl]amino methyl]piperidine-1-carboxylate,
(115) (4Z)-4-(1,3-Benzothiazol-6-ylmethylene)-2-[(7-methyl-7-azaspiro [3.5]nonan-2-yl) amino]-1H-imidazol-5-one,
(116) (4Z)-4-(1,3-Benzothiazol-6-ylmethylene)-2-(3-fluoro-4-methyl-anilino)-1H-imidazol-5-one,
(117) (4Z)-4-(1,3-Benzothiazol-6-ylmethylene)-2-(4-fluoroanilino)-1H-imidazol-5-one,
(118) (4Z)-4-(1,3-Benzothiazol-6-ylmethylene)-2-(4-hexylanilino)-1H-imidazol-5-one,
(119) (4Z)-4-(1,3-Benzothiazol-6-ylmethylene)-2-[4-(4-methylpiperazin-1-yl) anilino]-1H-imidazol-5-one,
(120) (4Z)-4-(1,3-Benzothiazol-6-ylmethylene)-2-[3-(difluoromethoxy) anilino]-1H-imidazol-5-one,
(121) (4Z)-2-[(1-Acetylindolin-6-yl) amino]-4-(1,3-benzothiazol-6-ylmethylene)-1H-imidazol-5-one,
(122) (4Z)-4-(1,3-Benzothiazol-6-ylmethylene)-2-[3-(trifluoromethyl) anilino]-1H-imidazol-5-one, (123) (4Z)-4-(1,3-Benzothiazol-6-ylmethylene)-2-(indan-5-ylamino)-1H-imidazol-5-one,
(124) (4Z)-4-(1,3-Benzothiazol-6-ylmethylene)-2-(4-morpholinoanilino)-1H-imidazol-5-one,
(125) (4Z)-4-(1,3-Benzothiazol-6-ylmethylene)-2-[(1-methylindazol-7-yl) amino]-1H-imidazol-5-one,
(126) (4Z)-4-(1,3-Benzothiazol-6-ylmethylene)-2-(pyrimidin-2-ylamino)-1H-imidazol-5-one,
(127) (4Z)-4-(1,3-Benzothiazol-6-ylmethylene)-2-(2-pyridylamino)-1H-imidazol-5-one,
(128) (4Z)-4-(1,3-Benzothiazol-6-ylmethylene)-2-[(1-methylpyrazol-3-yl) amino]-1H-imidazol-5-one,
(129) (4Z)-4-(1,3-Benzothiazol-6-ylmethylene)-2-[(2-methoxy-6-methyl-3-pyridyl) amino]-1H-imidazol-5-one,
(130) (4Z)-4-(1,3-Benzothiazol-6-ylmethylene)-2-(pyrimidin-5-ylamino)-1H-imidazol-5-one,
(131) (4Z)-4-(1,3-Benzothiazol-6-ylmethylene)-2-(3-pyridylamino)-1H-imidazol-5-one,
(132) (4Z)-4-(1,3-Benzothiazol-6-ylmethylene)-2-(1,3,4-thiadiazol-2-ylamino)-1H-imidazol-5-one,
(133) (4Z)-4-(1,3-Benzothiazol-6-ylmethylene)-2-[[5-(4-methylpiperazin-1-yl)-2-pyridyl]amino]-1H-imidazol-5-one,
(134) (4Z)-4-(1,3-Benzothiazol-6-ylmethylene)-2-[[6-(4-methylpiperazin-1-yl)-3-pyridyl]amino]-1H-imidazol-5-one,
(135) (4Z)-4-(1,3-Benzothiazol-6-ylmethylene)-2-[[2-(4-methylpiperazin-1-yl) pyrimidin-5-yl]amino]-1H-imidazol-5-one,
(136) (4Z)-4-(1,3-Benzothiazol-6-ylmethylene)-2-[[5-(4-methylpiperazin-1-yl) pyrimidin-2-yl]amino]-1H-imidazol-5-one,
(137) (4Z)-4-(1,3-Benzothiazol-6-ylmethylene)-2-[[5-(4-methylpiperazin-1-yl) pyrazin-2-yl]amino]-1H-imidazol-5-one,
(138) (4Z)-4-(1,3-Benzothiazol-6-ylmethylene)-2-[[6-(4-methylpiperazin-1-yl) pyridazin-3-yl]amino]-1H-imidazol-5-one,
(139) (4Z)-4-(1,3-Benzothiazol-6-ylmethylene)-2-(tetrahydropyran-4-ylamino)-1H-imidazol-5-one,
(140) Tert-butyl 4-[[(4Z)-4-(1,3-benzothiazol-6-ylmethylene)-5-oxo-1H-imidazol-2-yl]amino]piperidine-1-carboxylate,
(141) Ethyl 4-[[(4Z)-4-(1,3-benzothiazol-6-ylmethylene)-5-oxo-1H-imidazol-2-yl]amino]piperidine-1-carboxylate,
(142) (4Z)-4-(1,3-Benzothiazol-6-ylmethylene)-2-[(1-methyl-4-piperidyl) amino]-1H-imidazol-5-one,
(142) (+)-(4Z)-4-(1,3-Benzothiazol-6-ylmethylene)-2-[(1-methyl-3-piperidyl) amino]-1H-imidazol-5-one,
(144) (4Z)-4-(1,3-Benzothiazol-6-ylmethylene)-2-(oxetan-3-ylamino)-1H-imidazol-5-one,
(145) (4Z)-4-(1,3-Benzothiazol-6-ylmethylene)-2-[[(3R)-tetrahydrofuran-3-yl]amino]-1H-imidazol-5-one,
(146) (4Z)-4-(1,3-Benzothiazol-6-ylmethylene)-2-[[(3S)-tetrahydrofuran-3-yl]amino]-1H-imidazol-5-one,
(147) (4Z)-4-(1,3-Benzothiazol-6-ylmethylene)-2-[[(3R)-tetrahydropyran-3-yl]amino]-1H-imidazol-5-one,
(148) (4Z)-4-(1,3-Benzothiazol-6-ylmethylene)-2-[[(3S)-tetrahydropyran-3-yl]amino]-1H-imidazol-5-one,
(149) (+)-(4Z)-4-(1,3-Benzothiazol-6-ylmethylene)-2-[(6,6-dimethyltetrahydropyran-3-yl) amino]-1H-imidazol-5-one,
(149A). (4Z)-4-(1,3-Benzothiazol-6-ylmethylene)-2-[[(3R)/(3S)-6,6-dimethyltetrahydropyran-3-yl]amino]-1H-imidazol-5-one,
(149B). (4Z)-4-(1,3-Benzothiazol-6-ylmethylene)-2-[[(3R)/(3S)-6,6-dimethyltetrahydropyran-3-yl]amino]-1H-imidazol-5-one,
(150) (4Z)-4-(1,3-Benzothiazol-6-ylmethylene)-2-[[(3R,4R)-4-hydroxytetrahydropyran-3-yl]amino]-1H-imidazol-5-one,
(151) (+)-(4Z)-4-(1,3-Benzothiazol-6-ylmethylene)-2-(oxepan-3-ylamino)-1H-imidazol-5-one,
(152) (+)-3-[[(4Z)-4-(1,3-Benzothiazol-6-ylmethylene)-5-oxo-1H-imidazol-2-yl]amino]piperidin-2-one,
(153) (3S)-3-[[(4Z)-4-(1,3-Benzothiazol-6-ylmethylene)-5-oxo-1H-imidazol-2-yl]amino]piperidin-2-one,
(154) (5S)-5-[[(4Z)-4-(1,3-Benzothiazol-6-ylmethylene)-5-oxo-1H-imidazol-2-yl]amino]piperidin-2-one,
(155) (+)-(4Z)-4-(1,3-Benzothiazol-6-ylmethylene)-2-[(3,3-difluorocyclopentyl) amino]-1H-imidazol-5-one,
(156) (4Z)-4-(1,3-Benzothiazol-6-ylmethylene)-2-[(4,4-difluorocyclohexyl) amino]-1H-imidazol-5-one,
(157) (+)-(4Z)-4-(1,3-Benzothiazol-6-ylmethylene)-2-[(3,3-difluorocyclohexyl) amino]-1H-imidazol-5-one,
(158) (+)-(4Z)-4-(1,3-Benzothiazol-6-ylmethylene)-2-[(2,2-difluorocyclohexyl) amino]-1H-imidazol-5-one,
(159) (+)-(4Z)-4-(1,3-Benzothiazol-6-ylmethylene)-2-[(3,3-difluorocycloheptyl) amino]-1H-imidazol-5-one,
(160) (4Z)-4-(1,3-Benzothiazol-6-ylmethylene)-2-[[(1R)-1-(fluoromethyl)-3-methyl-butyl]amino]-1H-imidazol-5-one,
(161) (4Z)-4-(1,3-Benzothiazol-6-ylmethylene)-2-[[(1S)-1-(fluoromethyl)-3-methyl-butyl]amino]-1H-imidazol-5-one,
(162) [3-[[(4Z)-4-(1,3-Benzothiazol-6-ylmethylene)-5-oxo-1H-imidazol-2-yl]amino]-1-adamantyl]acetate,
(163) [3-[[(4Z)-4-(1,3-Benzothiazol-6-ylmethylene)-5-oxo-1H-imidazol-2-yl]amino]-1-adamantyl]2,2-dimethylpropanoate,
(164) (4Z)-4-(1,3-Benzothiazol-6-ylmethylene)-2-[[(1R,2R)-2-methoxycyclopentyl]amino]-1H-imidazol-5-one,
(165) (4Z)-4-(1,3-Benzothiazol-6-ylmethylene)-2-[[(1S,2S)-2-methoxycyclopentyl]amino]-1H-imidazol-5-one,
(166) (4Z)-4-(1,3-Benzothiazol-6-ylmethylene)-2-[[(1R,2R)-2-methoxycyclohexyl]amino]-1H-imidazol-5-one,
(167) (4Z)-4-(1,3-Benzothiazol-6-ylmethylene)-2-[[(1S,2S)-2-methoxycyclohexyl]amino]-1H-imidazol-5-one,
(168) (+)-(4Z)-4-(1,3-Benzothiazol-6-ylmethylene)-2-[[cis-3-methoxycyclohexyl]amino]-1H-imidazol-5-one,
(169) (+)-(4Z)-4-(1,3-Benzothiazol-6-ylmethylene)-2-[[trans-3-methoxycyclohexyl]amino]-1H-imidazol-5-one,
(169A). (4Z)-4-(1,3-Benzothiazol-6-ylmethylene)-2-[[(1R,3R)/(1S,3S)-3-methoxycyclohexyl]amino]-1H-imidazol-5-one,
(169B). (4Z)-4-(1,3-Benzothiazol-6-ylmethylene)-2-[[(1R,3R)/(1S,3S)-3-methoxycyclohexyl]amino]-1H-imidazol-5-one,
(170) (+)-(4Z)-4-(1,3-Benzothiazol-6-ylmethylene)-2-[[cis-4-hydroxycycloheptyl]amino]-1H-imidazol-5-one,
(171) (+)-(4Z)-4-(1,3-Benzothiazol-6-ylmethylene)-2-[[trans-4-hydroxycycloheptyl]amino]-1H-imidazol-5-one,
(171A). (4Z)-4-(1,3-Benzothiazol-6-ylmethylene)-2-[[(1R,4R)/(1S,4S)-4-hydroxycycloheptyl]amino]-1H-imidazol-5-one, (171B). (4Z)-4-(1,3-Benzothiazol-6-ylmethylene)-2-[[(1R,4R)/(1S,4S)-4-hydroxycycloheptyl]amino]-1H-imidazol-5-one,
(172) (+)-(4Z)-4-(1,3-Benzothiazol-6-ylmethylene)-2-[[cis-3-methoxycycloheptyl]amino]-1H-imidazol-5-one,
(173) (+)-(4Z)-4-(1,3-Benzothiazol-6-ylmethylene)-2-[[trans-3-methoxycycloheptyl]amino]-1H-imidazol-5-one,
(174) (+)-(4Z)-4-(1,3-Benzothiazol-6-ylmethylene)-2-[cis-4-methoxycycloheptyl]amino]-1H-imidazol-5-one,
(175) (+)-(4Z)-4-(1,3-benzothiazol-6-ylmethylene)-2-[[trans-4-methoxycycloheptyl]amino]-1H-imidazol-5-one,
(176) (4Z)-4-(1,3-Benzothiazol-6-ylmethylene)-2-[[(1R)-2-methoxy-1-phenyl-ethyl]amino]-1H-imidazol-5-one,
(177) (4Z)-4-(1,3-Benzothiazol-6-ylmethylene)-2-[[(1S)-2-methoxy-1-phenyl-ethyl]amino]-1H-imidazol-5-one,
(178) (4Z)-4-(1,3-Benzothiazol-6-ylmethylene)-2-[[(2R)-2-hydroxy-2-phenyl-ethyl]amino]-1H-imidazol-5-one,
(179) (4Z)-4-(1,3-Benzothiazol-6-ylmethylene)-2-[[(2S)-2-hydroxy-2-phenyl-ethyl]amino]-1H-imidazol-5-one,
(180) (4Z)-2-[[(1R)-2-Amino-1-phenyl-ethyl]amino]-4-(1,3-benzothiazol-6-ylmethylene)-1H-imidazol-5-one dihydrochloride,
(181) (4Z)-2-[[(1S)-2-Amino-1-phenyl-ethyl]amino]-4-(1,3-benzothiazol-6-ylmethylene)-1H-imidazol-5-one dihydrochloride,
(182) (4Z)-4-(1,3-Benzothiazol-6-ylmethylene)-2-[[(3R)-quinuclidin-3-yl]amino]-1H-imidazol-5-one,
(183) (4Z)-4-(1,3-Benzothiazol-6-ylmethylene)-2-[[(3S)-quinuclidin-3-yl]amino]-1H-imidazol-5-one,
(184) (+)-(4Z)-4-(1,3-Benzothiazol-6-ylmethylene)-2-(tetrahydrothiopyran-3-ylamino)-1H-imidazol-5-one,
(185) (+)-(4Z)-4-(1,3-Benzothiazol-6-ylmethylene)-2-(1,4-dioxepan-6-ylamino)-1H-imidazol-5-one,
(186) (+)-(4Z)-4-(1,3-Benzothiazol-6-ylmethylene)-2-[(2-oxopyrrolidin-3-yl) amino]-1H-imidazol-5-one,
(187) (+)-(4Z)-4-(1,3-Benzothiazol-6-ylmethylene)-2-[(1-methyl-2-oxo-pyrrolidin-3-yl) amino]-1H-imidazol-5-one,
(188) (+)-(4Z)-4-(1,3-Benzothiazol-6-ylmethylene)-2-[(4,4-dimethyl-2-oxo-pyrrolidin-3-yl) amino]-1H-imidazol-5-one,
(189) (3R)-3-[[(4Z)-4-(1,3-Benzothiazol-6-ylmethylene)-5-oxo-1H-imidazol-2-yl]amino]piperidin-2-one,
(190) (+)-3-[[(4Z)-4-(1,3-Benzothiazol-6-ylmethylene)-5-oxo-1H-imidazol-2-yl]amino]-1-methyl-piperidin-2-one,
(191) (+)-(4Z)-4-(1,3-Benzothiazol-6-ylmethylene)-2-[(3-methyl-2-oxo-pyrrolidin-3-yl) amino]-1H-imidazol-5-one,
(192) (+)-(4Z)-4-(1,3-Benzothiazol-6-ylmethylene)-2-[(1,3-dimethyl-2-oxo-pyrrolidin-3-yl) amino]-1H-imidazol-5-one,
(192A). (4Z)-4-(1,3-Benzothiazol-6-ylmethylene)-2-[[(3R)/(3S)-1,3-dimethyl-2-oxo-pyrrolidin-3-yl]amino]-1H-imidazol-5-one,
(192B). (4Z)-4-(1,3-Benzothiazol-6-ylmethylene)-2-[[(3R)/(3S)-1,3-dimethyl-2-oxo-pyrrolidin-3-yl]amino]-1H-imidazol-5-one,
(193) (4Z)-4-(1,3-Benzothiazol-6-ylmethylene)-2-[[(3S,4S)-4-hydroxytetrahydropyran-3-yl]amino]-1H-imidazol-5-one,
(194) (4Z)-2-(3-Noradamantylamino)-4-(1,3-benzothiazol-6-ylmethylene)-1H-imidazol-5-one,
(195) [3-[[(4Z)-4-(1,3-Benzothiazol-6-ylmethylene)-5-oxo-1H-imidazol-2-yl]amino]-1-adamantyl]N-tert-butylcarbamate,
(196) (4Z)-4-(1,3-Benzothiazol-6-ylmethylene)-2-[(3-fluoro-1-adamantyl) amino]-1H-imidazol-5-one,
(197) (4Z)-4-(1,3-Benzothiazol-6-ylmethylene)-2-[[(1R)-1-(tert-butoxymethyl)-3-methyl-butyl]amino]-1H-imidazol-5-one,
(198) (4Z)-4-(1,3-Benzothiazol-6-ylmethylene)-2-[[(1R)-2-tert-butoxy-1-phenyl-ethyl]amino]-1H-imidazol-5-one,
(199) N-[3-[[(4Z)-4-(1,3-Benzothiazol-6-ylmethylene)-5-oxo-1H-imidazol-2-yl]amino]-1-adamantyl]acetamide,
(200) N-[3-[[(4Z)-4-(1,3-Benzothiazol-6-ylmethylene)-5-oxo-1H-imidazol-2-yl]amino]-1-adamantyl]cyclopropanecarboxamide,
(201) N-[3-[[(4Z)-4-(1,3-Benzothiazol-6-ylmethylene)-5-oxo-1H-imidazol-2-yl]amino]-1-adamantyl]methanesulfonamide,
(202) N-[3-[[(4Z)-4-(1,3-Benzothiazol-6-ylmethylene)-5-oxo-1H-imidazol-2-yl]amino]-1-adamantyl]cyclopropanesulfonamide,
(203) (4Z)-4-(1,3-Benzothiazol-6-ylmethylene)-2-[[3-(dimethylamino)-1-adamantyl]amino]-1H-imidazol-5-one,
(204) Methyl 2-[[(4Z)-4-(1,3-benzothiazol-6-ylmethylene)-5-oxo-1H-imidazol-2-yl]amino]adamantane-2-carboxylate,
(205) (4Z)-2-(Cyclohexylamino)-4-[(2-methyl-1,3-benzothiazol-6-yl) methylene]-1H-imidazol-5-one,
(206) (4Z)-2-(Cycloheptylamino)-4-[(2-methyl-1,3-benzothiazol-6-yl) methylene]-1H-imidazol-5-one,
(207) (4Z)-2-[[(1R)-1-(Methoxymethyl)-3-methyl-butyl]amino]-4-[(2-methyl-1,3-benzothiazol-6-yl) methylene]-1H-imidazol-5-one,
(208) (4Z)-2-[[(1R)-2-Methoxy-1-phenyl-ethyl]amino]-4-[(2-methyl-1,3-benzothiazol-6-yl) methylene]-1H-imidazol-5-one,
(209) (4Z)-2-(1-Adamantylamino)-4-[(2-methyl-1,3-benzothiazol-6-yl) methylene]-1H-imidazol-5-one,
(210) (4Z)-2-[(3-Hydroxy-1-adamantyl) amino]-4-[(2-methyl-1,3-benzothiazol-6-yl) methylene]-1H-imidazol-5-one,
(211) (4Z)-4-(1,3-Benzothiazol-6-ylmethylene)-2-[(3,5-dihydroxy-1-adamantyl) amino]-1H-imidazol-5-one,
(212) (4Z)-4-(1,3-Benzothiazol-6-ylmethylene)-2-[(3,5,7-trifluoro-1-adamantyl) amino]-1H-imidazol-5-one,
(213) (4Z)-4-(1,3-Benzothiazol-6-ylmethylene)-2-[[(1R)-1-(ethoxymethyl)-3-methyl-butyl]amino]-1H-imidazol-5-one,
(214) (4Z)-4-(1,3-Benzothiazol-6-ylmethylene)-2-[[(1R)-1-(benzyloxymethyl)-3-methyl-butyl]amino]-1H-imidazol-5-one,
(215) (4Z)-4-(1,3-Benzothiazol-6-ylmethylene)-2-[[(1R)-1-[(4-fluorophenyl) methoxymethyl]-3-methyl-butyl]amino]-1H-imidazol-5-one,
(216) (4Z)-4-(1,3-Benzothiazol-6-ylmethylene)-2-[[(1R)-1-(cyclopropoxymethyl)-3-methyl-butyl]amino]-1H-imidazol-5-one, or anyone of their pharmaceutically acceptable salts.

13. A pharmaceutical composition comprising at least one compound as defined in claim 1 or any of its pharmaceutically acceptable salt or as defined in claim 12.

14. Synthesis process for manufacturing a compound of formula (I) as defined in claim 1 or any of its pharmaceutically acceptable salt or as defined in claim 12 or any of its pharmaceutically acceptable salts, comprising at least a step of coupling a compound of formula (II) below

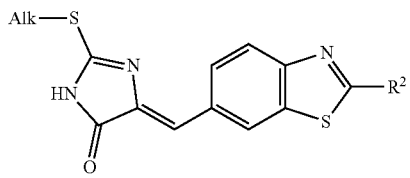

(II)

wherein Alk is a $(C_1-C_5)$ alkyl,
with an amine of formula $R^1NH_2$
wherein $R^1$ and $R^2$ are as defined in claim 1.

15. A synthetic intermediate of formula (II) below

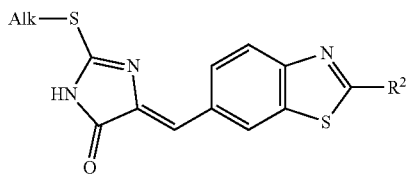

(II)

wherein Alk is a $(C_1-C_5)$ alkyl, in particular Alk is selected from the group consisting of an ethyl and a methyl and $R^2$ is as defined in claim 1.

16. Therapeutic method for the treatment of a disease selected from: cognitive deficits associated with Down syndrome (Trisomy 21); Alzheimer's disease and related diseases; dementia; tauopathies; and other neurodegenerative diseases (Parkinson's disease; Pick disease, including Niemann-Pick Type C Disease); CDKL5 Deficiency Disorder; McDermid syndrome; autism; type 1 and type 2 diabetes; abnormal folate and methionine metabolism; osteoarthritis, in particular knee osteoarthritis; Duchenne muscular dystrophy; several cancers, such as brain cancer, including glioblastoma, leukemia, including megakaryoblastic leukemia and acute lymphoblastic leukemia, head and neck squamous cell carcinoma, pancreatic cancer, including pancreatic ductal adenocarcinoma, prostate cancer, gastrointestinal cancer, breast cancer, such as Triple-negative breast cancer (TNBC), tissue cancer, including liposarcoma, Hedgehog/GLI-dependent cancer, liver cancer, including Hepatocellular carcinoma and viral infections, such as caused by Human immunodeficiency virus type 1 (HIV-1), Human cytomegalovirus (HCMV), Influenza A, Herpes virus, rhesus macaque cytomegalovirus, varicella-zoster virus, herpes simplex virus (HSV), Hepatitis C virus, Chikungunya virus, Dengue virus, Influenza virus and Severe acute respiratory syndrome (SARS) coronavirus, Cytomegalovirus and Human papillomavirus; neuroinflammation; anemia; infections caused by unicellular parasites, such as malaria, Leishmaniasis, Chagas and sleeping sickness (*Trypanosoma* sp.), and cattle diseases due to unicellular pathogens, and for regulating body temperature, in a patient in need thereof, comprising at least a step of administering a therapeutically effective amount of a compound of formula (I) according to claim 1.

17. The method according to claim 16, wherein the disease is selected from: Down syndrome, Alzheimer's disease, dementia, tauopathies, Parkinson's disease, Niemann-Pick Type C Disease, CDKL5 Deficiency Disorder and Phelan-McDermid syndrome and their associated cognitive and motor conditions and type 1 and type 2 diabetes.

18. Therapeutic method for the treatment of a disease selected from: cognitive deficits associated with Down syndrome (Trisomy 21); Alzheimer's disease and related diseases; dementia; tauopathies; and other neurodegenerative diseases (Parkinson's disease; Pick disease, including Niemann-Pick Type C Disease); CDKL5 Deficiency Disorder; McDermid syndrome; autism; type 1 and type 2 diabetes; abnormal folate and methionine metabolism; osteoarthritis, in particular knee osteoarthritis; Duchenne muscular dystrophy; several cancers, such as brain cancer, including glioblastoma, leukemia, including megakaryoblastic leukemia and acute lymphoblastic leukemia, head and neck squamous cell carcinoma, pancreatic cancer, including pancreatic ductal adenocarcinoma, prostate cancer, gastrointestinal cancer, breast cancer, such as Triple-negative breast cancer (TNBC), tissue cancer, including liposarcoma, Hedgehog/GLI-dependent cancer, liver cancer, including Hepatocellular carcinoma and viral infections, such as caused by Human immunodeficiency virus type 1 (HIV-1), Human cytomegalovirus (HCMV), Influenza A, Herpes virus, rhesus macaque cytomegalovirus, varicella-zoster virus, herpes simplex virus (HSV), Hepatitis C virus, Chikungunya virus, Dengue virus, Influenza virus and Severe acute respiratory syndrome (SARS) coronavirus, Cytomegalovirus and Human papillomavirus; neuroinflammation; anemia; infections caused by unicellular parasites, such as malaria, Leishmaniasis, Chagas and sleeping sickness (*Trypanosoma* sp.), and cattle diseases due to unicellular pathogens, and for regulating body temperature, in a patient in need thereof, comprising at least a step of administering a therapeutically effective amount of any of compounds (2) to (73) and (75) to (216) as defined in claim 12 or any of its pharmaceutically acceptable salts.

* * * * *